United States Patent
Nabel et al.

(10) Patent No.: US 11,993,636 B2
(45) Date of Patent: May 28, 2024

(54) ANTIGENIC OspA POLYPEPTIDES

(71) Applicant: Sanofi, Paris (FR)

(72) Inventors: Gary J. Nabel, Bridgewater, NJ (US); Chih-Jen Wei, Bridgewater, NJ (US); Heather Kamp, Bridgewater, NJ (US); Ronnie Wei, Bridgewater, NJ (US); Kurt Swanson, Bridgewater, NJ (US)

(73) Assignee: SANOFI, Paris (FR)

( * ) Notice: Subject to any disclaimer, the term of this patent is extended or adjusted under 35 U.S.C. 154(b) by 423 days.

(21) Appl. No.: 17/061,155

(22) Filed: Oct. 1, 2020

(65) Prior Publication Data

US 2021/0017238 A1 Jan. 21, 2021

Related U.S. Application Data

(63) Continuation of application No. PCT/US2019/025367, filed on Apr. 2, 2019.

(60) Provisional application No. 62/652,210, filed on Apr. 3, 2018.

(51) Int. Cl.
  *C07K 14/20* (2006.01)
  *C12N 15/10* (2006.01)

(52) U.S. Cl.
  CPC ............ *C07K 14/20* (2013.01); *C12N 15/102* (2013.01)

(58) Field of Classification Search
  CPC .... C07K 14/20; C07K 14/195; C07K 14/205; A61K 39/0225; A61K 2039/55555; A61K 2039/55577; A61K 2039/6031; A61P 31/00; A61P 31/04; C12N 15/102; C12N 15/62; C12N 9/1085; C12Y 205/01009; Y02A 50/30
  See application file for complete search history.

(56) References Cited

U.S. PATENT DOCUMENTS

| | | | | |
|---|---|---|---|---|
| 5,571,718 A | * | 11/1996 | Dunn | C07K 14/20 536/23.7 |
| 2011/0118449 A1 | * | 5/2011 | Kopacek | A61P 33/14 530/400 |
| 2012/0267258 A1 | | 10/2012 | Uraoka et al. | |

FOREIGN PATENT DOCUMENTS

| CA | 2485363 | * | 11/2003 | ......... C07K 14/005 |
|---|---|---|---|---|
| EP | 2515112 B1 | | 8/2015 | |
| JP | 2011506565 A | | 3/2011 | |
| JP | 2012225885 A | | 11/2012 | |
| JP | 2013529078 A | | 7/2013 | |
| JP | 2014513678 A | | 6/2014 | |
| JP | 2015530369 A | | 10/2015 | |
| JP | 2020520674 A | | 7/2020 | |
| JP | 2021504445 A | | 2/2021 | |
| WO | WO2002016421 | * | 2/2002 | ......... C07K 14/20 |
| WO | 2009080719 A1 | | 7/2009 | |
| WO | 2009126816 A1 | | 10/2009 | |
| WO | 2012139069 A2 | | 10/2012 | |

(Continued)

OTHER PUBLICATIONS

Calisti et al., Biochim Biophys Acta Gen Subj. Feb. 2017;1861(2):450-456. Epub Oct. 15, 2016. (Year: 2016).*

(Continued)

*Primary Examiner* — Jana A Hines
(74) *Attorney, Agent, or Firm* — McNeill Baur PLLC

(57) ABSTRACT

This disclosure relates to antigenic OspA polypeptides and their use in eliciting antibodies against OspA. Also disclosed are antigenic polypeptides comprising an OspA polypeptide and a ferritin protein.

6 Claims, 51 Drawing Sheets

Specification includes a Sequence Listing.

(56) References Cited

FOREIGN PATENT DOCUMENTS

| WO | WO2015169271 | * | 11/2015 | ......... C07K 16/1207 |
| WO | 2017096374 A1 | | 6/2017 | |
| WO | 2018193063 A2 | | 10/2018 | |
| WO | 2019103993 A1 | | 5/2019 | |

OTHER PUBLICATIONS

Merino et al., (Front. Cell. Infect. Microbiol., Jul. 9, 2013. Sec. Parasite and Host. vol. 3—2013). (Year: 2013) (Year: 2013) (Year: 2013) (Year: 2013) (Year: 2013) (Year: 2013) (Year: 2013).*

Turanek et al., (Molecular Vaccines from Prophylaxis to Therapy—vol. 2, Jun. 13, 2013, :561-577) (Year: 2013) (Year: 2013) (Year: 2013) (Year: 2013) (Year: 2013) (Year: 2013) (Year: 2013).*

Hajdusek, O., Almazán, C., Loosova, G., Villar, M., Canales, M., Grubhoffer, L., and et al. (2010). Characterization of ferritin 2 for the control of tick infestations. Vaccine 28, 2993-2998. (Year: 2010).*

Hajdusek, O., Sojka, D., Kopacek, P., Buresova, V., Franta, Z., Sauman, I., and et al. (2009). Knockdown of proteins involved in iron metabolism limits tick reproduction and development. Proc. Natl. Acad. Sci. U.S.A. 106, 1033-1038. (Year: 2009).*

Kopacek, P., Zdychova, J., Yoshiga, T., Weise, C., Rudenko, N., and Law, J. H. (2003). Molecular cloning, expression and isolation of ferritins from two tick species-Ornithodoros moubata and Ixodes ricinus. Insect. Biochem. Mol. Biol. 33, 103-113. (Year: 2003).*

Wille-Reece et al., "HIV Gag protein conjugated to a Toll-like receptor 7/8 agonist improves the magnitude and quality of Th1 and CD8+ T cell responses in nonhuman primates", Proc Natl Acad Sci, 102(42), pp. 15190-15194 (2005).

Wilske et al., "An OspA Serotyping System for Borrelia burgdorferi Based on Reactivity with Monoclonal Antibodies and OspA Sequence Analysis", J Clin Microbio, 31(2), pp. 340-350 (1993).

Wressnigg et al., "A Novel Multivalent OspA Vaccine against Lyme Borreliosis Is Safe and Immunogenic in an Adult Population Previously Infected with Borrelia burgdorferi Sensu Lato", Clinical and Vaccine Immunology, 21(11), pp. 1490-1499 (Nov. 2014).

Written Opinion of the International Searching Authority issued in PCT Application No. PCT/US2019/025422 dated Sep. 4, 2019 (13 pages).

Wu, Tom Y.-H., "Strategies for designing synthetic immune agonists", Immunology, 148(4), pp. 315-325 (Jul. 11, 2016).

Xu et al., "Trispecific broadly neutralizing HIV antibodies mediate potent SHIV protection in macaques", Science 358 (6359), pp. 85-90 (2017).

Yassine et al., "Hemagglutinin-stem nanoparticles generate heterosubtypic influenza protection", Nature Medicine 21(9), pp. 1065-1071 (2015).

Zhang et al., "Challenges of glycosylation analysis and control: an integrated approach to producing optimal and consistent therapeutic drugs", Drug Discovery Today, 21(5), pp. 740-765 (May 2016).

Lawson et al., "Solving the structure of human H ferritin by genetically engineering intermolecular crystal contacts", Nature, 349, pp. 541-544 (1991).

Balfour Jr., Henry, "Progress, prospects, and problems in Epstein-Barr virus vaccine development", Current Opinion in Virology, 6, pp. 1-5 (2014).

Calisti et al., "Probing bulky ligand entry in engineered archaeal ferritins", Biochimica et Biophysica Acia 1861, pp. 450-455 (2017).

Khoshnejad et al., "Ferritin-based drug delivery systems; Hybrid nanocarriers for vascular immunotargeting", J. Control Release, vol. 282, p. 13-24 (Mar. 6, 2018).

Moyle et al., "Site-Specific Incorporation of Three Toll-Like Receptor 2 Targeting Adjuvants into Semisynthetic, Molecularly Defined Nanoparticles: Application to Group A *Streptococcal* Vaccines", Bioconjugate Chem., 25, pp. 965-978 (2014).

Sequence #206 from U.S. Appl. No. 17/061,136, filed Mar. 24, 2023 (1 page).

Villar et al., "Reconstituted B cell receptor signaling reveals carbohydrate-dependent mode of activation", Scientific Reports, 6:36298, 11 pages (2016).

Zhen et al., "Ferritins as nanoplatforms for imaging and drug delivery", Expert Opin. Drug Deliv, 11(12), pp. 1913-1922 (2014).

* cited by examiner

OspA -GS- Ferritin
*Fig. 1A*
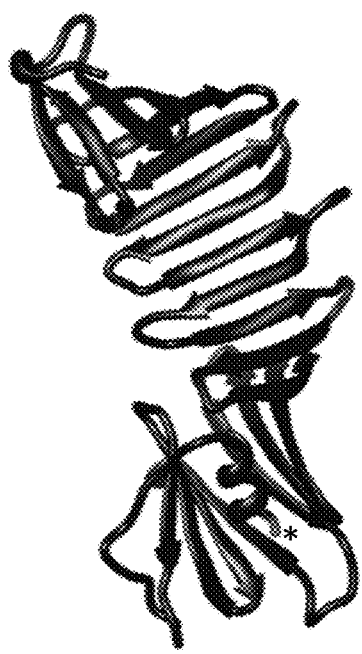
OspA
*Fig. 1B*
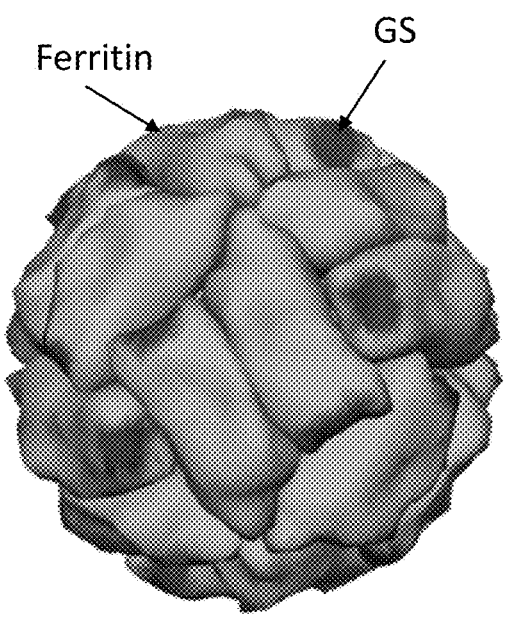
Ferritin
n = 24
*Fig. 1C*

| Serotype | Strain |
|---|---|
| 1 | *Borrelia burgdorferi* B31 |
| 2 | *Borrelia afzellii* Pko |
| 3 | *Borrelia garinii* PBr |
| 4 | *Borrelia bavariensis* Pbi |
| 5 | *Borrelia garinii* Phei |
| 7 | *Borrelia garinii* T25 |

- B. yangtzensis (0.0593)
- B. Afzelii (0.0799) Serotype 2
- B. spielmanii (0.0648)
- B. bissetti (0.0427)
- B. burgdorferi (-0.0131) Serotype 1
- B. bavariensis (0.0671) Serotype 4
- B. garinii (0.1271) Serotype 3, 5, 7
- hLFA-1 (0.4576) (0.1271)

*Fig. 5B*

OspA: YVLEGTLTA
S2  : FTLEGKVAN
S3  : FALEGTLTD
RD2 : YTLEGQLSD
Lfa1: YVIEGTSKQ

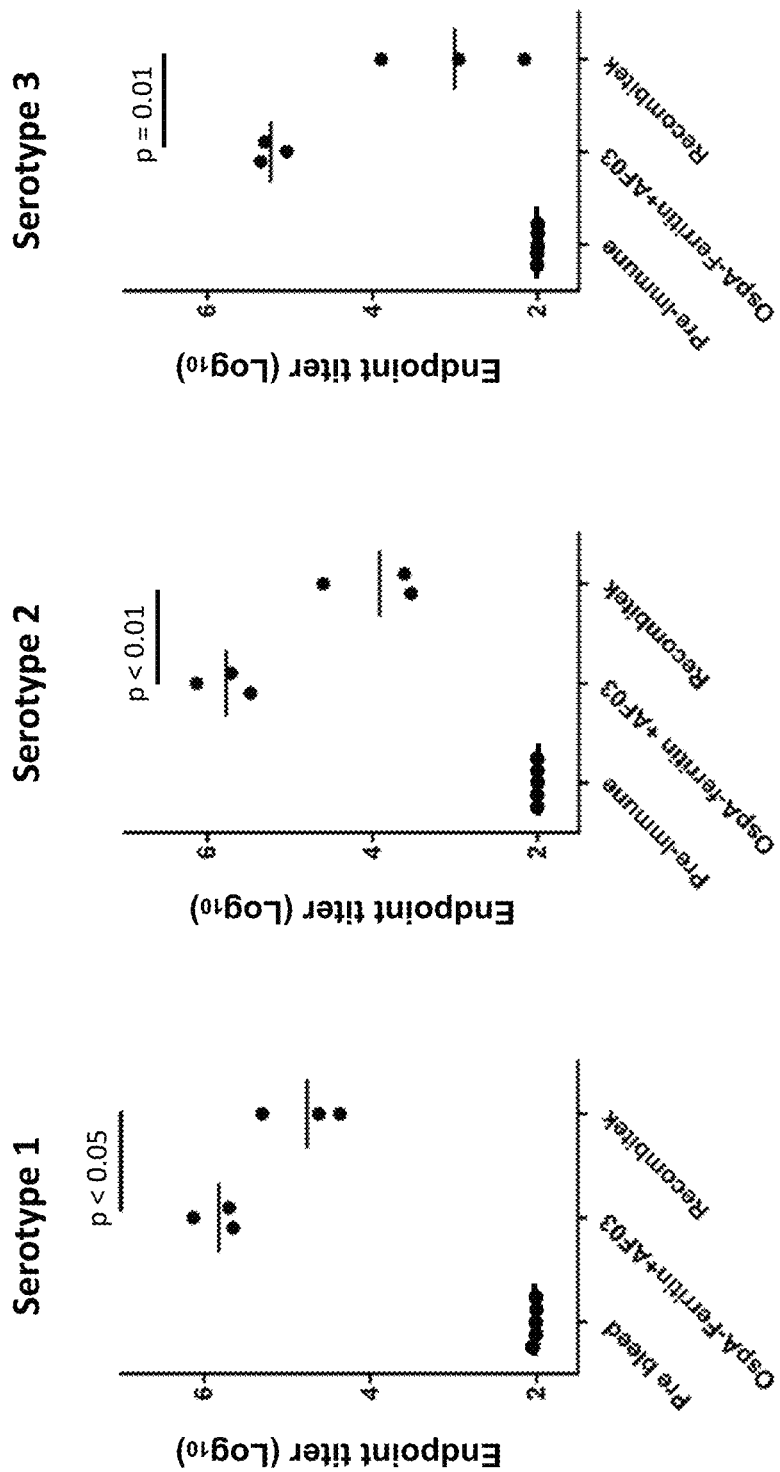

| Antigen | Mice/group | # mice culture positive | # mice infected (culture and PCR) | % infected | P value |
|---|---|---|---|---|---|
| Monovalent-3M-012 | 8 | 0 | 0 | 0 | P<0.0005 |
| Hexavalent-3M-012 | 8 | 0 | 1 | 12.5 | P<0.005 |
| Control particle | 9 | 6 | 7 | 77.8 | |

GS   OspA-GS-Ferritin
GS1  OspA- GGGS-Ferritin
GS2  OspA- GGGSGGGS-Ferritin
GS5  OspA- GGGSGGGSGGGSGGGSGGGS-Ferritin

GS5
Radius = 11.9 nm
% Pd = 13.3
%Mass = 100
<5 EU endotoxin
3 mg (from 100ml)

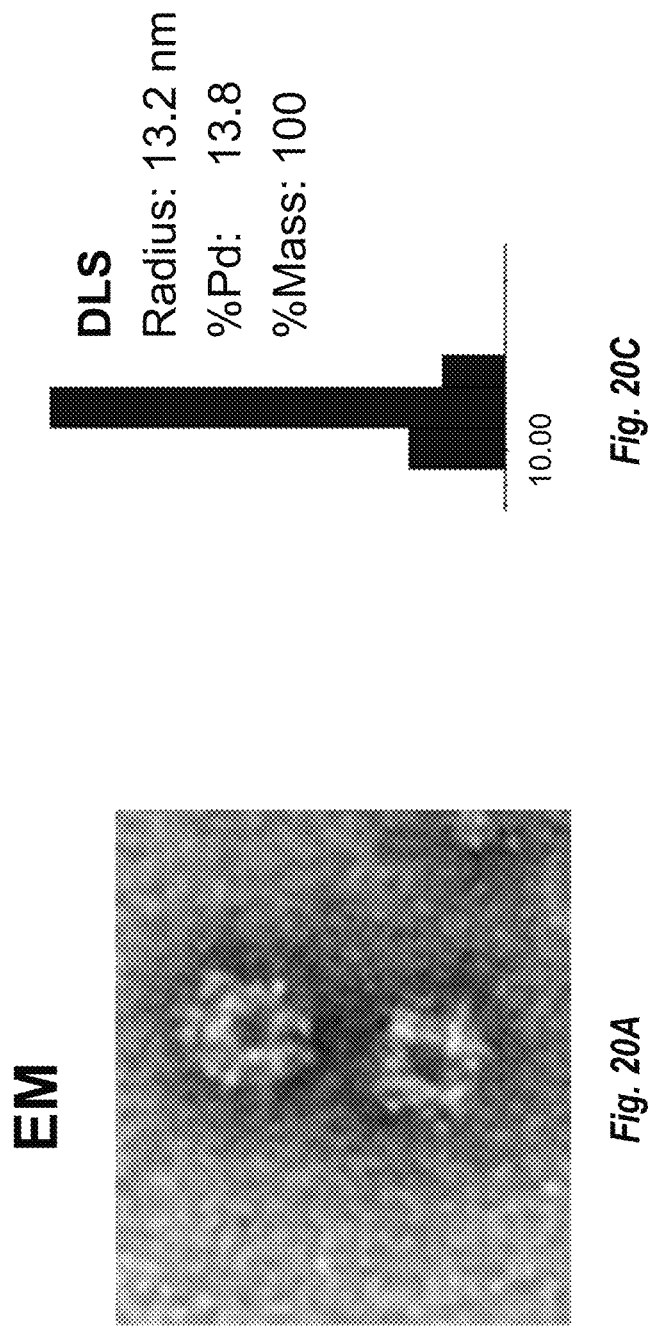

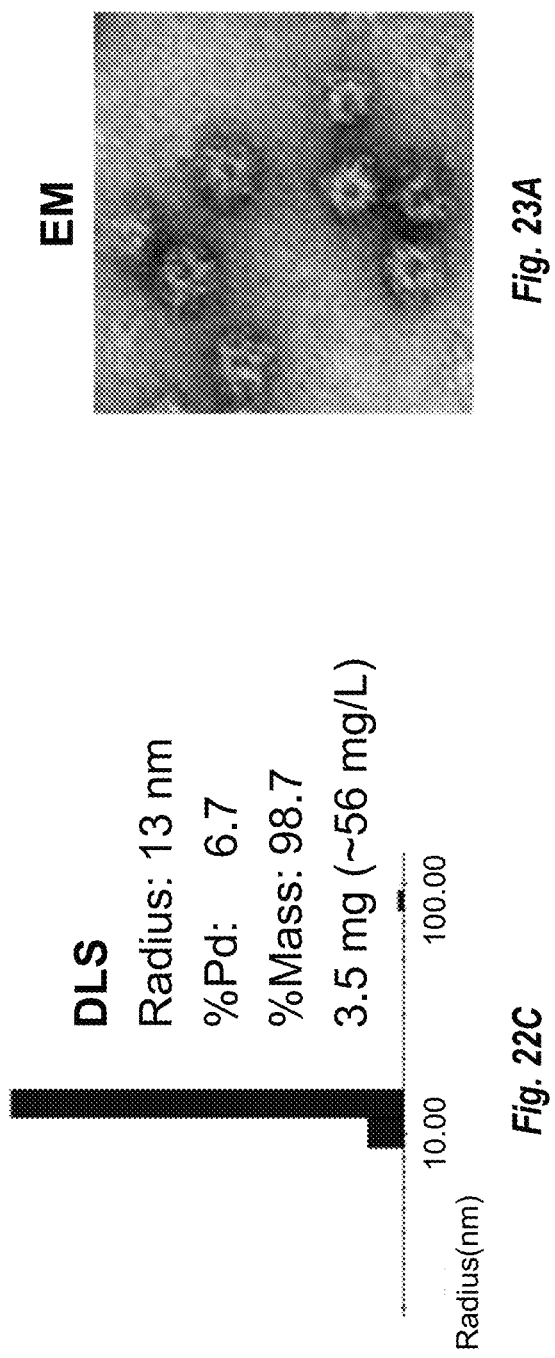

ANTIGENIC OspA POLYPEPTIDES

This application is a continuation of International Application No. PCT/US2019/025367, filed Apr. 2, 2019, which claims the benefit of priority of U.S. Provisional Patent Application No. 62/652,210, filed Apr. 3, 2018, the entire contents of which are incorporated herein by reference.

The instant application contains a Sequence Listing which has been submitted electronically in ASCII format and is hereby incorporated by reference in its entirety. Said ASCII copy, created on Sep. 29, 2020, is named 2020-09-29_01121-0033-00US_SL.txt and is 370,897 bytes in size.

Even with many successes in the field of vaccinology, new breakthroughs are needed to protect humans against many life-threatening infectious diseases. Many currently licensed vaccines rely on decade-old technologies to produce live-attenuated or inactivated killed pathogens, which carry inherent safety concerns and in many cases, stimulate only short-lived, weak immune responses that require the administration of multiple doses. While advances in genetic and biochemical engineering have made it possible to develop therapeutic agents to challenging disease targets, these applications to the field of vaccinology have not been fully realized. Recombinant protein technologies now allow the design of optimal antigens. Additionally, nanoparticles have increasingly demonstrated the potential for optimal antigen presentation and targeted drug delivery. Nanoparticles with multiple attached antigens have been shown to have increased binding avidity afforded by the multivalent display of their molecular cargos, and an ability to cross biological barriers more efficiently due to their nanoscopic size. *Helicobacter pylori* (*H. pylori*) ferritin nanoparticles fused to influenza virus haemagglutinin (HA) protein has allowed improved antigen stability and increased immunogenicity in mouse influenza models (see Kanekiyo et al., Nature 499:102-106 (2013)). This fusion protein self-assembled into an octahedrally-symmetric nanoparticle and presented 8 trimeric HA spikes to give a robust immune response in various pre-clinical models when used with an adjuvant.

Lyme borreliosis is a zoonotic disease caused by some bacterial species in the genus *Borrelia* and is transmitted to humans and canines by the bite of an infected *Ixodes* spp. tick. Lyme disease is a global public health problem, with cases reported from temperate climates across Europe, North America, and Asia. Outer surface protein A (OspA) of *Borrelia* is the major antigen that elicits an immune response. There are at least seven different serotypes (serotypes 1-7) of OspA that are found in *Borrelia* world-wide. Different genospecies of *Borrelia* exist worldwide, such that immunity to one genospecies may not confer immunity to other bacteria that can also cause Lyme borreliosis. Further, localized ranges of ticks that harbor *Borrelia* means that an OspA serotype that is associated with Lyme disease in patients in one geographic region might not be associated with Lyme disease in patients in another geographic region.

Here, a set of new polypeptides, nanoparticles, compositions, methods, and uses involving OspA polypeptides is presented. A modified OspA polypeptide was developed to provide protection from infection with *Borrelia* with reduced risk of stimulating an autoimmune reaction. Furthermore, self-adjuvanting antigenic polypeptides comprising an OspA polypeptide and ferritin were developed wherein immune-stimulatory moieties, such as adjuvants, were directly, chemically attached to the antigenic polypeptide. The direct conjugation of an immune-stimulatory moiety to the antigenic polypeptide allows for targeted co-delivery of the immune-stimulatory moiety and OspA polypeptide in a single macromolecular entity, which can greatly decrease the potential for systemic toxicity that is feared with traditional vaccines that comprise antigens and immune-stimulatory molecules such as adjuvants as separate molecules. The co-delivery of immune-stimulatory moieties together with OspA polypeptides in a macromolecular entity and their multivalent presentation may also reduce the overall dose needed to elicit protection, reducing manufacturing burdens and costs.

SUMMARY

It is an object of this disclosure to provide compositions, kits, methods, and uses that can provide one or more of the advantages discussed above, or at least provide the public with a useful choice. Accordingly, the following embodiments are disclosed herein.

Embodiment 1 is an antigenic OspA polypeptide comprising an OspA serotype 1 polypeptide of *Borrelia*, wherein the polypeptide does not comprise the sequence of SEQ ID NO: 77.

Embodiment 2 is the antigenic OspA polypeptide of embodiment 1, wherein the polypeptide lacks a transmembrane domain or a portion of a transmembrane domain.

Embodiment 3 is the antigenic OspA polypeptide of any one of the preceding embodiments, wherein the polypeptide is non-lipidated.

Embodiment 4 is the antigenic OspA polypeptide of any one of the preceding embodiments, wherein there is at least one amino acid substitution relative to the sequence of SEQ ID NO: 77, wherein the substitution reduces identity to SEQ ID NO: 78, or is non-conservative and does not result in higher identity to SEQ ID NO: 78.

Embodiment 5 is the antigenic OspA polypeptide of embodiment 4, wherein the substitution reduces identity to SEQ ID NO: 78.

Embodiment 6 is the antigenic OspA polypeptide of any one of the preceding embodiments, wherein one or more of the amino acids of SEQ ID NO: 77 is replaced with the corresponding amino acid(s) of a non-serotype 1 OspA.

Embodiment 7 is the antigenic OspA polypeptide of embodiment 6, wherein the non-serotype 1 OspA is serotype 2, 3, 4, 5, 6, or 7 OspA.

Embodiment 8 is the antigenic OspA polypeptide of embodiment 6, wherein each of the amino acids of SEQ ID NO: 77 are replaced with the corresponding amino acids of a serotype 2, 3, 4, 5, 6, or 7 OspA.

Embodiment 9 is the antigenic OspA polypeptide of any one of the preceding embodiments, wherein the polypeptide further comprises a modification to reduce or eliminate glycosylation.

Embodiment 10 is the antigenic OspA polypeptide of embodiment 9, wherein the modification comprises a substitution of at least one asparagine.

Embodiment 11 is the antigenic OspA polypeptide of embodiment 10, wherein the at least one asparagine comprises any one, two, three, or more of N71, N190, N202, and N251 of OspA serotype 1.

Embodiment 12 is the antigenic OspA polypeptide of embodiment 11, wherein the at least one asparagine comprises N71, N190, N202, and N251 of OspA serotype 1.

Embodiment 13 is the antigenic OspA polypeptide of any one of embodiments 10-12, wherein the one or more asparagines are substituted with glutamine.

Embodiment 14 is the antigenic OspA polypeptide of any one of embodiments 10-13, wherein the polypeptide lacks an N-glycosylation site.

Embodiment 15 is the antigenic OspA polypeptide of any one of the preceding embodiments, wherein the OspA is from *Borrelia burgdorferi, Borrelia mayonii, Borrelia afzelii, Borrelia garinii,* or *Borrelia bavariensis.*

Embodiment 16 is the antigenic OspA polypeptide of any one of the preceding embodiments, comprising a sequence with at least 85%, 90%, 95%, 97%, 98%, 99%, 99.5%, or 100% identity to the sequence of any one of SEQ ID NOS: 1, 3, 4, or 53.

Embodiment 17 is the antigenic OspA polypeptide of any one of the preceding embodiments, comprising the sequence of any one of SEQ ID NO: 1-10 or 12-76.

Embodiment 18 is the antigenic OspA polypeptide of any one of the preceding embodiments, comprising an OspA ectodomain.

Embodiment 19 is the antigenic OspA polypeptide of any one of the preceding embodiments, comprising a sequence with at least 85%, 90%, 95%, 97%, 98%, 99%, 99.5%, or 100% identity to the sequence of any one of SEQ ID NOS: 94-102.

Embodiment 20 is the antigenic OspA polypeptide of any one of the preceding embodiments, further comprising a ferritin protein.

Embodiment 21 is the antigenic OspA polypeptide of embodiment 20, wherein the ferritin comprises a mutation replacing a surface-exposed amino acid with a cysteine.

Embodiment 22 is an antigenic OspA polypeptide comprising an OspA polypeptide and a ferritin, wherein the ferritin comprises a mutation replacing a surface-exposed amino acid with a cysteine.

Embodiment 23 is the antigenic OspA polypeptide of any one of embodiments 20-22, wherein the ferritin comprises one or more of E12C, S26C, S72C, A75C, K79C, S100C, and S111C mutations of *H. pylori* ferritin or one or more corresponding mutations in a non-*H. pylori* ferritin as determined by pairwise or structural alignment.

Embodiment 24 is the antigenic OspA polypeptide of any one of embodiments 20-22, wherein the ferritin comprises an E12C mutation of *H. pylori* ferritin or a corresponding mutation in a non-*H. pylori* ferritin as determined by pairwise or structural alignment.

Embodiment 25 is the antigenic OspA polypeptide of any one of embodiments 20-22, wherein the ferritin comprises an S26C mutation of *H. pylori* ferritin or a corresponding mutation in a non-*H. pylori* ferritin as determined by pairwise or structural alignment.

Embodiment 26 is the antigenic OspA polypeptide of any one of embodiments 20-22, wherein the ferritin comprises an S72C mutation of *H. pylori* ferritin or a corresponding mutation in a non-*H. pylori* ferritin as determined by pairwise or structural alignment.

Embodiment 27 is the antigenic OspA polypeptide of any one of embodiments 20-22, wherein the ferritin comprises an A75C mutation of *H. pylori* ferritin or a corresponding mutation in a non-*H. pylori* ferritin as determined by pairwise or structural alignment.

Embodiment 28 is the antigenic OspA polypeptide of any one of embodiments 20-22, wherein the ferritin comprises a K79C mutation of *H. pylori* ferritin or a corresponding mutation in a non-*H. pylori* ferritin as determined by pairwise or structural alignment.

Embodiment 29 is the antigenic OspA polypeptide of any one of embodiments 20-22, wherein the ferritin comprises an S100C mutation of *H. pylori* ferritin or a corresponding mutation in a non-*H. pylori* ferritin as determined by pairwise or structural alignment.

Embodiment 30 is the antigenic OspA polypeptide of any one of embodiments 20-22, wherein the ferritin comprises an S111C mutation of *H. pylori* ferritin or a corresponding mutation in a non-*H. pylori* ferritin as determined by pairwise or structural alignment.

Embodiment 31 is the antigenic OspA polypeptide of any one of embodiments 20-30, comprising one or more immune-stimulatory moieties linked to the ferritin via a surface-exposed amino acid, optionally wherein the surface-exposed amino acid is a cysteine resulting from a mutation.

Embodiment 31a is the antigenic OspA polypeptide of embodiment 31, wherein the immune-stimulatory moiety is an agonist of TLR2, optionally wherein the agonist is PAM2CSK4, FSL-1, or PAM3CSK4.

Embodiment 31b is the antigenic OspA polypeptide of embodiment 31, wherein the immune-stimulatory moiety is an agonist of TLR7/8, optionally wherein the agonist is a single-stranded RNA, an imidazoquinoline, a nucleoside analog, 3M-012, or SM7/8a.

Embodiment 31c is the antigenic OspA polypeptide of embodiment 31, wherein the immune-stimulatory moiety is an agonist of TLR9, optionally wherein the agonist is a CpH oligodeoxynucleotide (ODN), an ODN comprising one or more 6mer CpG motif comprising 5' Purine (Pu)-Pyrimidine (Py)-C-G-Py-Pu 3', an ODN comprising the sequence of SEQ ID NO: 210, or ISS-1018.

Embodiment 31d is the ferritin protein of embodiment 31c, wherein the agonist of TLR9 comprises a backbone comprising phosphorothioate linkages.

Embodiment 31e is the antigenic OspA polypeptide of embodiment 31, wherein the immune-stimulatory moiety is an agonist of STING, optionally wherein the agonist is a cyclic dinucleotide (CDN), cdA, cdG, cAMP-cGMP, and 2'-5',3'-5' cGAMP, or DMXAA.

Embodiment 32 is the antigenic OspA polypeptide of any one of embodiments 20-31e, wherein the ferritin comprises a mutation replacing a surface-exposed asparagine with a non-asparagine amino acid, optionally wherein the asparagine is at position 19 of *H. pylori* ferritin, or an analogous position in a non-*H. pylori* ferritin as determined by pairwise or structural alignment.

Embodiment 33 is the antigenic OspA polypeptide of any one of embodiments 20-32, wherein the ferritin comprises a mutation replacing an internal cysteine with a non-cysteine amino acid, optionally wherein the internal cysteine is at position 31 of *H. pylori* ferritin, or a position that corresponds to position 31 of *H. pylori* ferritin as determined by pair-wise or structural alignment.

Embodiment 34 is the antigenic OspA polypeptide of any one of embodiments 20-33, wherein the antigenic OspA polypeptide comprises a peptide linker between the OspA polypeptide and the ferritin.

Embodiment 35 is the antigenic OspA polypeptide of embodiment 34, wherein the peptide linker is N-terminal to the ferritin.

Embodiment 35a is the antigenic OspA polypeptide of embodiment 34, wherein the peptide linker is C-terminal to the ferritin.

Embodiment 36 is the antigenic OspA polypeptide of any one of the preceding embodiments, wherein the ferritin comprises an amino acid sequence with 80%, 85%, 90%, 95%, 98%, or 99% identity to any one of SEQ ID NOs: 201-207 or 211-215.

Embodiment 36a is the antigenic OspA polypeptide of embodiment 36, comprising an amino acid sequence with 80%, 85%, 90%, 95%, 98%, or 99% identity to any one of SEQ ID NOs: 201.

Embodiment 36b is the antigenic OspA polypeptide of embodiment 36, comprising an amino acid sequence with 80%, 85%, 90%, 95%, 98%, or 99% identity to any one of SEQ ID NOs: 202.

Embodiment 36c is the antigenic OspA polypeptide of embodiment 36, comprising an amino acid sequence with 80%, 85%, 90%, 95%, 98%, or 99% identity to any one of SEQ ID NOs: 203.

Embodiment 36d is the antigenic OspA polypeptide of embodiment 36, comprising an amino acid sequence with 80%, 85%, 90%, 95%, 98%, or 99% identity to SEQ ID NO: 215.

Embodiment 36e is the antigenic OspA polypeptide of embodiment 36, comprising an amino acid sequence with 80%, 85%, 90%, 95%, 98%, or 99% identity to SEQ ID NO: 204.

Embodiment 36f is the antigenic OspA polypeptide of embodiment 36, comprising an amino acid sequence with 80%, 85%, 90%, 95%, 98%, or 99% identity to SEQ ID NO: 205.

Embodiment 36g is the antigenic OspA polypeptide of embodiment 36, comprising an amino acid sequence with 80%, 85%, 90%, 95%, 98%, or 99% identity to SEQ ID NO: 206.

Embodiment 36h is the antigenic OspA polypeptide of embodiment 36, comprising an amino acid sequence with 80%, 85%, 90%, 95%, 98%, or 99% identity to SEQ ID NO: 207.

Embodiment 36i is the antigenic OspA polypeptide of embodiment 36, comprising an amino acid sequence with 80%, 85%, 90%, 95%, 98%, or 99% identity to SEQ ID NO: 211.

Embodiment 36j is the antigenic OspA polypeptide of embodiment 36, comprising an amino acid sequence with 80%, 85%, 90%, 95%, 98%, or 99% identity to SEQ ID NO: 212.

Embodiment 36k is the antigenic OspA polypeptide of embodiment 36, comprising an amino acid sequence with 80%, 85%, 90%, 95%, 98%, or 99% identity to SEQ ID NO: 213.

Embodiment 36l is the antigenic OspA polypeptide of embodiment 36, comprising an amino acid sequence with 80%, 85%, 90%, 95%, 98%, or 99% identity to SEQ ID NO: 214.

Embodiment 37 is a ferritin particle comprising the antigenic OspA polypeptide of any one of embodiments 20-36l.

Embodiment 38 is the antigenic OspA polypeptide of any one of embodiments 1-19, further comprising a lumazine synthase protein.

Embodiment 39 is a lumazine synthase particle comprising the antigenic OspA polypeptide of embodiment 38.

Embodiment 40 is a composition comprising the antigenic OspA polypeptide, ferritin particle, or lumazine synthase particle of any one of the preceding embodiments, further comprising a pharmaceutically acceptable carrier.

Embodiment 41 is the composition of embodiment 40, further comprising an adjuvant, optionally wherein the adjuvant is AF03.

Embodiment 42 is the composition of embodiment 40 or 41, which comprises a first and second antigenic OspA polypeptide, wherein the first and second antigenic OspA polypeptides comprise OspA polypeptides of different serotypes.

Embodiment 43 is the composition of embodiment 42, comprising one, two, three, four, five, six, or seven antigenic OspA polypeptides selected from: an antigenic OspA polypeptide comprising an OspA serotype 1 polypeptide; an antigenic OspA polypeptide comprising an OspA serotype 2 polypeptide; an antigenic OspA polypeptide comprising an OspA serotype 3 polypeptide; an antigenic OspA polypeptide comprising an OspA serotype 4 polypeptide; an antigenic OspA polypeptide comprising an OspA serotype 5 polypeptide; an antigenic OspA polypeptide comprising an OspA serotype 6 polypeptide; and an antigenic OspA polypeptide comprising an OspA serotype 7 polypeptide.

Embodiment 44 is the composition of embodiment 43, comprising an antigenic OspA polypeptide comprising an OspA serotype 1 polypeptide; an antigenic OspA polypeptide comprising an OspA serotype 2 polypeptide; an antigenic OspA polypeptide comprising an OspA serotype 3 polypeptide; an antigenic OspA polypeptide comprising an OspA serotype 4 polypeptide; an antigenic OspA polypeptide comprising an OspA serotype 5 polypeptide; and an antigenic OspA polypeptide comprising an OspA serotype 7 polypeptide.

Embodiment 45 is the antigenic OspA polypeptide, ferritin particle, lumazine synthase particle, or composition of any one of embodiments 1-44 for use in a method of eliciting an immune response to *Borrelia* or in protecting a subject against Lyme Disease.

Embodiment 46 is a method of eliciting an immune response to *Borrelia* or protecting a subject against Lyme Disease comprising administering any one or more of the antigenic OspA polypeptide, ferritin particle, lumazine synthase particle, or composition of any one of embodiments 1-44 to a subject.

Embodiment 47 is the antigenic OspA polypeptide, ferritin particle, lumazine synthase particle, composition, or method of any one of embodiments 45-46, wherein the subject is human.

Embodiment 47a is the antigenic OspA polypeptide, ferritin particle, lumazine synthase particle, composition, or method of any one of embodiments 45-46, wherein the subject is a mammal, optionally wherein the mammal is a primate or domesticated mammal, further optionally wherein the primate is a non-human primate, monkey, macaque, rhesus or cynomolgus macaque, or ape, or the domesticated mammal is a dog, rabbit, cat, horse, sheep, cow, goat, camel, or donkey.

Embodiment 48 is a kit comprising any one or more of the antigenic OspA polypeptide, ferritin particle, lumazine synthase particle, and compositions of embodiments 1-44, optionally with instructions for use in immunizing subjects against Lyme Disease.

Embodiment 49 is a nucleic acid encoding the antigenic OspA polypeptide of any one of embodiments 1-36l, optionally wherein the nucleic acid is RNA.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate several embodiments and together with the description, serve to explain the principles described herein.

BRIEF DESCRIPTION OF THE DRAWINGS

FIGS. 1A-1D show exemplary designs of OspA-Ferritin nanoparticles. FIG. 1A. OspA genetically fused to ferritin to form a fusion protein. The OspA and ferritin sequences are separated by a glycine-serine linker (-GS-). FIG. 1B. A structure of the ectodomain of OspA is depicted. The C-terminus where OspA is attached to ferritin is indicated with an asterisk. FIG. 1C. An exemplary ferritin nanoparticle composed of 24 monomers of *H. pylori* ferritin. FIG. 1D. An exemplary OspA-ferritin fusion protein nanoparticle. Ferritin (light gray), the location of the glycine-serine linker (GS), and OspA (dark gray and black) are depicted (n: number of subunits).

FIG. 2A. Size exclusion chromatography (SEC) profile of an exemplary OspA-Ferritin nanoparticle purified on a Superose 6 column. FIG. 2B. SDS-PAGE gel of a purified exemplary OspA-Ferritin from Expi293 cells. FIG. 2C. Dynamic Light Scattering (DLS) profile of exemplary OspA-Ferritin nanoparticles. Radius is 13 nm, % Pd (measure of normalized polydispersity) is 7.4, and mass is 100%. FIG. 2D. Composite image of an exemplary OspA-Ferritin constructed from class averaging of transmission electron micrographs of 318 particles at 67,000× magnification. Ferritin nanoparticles appear on transmission electron microscopy as a strong circular density with a hollow center. Each nanoparticle is surrounded by numerous, short shapes corresponding to OspA that appear circular or slightly oblong.

FIG. 3A. Biochemical analysis by SDS-PAGE of OspA-Ferritin Serotypes 1-5 and 7 purified by size exclusion chromatography. FIG. 3B. Transmission electron microscopy of OspA-Ferritin Serotypes 1-5 and 7 (98,000×).

FIGS. 5A-5C present information regarding exemplary OspA-Ferritin, wherein the OspA polypeptide is modified at an epitope of OspA serotype 1 that has homology with a fragment of the sequence of human leukocyte function-associated antigen-1 (hLFA-1). FIG. 5A. Structure showing the location of the LFA-1 homology site (amino acids 165-173 of SEQ ID NO: 83) within an OspA ectodomain. FIG. 5B. Dendrogram showing the relationship of OspA amino acids 165-173 of SEQ ID NO: 83 (*B. burgdorferi* Serotype 1 OspA) to corresponding sequences in hLFA-1 and other *Borrelia* species and serotypes. FIG. 5C. The nine-amino-acid segment (nonapeptide) at amino acids 165-173 of SEQ ID NO: 83 (labeled "OspA") is compared with the corresponding nonapeptides from Serotype 2 and Serotype 3 OspA ("S2" (SEQ ID NO: 79) and "S3" (SEQ ID NO: 80) respectively), a rationally designed substitute nonapeptide ("RD2"; SEQ ID NO: 81), and the corresponding nonapeptide from hLFA-1 (SEQ ID NO: 78). FIG. 5C discloses SEQ ID NOS 77, 79-81, and 78, respectively, in order of appearance. FIG. 5D. C3H mice (n=5) were immunized intramuscularly (IM) at week 0 and week 4 with 1 μg doses of OspA Serotype 1-ferritin nanoparticles with AddaVax™ adjuvant (squalene-based oil-in-water nano-emulsion; available from InvivoGen, Cat. No. vac-adx-10). The OspA sequence comprised the wild-type hLFA-1 homology site (i.e., amino acids 165-173 of SEQ ID NO: 83; "Sero1") or a substitute sequence as follows: SEQ ID NO: 81 ("RD"); SEQ ID NO: 80 ("Sero 3 Replacement"); SEQ ID NO: 79 ("Sero 2 replacement"). Antibody response was assessed via endpoint titer measured by ELISA 2 weeks after the $2^{nd}$ immunization of the indicated constructs.

FIG. 6A. A 2-step click chemistry strategy was used to attach the 3M-012 to ferritin. A DBCO-PEG4-maleimide linker was first attached to a surface exposed cysteine on ferritin. After excess linker was removed, azide-3M-012 was added. FIG. 6B. C3H mice (n=5) were immunized intramuscularly with 1 μg of the indicated composition at weeks 0 and 4 and analyzed 2 weeks later. "Conjugate" indicates OspA-ferritin-3M-012 conjugated nanoparticle. "Admix" indicates a non-conjugated mix of the same OspA-ferritin administered with 29 ng or 20 μg 3M-012 or Alum. The 29 ng "admix" mixture of OspA-ferritin and 3M-012 represents the molar equivalent amount of 3M-012 on the conjugated nanoparticle.

FIG. 7A. A 2-step click chemistry strategy was used to attach the CPG to ferritin. A DBCO-PEG4-maleimide linker was first attached to a surface exposed cysteine on ferritin. After excess linker was removed, azide-CpG was added. FIG. 7A discloses SEQ ID NO: 228. FIG. 7B. Biochemical analysis of CpG-conjugation by a SDS-PAGE gel reveals a shift in molecular weight after conjugation to CpG with 92% of OspA-Ferritin conjugated to CpG. FIG. 7C. C3H mice (n=5) were immunized intramuscularly with 1 μg of the indicated composition and at weeks 0 and 4 and analyzed 2 weeks later. "Conjugate" indicates OspA-ferritin-CPG conjugated nanoparticle. "Admix" indicates a non-conjugated mix of the same OspA-ferritin administered with 339 ng or 50 μg CpG or Alum. The 339 ng "admix" mixture of OspA-ferritin and CPG represents the molar equivalent amount of CpG on the conjugated nanoparticle.

FIGS. 10A-10G show antibody responses to serotypes 1-7, respectively, in Rhesus monkeys (n=3 per group) to hexavalent OspA-ferritin nanoparticle compositions, which were as described for FIGS. 9A-G except that doses were 60 μg total (10 μg each serotype) and contained non-conjugated AF03 adjuvant. Monkeys were immunized intramuscularly at week 0 and week 6. Antibody response was analyzed 2 weeks after immunization via endpoint titer measured by ELISA. RECOMBITEK® Lyme was used as a comparative reference at 10 μg dose. For all experiments, an ELISA plate was coated with the OspA serotype indicated in each panel.

FIG. 11 shows results from tick challenge testing of 3M-012 conjugated OspA-ferritin compositions. Mice were immunized with a 1 μg dose of the indicated compositions at week 0 and week 4. The monovalent composition contained 1 μg of OspA-ferritin serotype 1 conjugated to 3M-012. The "Hexavalent-3M-012" composition was as described for FIGS. 9A-G. The control particle lacked an OspA polypeptide. Mice were challenged with 5-6 ticks infected with Borrelia burgdorferi N40 strain (serotype 1) for 5 days two weeks after the second immunization and sacrificed two weeks later. Tissue samples from the heart, ankle and ear were cultured in BSK media with antibiotics for B. burgdorferi for 6 weeks. Negative samples were tested by PCR for the presence of B. burgdorferi. A positive sample was positive either by culture or PCR.

Figure 14:
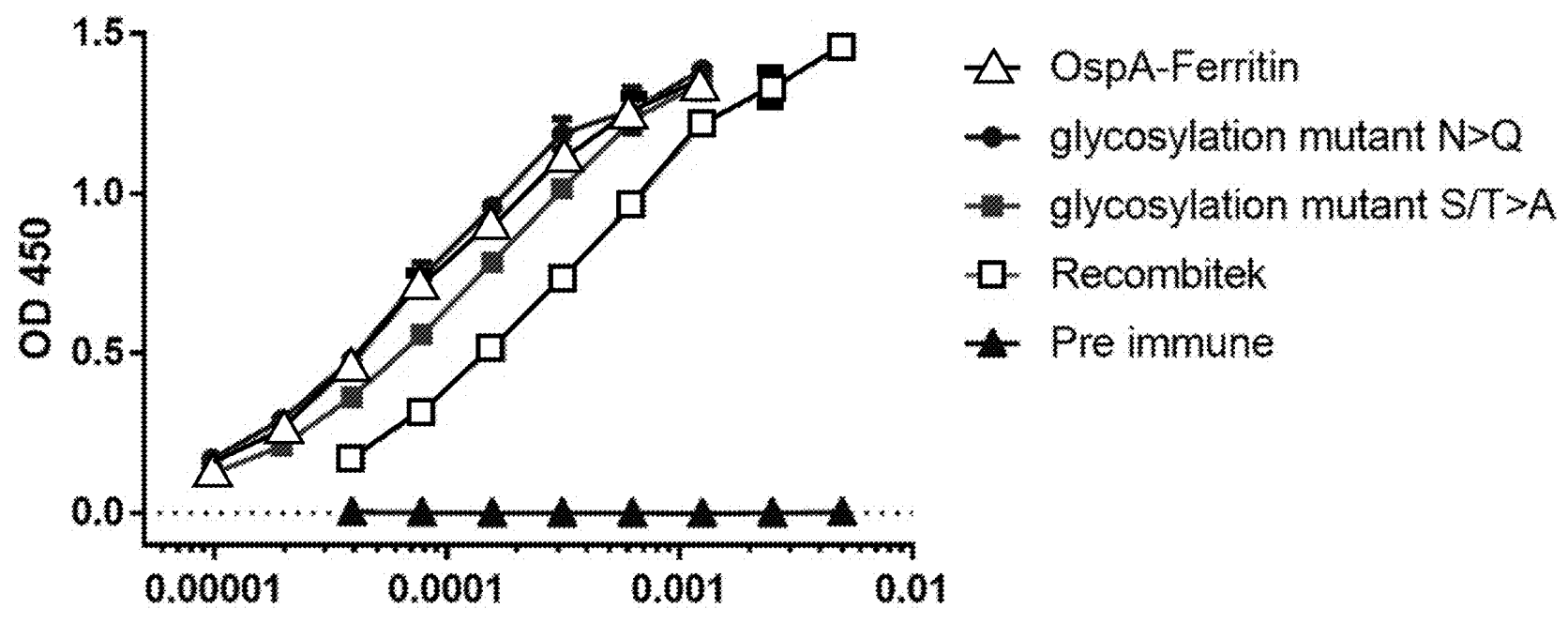

FIG. 14 shows antibody response in mice to OspA-ferritin (SEQ ID NO: 52). OspA-ferritin glycosylation mutant N>Q (SEQ ID NO: 53), and glycosylation mutant S/T>A (SEQ ID NO: 63) compared to RECOMBITEK® Lyme and negative (Pre immune) controls, measured by ELISA across a dilution series as shown.

FIG. 15A. Coomassie staining of purified OspA constructs comprising linkers as indicated. FIG. 15A discloses SEQ ID NOS 226 and 91-92, respectively, in order of appearance. FIG. 15B. Dynamic Light Scattering (DLS) of OspA-ferritin nanoparticle comprising GS1 (SEQ ID NO: 60). FIG. 15C. DLS of OspA-ferritin nanoparticle comprising GS2 (SEQ ID NO: 61). FIG. 15D. Electron micrograph (EM) of OspA-ferritin nanoparticle comprising GS5 (SEQ ID NO: 62). FIG. 15E. DLS of OspA-ferritin nanoparticle comprising GS5 (SEQ ID NO: 62).

FIG. 17A. DLS data. FIG. 17B. Coomassie gel of indicated fractions 22-64 of size exclusion chromatography (SEC) trace. FIG. 17C. EM data.

FIG. 19A. EM data. FIG. 19B. Coomassie gel of indicated fractions 20-40 of the SEC trace. FIG. 19C. DLS data.

FIGS. 20A-20C show characterization of a OspA serotype 2-lumazine synthase construct (SEQ ID NO: 16). FIG. 20A. EM data. FIG. 20B. Coomassie gel of indicated fractions 27-56 of the SEC trace. FIG. 20C. DLS data.

FIGS. 21A-21B show characterization of a OspA serotype 3-lumazine synthase construct (SEQ ID NO: 17). FIG. 21A. Coomassie gel of indicated fractions 23-39 of the SEC trace. FIG. 21B. DLS data.

FIGS. 22A-22C show characterization of a OspA serotype 5-lumazine synthase construct (SEQ ID NO: 19). FIG. 22A. EM data. FIG. 22B. Coomassie gel of indicated fractions 22-38 of the SEC trace. FIG. 22C. DLS data.

FIGS. 23A-23C show characterization of a OspA serotype 7-lumazine synthase construct (SEQ ID NO: 21). FIG. 23A. EM data. FIG. 23B. Coomassie gel of indicated fractions 20-38 of the SEC trace. FIG. 23C. DLS data.

DETAILED DESCRIPTION

Figure 1D:
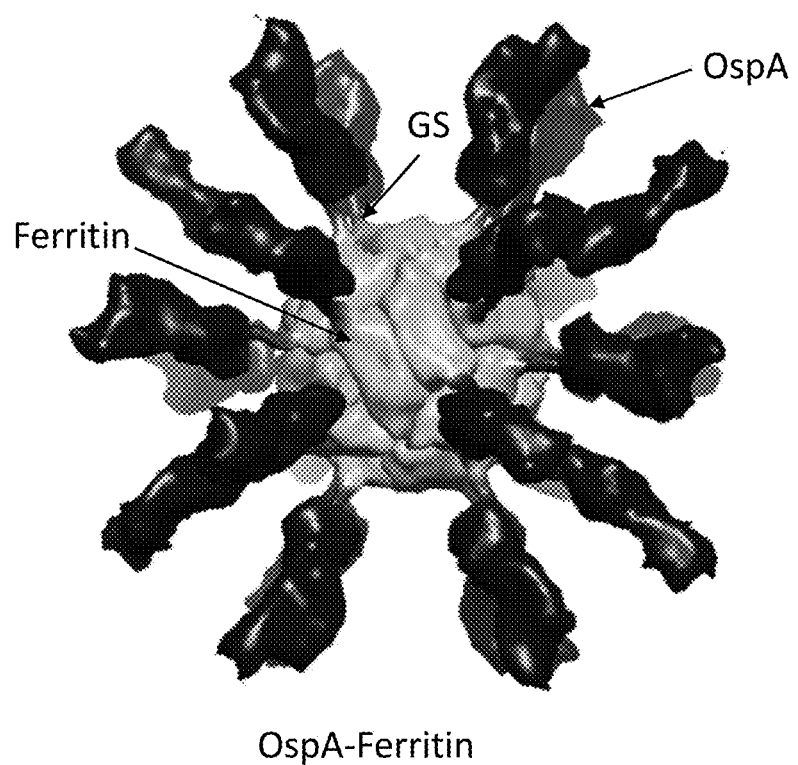

Provided herein are novel antigens for vaccination against Lyme disease. Lyme disease is caused by bacteria belonging to the *Borrelia burgdorferi* sensu law (s.l.) complex (herein referred to as "*Borrelia*"). The antigens described herein include antigenic polypeptides, fusion proteins, nanoparticles, and compositions that can be used by themselves or with non-conjugated adjuvant to vaccinate subjects against Lyme disease. The fusion proteins may comprise antigenic polypeptides fused to ferritin. Ferritin may be wild-type or may comprise one or more mutations, e.g., a mutation replacing a surface-exposed amino acid with a cysteine so that immune-stimulatory moieties may be directly conjugated to the engineered surface-exposed cysteine. A cysteine resulting from such a mutation may eliminate or reduce the need for separately administered adjuvant, and also potentially reduce the amount of adjuvant/immune-stimulatory moiety needed to elicit an immune response to the antigen. Nucleic acids that encode the antigenic polypeptides described herein are also provided.

A. Definitions

"Adjuvant," as used herein, refers to a substance or vehicle that non-specifically enhances the immune response to an antigen. Adjuvants can include, without limitation, a suspension of minerals (e.g., alum, aluminum hydroxide, or phosphate) on which antigen is adsorbed; a water-in-oil or oil-in-water emulsion in which antigen solution is emulsified in mineral oil or in water (e.g., Freund's incomplete adjuvant). Sometimes killed mycobacteria is included (e.g., Freund's complete adjuvant) to further enhance antigenicity. Immuno-stimulatory oligonucleotides (e.g., a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants can also include biological molecules, such as Toll-Like Receptor (TLR) agonists and costimulatory molecules. An adjuvant may be administered as a separate molecule in a composition or covalently bound (conjugated) to modified ferritin or an antigenic ferritin polypeptide.

As used herein, an "antigen" refers to an agent that elicits an immune response, and/or an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism. Alternatively, or additionally, in some embodiments, an antigen elicits a cellular response (e.g., involving T-cells whose receptors specifically interact with the antigen) in an organism. A particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In some embodiments, an antigen reacts with the products of specific humoral or cellular immunity, including those induced by heterologous immunogens. Antigens include antigenic ferritin proteins comprising ferritin (e.g., comprising one or more mutations) and a non-ferritin polypeptide as described herein.

"Ferritin" or "ferritin protein," as used herein, refers to a protein with detectable sequence identity to *H. pylori* ferritin (SEQ ID NO: 208 or 209) or another ferritin discussed herein, such as *P. furiosus* ferritin, *Trichoplusia ni* ferritin, or human ferritin, that serves to store iron, e.g., intracellularly or in tissues or to carry iron in the bloodstream. Such exemplary ferritins, including those that occur as two polypeptide chains, known as the heavy and light chains (e.g., *T. ni* and human ferritin), are discussed in detail below. In some embodiments, a ferritin comprises a sequence with at least 15%, 20%, 30%, 40%, 50%, 60%, 70%, 75%, 80%, 85%, 90%, 95%, 97%, 98%, 99%, or 99.5% identity to a ferritin sequence disclosed herein, e.g., in Table 1 (Sequence Table). A ferritin may be a fragment of a full-length naturally-occurring sequence. "Wild-type ferritin," as used herein, refers to a ferritin whose sequence consists of a naturally-occurring sequence. Ferritins also include full-length occurring sequence or a fragment of ferritin with one or more differences in its amino acid sequence from a wild-type ferritin.

As used herein, a "ferritin monomer" refers to a single ferritin molecule (or, where applicable, a single ferritin heavy or light chain) that has not assembled with other ferritin molecules. A "ferritin multimer" comprises multiple associated ferritin monomers. A "ferritin protein" includes monomeric ferritin and multimeric ferritin.

As used herein, "ferritin particle," refers to ferritin that has self-assembled into a globular form. Ferritin particles are sometimes referred to as "ferritin nanoparticles" or simply "nanoparticles". In some embodiments, a ferritin particle comprises 24 ferritin monomers (or, where applicable, 24 total heavy and light chains).

"Hybrid ferritin," as used herein, refers to ferritin comprising *H. pylori* ferritin with an amino terminal extension of bullfrog ferritin. An exemplary sequence used as an amino terminal extension of bullfrog ferritin appears as SEQ ID NO: 217. In hybrid ferritin, the amino terminal extension of bullfrog ferritin can be fused to *H. pylori* ferritin such that immune-stimulatory moiety attachment sites are distributed evenly on the ferritin particle surface. "Bullfrog linker" as used herein is a linker comprising the sequence of SEQ ID NO: 217. Hybrid ferritin is also sometimes referred to as "bfpFerr" or "bfp ferritin." Any of the constructs comprising a bullfrog sequence can be provided without the bullfrog sequence, such as, for example, without a linker or with an alternative linker. Exemplary bullfrog linker sequences are provided in Table 1. Where Table 1 shows a bullfrog linker, the same construct may be made without a linker or with an alternative linker.

"Glycosylation," as used herein, refers to the addition of a saccharide unit to a protein.

"Immune response," as used herein, refers to a response of a cell of the immune system, such as a B cell, T cell, dendritic cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate and/or adaptive immune response. As used herein, a "protective immune response" refers to an immune response that protects a subject from infection (e.g., prevents infection or prevents the development of disease associated with infection). Methods of measuring immune responses are well known in the art and include, for example, by measuring proliferation and/or activity of lymphocytes (such as B or T cells), secretion of cytokines or chemokines, inflammation, antibody production and the like. An "antibody response" is an immune response in which antibodies are produced.

An "immune-stimulatory moiety," as used herein, refers to a moiety that is covalently attached to a ferritin or antigenic ferritin polypeptide and that can activate a component of the immune system (either alone or when attached to ferritin or antigenic ferritin polypeptide). Exemplary immune-stimulatory moieties include agonists of toll-like receptors (TLRs), e.g., TLR 4, 7, 8, or 9. In some embodiments, an immune-stimulatory moiety is an adjuvant.

As used herein, the term "kit" refers to a packaged set of related components, such as one or more compounds or compositions and one or more related materials such as solvents, solutions, buffers, instructions, or desiccants.

"N-glycan," as used herein, refers to a saccharide chain attached to a protein at the amide nitrogen of an N (asparagine) residue of the protein. As such, an N-glycan is formed by the process of N-glycosylation. This glycan may be a polysaccharide.

An "OspA ectodomain" as used herein refers to about amino acid residues 27-273 of *B. burgdorferi* OspA (UniProt Accession No. P0CL66) or the corresponding positions of a homolog thereof as identified by pairwise or structural alignment. Further examples of OspA ectodomains include positions 27-X of any of SEQ ID NOs: 83-89 where X is the C-terminal position of the relevant sequence, optionally wherein the C-terminal Lys is omitted. In some embodiments, an ectodomain further comprises at its N-terminus the 26th residue, or the 25th and 26th residues, of the corresponding full-length wild-type sequence; in SEQ ID NOs: 83-89, the 25th and 26th residues are Asp and Glu. Still further examples of OspA ectodomains include any of SEQ ID NOs: 94-102, optionally wherein the N-terminal 1, 2, or 3 residues (Met-Asp-Glu) are omitted, further optionally wherein the C-terminal Lys is omitted.

An "OspA transmembrane domain" as used herein refers to about amino acid residues 2-24 of *B. burgdorferi* OspA (UniProt Accession No. P0CL66) or the corresponding positions of a homolog thereof as identified by pairwise or structural alignment.

"Self-adjuvanting," as used herein, refers to a composition or polypeptide comprising a ferritin and an immune-stimulatory moiety directly conjugated to the ferritin so that the ferritin and immune-stimulatory moiety are in the same molecular entity. An antigenic ferritin polypeptide comprising a non-ferritin polypeptide may be conjugated to an immune-stimulatory moiety to generate a self-adjuvanting polypeptide.

An "antigenic OspA polypeptide" is used herein to refer to a polypeptide comprising all or part of an OspA of sufficient length that the polypeptide is antigenic with respect to OspA. Full-length OspA comprises a transmembrane domain and an ectodomain, defined below. Antigenicity may be a feature of the OspA sequence as part of a construct further comprising a heterologous sequence, such as a ferritin or lumazine synthase protein. That is, if an OspA is part of a construct further comprising a heterologous sequence, then it is sufficient that the construct can serve as an antigen that generates anti-OspA antibodies, regardless of whether the OspA sequence without the heterologous sequence could do so.

Antigenic ferritin polypeptide" and "antigenic ferritin protein" are used interchangeably herein to refer to a polypeptide comprising a ferritin and a non-ferritin polypeptide, such as OspA, of sufficient length that the molecule is antigenic with respect to the non-ferritin polypeptide. The antigenic ferritin polypeptide may further comprise an immune-stimulatory moiety. Antigenicity may be a feature of the non-ferritin sequence as part of the larger construct. That is, it is sufficient that the construct can serve as an antigen against the non-ferritin polypeptide, regardless of whether the non-ferritin polypeptide without the ferritin (and immune-stimulatory moiety if applicable) could do so. In some embodiments, the non-ferritin polypeptide is an OspA polypeptide, in which case the antigenic ferritin polypeptide is also an "antigenic OspA polypeptide". To be clear, however, an "antigenic OspA polypeptide" does not need to comprise ferritin. "Antigenic polypeptide" is used herein to refer to a polypeptide which is either or both of an antigenic ferritin polypeptide and an antigenic OspA polypeptide. The disclosure describes nucleic acid sequences and amino acid sequences having a certain degree of identity to a given nucleic acid sequence or amino acid sequence, respectively (a references sequence).

"Sequence identity" between two nucleic acid sequences indicates the percentage of nucleotides that are identical between the sequences. "Sequence identity" between two amino acid sequences indicates the percentage of amino acids that are identical between the sequences.

The terms "% identical", "% identity" or similar terms are intended to refer, in particular, to the percentage of nucleotides or amino acids which are identical in an optimal alignment between the sequences to be compared. Said percentage is purely statistical, and the differences between the two sequences may be but are not necessarily randomly distributed over the entire length of the sequences to be compared. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Needleman and Wunsch, 1970, J. Mol. Biol. 48, 443, with the aid of the similarity search algorithm by Pearson and Lipman, 1988, Proc. Natl Acad. Sci. USA 88, 2444, or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions at which the sequences to be compared correspond, dividing this number by the number of positions compared (e.g., the number of positions in the reference sequence) and multiplying this result by 100.

In some embodiments, the degree of identity is given for a region which is at least about 50%, at least about 60%, at least about 70%, at least about 80%, at least about 90% or about 100% of the entire length of the reference sequence. For example, if the reference nucleic acid sequence consists of 200 nucleotides, the degree of identity is given for at least about 100, at least about 120, at least about 140, at least about 160, at least about 180, or about 200 nucleotides, in some embodiments in continuous nucleotides. In some embodiments, the degree of identity is given for the entire length of the reference sequence.

Nucleic acid sequences or amino acid sequences having a particular degree of identity to a given nucleic acid sequence or amino acid sequence, respectively, may have at least one functional property of said given sequence, e.g., and in some instances, are functionally equivalent to said given sequence. One important property includes the ability to act as a cytokine, in particular when administered to a subject. In some embodiments, a nucleic acid sequence or amino acid sequence having a particular degree of identity to a given nucleic acid sequence or amino acid sequence is functionally equivalent to said given sequence.

As used herein, a "subject" refers to any member of the animal kingdom. In some embodiments, "subject" refers to humans. In some embodiments, "subject" refers to non-human animals. In some embodiments, subjects include, but are not limited to, mammals, birds, reptiles, amphibians, fish, insects, and/or worms. In certain embodiments, the non-human subject is a mammal (e.g., a rodent, a mouse, a rat, a rabbit, a monkey, a dog, a cat, a sheep, cattle, a primate, and/or a pig). In some embodiments, a subject may be a transgenic animal, genetically-engineered animal, and/or a clone. In certain embodiments of the present invention the subject is an adult, an adolescent or an infant. In some embodiments, terms "individual" or "patient" are used and are intended to be interchangeable with "subject".

A "surface-exposed" amino acid, as used herein, refers to an amino acid residue in a protein (e.g., a ferritin) with a side chain that can be contacted by solvent molecules when the protein is in its native three-dimensional conformation after multimerization, if applicable. Thus, for example, in the case of ferritin that forms a 24-mer, a surface-exposed amino acid residue is one whose side chain can be contacted by solvent when the ferritin is assembled as a 24-mer, e.g., as a ferritin multimer or ferritin particle.

As used herein, the term "vaccination" or "vaccinate" refers to the administration of a composition intended to generate an immune response, for example to a disease-causing agent. Vaccination can be administered before, during, and/or after exposure to a disease-causing agent, and/or to the development of one or more symptoms, and in some embodiments, before, during, and/or shortly after exposure to the agent. In some embodiments, vaccination includes multiple administrations, appropriately spaced in time, of a vaccinating composition.

B. OspA Polypeptides

OspA polypeptides are provided, which can be antigenic when administered alone, with adjuvant as a separate molecule, and/or as part of a nanoparticle (e.g., ferritin particle or lumazine synthase particle), which can be self-adjuvanting. In some embodiments, an OspA polypeptide comprises a modified outer surface protein A (OspA) of *Borrelia*. OspA exists in a number of serotypes, as defined by their reactivity with monoclonal antibodies against different epitopes of OspA (see Wilske et al., J Clin Microbio 31(2):340-350 (1993)). These serotypes are correlated with different geno-species of *Borrelia* bacteria. In some embodiments, the OspA is any one of serotypes 1-7. In some embodiments, the OspA is from *Borrelia burgdorferi, Borrelia mayonii, Borrelia afzelii, Borrelia garinii*, or *Borrelia bavariensis*. In some embodiments, the OspA is *Borrelia burgdorferi* OspA. In some embodiments, the *Borrelia* can be carried by a tick of the *Ixodes* genus. In some embodiments, the *Borrelia* is *Borrelia burgdorferi, Borrelia mayonii, Borrelia afzelii, Borrelia garinii*, or *Borrelia bavariensis*.

In some embodiments, the OspA polypeptide is an OspA serotype 1 polypeptide, such as an OspA serotype 1 ectodomain. The literature has reported that an epitope of OspA serotype 1 at amino acids 165-173 of SEQ ID NO: 83 has homology with a fragment of the sequence of human leukocyte function-associated antigen-1 (hLFA-1)—i.e., SEQ ID NO: 78 (see Gross, D. M., et al., Science 281(5377): p. 703-6 (1998)). Amino acids 165-173 of SEQ ID NO: 83 are shown as an isolated nonapeptide in SEQ ID NO: 77 and are referred to as the hLFA-1 homology site. SEQ ID NO: 83 is an exemplary wild-type serotype 1 OspA sequence, which is used herein as a reference sequence for discussion of amino acid positions in OspA. This homology site may play a role in the development of Lyme arthritis, including antibiotic-resistant Lyme arthritis. Described herein are antigenic OspA polypeptides comprising a modified OspA serotype 1 polypeptide of *Borrelia*, wherein the modified OspA does not comprise the sequence of SEQ ID NO: 77. Such polypeptides, when used to elicit antibodies, may have improved safety, e.g., reduced risk of triggering an autoimmune response. In some embodiments, the OspA serotype 1 polypeptide has one or more modifications that reduce identity with hLFA-1. Any modification to reduce homology to SEQ ID NO: 78, to reduce identity to SEQ ID NO: 78, or to introduce one or more non-conservative substitutions relative to SEQ ID NO: 78 is encompassed. In some embodiments, an antigenic polypeptide comprising OspA serotype 1 polypeptide of *Borrelia*, wherein the polypeptide does not comprise the sequence of SEQ ID NO: 77 is provided. In some embodiments, the antigenic polypeptide comprises the ectodomain of OspA serotype 1, wherein the ectodomain does not comprise the sequence of SEQ ID NO: 77. In some embodiments, the antigenic OspA serotype 1 polypeptide comprises a sequence with at least 85%, 90%, 95%, 97%, 98%, 99%, 99.5%, or 100% identity to the sequence of any one of SEQ ID NOS: 94-102.

"Reducing homology" encompasses reducing sequence identity and/or reducing sequence similarity, wherein each member of a set of amino acids listed as conservative substitutions in the Table below is considered similar to the listed original residue and to the other members of the set; for example, the first line of the table indicates that alanine, valine, leucine, and isoleucine are similar to each other, and the eighth line indicates that alanine and glycine are similar to each other. Similarity is not transitive, so for example, isoleucine and glycine are not considered similar. In some embodiments, a modified OspA comprises an OspA serotype 1 protein with reduced homology to hLFA-1 compared to wild-type OspA serotype 1. In some embodiments, a modified OspA comprises an OspA serotype 1 comprising a modification to any one or more of the amino acids of SEQ ID NO: 77. In some embodiments, the modification to SEQ ID NO: 77 is a non-conservative amino acid substitution. A non-conservative substitution is a substitution different from the conservative substitutions shown in the following Table.

TABLE 3

Conservative Amino Acid Substitutions

| Original Residue | Conservative Substitutions |
|---|---|
| Ala (A) | Val; Leu; Ile |
| Arg (R) | Lys; Gln; Asn |

TABLE 3-continued

Conservative Amino Acid Substitutions

| Original Residue | Conservative Substitutions |
|---|---|
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

In some embodiments, one or more of the amino acids of SEQ ID NO: 77 is replaced with the corresponding amino acid(s) of a non-serotype 1 OspA, such as serotype 2, 3, 4, 5, 6, or 7 OspA. In some embodiments, each of the amino acids of SEQ ID NO: 77 are replaced with the corresponding amino acid(s) of a serotype 2, 3, 4, 5, 6, or 7 OspA. In some embodiments, the amino acids of SEQ ID NO: 77 are replaced with corresponding amino acids of serotype 2 (S2, SEQ ID NO: 79) or serotype 3 (S3, SEQ ID NO: 80).

In some embodiments, a modified OspA comprises SEQ ID NO: 81. In some embodiments, a modified OspA comprises SEQ ID NO: 82. SEQ ID NOS: 81 and 82 are intended to replace SEQ ID NO: 77 and thereby reduce homology to SEQ ID NO: 78.

In some embodiments, the polypeptide is a full-length OspA (e.g., including a transmembrane domain and an ectodomain, which may or may not comprise a modification to reduce homology to hLFA-1 as described herein).

In some embodiments, the polypeptide lacks a transmembrane domain. In some embodiments, the polypeptide lacks a portion of a transmembrane domain, e.g., the N-terminal 2, 3, 4, 5, 6, 7, 8, 9, 10, 11, 12, 13, 14, 15, 16, 17, 18, 19, 20, 21, 22, 23, or 24 amino acids of a wild-type OspA sequence. In some embodiments, the polypeptide lacks a segment including amino acid 17 of OspA serotype 1 or the corresponding position of a homolog thereof as identified by pairwise or structural alignment. In some embodiments, the polypeptide lacks at least amino acids 1-17 of OspA, such as OspA serotype 1, or the counterpart amino acids in a homolog thereof as identified by pairwise or structural alignment. In some embodiments, the polypeptide lacks at least the N-terminal 18, 19, 20, 21, 22, 23, or 24 amino acids of OspA, such as OspA serotype 1, or the counterpart amino acids in a homolog thereof as identified by pairwise or structural alignment. In some embodiments, the polypeptide lacks amino acids 1-25 of OspA, such as OspA serotype 1, or the counterpart amino acids in a homolog thereof as identified by pairwise or structural alignment. In some embodiments, the polypeptide lacks amino acids 1-26 of OspA serotype 1, or the counterpart amino acids in a homolog thereof as identified by pairwise or structural alignment. For the avoidance of doubt, lacking a transmembrane domain does not require that a polypeptide lack an N-terminal methionine; for example, a polypeptide in which the first residue is methionine and the second residue corresponds to residue 26 of a wild-type OspA, followed by residues corresponding to the 27th, 28th, etc., wild-type OspA residues, is considered to lack a transmembrane domain. In some embodiments, the polypeptide comprising an OspA lacks a lipidation site, such as the lipidation site contained within the transmembrane domain of wild-type OspA serotype 1. In some embodiments, the polypeptide lacks cysteine 17 of OspA serotype 1. In some embodiments, the polypeptide does not comprise a cysteine that corresponds to any of positions 1-25 of a wild-type OspA, e.g., any of SEQ ID NOs: 83-89. In some embodiments, the polypeptide lacks or has a substitution at cysteine 17 of OspA serotype 1. In some embodiments, the polypeptide lacks at least part of a wild-type OspA transmembrane domain, such that it lacks a lipidation site. In some embodiments, the polypeptide lacks amino acids that align to amino acids 1-17 of OspA serotype 1.

In some embodiments, the polypeptide does not comprise a palmitoyl group. In some embodiments, the polypeptide does not comprise a diacylglycerol group. In some embodiments, the polypeptide is non-lipidated. In some embodiments, the polypeptide lacks a lipidation site. In some embodiments, this lipidation site is contained within the transmembrane domain. In some embodiments, the lipidation site that is removed is cysteine 17 of OspA serotype 1. In some embodiments, the polypeptide lacks or has a substitution at cysteine 17 of OspA serotype 1.

In some embodiments, removal of an OspA lipidation site and/or transmembrane domain or portion thereof, and/or the lack of a palmitoyl and/or diacylglycerol group, allows easier protein purification, e.g., by improving the solubility of the protein and/or making the protein more amenable to purification by techniques such as ion exchange and other forms of chromatography.

In some embodiments, the polypeptide comprises a mammalian leader sequence (also known as a signal sequence). In some embodiments, the mammalian leader sequence results in secretion of the polypeptide when expressed in mammalian cells.

In some embodiments, the polypeptide lacks a glycosylation site. Modifications to remove glycosylation sites are described in detail herein. The OspA polypeptides according to this disclosure can comprise any such modification, which can be combined with any of the other modifications described herein, including modifications to the hLFA-1 homology site and/or deletion of part or all of a transmembrane domain. In some embodiments, the polypeptide does not comprise SEQ ID NO: 77 (e.g., has reduced homology to hLFA-1a) and has modifications to reduce glycosylation and/or lacks a transmembrane domain.

1. Modification of Glycosylation

N-linked glycosylation is the attachment of glycan to an amide nitrogen of an asparagine (Asn; N) residue of a protein. The process of attachment results in a glycosylated protein. Glycosylation can occur at any asparagine residue in a protein that is accessible to and recognized by glycosylating enzymes following translation of the protein, and is most common at accessible asparagines that are part of an NXS/TX site, wherein the second amino acid residue following the asparagine is a serine or threonine. A non-human glycosylation pattern can render a polypeptide undesirably reactogenic when used to elicit antibodies. Additionally, glycosylation of a polypeptide that is not normally glycosylated can alter its immunogenicity. For example, glycosylation can mask important immunogenic epitopes within a protein. Thus, to reduce or eliminate glycosylation, either asparagine residues or serine/threonine residues can be modified, for example, by substitution to another amino acid.

In some embodiments, a polypeptide comprising an OspA is modified to reduce or eliminate glycosylation. In some embodiments, one or more N-glycosylation sites in OspA are removed. In some embodiments, the removal of an N-glycosylation site decreases glycosylation of OspA. In some embodiments, the polypeptide has decreased glycosylation relative to wild-type OspA, such as wild-type serotype 1 OspA. In some embodiments, the removal of N-glycosylation sites eliminates glycosylation of OspA.

In some embodiments, one or more asparagines in OspA are replaced with a non-asparagine amino acid. In some embodiments, each asparagine in OspA is replaced with a non-asparagine amino acid. Any natural or non-natural amino acid found in proteins, e.g., glutamine, may be used to replace asparagine. In some embodiments, the modification to reduce or eliminate glycosylation modifies an NXS/TX glycosylation site (wherein the second residue following the N is an S or T). In some embodiments, the first X in the NXS/TX site is not proline and/or the second X in the NXS/TX site is not proline. In some embodiments, the modification to reduce or eliminate glycosylation is an N to Q substitution. In some embodiments, the modification to reduce or eliminate glycosylation is an S/T to A substitution.

A detailed discussion of positions that can be modified to reduce or eliminate glycosylation below. Position numbers refer to the positions in full-length OspA sequences provided as SEQ ID NOs: 83-89. It is understood that position numbers should be adjusted appropriately for partial and modified OspA sequences (e.g., if an N-terminal deletion results in a net shortening by 25 amino acid residues, then position numbers should be decremented by 25).

In some embodiments, the modification to reduce or eliminate glycosylation comprises a substitution of any one or more of N20, N71, N190, N202, and N251 of OspA serotype 1 (SEQ ID NO: 83). In some embodiments, the modification comprises modifications at each of N71, N190, N202, and N251 of OspA serotype 1. In some embodiments, the modification to reduce or eliminate glycosylation comprises one or more of N20Q, N71Q, N190Q, N202Q, or N251Q of OspA serotype 1. Corresponding amino acids can be found in OspA of different serotypes by pair-wise alignment. Thus, in some embodiments, the asparagine residues replaced in OspA of serotypes 2-7 are amino acid residues that align with N20, N71, N190, N202, and N251 of OspA serotype 1. In some embodiments, the modification to reduce or eliminate glycosylation comprises a substitution of any one or more of a Ser or Thr residue at position 22, 73, 192, 204, and 253 of OspA serotype 1. In some embodiments, the modification comprises a substitution of one or more of a Ser or Thr residue at position 22, 73, 192, 204, and 253 of OspA serotype 1 with an alanine.

In some embodiments, the modification to reduce or eliminate glycosylation comprises substitutions any one or more of N20, N71, N141, N164, N202, and N205 of OspA serotype 2 (SEQ ID NO: 84). In some embodiments, the modification comprises modifications at each of N20, N71, N141, N164, N202, and N205 of OspA serotype 2. In some embodiments, the modification to reduce or eliminate glycosylation comprises one or more of N20Q, N71Q, N141Q, N164Q, N202Q, or N205Q of OspA serotype 2. Analogous amino acids can be found in OspA of different serotypes by pair-wise alignment. Thus, in some embodiments, the asparagine residues replaced in OspA of serotypes 1 or 3-7 are amino acid residues that align with N20, N71, N141, N164, N202, and N205 of OspA serotype 2. In some embodiments, the modification to reduce or eliminate glycosylation comprises a substitution of any one or more of a Ser or Thr residue at position 22, 73, 143, 166, 204, and 207 of OspA serotype 2. In some embodiments, the modification comprises a substitution of one or more of a Ser or Thr residue at position 22, 73, 143, 166, 204, and 207 of OspA serotype 2 with an alanine.

In some embodiments, the modification to reduce or eliminate glycosylation comprises substitutions of any one or more of N20, N71, N95, N141, N191, and N203 of OspA serotype 3 (SEQ ID NO: 85). In some embodiments, the modification comprises modifications at each of N20, N20, N71, N95, N141, N191, and N203 of OspA serotype 3. In some embodiments, the modification to reduce or eliminate glycosylation comprises one or more of N20Q, N71Q, N95Q, N141Q, N191Q, or N203Q of OspA serotype 3. Analogous amino acids can be found in OspA of different serotypes by pair-wise alignment. Thus, in some embodiments, the asparagine residues replaced in OspA of serotypes 1-2 or 4-7 are amino acid residues that align with N20, N20, N71, N95, N141, N191, and N203 of OspA serotype 3. In some embodiments, the modification to reduce or eliminate glycosylation comprises a substitution of any one or more of a Ser or Thr residue at position 22, 73, 97, 143, 193, and 205 of OspA serotype 3. In some embodiments, the modification comprises a substitution of one or more of a Ser or Thr residue at position 22, 73, 97, 143, 193, and 205 of OspA serotype 3 with an alanine.

In some embodiments, the modification to reduce or eliminate glycosylation comprises substitutions of any one or more of N20, N71, N141, N202, N205, and N219 of OspA serotype 4 (SEQ ID NO: 86). In some embodiments, the modification comprises modifications at each of N20, N71, N141, N202, N205, and N219 of OspA serotype 4. In some embodiments, the modification to reduce or eliminate glycosylation comprises one or more of N20Q, N71Q, N141Q, N202Q, N205Q, or N219Q of OspA serotype 4. Analogous amino acids can be found in OspA of different serotypes by pair-wise alignment. Thus, in some embodiments, the asparagine residues replaced in OspA of serotypes 1-3 or 5-7 are amino acid residues that align with N20, N71, N141, N202, N205, and N219 of OspA serotype 4. In some embodiments, the modification to reduce or eliminate glycosylation comprises a substitution of any one or more of a Ser or Thr residue at position 22, 73, 143, 204, 207, and 221 of OspA serotype 4. In some embodiments, the modification comprises a substitution of one or more of a Ser or Thr residue at position 22, 73, 143, 204, 207, and 221 of OspA serotype 4 with an alanine.

In some embodiments, the modification to reduce or eliminate glycosylation comprises substitutions of any one or more of N20, N71, and N141 of OspA serotype 5. (Certain serotypes, including serotypes 5-7, contain fewer glycosylation sites than certain other OspA sequences such as serotype 1). In some embodiments, the modification comprises modifications at each of N20, N71, and N141 of OspA serotype 5 (SEQ ID NO: 87). In some embodiments, the modification to reduce or eliminate glycosylation comprises one or more of N20Q, N71Q, or N141Q of OspA serotype 5. Analogous amino acids can be found in OspA of different serotypes by pair-wise alignment. Thus, in some embodiments, the asparagine residues replaced in OspA of serotypes 1-4 or 6-7 are amino acid residues that align with N20, N71, and N141 of OspA serotype 5. In some embodiments, the modification to reduce or eliminate glycosylation comprises a substitution of any one or more of a Ser or Thr residue at position 22, 73, and 143 of OspA serotype 5. In some embodiments, the modification comprises a substitution of one or more of a Ser or Thr residue at position 22, 73, and 143 of OspA serotype 5 with an alanine.

In some embodiments, the modification to reduce or eliminate glycosylation comprises substitutions of any one or more of N20, N71, and N141 of OspA serotype 6 (SEQ ID NO: 88). In some embodiments, the modification comprises modifications at each of N20, N71, and N141 of OspA serotype 6. In some embodiments, the modification to reduce or eliminate glycosylation comprises one or more of N20Q, N71Q, or N141Q of OspA serotype 6. Analogous amino acids can be found in OspA of different serotypes by pair-wise alignment. Thus, in some embodiments, the asparagine residues replaced in OspA of serotypes 1-5 or 7 are amino acid residues that align with N20, N71, and N141 of OspA serotype 6. In some embodiments, the modification to reduce or eliminate glycosylation comprises a substitution of any one or more of a Ser or Thr residue at position 22, 73, and 143 of OspA serotype 6. In some embodiments, the modification comprises a substitution of one or more of a Ser or Thr residue at position 22, 73, and 143 of OspA serotype 6 with an alanine.

In some embodiments, the modification to reduce or eliminate glycosylation comprises substitutions of any one or more of N20, N71, N141, and N191 of OspA serotype 7 (SEQ ID NO: 89). In some embodiments, the modification comprises modifications at each of N20, N71, N141, and N191 of OspA serotype 7. In some embodiments, the modification to reduce or eliminate glycosylation comprises one or more of N20Q, N71Q, N141Q, or N191Q of OspA serotype 7. Analogous amino acids can be found in OspA of different serotypes by pair-wise alignment. Thus, in some embodiments, the asparagine residues replaced in OspA of serotypes 1-6 are amino acid residues that align with N20, N71, N141, and N191 of OspA serotype 7. In some embodiments, the modification to reduce or eliminate glycosylation comprises a substitution of any one or more of a Ser or Thr residue at position 22, 73, 143, and 193 of OspA serotype 7. In some embodiments, the modification comprises a substitution of one or more of a Ser or Thr residue at position 22, 73, 143, and 193 of OspA serotype 7 with an alanine.

C. Antigenic OspA Polypeptides Comprising an OspA Polypeptide and Ferritin or Lumazine Synthase In some embodiments, an antigenic polypeptide is provided, comprising an OspA polypeptide and ferritin or lumazine synthase. It is to be understood that such antigenic OspA polypeptides disclosed herein are antigenic with respect to the OspA component, e.g., they can be administered to a mammal, such as a human, to elicit the production of anti-OspA antibodies. The ferritin component of the antigenic polypeptide may be wild type ferritin of any species, or ferritin of any species which comprises one or more mutations, both as described herein. In some embodiments, the antigenic polypeptide comprises the amino acids of any one of SEQ ID NOS: 1-76. In some embodiments, the antigenic polypeptide comprises a sequence with at least 85%, 90%, 95%, 97%, 98%, 99%, 99.5%, or 100% identity to the sequence of any one of SEQ ID NOS: 1-76. The lumazine synthase component of the antigenic polypeptide may be lumazine synthase of any species.

In some embodiments, the antigenic polypeptide comprises a mammalian leader sequence (also known as a signal sequence). In some embodiments, the mammalian leader sequence results in secretion of the antigenic polypeptide when expressed in mammalian cells.

1. OspA Polypeptide Component

The antigenic OspA polypeptide can comprise any of the modified OspA polypeptides described herein.

For example, in some embodiments, the OspA component of the antigenic OspA polypeptide comprises the ectodomain of OspA. In some embodiments, the ectodomain of OspA is from any one of serotypes 1, 2, 3, 4, 5, 6, or 7. Exemplary wild-type OspA sequences are provided as SEQ ID NOS: 83-89. The N-terminal 25 amino acids thereof can be removed to, for example, remove the lipidation site. Accession numbers for exemplary OspA sequences are also provided in the examples. In some embodiments, the ectodomain is from *Borrelia burgdorferi*, *Borrelia mayonii*, *Borrelia afzelii*, *Borrelia garinii*, or *Borrelia bavariensis*. In some embodiments, the ectodomain is *Borrelia burgdorferi*.

In some embodiments, the ectodomain is a wild-type ectodomain.

In some embodiments, the ectodomain is a modified ectodomain, e.g., an ectodomain modified to reduce glycosylation. Introductory discussion of glycosylation is provided in the previous section and is not repeated here in the interest of brevity. The OspA component of the antigenic OspA polypeptide can comprise any of the modifications described herein to reduce or eliminate glycosylation, including without limitation removal of one or more N-glycosylation sites in the ectodomain are removed, e.g., by amino acid substitutions, as discussed in detail herein.

In some embodiments, the OspA ectodomain is present as part of a larger OspA sequence in the antigenic polypeptide, e.g., including part or all of a transmembrane domain. In some embodiments, the OspA ectodomain is present in a full-length OspA sequence within the antigenic polypeptide. In some embodiments, the full-length OspA sequence is a wild-type full-length OspA sequence. In some embodiments, the antigenic polypeptide does not comprise a transmembrane domain.

Any of the modifications discussed above can be combined in the antigenic polypeptide. In some embodiments, the antigenic polypeptide comprises at least one modification to reduce glycosylation and at least one further modification described herein.

In some embodiments, the OspA ectodomain of the antigenic polypeptide is any one of the modified OspA ectodomains described in section B above.

Any of the OspA ectodomains (or the sequence comprising the OspA ectodomain, such as full-length OspA) described herein can be combined in the antigenic polypeptide with any of the ferritins described below.

2. Ferritin Component

In some embodiments, a fusion protein comprising the antigenic OspA polypeptide described herein and ferritin is encompassed. The ferritin in the antigenic polypeptide can be wild-type or comprise one or more mutations (see the following section). In some embodiments, the ferritin is bacterial, insect, fungal, bird, or mammalian. In some embodiments, the ferritin is human. In some embodiments, the ferritin is bacterial. In some embodiments, the ferritin is *Trichoplusia ni* ferritin (PDB: 1Z6O_X, SEQ ID NOS: 211 and 212).

In some embodiments, the ferritin is a light chain and/or heavy chain ferritin. In some embodiments, the ferritin is human heavy chain ferritin (FTH1, GENE ID No: 2495) or human light chain ferritin (FTL, GENE ID No: 2512). In some embodiments, the ferritin is a multimeric protein referred to herein as a "ferritin particle" or a "ferritin nanoparticle" comprising 24 total subunits of heavy chain ferritin and light chain ferritin.

In some embodiments, an antigenic OspA polypeptide comprises a light chain ferritin and an OspA polypeptide. In some embodiments, an antigenic polypeptide comprises a heavy chain ferritin and an OspA polypeptide. In some embodiments, an antigenic polypeptide comprising a light chain ferritin and an OspA polypeptide can assemble with a heavy chain ferritin that is not linked to a non-ferritin polypeptide. In some embodiments, an antigenic polypeptide comprising a heavy chain ferritin and an OspA polypeptide can assemble with a light chain ferritin that is not linked to a non-ferritin polypeptide. A ferritin not linked to a non-ferritin polypeptide may be referred as a "naked ferritin."

In some embodiments, an antigenic polypeptide comprising a heavy chain ferritin and an OspA polypeptide can assemble with an antigenic polypeptide comprising a light chain ferritin and an OspA polypeptide to allow expression of 2 of the same or different antigens on a single ferritin particle. In some embodiments, the 2 different antigens are encoded by a single infectious agent. In some embodiments, the 2 different antigens are encoded by 2 different infectious agents, e.g., *Borrelia* of different serotypes or species.

In some embodiments, an antigenic polypeptide comprising a heavy chain ferritin and an OspA polypeptide can assemble with an antigenic polypeptide comprising a light chain ferritin and an OspA polypeptide to produce a bivalent composition. In some embodiments, the ferritin is *H. pylori* ferritin (see SEQ ID NO: 90 for an exemplary wild-type *H. pylori* ferritin sequence comprising an 8-amino acid extension from bullfrog ferritin at its N-terminus). In some embodiments, the lower sequence homology between *H. pylori* ferritin (or other bacterial ferritins) and human ferritin may decrease the potential for autoimmunity when used as a platform for constructing antigenic polypeptides (see Kanekiyo et al., Cell 162, 1090-1100 (2015)).

In some embodiments, the ferritin is *Pyrococcus furiosus* ferritin (NCBI seq WP_011011871.1), optionally with one or more mutations described herein.

In some embodiments, the ferritin comprises a sequence having greater than 70%, greater than 75%, greater than 80%, greater than 85%, greater than 90%, greater than 95%, greater than 97%, greater than 98%, or greater than 99% identity to a wild-type ferritin.

In some embodiments, the ferritin is an insect ferritin. In some embodiments, the ferritin is *Trichoplusia Ni* ferritin (PDB: 1Z6O_X, SEQ ID NOS: 211 and 212), optionally with one or more mutations described herein.

a) Ferritin Mutations

In some embodiments, the ferritin comprises one or more mutations are disclosed herein. In some embodiments, the one or more mutations comprise changes to the amino acid sequence of a wild-type ferritin and/or an insertion, e.g., at the N- or C-terminus. In some embodiments, one, two, three, four, five, or more different amino acids are mutated in the ferritin as compared to wild-type ferritin (in some embodiments, in addition to any N-terminal insertion). The one or more mutations can change functional properties of the ferritin, e.g., as discussed in detail below. In general, a mutation simply refers to a difference in the sequence (such as a substituted, added, or deleted amino acid residue or residues) relative to the corresponding wild-type ferritin.

(1) Cysteine for Conjugation

In some embodiments, ferritin is mutated to provide a chemical handle for conjugation of an immune-stimulatory moiety and/or non-ferritin polypeptide. This can be achieved with a mutation replacing a surface-exposed non-cysteine amino acid with a cysteine. For the avoidance of doubt, language such as "replacing a surface-exposed amino acid with a cysteine" necessarily implies that the surface-exposed amino acid in the wild-type or pre-mutation sequence is not cysteine. Another approach for providing a chemical handle for conjugation of an immune-stimulatory moiety or non-ferritin polypeptide is to include a segment of amino acids, such as a linker, N- or C-terminal to the ferritin, wherein the segment of amino acids comprises a cysteine. In some embodiments, this cysteine (whether replacing a surface-exposed amino acid or in an N- or C-terminal linker) is unpaired, which means that it does not have an appropriate partner cysteine to form a disulfide bond. In some embodiments, this cysteine does not change the secondary structure of ferritin. In some embodiments, this cysteine does not change the tertiary structure of ferritin.

In some embodiments, this cysteine can be used to conjugate agents, such as immune-stimulatory moieties, to ferritin. In some embodiments, this cysteine provides a free thiol group that is reactive. In some embodiments, agents conjugated to this cysteine on ferritin are exposed on the surface of an assembled ferritin particle. In some embodiments, this cysteine can interact with molecules and cells of the subject after administration while the ferritin particle is assembled.

In some embodiments, the presence of this cysteine allows conjugation of one or more immune-stimulatory moieties, e.g., adjuvants. In some embodiments, conjugation of the immune-stimulatory moiety would not occur in the absence of this cysteine.

In some embodiments, the non-cysteine amino acid that is replaced with a cysteine is selected from E12, S72, A75, K79, S100, and S111 of *H. pylori* ferritin. Thus, in some embodiments, the surface-exposed amino acid that is replaced in favor of cysteine is an amino acid residue that corresponds to E12, S26, S72, A75, K79, S100, or S111 of *H. pylori* ferritin. Analogous amino acids can be found in non-*H. pylori* ferritin by pair-wise or structural alignment. In some embodiments, the non-cysteine amino acid that is replaced with a cysteine can be selected from an amino acid that corresponds to S3, S19, S33, I82, A86, A102, and A120 of human light chain ferritin. In some embodiments, the surface-exposed amino acid to be replaced with a cysteine is selected based on the understanding that if the native amino acid were replaced with cysteine, it would be reactive in an assembled ferritin multimer or particle and/or that this cysteine does not disrupt the stability of the ferritin multimer or particle and/or that this cysteine does not lead to reduction in expression levels of ferritin.

In some embodiments, the ferritin comprises an E12C mutation. In some embodiments, the E12C residue can be used to conjugate agents (e.g., immune-stimulatory moieties and/or non-ferritin polypeptides) to ferritin. In some embodiments, the E12C residue provides a free thiol group that is reactive. In some embodiments, agents conjugated to the E12C residue on ferritin monomers are expressed on the surface on an assembled ferritin multimer or particle. In some embodiments, twenty-four E12C residues (one from each monomer) are present on the surface of a ferritin multimer or particle.

In some embodiments, the ferritin comprises an S26C mutation. In some embodiments, the S26C residue can be used to conjugate agents (e.g., immune-stimulatory moieties and/or non-ferritin polypeptides) to ferritin. In some embodiments, the S26C residue provides a free thiol group that is reactive. In some embodiments, agents conjugated to the S26C residue on ferritin monomers are expressed on the surface on an assembled ferritin multimer or particle. In some embodiments, twenty-four S26C residues (one from each monomer) are present on the surface of a ferritin multimer or particle.

In some embodiments, the ferritin comprises an S72C mutation. In some embodiments, the S72C residue can be used to conjugate agents (e.g., immune-stimulatory moieties and/or non-ferritin polypeptides) to ferritin. In some embodiments, the S72C residue provides a free thiol group that is reactive. In some embodiments, agents conjugated to the S72C residue on ferritin monomers are expressed on the surface on an assembled ferritin multimer or particle. In some embodiments, twenty-four S72C residues (one from each monomer) are present on the surface of a ferritin multimer or particle.

In some embodiments, the ferritin comprises an A75C mutation. In some embodiments, the A75C residue can be used to conjugate agents (e.g., immune-stimulatory moieties and/or non-ferritin polypeptides) to ferritin. In some embodiments, the A75C residue provides a free thiol group that is reactive. In some embodiments, agents conjugated to the A75C residue on ferritin monomers are expressed on the surface on an assembled ferritin multimer or particle. In some embodiments, twenty-four A75C residues (one from each monomer) are present on the surface of a ferritin multimer or particle.

In some embodiments, the ferritin comprises an K79C mutation. In some embodiments, the K79C residue can be used to conjugate agents (e.g., immune-stimulatory moieties and/or non-ferritin polypeptides) to ferritin. In some embodiments, the K79C residue provides a free thiol group that is reactive. In some embodiments, agents conjugated to the K79C residue on ferritin monomers are expressed on the surface on an assembled ferritin multimer or particle. In some embodiments, twenty-four K79C residues (one from each monomer) are present on the surface of a ferritin multimer or particle.

In some embodiments, the ferritin comprises an S100C mutation. In some embodiments, the S100C residue can be used to conjugate agents (e.g., immune-stimulatory moieties and/or non-ferritin polypeptides) to ferritin. In some embodiments, the S100C residue provides a free thiol group that is reactive. In some embodiments, agents conjugated to the S100C residue on ferritin monomers are expressed on the surface on an assembled ferritin multimer or particle. In some embodiments, twenty-four S100C residues (one from each monomer) are present on the surface of a ferritin multimer or particle.

In some embodiments, the ferritin comprises an S111C mutation. In some embodiments, the S111C residue can be used to conjugate agents (e.g., immune-stimulatory moieties and/or non-ferritin polypeptides) to ferritin. In some embodiments, the S111C residue provides a free thiol group that is reactive. In some embodiments, agents conjugated to the S111C residue on ferritin monomers are expressed on the surface on an assembled ferritin multimer or particle. In some embodiments, twenty-four S111C residues (one from each monomer) are present on the surface of a ferritin multimer or particle.

(2) Removal of Internal Cysteine

In some embodiments, the ferritin comprises a mutation replacing an internal cysteine with a non-cysteine amino acid. Removal of a native internal cysteine residue can ensure that there is only one unpaired cysteine per ferritin monomer and avoid undesired reactions such as disulfide formation and may result in a more stable and efficient result (e.g., adjuvant presentation). In some embodiments, C31 of H. pylori ferritin is replaced with a non-cysteine amino acid. In some embodiments, C31 of H. pylori ferritin is replaced with a serine (C31S), although any non-cysteine residue may be used, e.g., alanine, glycine, threonine, or asparagine. Analogous amino acids can be found in non-H. pylori ferritin by pair-wise or structural alignment. Thus, in some embodiments, the internal cysteine that is replaced in favor of non-cysteine is an amino acid residue that aligns with C31 of H. pylori ferritin. Exemplary ferritin sequences showing a C31S mutation are shown in SEQ ID NOS: 201-207. In some embodiments, when more than one internal cysteine is present in ferritin, two or more (e.g., each) internal cysteine is replaced with a non-cysteine amino acid, such as serine or an amino acid selected from serine, alanine, glycine, threonine, or asparagine.

(3) Glycosylation

Human-compatible glycosylation can contribute to safety and efficacy in recombinant drug products. Regulatory approval may be contingent on demonstrating appropriate glycosylation as a critical quality attribute (see Zhang et al., Drug Discovery Today 21(5):740-765 (2016)). N-glycans can result from glycosylation of asparagine side chains and can differ in structure between humans and other organisms such as bacteria and yeast. Thus, it may be desirable to reduce or eliminate non-human glycosylation and/or N-glycan formation in ferritin according to the disclosure. In some embodiments, controlling glycosylation of ferritin improves the efficacy and/or safety of the composition, especially when used for human vaccination.

In some embodiments, ferritin is mutated to inhibit formation of an N-glycan. In some embodiments, a mutated ferritin has reduced glycosylation as compared to its corresponding wild type ferritin.

In some embodiments, the ferritin comprises a mutation replacing a surface-exposed asparagine with a non-asparagine amino acid. In some embodiments, the surface-exposed asparagine is N19 of H. pylori ferritin or a position that corresponds to position 31 of H. pylori ferritin as determined by pair-wise or structural alignment In some embodiments, mutating such an asparagine, e.g., N19 of H. pylori ferritin, decreases glycosylation of ferritin. In some embodiments, the mutation replaces the asparagine with a glutamine. In some embodiments, the ferritin is an H. pylori ferritin comprising an N19Q mutation. SEQ ID NOS: 201-207 are exemplary ferritin sequences comprising N19Q mutations.

A mammal exposed to a glycosylated protein produced in bacteria or yeast may generate an immune response to the glycosylated protein, because the pattern of glycosylation of a given protein in bacterial or yeast could be different from the pattern of glycosylation of the same protein in a mammal. Thus, some glycosylated therapeutic proteins may not be appropriate for production in bacteria or yeast.

In some embodiments, decreased glycosylation of ferritin by amino acid mutation facilitates protein production in bacteria or yeast. In some embodiments, decreased glycosylation of ferritin reduces the potential for adverse effects in mammals upon administration of mutated ferritin that is expressed in bacteria or yeast. In some embodiments, the reactogenicity in a human subject of a mutated ferritin produced in bacteria or yeast is lower because glycosylation is decreased. In some embodiments, the incidence of hypersensitivity responses in human subjects is lower following treatment with a mutated ferritin with reduced glycosylation compared to wildtype ferritin.

In some embodiments, degradation in a subject of a composition comprising a mutated ferritin with reduced glycosylation is slower compared with a composition comprising a wild-type ferritin, or a composition comprising a corresponding ferritin with wild-type glycosylation. In some embodiments, a composition comprising a mutated ferritin with reduced glycosylation has reduced clearance in a subject compared with a composition comprising a wild-type ferritin, or a composition comprising a corresponding ferritin with wild-type glycosylation. In some embodiments, a composition comprising a mutated ferritin with reduced glycosylation has a longer-serum half-life compared to wild-type ferritin, or a composition comprising a corresponding ferritin with wild-type glycosylation.

(4) Combinations of Mutations

In some embodiments, a ferritin comprises more than one type of mutation described herein. In some embodiments, the ferritin comprises one or more mutations independently selected from: a mutation to decrease glycosylation, a mutation to remove an internal cysteine, and a mutation to generate a surface-exposed cysteine. In some embodiments, the ferritin comprises a mutation to decrease glycosylation, a mutation to remove an internal cysteine, and a mutation to generate a surface-exposed cysteine.

In some embodiments, the ferritin comprises an N19Q mutation, a C31S mutation, and a mutation to generate a surface-exposed cysteine. In some embodiments, the ferritin comprises an N19Q mutation, a C31S mutation, and an E12C mutation. In some embodiments, the ferritin comprises an N19Q mutation, a C31S mutation, and an S72C mutation. In some embodiments, the ferritin comprises an N19Q mutation, a C31S mutation, and an A75C mutation. In some embodiments, the ferritin comprises an N19Q mutation, a C31S mutation, and an K79C mutation. In some embodiments, the ferritin comprises an N19Q mutation, a C31S mutation, and an S100C mutation. In some embodiments, the ferritin comprises an N19Q mutation, a C31S mutation, and an S111C mutation. In some embodiments, the ferritin comprises mutations corresponding to any of the foregoing sets of mutations, wherein the corresponding mutations change an N to a Q, a C to an S, and a non-cysteine surface-exposed amino acid to a cysteine at positions determined by pair-wise alignment of the ferritin amino acid sequence to an *H. pylori* ferritin amino acid sequence (SEQ ID NO: 208 OR 209).

Exemplary ferritins comprising more than one type of mutation are provided in SEQ ID NOS: 201-207.

3. Structural Alignment

As discussed herein, positions of mutations corresponding to those described with respect to a given polypeptide (e.g, *H. pylori* ferritin) can be identified by pairwise or structural alignment. Structural alignment is relevant to large protein families such as ferritin where the proteins share similar structures despite considerable sequence variation and many members of the family have been structurally characterized, and can also be used to identify corresponding positions in different versions of other polypeptides described herein, such as *Borrelia* polypeptides (e.g., OspA). The protein databank (PDB) comprises 3D structures for many ferritins, including those listed below with their accession numbers.

2jd6, 2jd7-PfFR-*Pyrococcus furiosus*. 2jd8-PfFR+Zn. 3a68-soFR from gene SferH4-soybean. 3a9q-soFR from gene SferH4 (mutant). 3egm, 3bvf, 3bvi, 3bvk, 3bvl-HpFR-*Heliobacter pylori*. 5c6f-HpFR (mutant)+Fe. 1z4a, 1v1g-FR-*Thermotoga maritime*. 1s3q, 1sq3, 3kx9-FR-*Archaeoglubus fulgidus*. 1krq-FR-*Campylobacter jejuni*. 1eum-EcFR-*Escherichia coli*. 4reu-EcFR+Fe. 4xgs-EcFR (mutant)+Fe2O2. 4ztt-EcFR (mutant)+Fe2O+Fe2+Fe+O2. 1qgh-LiFR-*Listeria innocua*. 3qz3-VcFR-*Vibrio cholerae*. 3vnx-FR-*Ulva pertusa*. 4ism, 4isp, 4itt, 4itw, 4iwj, 4iwk, 4ixk, 3e6s-PnmFR-*Pseudo-nitschia* multiseries. 4zkh, 4zkw, 4zkx, 4zl5, 4zl6, 4zlw, 4zmc-PnmFR (mutant)+Fe. 1z6o-FR-*Trichoplusia ni*. 4cmy-FR+Fe-*Chlorobaculum tepidum*. Ferritin light chain (FTL). 1lb3, 1h96-mFTL-mouse. 1rcc, 1rcd, 1rci-bFTL+tartrate+Mg. 1rce, 1rcg-bFTL+tartrate+Mn. 3noz, 3np0, 3np2, 3o7r-hoFTL (mutant)-horse. 3o7s, 3u90-hoFTL. 4v1w-hoFTL-cryo EM. 3rav, 3rd0-hoFTL+barbiturate. Ferritin light+heavy chains: 5gn8-hFTH+Ca.

Structural alignment involves identifying corresponding residues across two (or more) polypeptide sequences by (i) modeling the structure of a first sequence using the known structure of the second sequence or (ii) comparing the structures of the first and second sequences where both are known, and identifying the residue in the first sequence most similarly positioned to a residue of interest in the second sequence. Corresponding residues are identified in some algorithms based on alpha-carbon distance minimization in the overlaid structures (e.g., what set of paired alpha carbons provides a minimized root-mean-square deviation for the alignment). When identifying positions in a non-*H. pylori* ferritin corresponding to positions described with respect to *H. pylori* ferritin, *H. pylori* ferritin can be the "second" sequence. Where a non-*H. pylori* ferritin of interest does not have an available known structure, but is more closely related to another non-*H. pylori* ferritin that does have a known structure than to *H. pylori* ferritin, it may be most effective to model the non-*H. pylori* ferritin of interest using the known structure of the closely related non-*H. pylori* ferritin, and then compare that model to the *H. pylori* ferritin structure to identify the desired corresponding residue in the ferritin of interest. There is an extensive literature on structural modeling and alignment; representative disclosures include U.S. Pat. Nos. 6,859,736; 8,738,343; and those cited in Aslam et al., Electronic Journal of Biotechnology 20 (2016) 9-13. For discussion of modeling a structure based on a known related structure or structures, see, e.g., Bordoli et al., Nature Protocols 4 (2009) 1-13, and references cited therein.

4. Lumazine Synthase

In some embodiments, the antigenic polypeptide comprises a lumazine synthase protein (see Ra et al., Clin Exp Vaccine Res 3:227-234 (2014)). In some embodiments, this protein is lumazine synthase serotype 1, 2, 3, 4, 5, 6, or 7. Exemplary lumazine synthase sequences are provided as SEQ ID NO: 216 and 219. In some embodiments, the lumazine synthase comprises a sequence with 80%, 85%, 90%, 95%, 98%, or 99% identity to SEQ ID NO: 216 or 219. Lumazine synthases can form higher-order structures, e.g., a 60-subunit lumazine synthase particle. Exemplary lumazine synthases are *Aquifex aeolicus* lumazine synthase and *E. coli* lumazine synthase. The lumazine synthase can be located C-terminal to the OspA (e.g., the sequence comprising the OspA ectodomain, such as full-length OspA) and can be separated from the OspA by a linker as discussed herein. Exemplary antigenic polypeptides comprising a lumazine synthase protein are SEQ ID NOS: 12-21. In some embodiments, the antigenic polypeptide comprises a sequence with 80%, 85%, 90%, 95%, 98%, or 99% identity to any one of SEQ ID NOs: 12-21.

5. Linker

In some embodiments, ferritin or lumazine synthase is joined (e.g., fused) to the OspA (e.g., the sequence comprising the OspA ectodomain, such as full-length OspA) via a linker.

In some embodiments, a linker separates the amino acid sequence of a non-ferritin polypeptide (e.g., OspA) from the amino acid sequence of ferritin. Any linker may be used. In some embodiments, the linker is a peptide linker, which can facilitate expression of the antigenic ferritin polypeptide as a fusion protein (e.g., from a single open reading frame). In some embodiments, the linker is a glycine-serine linker. In some embodiments, the glycine-serine linker is GS, GGGS (SEQ ID NO: 226), 2XGGGS (SEQ ID NO: 91) (i.e., GGGSGGGS (SEQ ID NO: 91)), or SXGGGS (SEQ ID NO: 92). The linker may be N- or C-terminal to ferritin.

In some embodiments, the linker is 2, 3, 4, 5, 6, 7, 8, 9, or 10 amino acids in length. In some embodiments, the linker is about 2-4, 2-6, 2-8, 2-10, 2-12, or 2-14 amino acids in length. In some embodiments, the linker is at least 15 amino acids in length. In some embodiments, the linker is at least 25 amino acids in length. In some embodiments, the linker is at least 30 amino acids in length. In some embodiments, the linker is at least 35 amino acids in length. In some embodiments, the linker is at least 40 amino acids in length. In some embodiments, the linker is less than or equal to 60 amino acids in length. In some embodiments, the linker is less than or equal to 50 amino acids in length. In some embodiments, the linker is about 16, 28, 40, 46, or 47 amino acids in length. In some embodiments, the linker is flexible. In some embodiments, the linker comprises a cysteine, e.g., for use as a site for conjugation of an immune-stimulatory moiety (e.g., adjuvant); an exemplary linker comprising a cysteine is provided as SEQ ID NO: 225. In some embodiments, the linker comprises a sequence with at least 75%, 80%, 85%, 90%, or 95% identity to SEQ ID NO: 225, and further comprises a cysteine corresponding to the cysteine in SEQ ID NO: 225. In some embodiments, the linker comprises at least 25 amino acids (e.g., 25 to 60 amino acids), wherein a cysteine is located at a position ranging from the $8^{th}$ amino acid from the N-terminus to the $8^{th}$ amino acid from the C-terminus, or within 10 amino acids of the central residue or bond of the linker.

In some embodiments, the linker comprises glycine (G) and/or serine (S) amino acids. In some embodiments, the linker comprises or consists of glycine (G), serine (S), asparagine (N), and/or alanine (A) amino acids, and optionally a cysteine as discussed above. In some embodiments, the linker comprises an amino acid sequence with at least 80%, 85%, 90%, 95%, 97%, 98%, 99%, or 100% identity to SEQ ID NO: 222. In some embodiments, the linker is GGGGSGGGGSGGGGSG (SEQ ID NO: 220), GGSGSG-SNSSASSGASSGGASGGSGGSG (SEQ ID NO: 221), GGSGSASSGASASGSSNGSGSGSGSNSSASSGASSG-GASGGSGGSG (SEQ ID NO: 222), or GS. In some embodiments, the linker is FR1 (SEQ ID NO: 223) or FR2 (SEQ ID NO: 224).

In some embodiments, the ferritin comprises *H. pylori* ferritin with the amino terminal extension of bullfrog ferritin (which will be referred to as hybrid ferritin). In some embodiments, this hybrid ferritin forms multimers with non-ferritin polypeptide-attachment sites distributed evenly on the surface (see Kanekiyo 2015). In some embodiments, N-terminal fusion proteins with hybrid ferritin allow presentation of a non-ferritin polypeptide on the ferritin nanoparticle surface. In some embodiments, the non-ferritin polypeptide is a viral or bacterial polypeptide. In some embodiments, a ferritin comprises a glutamate at a position corresponding to position 13 of SEQ ID NO: 208 (hybrid ferritin, which comprises this glutamate) or position 6 in SEQ ID NO: 209 (wild-type *H. pylori* ferritin, in which position 6 is isoleucine). In combination with a bullfrog linker, this glutamate is thought to preserve the conserved salt bridge found in human and bullfrog ferritins (6R and 14E in both human light chain and bullfrog lower-subunit ferritins). See Kanekiyo et al., Cell 162, 1090-1100 (2015)).

In some embodiments, an antigenic OspA polypeptide is linked to ferritin via a cysteine-thrombin-histidine linker. In some embodiments, this linker is used to directly conjugate a moiety (e.g., immune-stimulatory moiety or non-ferritin polypeptide) to ferritin via click chemistry. An exemplary sequence comprising a cysteine-thrombin-histidine linker is SEQ ID NO: 218. Click chemistry suitable for conjugation reactions involving the cysteine-thrombin-histidine linker is discussed above.

In some embodiments, a linker comprising a cysteine as a conjugation site for an immune-stimulatory moiety such as an adjuvant is used in a construct comprising a ferritin molecule lacking an unpaired, surface-exposed cysteine, or in a construct comprising a ferritin molecule comprising an unpaired, surface-exposed cysteine.

In some embodiments, a construct does not comprise a linker. In some embodiments, a construct comprises one linker. In some embodiments, a construct comprises two or more than two linkers.

6. Immune-Stimulatory Moieties; Adjuvants; Conjugated Polypeptides

In some embodiments, a non-ferritin polypeptide (e.g., an OspA polypeptide) and/or an immune-stimulatory moiety, such as an adjuvant, is attached to a surface-exposed amino acid of ferritin or a linker. In some embodiments, the surface-exposed amino acid is a cysteine, e.g., resulting from a mutation discussed above. In some embodiments, the surface-exposed amino acid is a lysine, aspartate, or glutamate. Conjugation procedures using glutaraldehyde (for conjugation of a lysine with an amino-bearing linker or moiety) or a carbodiimide (e.g., 1-Cyclohexyl-3-(2-morpholin-4-yl-ethyl) carbodiimide or 1-Ethyl-3-(3-dimethyl-aminopropyl) carbodiimide (EDC; EDAC) for conjugating an aspartate or glutamate to an amino-bearing linker or moiety, or a lysine to a carboxyl-bearing linker or moiety) are described in, e.g., Chapter 4 of Holtzhauer, M., Basic Methods for the Biochemical Lab, Springer 2006, ISBN 978-3-540-32785-1, available from on the world wide web atspringer.com.

In some embodiments, an immune-stimulatory moiety, such as an adjuvant, is attached to a surface-exposed amino acid of ferritin. In some embodiments, more than one immune-stimulatory moiety, such as an adjuvant, is attached to a surface-exposed amino acid of ferritin. In some embodiments, twenty-four immune-stimulatory moieties are attached to a ferritin multimer or particle (e.g., one moiety for each monomer in the *H. pylori* ferritin particle). In some embodiments with multiple immune-stimulatory moieties attached to a ferritin nanoparticle, all of the immune-stimulatory moieties are identical. In some embodiments with multiple immune-stimulatory moieties attached to a ferritin nanoparticle, all of the immune-stimulatory moieties are not identical.

a) Types of Immune-Stimulatory Moieties; Adjuvants

Any immune-stimulatory moiety that can be attached to a surface-exposed amino acid (e.g., cysteine) can be used in ferritins (or linkers) according to this disclosure. In some embodiments, the immune-stimulatory moiety is a B cell agonist.

In some embodiments, the immune-stimulatory moiety is not hydrophobic. In some embodiments, the immune-stimulatory moiety is hydrophilic. In some embodiments, the immune-stimulatory moiety is polar. In some embodiments, the immune-stimulatory moiety is capable of hydrogen bonding or ionic bonding, e.g., comprises a hydrogen bond donor, hydrogen bond acceptor, cationic moiety, or anionic moiety. A moiety is considered cationic or anionic if it would be ionized in aqueous solution at a physiologically relevant pH, such as pH 6, 7, 7.4, or 8.

In some embodiments, the immune-stimulatory moiety is an adjuvant. In some embodiments, the adjuvant comprises a pathogen associated molecular pattern (PAMP). In some embodiments, the adjuvant is a toll-like receptor (TLR) agonist or stimulator of interferon genes (STING) agonist. In some embodiments, the adjuvant activates TLR signaling in B and/or T cells. In some embodiments, the adjuvant regulates the adaptive immune response.

(1) TLR2 Agonists

In some embodiments, the immune-stimulatory moiety is a TLR2 agonist. In some embodiments, the immune-stimulatory moiety stimulates TLR2 signaling. In some embodiments, the immune-stimulatory moiety is a synthetic small molecule ligand of TLR2. In some embodiments, the immune-stimulatory moiety is a synthetic small molecule agonist of TLR2 signaling.

In some embodiments, the TLR2 agonist is PAM2CSK4, FSL-1, or PAM3CSK4.

(2) TLR7/8 Agonists

In some embodiments, the immune-stimulatory moiety is a TLR7 and/or TLR8 agonist (i.e., an agonist of at least one of TLR7 and TLR8). In some embodiments, the immune-stimulatory moiety stimulates TLR7 and/or TLR8 signaling. In some embodiments, the immune-stimulatory moiety is a synthetic small molecule ligand of TLR7 and/or TLR8. In some embodiments, the immune-stimulatory moiety is a synthetic small molecule agonist of TLR7 and/or TLR8 signaling.

In some embodiments, the TLR7 and/or TLR8 agonist is single-stranded (ssRNA). In some embodiments, the TLR7 and/or TLR8 agonist is an imidazoquinoline. In some embodiments, the TLR7 and/or TLR8 agonist is a nucleoside analog.

In some embodiments, the TLR7 and/or TLR8 agonist is an imidazoquinolinamine Toll-like receptor (TLR) agonist, such as 3M-012 (3M Pharmaceuticals). The structure of free 3M-012 is:

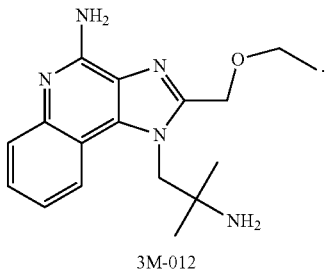 [SMILES: CCOCc1nc2c(N)nc3ccccc3c2n1CC(C)(C)N]

3M-012

It is understood that an immune-stimulatory moiety such as 3M-012 or any moiety discussed herein can be conjugated to a ferritin by substituting an appropriate peripheral atom of the moiety (e.g., a hydrogen) with a bond to a ferritin described herein, e.g., at the sulfur of a surface-exposed cysteine or a linker attached to such a sulfur. Thus, when conjugated to a ferritin, the structure of the immune-stimulatory moiety will differ slightly from the structure of the free molecule.

In some embodiments the TLR7 and/or TLR8 agonist is SM7/8a. The structure of free SM7/8a is:

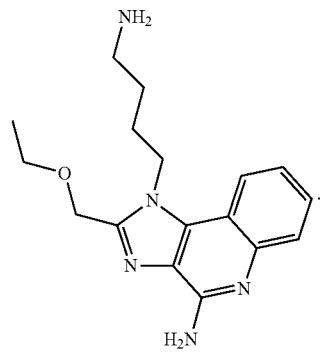 [SMILES: CCOCc1nc2c(N)nc3ccccc3c2n1CCCCN]

See, e.g., Lynn et al., Nat Biotechnol. 2015 November; 33(11):1201-10. doi: 10.1038/nbt.3371.

(3) TLR9 Agonists

In some embodiments, the immune-stimulatory moiety is a TLR9 agonist. In some embodiments, the immune-stimulatory moiety stimulates TLR9 signaling. In some embodiments, the immune-stimulatory moiety is a synthetic small molecule ligand of TLR9. In some embodiments, the immune-stimulatory moiety is a synthetic small molecule agonist of TLR9 signaling.

In some embodiments, the TLR9 agonist is a CpG oligodeoxynucleotide (ODN). In some embodiments, the TLR9 agonist is an unmethylated CpG ODN. In some embodiments, the CpG ODN comprises a partial or complete phosphorothioate (PS) backbone instead of the natural phosphodiester (PO) backbone found in ordinary DNA.

In some embodiments, the CpG ODN is a Class B ODN, which comprises one or more 6mer CpG motif comprising 5' Purine (Pu)-Pyrimidine (Py)-C-G-Py-Pu 3'; has a fully phosphorothioated (i.e., PS-modified) backbone; and has a length of 18-28 nucleotides. In some embodiments, the CpG ODN comprises the sequence of SEQ ID NO: 210, optionally comprising phosphorothioate linkages in the backbone.

In some embodiments, the TLR9 agonist comprises an immune-stimulatory sequence (ISS). In some embodiments the TLR9 agonist is ISS-1018 (Dynavax) (SEQ ID NO: 210).

(4) STING Agonists

In some embodiments, the immune-stimulatory moiety is a STING (Stimulator of Interferon Genes Protein, also known as Endoplasmic Reticulum IFN Stimulator) agonist. In some embodiments, the immune-stimulatory moiety stimulates STING signaling. In some embodiments, the immune-stimulatory moiety is a synthetic small molecule ligand of STING. In some embodiments, the immune-stimulatory moiety is a synthetic small molecule agonist of STING signaling.

In some embodiments the STING agonist is a cyclic dinucleotide (CDN). See, e.g., Danilchanka et al., Cell 154:962-970 (2013). Exemplary CDNs include cdA, cdG, cAMP-cGMP, and 2'-5',3'-5' cGAMP (see Danilchanka et al. for structures). STING agonists also include synthetic agonists such as DMXAA

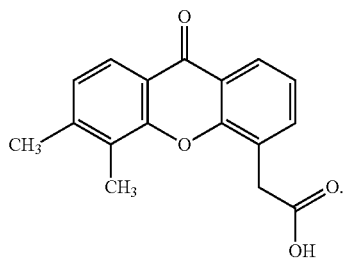 [SMILES: Cc1ccc2c(=O)c3cccc(CC(=O)O)c3oc2c1C]

b) Conjugated Non-Ferritin Polypeptides

In some embodiments, an antigenic OspA polypeptide is conjugated to a surface-exposed amino acid of ferritin. In some embodiments, the antigenic OspA polypeptide is antigenic alone, whereas in some embodiments, the antigenic OspA polypeptide is antigenic because of its association with ferritin.

7. Conjugation

In some embodiments, a surface-exposed cysteine is used to conjugate an immune-stimulatory moiety, such as an adjuvant, or an antigenic OspA polypeptide to a ferritin. In some embodiments, a surface-exposed cysteine is used to conjugate a linker to the ferritin, which linker can be subsequently conjugated to an immune-stimulatory moiety, such as an adjuvant, or an antigenic OspA polypeptide. In some embodiments, a surface-exposed cysteine creates a chemical handle for conjugation reactions to attach an adjuvant, linker, or an antigenic OspA polypeptide.

In some embodiments, bioconjugates are produced, wherein an immune-stimulatory moiety, such as an adjuvant, or an antigenic OspA polypeptide is linked to a ferritin after reduction of an unpaired, surface-exposed cysteine of the ferritin. An unpaired surface-exposed cysteine is one that lacks a partner cysteine in an appropriate position to form a disulfide bond. In some embodiments, an unpaired cysteine comprises a free thiol side chain.

a) Types of Conjugation Chemistries

Any type of chemistry can be used to conjugate the immune-stimulatory moiety, such as an adjuvant, or an antigenic OspA polypeptide to the ferritin, e.g., via reaction a surface-exposed amino acid such as cysteine or another amino acid such as Lys, Glu, or Asp.

In some embodiments, the conjugation is performed using click chemistry. As used herein, "click chemistry" refers to a reaction between a pair of functional groups that rapidly and selective react (i.e., "click") with each other. In some embodiments, the click chemistry can be performed under mild, aqueous conditions. In some embodiments, a click chemistry reaction takes advantage of a cysteine on the surface of the ferritin, such as a cysteine resulting from mutation of a surface-exposed amino acid, to perform click chemistry using a functional group that can react with the cysteine.

A variety of reactions that fulfill the criteria for click chemistry are known in the field, and one skilled in the art could use any one of a number of published methodologies (see, e.g., Hein et al., Pharm Res 25(10):2216-2230 (2008)). A wide range of commercially available reagents for click chemistry could be used, such as those from Sigma Aldrich, Jena Bioscience, or Lumiprobe. In some embodiments, conjugation is performed using click chemistry as described in the Examples below.

In some embodiments, the click chemistry reaction occurs after reduction of the ferritin.

In some embodiments, the click chemistry may be a 1-step click reaction. In some embodiments, the click chemistry may be a 2-step click reaction.

In some embodiments, the reaction(s) comprises metal-free click chemistry. In some embodiments, the reaction(s) comprise thiol-maleimide and/or disulfide exchange.

Metal Free Click Chemistry

Metal-free click chemistry can be used for conjugation reactions to avoid potential oxidation of proteins. Metal-free click chemistry has been used to form antibody conjugates (see van Geel et al., Bioconjugate Chem. 2015, 26, 2233-2242).

In some embodiments, metal-free click chemistry is used in reactions to attach adjuvant to ferritin. In some embodiments, copper-free conjugation is used in reactions to attach adjuvant to ferritin. In some embodiments, the metal-free click chemistry uses bicyclo[6.1.0]nonyne (BCN). In some embodiments, the metal-free click chemistry uses dibenzoazacyclooctyne (DBCO). In some embodiments BCN or DBCO reacts with an azide group.

DBCO has high specificity for azide groups via a strain-promoted click reaction in the absence of a catalyst, resulting in high yield of a stable triazole. In some embodiments, DBCO reacts with azide in the absence of copper catalyst.

In some embodiments, metal-free click chemistry is used in a 1-step click reaction. In some embodiments, metal-free click chemistry is used in a 2-step click reaction.

Thiol-Maleimide and Disulfide Exchange

Ferritins described herein can comprise a cysteine comprising a thiol, also known as a sulfhydryl, which is available for reaction with sulfhydryl-reactive chemical groups (or which can be made available through reduction). Thus, the cysteine allows chemoselective modification to add an immune-stimulatory moiety, such as an adjuvant, to the ferritin. Under basic conditions, the cysteine will be deprotonated to generate a thiolate nucleophile, which can react with soft electrophiles, such as maleimides and iodoacetamides. The reaction of the cysteine with a maleimide or iodoacetamide results in a carbon-sulfur bond.

In some embodiments, a sulfhydryl-reactive chemical group reacts with the surface-exposed cysteine or cysteine in the linker of the ferritin. In some embodiments, the sulfhydryl-reactive chemical group is a haloacetyl, maleimide, aziridine, acryloyl, arylating agent, vinylsulfone, pyridyl disulfide, or TNB-thiol.

In some embodiments, the sulfhydryl-reactive chemical group conjugates to the sulfhydryl of the cysteine by alkylation (i.e., formation of a thioether bond)). In some embodiments, the sulfhydryl-reactive chemical group conjugates to the sulfhydryl of the cysteine by disulfide exchange (i.e., formation of a disulfide bond).

In some embodiments, the reaction to conjugate an immune-stimulatory moiety, such as an adjuvant, to the ferritin is a thiol-maleimide reaction.

In some embodiments, the sulfhydryl-reactive chemical group is a maleimide. In some embodiments, reaction of a maleimide with the cysteine results in formation of a stable thioester linkage, e.g., that is not reversible. In some embodiments, the maleimide does not react with tyrosines, histidines, or methionines in the ferritin. In some embodiments, unreacted maleimides are quenched at the end of the reaction by adding a free thiol, e.g., in excess.

In some embodiments, the reaction to conjugate an immune-stimulatory moiety, such as an adjuvant, to the ferritin is a thiol-disulfide exchange, also known as a disulfide interchange. In some embodiments, the reaction involves formation of a mixed disulfide comprising a portion of the original disulfide. In some embodiments, the original disulfide is the cysteine introduced in the ferritin by mutation of a surface-exposed amino acid or addition of an N-terminal linker.

In some embodiments, the sulfhydryl-reactive chemical group is a pyridyl dithiol. In some embodiments, the sulfhydryl-reactive chemical group is a TNB-thiol group.

b) Linkers

In some embodiments, an immune-stimulatory moiety, such as an adjuvant, or an antigenic OspA polypeptide is attached to the ferritin via a linker that is covalently bound to a surface-exposed amino acid such as a cysteine. In some embodiments, the linker comprises a polyethylene glycol, e.g., a PEG linker. In some embodiments, the polyethylene glycol (e.g., PEG) linker increases water solubility and ligation efficiency of the ferritin linked to the immune-stimulatory moiety, such as an adjuvant. The PEG linker is between 2 and 18 PEGs long, e.g., PEG4, PEG5, PEG6, PEG7, PEG8, PEG9, PEG10, PEG11, PEG12, PEG13, PEG14, PEG15, PEG16, PEG17, and PEG18.

In some embodiments, the linker comprises a maleimide. In some embodiments, the linker comprises the components of immune-stimulatory moiety (ISM)-linker-maleimide. In some embodiments, the ISM-linker-maleimide is conjugated to ferritin in a 1-step click chemistry reaction by reaction of the maleimide with a cysteine of the ferritin. In some embodiments, the ISM of the adjuvant-linker-maleimide is SM7/8a. In some embodiments, the linker of the ISM-linker-maleimide is PEG4. In some embodiments, the ISM-linker-maleimide is SM7/8a-PEG4-maleimide.

In some embodiments, a 2-step click chemistry protocol is used with a linker comprising a sulfhydryl-reactive chemical group at one end and an amine-reactive group at the other end. In such a 2-step click chemistry protocol, a sulfhydryl-reactive chemical group reacts with a cysteine of the ferritin, while the amine-reactive group reacts with a reagent attached to the ISM. In this way, the ISM is conjugated to the ferritin via a set of 2 click chemistry reagents.

In some embodiments of the 2-step click chemistry protocol, the sulfhydryl-reactive chemical group is maleimide. In some embodiments of the 2-step click chemistry protocol, the maleimide reacts with the cysteine introduced in the ferritin by mutation of a surface-exposed amino acid or addition of an N-terminal linker.

In some embodiments of the 2-step click chemistry protocol, the amine-reactive group is DBCO. In some embodiments of the 2-step click chemistry protocol, the DBCO reacts with an azide group attached to an ISM.

In some embodiments, a maleimide-linker-DBCO is used. In some embodiments, the maleimide-linker-DBCO is conjugated to ferritin after the ferritin is reduced. In some embodiments, the maleimide-linker-reagent is conjugated to ferritin by reaction of the maleimide with the cysteine of the ferritin in a first step. In some embodiments, the DBCO is used to link to an ISM attached to azide. In some embodiments, the ISM coupled to azide is ISS-1018. In some embodiments, the adjuvant coupled to azide is 3M-012 or CpG.

In some embodiments, a linker with a reactive group is added to the ISM. In some embodiments, the linker is a PEG4-azide linker or a PEG4-maleimide linker.

In some embodiments, a PEG4-azide linker is conjugated to 3M-012. An exemplary structure of 3M-012 conjugated to a PEG4-azide linker is:

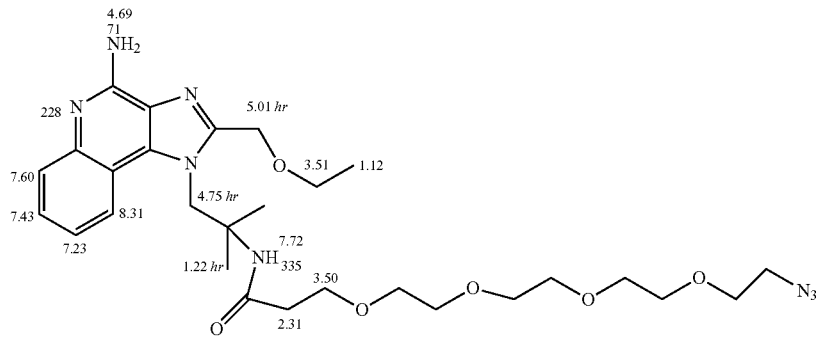 [SMILES: CCOCc1nc2c(N)nc3ccccc3c2n1CC(C)(C)NC(=O)CCOCCOCCOCCOCCN=[N+]=[N-]]

In some embodiments, a PEG4-azide linker is conjugated to SM7/8a. An exemplary structure of SM7/8a conjugated to a PEG4-azide linker is:

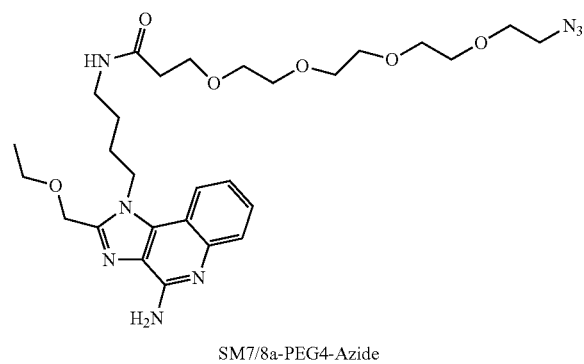 [SMILES: CCOCc1nc2c(N)nc3ccccc3c2n1CCCCNC(=O)CCOCCOCCOCCOCCN=[N+]=[N-]]

SM7/8a-PEG4-Azide

In some embodiments, a PEG4-maleimide linker is conjugated to SM7/8a. An exemplary structure of SM7/8a conjugated to a PEG4-maleimide linker is:

SM7/8 a-PEG4-Maleimide

In some embodiments, an azide group is conjugated to ISS-1018. An exemplary structure of ISS-1018 conjugated to an NHS ester-azide linker is:

D. Exemplary Compositions, Kits, Nucleic Acids, Uses, and Methods

In some embodiments, a composition comprising any one or more of the antigenic polypeptides described herein and a pharmaceutically acceptable vehicle, adjuvant, or excipient is provided.

In some embodiments, an antigenic polypeptide, or composition described herein is administered to a subject, such as a human, to immunize against infection caused by *Borrelia*, e.g., Lyme disease. In some embodiments, an antigenic polypeptide described herein is administered to a subject, such as a human, to produce a protective immune response to future infection with *Borrelia*. In some embodiments, a polypeptide comprising a modified OspA serotype 1 polypeptide as described herein is administered. In some embodiments, an antigenic polypeptide comprising an OspA and ferritin as described herein is administered.

In some embodiments, the protective immune response decreases the incidence of hospitalization. In some embodiments, the protective immune response decreases the incidence of acute or chronic Lyme disease, including joint inflammation, neurological symptoms, cognitive deficits, or heart rhythm irregularities.

In some embodiments, a composition comprises an OspA serotype 1 polypeptide. In some embodiments, a composition comprises an OspA serotype 2 polypeptide. In some embodiments, a composition comprises an OspA serotype 3 polypeptide. In some embodiments, a composition comprises an OspA serotype 4 polypeptide. In some embodiments, a composition comprises an OspA serotype 5 polypeptide. In some embodiments, a composition comprises an OspA serotype 6 polypeptide. In some embodiments, a composition comprises an OspA serotype 7 polypeptide. In some embodiments, a composition comprises only one OspA polypeptide. In some embodiments, a composition comprises on or more of an OspA serotype 1, 2, 3, 4, 5, 6, and 7.

In some embodiments, a composition comprises more than one OspA polypeptide, e.g., from more than one OspA serotype. In some embodiments, such a composition allows vaccination against multiple types of *Borrelia*, for example, one, two, three, four, five, six, or seven of serotypes 1-7. As the serotypes of OspA are related to genospecies of *Borrelia* (see Wilske 1993), vaccination with such a composition comprising OspA of multiple serotypes may produce immunity to a range of bacteria that can cause Lyme disease.

In some embodiments, a composition comprising OspA of multiple serotypes produces immunity against *Borrelia* that express different OspA serotypes. For example, it has been observed as discussed in the Examples that a composition comprising OspA polypeptides of serotypes 1-5 and 7 can elicit antibodies that recognize OspA serotype 6. In some embodiments, such a composition produces immunity against multiple genospecies of *Borrelia*.

In some embodiments, a composition comprises two different OspA serotypes. In some embodiments, a multivalent composition comprises three different OspA serotypes. In some embodiments, a multivalent composition comprises four different OspA serotypes. In some embodiments, a multivalent composition comprises five different OspA serotypes. In some embodiments, a multivalent composition comprises six different OspA serotypes. In some embodiments, a multivalent composition comprises seven different OspA serotypes.

In some embodiments, a composition comprises an OspA serotype 1 and any one or more of OspA serotypes 2-7. In some embodiments, a composition comprises an OspA serotype 2 and any one or more of OspA serotypes 1 and 3-7. In some embodiments, a composition comprises an OspA serotype 3 and any one or more of OspA serotypes 1-2 and 4-7. In some embodiments, a composition comprises an OspA serotype 4 and any one or more of OspA serotypes 1-3 and 5-7. In some embodiments, a composition comprises an OspA serotype 5 and any one or more of OspA serotypes 1-4 and 6-7. In some embodiments, a composition comprises an OspA serotype 6 and any one or more of OspA serotypes 1-5 and 7. In some embodiments, a composition comprises an OspA serotype 7 and any one or more of OspA serotypes 1-6. In some embodiments, a composition comprises at least 2, 3, 4, 5, or 6 of OspA polypeptides of serotypes 1-5 and 7.

In some embodiments, any one or more of the antigenic polypeptides, or compositions described herein are provided for use in immunizing against infection caused by *Borrelia*, e.g., Lyme disease. In some embodiments, any one or more of the antigenic polypeptides, or compositions described herein are provided for use in producing a protective immune response to future infection with *Borrelia*. In some embodiments, any one or more of the antigenic polypeptides, or compositions described herein are for use in a mammal, such as a primate (e.g., non-human primate, such as a monkey (e.g., a macaque, such as rhesus or cynomolgus) or ape), rodent (e.g., mouse or rat), or domesticated mammal (e.g., dog, rabbit, cat, horse, sheep, cow, goat, camel, or donkey).

1. Adjuvants

An adjuvant may be administered together with the antigenic polypeptides described herein to a subject, wherein such administration produces a higher titer of antibodies against the OspA in the subject as compared to administration of the OspA without the adjuvant. An adjuvant may promote earlier, more potent, or more persistent immune response to the OspA.

In some embodiments, a composition comprises one adjuvant. In some embodiments, a composition comprises more than one adjuvant. In some embodiments, a composition does not comprise an adjuvant.

In some embodiments, an adjuvant comprises aluminum. In some embodiments, an adjuvant is aluminum phosphate. In some embodiments, an adjuvant is Alum (Alyhydrogel '85 2%; Brenntag—Cat #21645-51-2).

In some embodiments, an adjuvant is an organic adjuvant. In some embodiments, an adjuvant is an oil-based adjuvant. In some embodiments, an adjuvant comprises an oil-in-water nanoemulsion.

In some embodiments, an adjuvant comprises squalene. In some embodiments, the adjuvant comprising squalene is Ribi (Sigma adjuvant system Cat #S6322-1v1), AddaVax™ (squalene-based oil-in-water nano-emulsion), MF59, AS03, or AF03 (see U.S. Pat. No. 9,703,095). In some embodiments, the adjuvant comprising squalene is a nanoemulsion.

In some embodiments, an adjuvant comprises a polyacrylic acid polymer (PAA). In some embodiments, the adjuvant comprising PAA is SPA09 (see WO 2017218819).

In some embodiments, an adjuvant comprises non-metabolizable oils. In some embodiments, the adjuvant is Incomplete Freund's Adjuvant (IFA).

In some embodiments, an adjuvant comprises non-metabolizable oils and killed *Mycobacterium tuberculosis*. In some embodiments, the adjuvant is Complete Freund's Adjuvant (CFA).

In some embodiments, an adjuvant is a lipopolysaccharide. In some embodiments, an adjuvant is monophosphoryl A (MPL or MPLA).

2. Subjects

In some embodiments, the subject is a mammal. In some embodiments, the subject is a human.

In some embodiments, the subject is an adult (greater than or equal to 18 years of age). In some embodiments, the subject is a child or adolescent (less than 18 years of age). In some embodiments, the subject is elderly (greater than 60 years of age). In some embodiments, the subject is a non-elderly adult (greater than or equal to 18 years of age and less than or equal to 60 years of age).

In some embodiments, more than one administration of the composition is administered to the subject. In some embodiments, a booster administration improves the immune response.

In some embodiments, any one or more of the antigenic polypeptides, or compositions described herein are for use in a mammal, such as a primate (e.g., non-human primate, such as a monkey (e.g., a macaque, such as rhesus or cynomolgus) or ape), rodent (e.g., mouse or rat), or domesticated mammal (e.g., dog, rabbit, cat, horse, sheep, cow, goat, camel, or donkey).

In some embodiments, the composition is suitably formulated for an intended route of administration. Examples of suitable routes of administration include intramuscular, transcutaneous, subcutaneous, intranasal, oral, or transdermal.

In some embodiments, more than one administration of the composition is administered to the subject. In some embodiments, a booster administration improves the immune response.

3. Pharmaceutical Compositions

In various embodiments, a pharmaceutical composition comprising an antigenic ferritin polypeptide described herein and/or related entities is provided. In some embodiments, the pharmaceutical composition is an immunogenic composition (e.g., a vaccine) capable of eliciting an immune response such as a protective immune response against *Borrelia*.

For example, in some embodiments, the pharmaceutical compositions may comprise one or more of the following: (1) an antigenic ferritin protein comprising (i) a mutation replacing a surface-exposed amino acid with a cysteine and (ii) an antigenic OspA polypeptide; (2) an antigenic ferritin protein comprising (i) a mutation replacing a surface exposed amino acid with a cysteine and an immune-stimulatory moiety linked to the cysteine; and (ii) an antigenic OspA polypeptide; (3) antigenic ferritin protein comprising (i) a surface-exposed cysteine, (ii) a peptide linker N-terminal to the ferritin protein, and (iii) an antigenic OspA polypeptide N-terminal to the peptide linker; (4) an antigenic ferritin protein comprising: (i) a mutation replacing a surface exposed amino acid with a cysteine and an immune-stimulatory moiety linked to the cysteine, (ii) a mutation replacing the internal cysteine at position 31 of *H. pylori* ferritin, or a mutation of an internal cysteine at a position that is analogous to position 31 of a non-*H. pylori* ferritin as determined by pair-wise or structural alignment, with a non-cysteine amino acid, (iii) a mutation replacing a surface-exposed asparagine with a non-asparagine amino acid, and (iv) an antigenic OspA polypeptide; or (5) a ferritin particle comprising any of the foregoing ferritin proteins.

In some embodiments, the present invention provides pharmaceutical compositions comprising antibodies or other agents related to the antigenic polypeptides described herein. In an embodiment, the pharmaceutical composition comprises antibodies that bind to and/or compete with an antigenic polypeptide described herein. Alternatively, the antibodies may recognize viral particles or bacteria comprising the non-ferritin polypeptide component of an antigenic polypeptide described herein.

In some embodiments, the pharmaceutical compositions as described herein are administered alone or in combination with one or more agents to enhance an immune response, e.g., an adjuvant described above. In some embodiments, a pharmaceutical composition further comprises an adjuvant described above.

In some embodiments, the pharmaceutical composition further comprises a pharmaceutically acceptable carrier or excipient. As used herein, the term "carrier" refers to a diluent, adjuvant, excipient, or vehicle with which a pharmaceutical composition is administered. In exemplary embodiments, carriers can include sterile liquids, such as, for example, water and oils, including oils of petroleum, animal, vegetable, or synthetic origin, such as, for example, peanut oil, soybean oil, mineral oil, sesame oil and the like. In some embodiments, carriers are or include one or more solid components. Pharmaceutically acceptable carriers can also include, but are not limited to, saline, buffered saline, dextrose, glycerol, ethanol, and combinations thereof. As used herein, an excipient is any non-therapeutic agent that may be included in a pharmaceutical composition, for example to provide or contribute to a desired consistency or stabilizing effect. Suitable pharmaceutical excipients include, but are not limited to, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In various embodiments, the pharmaceutical composition is sterile.

In some embodiments, the pharmaceutical composition contains minor amounts of wetting or emulsifying agents, or pH buffering agents. In some embodiments, the pharmaceutical compositions of may include any of a variety of additives, such as stabilizers, buffers, or preservatives. In addition, auxiliary, stabilizing, thickening, lubricating, and coloring agents can be included.

In various embodiments, the pharmaceutical composition may be formulated to suit any desired mode of administration. For example, the pharmaceutical composition can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, desiccated powder, or any other form suitable for use. General considerations in the formulation and manufacture of pharmaceutical agents may be found, for example, in Remington's Pharmaceutical Sciences, 19th ed., Mack Publishing Co., Easton, Pa., 1995; incorporated herein by reference.

The pharmaceutical composition can be administered via any route of administration. Routes of administration include, for example, oral, intradermal, intramuscular, intraperitoneal, intravenous, subcutaneous, intranasal, mucosal, epidural, sublingual, intranasal, intracerebral, intravaginal, transdermal, rectally, by intratracheal instillation, bronchial instillation, inhalation, or topically. Administration can be local or systemic. In some embodiments, administration is carried out orally. In another embodiment, the administration is by parenteral injection. In some instances, administration results in the release of the antigenic ferritin polypeptide described herein into the bloodstream. The mode of administration can be left to the discretion of the practitioner.

In some embodiments, the pharmaceutical composition is suitable for parenteral administration (e.g. intravenous, intramuscular, intraperitoneal, and subcutaneous). Such compositions can be formulated as, for example, solutions, suspensions, dispersions, emulsions, and the like. They may also be manufactured in the form of sterile solid compositions (e.g. lyophilized composition), which can be dissolved or suspended in sterile injectable medium immediately before use. For example, parenteral administration can be achieved by injection. In such embodiments, injectables are prepared in conventional forms, i.e., either as liquid solutions or suspensions, solid forms suitable for solution or suspension in liquid prior to injection, or as emulsions. In some embodiments, injection solutions and suspensions are prepared from sterile powders, lyophilized powders, or granules.

In a further embodiment, the pharmaceutical composition is formulated for delivery by inhalation (e.g., for direct delivery to the lungs and the respiratory system). For example, the composition may take the form of a nasal spray or any other known aerosol formulation. In some embodiments, preparations for inhaled or aerosol delivery comprise a plurality of particles. In some embodiments, such preparations can have a mean particle size of about 1, about 2, about 3, about 4, about 5, about 6, about 7, about 8, about 9, about 10, about 11, about 12, or about 13 microns. In some embodiments, preparations for inhaled or aerosol delivery are formulated as a dry powder. In some embodiments, preparations for inhaled or aerosol delivery are formulated as a wet powder, for example through inclusion of a wetting agent. In some embodiments, the wetting agent is selected from the group consisting of water, saline, or other liquid of physiological pH.

In some embodiments, the pharmaceutical composition in accordance with the invention are administered as drops to the nasal or buccal cavity. In some embodiments, a dose may comprise a plurality of drops (e.g., 1-100, 1-50, 1-20, 1-10, 1-5, etc.).

The present pharmaceutical composition may be administered in any dose appropriate to achieve a desired outcome. In some embodiments, the desired outcome is the induction of a long-lasting adaptive immune response against a pathogen, such as the source of a non-ferritin polypeptide present in an antigenic ferritin polypeptide present in the composition. In some embodiments, the desired outcome is a reduction in the intensity, severity, frequency, and/or delay of onset of one or more symptoms of infection. In some embodiments, the desired outcome is the inhibition or prevention of infection. The dose required will vary from subject to subject depending on the species, age, weight, and general condition of the subject, the severity of the infection being prevented or treated, the particular composition being used, and its mode of administration.

In some embodiments, pharmaceutical compositions in accordance with the invention are administered in single or multiple doses. In some embodiments, the pharmaceutical compositions are administered in multiple doses administered on different days (e.g., prime-boost vaccination strategies). In some embodiments, the pharmaceutical composition is administered as part of a booster regimen.

In various embodiments, the pharmaceutical composition is co-administered with one or more additional therapeutic agents. Co-administration does not require the therapeutic agents to be administered simultaneously, if the timing of their administration is such that the pharmacological activities of the additional therapeutic agent and the active ingredient(s) in the pharmaceutical composition overlap in time, thereby exerting a combined therapeutic effect. In general, each agent will be administered at a dose and on a time schedule determined for that agent.

4. Nucleic Acid/RNA

Also provided is a nucleic acid encoding an antigenic OspA polypeptide described herein. In some embodiments, the nucleic acid is an mRNA. Any nucleic acid capable of undergoing translation resulting in a polypeptide is considered an mRNA for purposes of this disclosure.

5. Kits

Also provided herein are kits comprising one or more antigenic polypeptides, nucleic acids, antigenic ferritin particles, antigenic lumazine synthase particles, compositions, or pharmaceutical compositions described herein. In some embodiments, a kit further comprises one or more of a solvent, solution, buffer, instructions, or desiccant.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. "About" indicates a degree of variation that does not substantially affect the properties of the described subject matter, e.g., within 10%, 5%, 2%, or 1%. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed considering the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items. The term "or" is used in the inclusive sense, i.e., equivalent to "and/or," unless the context dictates otherwise.

TABLE 1

(Sequence Table): Description of sequences

```
Sequences
Key for sequences 1-102:
Leader sequences are sometimes underlined
Modified LFA-1 site is Italicized and underlined (if present)
Mutations other than modified LFA-1 site are in BOLD and curvy underlined
Linker is double underlined
Bullf TABLE 1-continued (Sequence Table): Description of sequences

| Description ("ferritin" refers to H. pylori ferritin optionally with one or more mutations unless otherwise indicated) | Sequences<br>Key for sequences 1-102:<br>Leader sequences are sometimes underlined<br>Modified LFA-1 site is Italicized and underlined (if present)<br>Mutations other than modified LFA-1 site are in BOLD and curvy underlined<br>Linker is double underlined<br>Bullfrog sequence is Italicized and curvy underlined (if present)<br>Human heavy chain ferritin sequence is in BOLD (if present)<br>Transmembrane domain is italicized (if present)<br>lipidation site is in Bold, italicized, and underlined (if present) | SEQ ID NO: |
|---|---|---|
| Serotype 3 OspA-ferritin | MSMSSWSYTHSLDGAGLFLFDHAAEEYEHAKKLIIFLNENNVPVQLTSISAPEHKFEGLTQIFQKAYEHEQHISESINNIVDHAIKCKDHATFN<br>FL*QWYVAEQHEEEVLFKDILDKIELIGNENHGLYLADQYVKGIAKSRKS* | 6 |
| Serotype 3 OspA-ferritin | MDEKNSVSVDLPGGMKVLVSKEKDKDGKYSLMATVEKLELKGTSDKNGSGVLEGEKADKSKAKLTISQDLNQTTFEIFKEDGKTLVSRKVNSK<br>DKSSTEEKFNDKGKLSEKVTRANGTRLEYTEIKNDGSGKAEVLKGFALEGTLTDGGETKLTVTEGTVVLSKNISKSGEITVALNDTETTPAD<br>KKTGEWKSDTSTLTISKNSQKPKQLVFTKENTITVQNYNRAGNALEGSPAEIKDLAELKAALKGSES*QVRQQF*SKDIEKLLNEQVNKEMQSSNL<br>YMSMSSWSYTHSLDGAGLFLFDHAAEEYEHAKKLIIFLNENNVPVQLTSISAPEHKFEGLTQIFQKAYEHEQHISESINNIVDHAIKCKDHATF<br>NFL*QWYVAEQHEEEVLFKDILDKIELIGNENHGLYLADQYVKGIAKSRKS* | 7 |
| Serotype 4 OspA-ferritin | MDEKNSVSVDLPGEMKVLVSKEKDKDGKYSLMATVDKLELKGTSDKNGSGTLEGESDKSKAKLTISEDLSKTTFEIFKEDGKTLVSKKVNSK<br>DKSSIEEKFNAKGELSEKTILRANGTRLEYTEIKSDGTGKAKEVLKDFALEGTLAADKTTLKVTEGTVVLSKHIPNSGEITVELNDSNSTQATK<br>KTGKWDSNTSTLTISVNSKKTKNIVFTKEDTITVQKYDSAGTNLEGNAVEIKTLDELKNALKGS*ESQVKQQF*SKDIEKLLNEQVNKEMQSSNLY<br>MSMSSWSYTHSLDGAGLFLFDHAAEEYEHAKKLIIFLNENNVPVQLTSISAPEHKFEGLTQIFQKAYEHEQHISESINNIVDHAIKCKDHATFN<br>FL*QWYVAEQHEEEVLFKDILDKIELIGNENHGLYLADQYVKGIAKSRKS* | 8 |
| Serotype 5 OspA-ferritin | MDEKNSVSVDLPGGMKVLVSKEKDKDGKYSLMATVEKLELKGTSDKNNGSGTLEGEKTDKSKVKLTIAEDLSKTTFEIFKEDGKTLVSKKVTLK<br>DKSSTEEKFNEKGEISEKTIVRANGTRLEYTDIKSDGSGKAKEVLKDFTLEGTLAADGKTTLKDALKGSEITVALDDSDTTQAT<br>KKTGKWDSKTSTLTISVNSQKTKNLVFTKEDTITVQKYDSAGTNLEGKAVEITTLEKLIKDALKGS*ESQVKQQF*SKDIEKLLNEQVNKEMQSSNL<br>YMSMSSWSYTHSLDGAGLFLFDHAAEEYEHAKKLIIFLNENNVPVQLTSISAPEHKFEGLTQIFQKAYEHEQHISESINNIVDHAIKCKDHATF<br>NFL*QWYVAEQHEEEVLFKDILDKIELIGNENHGLYLADQYVKGIAKSRKS* | 9 |
| Serotype 6 OspA-ferritin | MDEKNSVSVDLPGGMTVLVSKEKDKDGKYSLEATVDKLELKGTSDKNNGSGTLEGEKTDKSKVKSTIADDLSQTKFEIFKEDGKTLVSKKVTLK<br>DKSSTEEKFNGKGETSEKTIVRANGTRLEYTDIKSDGSGKAKEVLKDFTLEGTLAADGKTTLKVTEGTVVLSKNILKSGEITAALDDSDTTRAT<br>KKTGKWDSKTSTLTISVNSQKTKNLVFTKEDTITVQRYDSAGTNLEGKAVEITTLKELKNALKGS*ESQVRQQF*SKDIEKLLNEQVNKEMQSSNL<br>YMSMSSWSYTHSLDGAGLFLFDHAAEEYEHAKKLIIFLNENNVPVQLTSISAPEHKFEGLTQIFQKAYEHEQHISESINNIVDHAIKCKDHATF<br>NFL*QWYVAEQHEEEVLFKDILDKIELIGNENHGLYLADQYVKGIAKSRKS* | 10 |
| Serotype 7 OspA-ferritin | MDEKNSVSVDLPGEMKVLVSKEKDKDGKYSLEATVDKLELKGTSDKNNGSGVLEGVKAAKSKAKLTIADLNEAKAKLTIVEAGTVLSLTLEGTLTADGETKLTVEAGTVTLKSLKNISESGEITVELKDTETTPAD | 11 |

TABLE 1 -continued (Sequence Table): Description of sequences

| Description ("ferritin" refers to H. pylori ferritin optionally with one or more mutations unless otherwise indicated) | Sequences<br>Key for sequences 1-102:<br>Leader sequences are sometimes underlined<br>Modified LFA-1 site is Italicized and underlined (if present)<br>Mutations other than modified LFA-1 site are in BOLD and curvy underlined<br>Linker is double underlined<br>Bullfrog sequence is Italicized and curvy underlined (if present)<br>Human heavy chain ferritin sequence is in BOLD (if present)<br>Transmembrane domain is italicized (if present)<br>lipidation site is in Bold, italicized, and underlined (if present) | SEQ ID NO: |
|---|---|---|
| | KKSGTWDSKTSTLTISKNSQKITKQLVFTKENTITVQKYNTAGTKLEGSPAEIKDLEALKAALKGSES*QVRQQ*FSKDIEKLLNEQVNKEMQSSNL | 11 |
| | YMSMSSWSYTHSLDGAGLFLPDHAAEEYEHAKKLIIFLNENNVPVQLTSISAPEHKFEGLTQIFQKAYEHEQHISESINNIVDHAIKCKDHATF | 12 |
| | NFLQWYVAEQHEEEVLFKDILDKIELIGNENHGLYLADQYVKGIAKSRKS | 13 |
| Serotype 4 OspA-Cysteine-Thrombin-His | MDEKNSVSVDLPGEMKVLVSKEKDKDGKYSLMATVDKLELKGT TABLE 1 -continued (Sequence Table): Description of sequences

| Description ("ferritin" refers to H. pylori ferritin optionally with one or more mutations unless otherwise indicated) | Sequences<br>Key for sequences 1-102:<br>Leader sequences are sometimes underlined<br>Modified LFA-1 site is Italicized and underlined (if present)<br>Mutations other than modified LFA-1 site are in BOLD and curvy underlined<br>Linker is double underlined<br>Bullfrog sequence is Italicized and curvy underlined (if present)<br>Human heavy chain ferritin sequence is in BOLD (if present)<br>Transmembrane domain is italicized (if present)<br>lipidation site is in Bold, italicized, and underlined (if present) | SEQ ID NO: |
|---|---|---|
| Serotype 3 OspA-l TABLE 1 -continued Description of sequences (Sequence Table):
Key for sequences 1-102:
Leader sequences are sometimes underlined
Modified LFA-1 site is Italicized and underlined (if present)
Mutations other than modified LFA-1 site are in BOLD and curvy underlined
Linker is double underlined
Bullfrog sequence is Italicized and curvy underlined (if present)
Human heavy chain ferritin sequence is in BOLD (if present)
Transmembrane domain is italicized (if present)
lipidation site is in Bold, italicized, and underlined (if present)

| Description ("ferritin" refers to H. pylori ferritin optionally with one or more mutations unless otherwise indicated) | Sequences | SEQ ID NO: |
|---|---|---|
| | KNDPHLCDFIETHYLNEQVKAIKELGDHVTNLRKMGAPESGLAEYLFDKHTLGDSDNES | |
| OspA Serotype1; LFA-1 repl TABLE 1-continued (Sequence Table): Description of sequences

| Description ("ferritin" refers to H. pylori ferritin optionally with one or more mutations unless otherwise indicated) | Sequences<br>Key for sequences 1-102:<br>Leader sequences are sometimes underlined<br>Modified LFA-1 site is Italicized and underlined (if present)<br>Mutations other than modified LFA-1 site are in BOLD and curvy underlined TABLE 1-continued (Sequence Table): Description of sequences Sequences
Key for sequences 1-102:
Leader sequences are sometimes underlined
Modified LFA-1 site is Italicized and underlined (if present)
Mutations other than modified LFA-1 site are in BOLD and curvy underlined
Linker is double underlined
Bullfrog sequence is Italicized and curvy underlined (if present)
Human heavy chain ferritin sequence is in BOLD (if present)
Transmembrane domain is italicized (if present)
lipidation site is in Bold, italicized, and underlined (if present)

| Description ("ferritin" refers to *H. pylori* ferritin optionally with one or more mutations unless otherwise indicated) | Sequences | SEQ ID NO: |
|---|---|---|
| OspA Serotype 2-*Pyrococcus furiosus* ferritin | MDEKNSASVDLPGEMKVLVSKEKDKDGKYSLKATVDKIELKGTSDKDNGSGVLEGTKDDKSKAKLTIADDLSKTTFEIFKEDGKTLVSRKVSSK DKTSTDEMFNEKGELSAKTMTRENGTKLEYTEMKSDGTGKAKEVLKNFTLEVKGTVTLSKEIAKSGEVTVALNDTNTTQATK KTGAWDSKTSTLTISVNSKKTTQLVFTKQDTITVQKYDSAGTNLEGTAVEIKTLDELKNALKGSMLSERMLKALNDQLNRELYSAYLYFAMAAY FEDLGLEGFANWMKAQAEEEIGHALRFYNYIYDRNGRVELDEIPKPPKEWESPLKAFEAAYEHEKFISKSIYELAALAEEEKDYSTRAFLEWFI NEQVEEEASVKKILDKLKFAKDSPQILFMLDKELSARAPKLPGLLMQGGE | 36 |
| OspA Serotype 3-*Pyrococcus furiosus* ferritin | MDEKNSVSVDLPGGMKVLVSKEKDKDGKYSLMATVEKLELKGTSDKSNGSGVLEGEKADKSKAKLTISQDLNQTTFEIFKEDGKTLVSRKVNSK DKSSTEEKFNDKGKLSEKVVTRANGTRLEYTEIKNDGSGKAKEVLKGFALEGTLTDGGETKLTVTEGTVTLSKNISKSGEITVALNDTETTPAD KKTGEWKSDTSTLTISKNSQKPKQLVFTKENTITVQNYNRAGNALEGSPAEIKDLAELIKAALKGSMLSERMLKALNDQLNRELYSAYLYFAMAA YFEDLGLEGFANWMKAQAEEEIGHALRFYNYIYDRNGRVELDEIPKPPKEWESPLKAFEAAYEHEKFISKSIYELAALAEEEKDYSTRAFLEWF INEQVEEEASVKKILDKLKFAKDSPQILFMLDKELSARAPKLPGLLMQGGE | 37 |
| OspA Serotype 4-*Pyrococcus furiosus* ferritin | MDEKNSVSVDLPGGMKVLVSKEKDKDGKYSLMATVEKLELKGTSDKSNGSGTLEGEKSDKSKAKLTISEDLSKTTFEIFKEDGKTLVSKKVNSK DKSSIEEKFNAKGELSEKTILRANGTRLEYTEIKSDGTGKAKEVLKDFALEGTLAADKTTLKVTEGTVLSKHIPNSGEITVELNDSNSTQATK KTGKWDSNTSTLTISVNSKKTNIVFTKEDTITVQKYDSAGTNLEGNAVEIKTLDELKNALKGSMLSERMLKALNDQLNRELYSAYLYFAMAAY FEDLGLEGFANWMKAQAEEEIGHALRFYNYIYDRNGRVELDEIPKPPKEWESPLKAFEAAYEHEKFISKSIYELAALAEEEKDYSTRAFLEWFI NEQVEEEASVKKILDKLKFAKDSPQILFMLDKELSARAPKLPGLLMQGGE | 38 |
| OspA Serotype 5-*Pyrococcus furiosus* ferritin | MDEKNSVSVDLPGGMKVLVSKEKDKDGKYSLMATVEKLELKGTSDKNNGSGTLEGEKTDKSKVLKTIAEDLSKTTFEIFKEDGKTLVSKKVTLK DKSSTEEKFNEKGEISEKTIVRANGTRLEYTDIKSDGSGKAKEVLKDFTLEGTLAADGKTTLKDALKGSMLSERMLKALNDQLNRELYSAYLYFAMAA KKTGKWDSKTSTLTISVNSQKTKNLVFTKEDTITVQRYDSAGTNLEGKAVEITTLKELKNALKGSMLSERMLKALNDQLNRELYSAYLYFAMAA YFEDLGLEGFANWMKAQAEEEIGHALRFYNYIYDRNGRVELDEIPKPPKEWESPLKAFEAAYEHEKFISKSIYELAALAEEEKDYSTRAFLEWF INEQVEEEASVKKILDKLKFAKDSPQILFMLDKELSARAPKLPGLLMQGGE | 39 |
| OspA Serotype 6-*Pyrococcus furiosus* ferritin | MDEKNSVSVDLPGGMTVLVSKEKDKDGKYSLEATVDKLELKGTSDKNNGSGTLEGEKTDKSKVKSTIADDLSQTKFEIFKEDGKTLVSKKVTLK DKSSTEEKFNGKGETSEKTIVRANGTRLEYTDIKSDGSGKAKEVLKDFTLEGTLAADGKTTLAADGKTTLKVTEGTVVLSKNILKSGEITAALDDSDTTRAT KKTGKWDSKTSTLTISVNSQKTKNLVFTKEDTITVQRYDSAGTNLEGKAVEITTLKELKNALKGSMLSERMLKALNDQLNRELYSAYLYFAMAA YFEDLGLEGFANWMKAQAEEEIGHALRFYNYIYDRNGRVELDEIPKPPKEWESPLKAFEAAYEHEKFISKSIYELAALAEEEKDYSTRAFLEWF INEQVEEEASVKKILDKLKFAKDSPQILFMLDKELSARAPKLPGLLMQGGE | 40 |
| OspA Serotype 7-*Pyrococcus furiosus* ferritin | MDEKNSVSVDLPGEMKVLVSKEKDKDGKYSLEATVDKLELKGTSDKNNGSGVLEGVKAAKSKAKLTIADDLSQTKFEIFKEDGKTLVSKKVTLK DKSSTEEKFNDKGKLSEKVVTRANGTRLEYTEIQNDGSGKAKEVLKSLTLEGTITADGETKLTVEAGTVTLSKNISESGEITVELKDTETTPAD KKSGTWDSKTSTLTISKNSQKTKQLVFTKENTITVQKYNTAGTKLEGSPAEIKDLEALKAALKGSMLSERMLKALNDQLNRELYSAYLYFAMAA YFEDLGLEGFANWMKAQAEEEIGHALRFYNYIYDRNGRVELDEIPKPPKEWESPLKAFEAAYEHEKFISKSIYELAALAEEEKDYSTRAFLEWF INEQVEEEASVKKILDKLKFAKDSPQILFMLDKELSARAPKLPGLLMQGGE | 41 |

TABLE 1 -continued (Sequence Table): Description of sequences

| Description ("ferritin" refers to *H. pylori* ferritin optionally with one or more mutations unless otherwise indicated) | Sequences<br>Key for sequences 1-102:<br>Leader sequences are sometimes underlined<br>Modified LFA-1 site is Italicized and underlined (if present)<br>Mutations other than modified LFA-1 site are in BOLD and curvy underlined<br>Linker is double underlined<br>Bullfrog sequence is Italicized and curvy underlined (if present)<br>Human heavy chain ferritin sequence is in BOLD (if present)<br>Transmembrane domain is italicized (if present)<br>lipidation site is in Bold, italicized, and underlined (if present) | SEQ ID NO: |
|---|---|---|
| OspA Serotype 1; LFA-1 replacement RD2-*Trichoplusia Ni* ferritin | MDEKNSVSVDLPGEMKVLVSKEKNKDGKYDLIATVDKLELKGTSDKNNGSGVLEGVKADKSKVKLTISDDLGQTTLEVFKEDGKTLVSKKVTSK<br>DKSSTEEKFNEKGEVSEKIITRADGTRLEYTGIKSDGSGKAKEVLKG*YTLEGQLSD*EKTTLVVKEGTVTLSKNISKSGEVSVELNDTDSSAATK<br>KTAAWNSGTSTLTITVNSKKTKDLVFTKENTITVQQYDSNGTKLEGSAVEITKLDEIKNALKGSTQCNVNPVQIPKDWITMHRSCRNSMRQQIQ<br>MEVGASLQYLAMGAHFSKDVVNRPGFAQLFFDAASEEREHAMKLIEYLLMRGELTNDVSSLLQVRPPTRSSWKGGVEALEHALSMESDVTKSIR<br>NVIKACEDDSEFNDYHLVDYLTGDFLEEQYKGQRDLAGKASTLKKLMDRHEALGEFIFDKKLLGIDV | 42 |
| OspA Serotype 1; LFA-1 replacement RD1-*Trichoplusia Ni* ferritin | MDEKNSVSVDLPGEMKVLVSKEKNKDGKYDLIATVDKLELKGTSDKNNGSGVLEGVKADKSKVKLTISDDLGQTTLEVFKEDGKTLVSKKVTSK<br>DKSSTEEKFNEKGEVSEKIITRADGTRLEYTGIKSDGSGKAKEVLKG*YDLKGELSS*EKTTLVVKEGTVTLSKNISKSGEVSVELNDTDSSAATK<br>KTAAWNSGTSTLTITVNSKKTKDLVFTKENTITVQQYDSNGTKLEGSAVEITKLDEIKNALKGSTQCNVNPVQIPKDWITMHRSCRNSMRQQIQ<br>MEVGASLQYLAMGAHFSKDVVNRPGFAQLFFDAASEEREHAMKLIEYLLMRGELTNDVSSLLQVRPPTRSSWKGGVEALEHALSMESDVTKSIR<br>NVIKACEDDSEFNDYHLVDYLTGDFLEEQYKGQRDLAGKASTLKKLMDRHEALGEFIFDKKLLGIDV | 43 |
| OspA Serotype 1; LFA-1 replacement Serotype 2-*Trichoplusia Ni* ferritin | MDEKNSVSVDLPGEMKVLVSKEKNKDGKYDLIATVDKLELKGTSDKNNGSGVLEGVKADKSKVKLTISDDLGQTTLEVFKEDGKTLVSKKVTSK<br>DKSSTEEKFNEKGEVSEKIITRADGTRLEYTGIKSDGSGKAKEVLKG*FTLEGKVAN*EKTTLVVKEGTVTLSKNISKSGEVSVELNDTDSSAATK<br>KTAAWNSGTSTLTITVNSKKTKDLVFTKENTITVQQYDSNGTKLEGSAVEITKLDEIKNALKGSTQCNVNPVQIPKDWITMHRSCRNSMRQQIQ<br>MEVGASLQYLAMGAHFSKDVVNRPGFAQLFFDAASEEREHAMKLIEYLLMRGELTNDVSSLLQVRPPTRSSWKGGVEALEHALSMESDVTKSIR<br>NVIKACEDDSEFNDYHLVDYLTGDFLEEQYKGQRDLAGKASTLKKLMDRHEALGEFIFDKKLLGIDV | 44 |
| OspA Serotype1; LFA-1 replacement Serotype 3-*Trichoplusia Ni* ferritin | MDEKNSVSVDLPGEMKVLVSKEKNKDGKYDLIATVDKLELKGTSDKNNGSGVLEGVKADKSKVKLTISDDLGQTTLEVFKEDGKTLVSKKVTSK<br>DKSSTEEKFNEKGEVSEKIITRADGTRLEYTGIKSDGSGKAKEVLKG*FALEGTLTD*EKTTLVVKEGTVTLSKNISKSGEVSVELNDTDSSAATK<br>KTAAWNSGTSTLTITVNSKKTKDLVFTKENTITVQQYDSNGTKLEGSAVEITKLDEIKNALKGSTQCNVNPVQIPKDWITMHRSCRNSMRQQIQ<br>MEVGASLQYLAMGAHFSKDVVNRPGFAQLFFDAASEEREHAMKLIEYLLMRGELTNDVSSLLQVRPPTRSSWKGGVEALEHALSMESDVTKSIR<br>NVIKACEDDSEFNDYHLVDYLTGDFLEEQYKGQRDLAGKASTLKKLMDRHEALGEFIFDKKLLGIDV | 45 |
| OspA Serotype 2-*Trichoplusia Ni* ferritin | MDEKNSASVDLPGEMKVLVSKEKDKDGKYSLKATVDKIELKGTSDKDNGSGVLEGTKDDKSKAKLTIADDLSKTTFELFKEDGKTLVSRKVSSK<br>DKTSTDEMFNEKGELSAKTMTRENGTKLEYTEMKSDGTGKAKEVLKNFTLEGKVANDKVTLEVKEGTVTLSKEIAKSGEVTVALNDTNTTQATK<br>KTGAWDSKTSTLTISVNSKKTTQLVFTKQDTITVQKYDSAGTNLEGTAVEIKTLDELKNALKGSTQCNVNPVQIPKDWITMHRSCRNSMRQQIQ<br>MEVGASLQYLAMGAHFSKDVVNRPGFAQLFFDAASEEREHAMKLIEYLLMRGELTNDVSSLLQVRPPTRSSWKGGVEALEHALSMESDVTKSIR<br>NVIKACEDDSEFNDYHLVDYLTGDFLEEQYKGQRDLAGKASTLKKLMDRHEALGEFIFDKKLLGIDV | 46 |
| OspA Serotype 3 *Trichoplusia Ni* ferritin | MDEKNSVSVDLPGGMKVLVSKEKDKDGKYSLMATVEKLELKGTSDKSNGSGVLEGEKADKSKAKLTISQDLNQTTFEIFKEDGKTLVSRKVNSK<br>DKSSTEEKFNDKGKLSEKVVTRANGTRLEYTEIKNDGSGKAKEVLKGFALEGTLTDGGETKLTVTEGTVTLSKNISKSGEITVALNDTETTPAD<br>KKTGEWKSDTSTLTISKNSQKPKQLVFTKENTITVQNYNRAGNALEGSPAEIKDLAELKAALKGSTQCNVNPVQIPKDWITMHRSCRNSMRQQI<br>QMEVGASLQYLAMGAHFSKDVVNRPGFAQLFFDAASEEREHAMKLIEYLLMRGELTNDVSSLLQVRPPTRSSWKGGVEALEHALSMESDVTKSI<br>RNVIKACEDDSEFNDYHLVDYLTGDFLEEQYKGQRDLAGKASTLKKLMDRHEALGEFIFDKKLLGIDV | 47 |

TABLE 1 -continued (Sequence Table): Description of sequences

| Description ("ferritin" refers to *H. pylori* ferritin optionally with one or more mutations unless otherwise indicated) | Sequences<br>Key for sequences 1-102:<br>Leader sequences are sometimes underlined<br>Modified LFA-1 site is Italicized and underlined (if present)<br>Mutations other than modified LFA-1 site are in BOLD and curvy underlined<br>Linker is double underlined<br>Bullfrog sequence is Italicized and curvy underlined (if present)<br>Human heavy chain ferritin sequence is in BOLD (if present)<br>Transmembrane domain is italicized (if present)<br>lipidation site is in Bold, italicized, and underlined (if present) | SEQ ID NO: |
|---|---|---|
| OspA Serotype 4-*Trichoplusia Ni* ferritin | MDEKNSVSVDLPGEMKVLVSKEKDKDGKYSLMATVDKLELKGTSDKSNGSGTLEGEKSDKSKAKLTISEDLSKTTFEIFKEDGKTLVSKKVNSK<br>DKSSIEEKFNAKGELSEKTILRANGTRLEYTEIKSDGTGKAKEVLKDFALEGTLAADKTTLKVTEGTVVLSKHIPNSGEITVELNDSNSTQATK<br>KTGKWDSNTSTLTISVNSKKTKNIVFTKEDTITVQKYDSAGTNLEGNAVEIKTLDELKNALKGSTQCNVNPVQIPKDWITMHRSCRNSMRQQIQ<br>MEVGASLQYLAMGAHFSKDVVNRPGFAQLFFDAASEEREHAMKLIEYLLMRGELTNDVSSLLQVRPPTRSSWKGGVEALEHALSMESDVTKSIR<br>NVIKACEDDSEFNDYHLVDYLTGDFLEEQYKGQRDLAGKASTLKKLMDRHEALGEFIFDKKLLGIDV | 48 |
| OspA Serotype 5-*Trichoplusia Ni* ferritin | MDEKNSVSVDLPGGMKVLVSKEKDKDGKYSLMATVEKLELKGTSDKNNGSGTLEGEKTDKSKVKLTIAEDLSKTTFEIFKEDGKTLVSKKVTLK<br>DKSSTEEKFNEKGEISEKTIVRANGTRLEYTDIKSDGSGKAKEVLKDFTLEGTLAADGKTTLKVTEGTVVLSKNILKSGEITVALDDSDTTQAT<br>KKTGKWDSKTSTLTISVNSQKTKNLVFTKEDTITVQKYDSAGTNLEGKAVEITTLEKLKDALKGSTQCNVNPVQIPKDWITMHRSCRNSMRQQI<br>QMEVGASLQYLAMGAHFSKDVVNRPGFAQLFFDAASEEREHAMKLIEYLLMRGELTNDVSSLLQVRPPTRSSWKGGVEALEHALSMESDVTKSI<br>RNVIKACEDDSEFNDYHLVDYLTGDFLEEQYKGQRDLAGKASTLKKLMDRHEALGEFIFDKKLLGIDV | 49 |
| OspA Serotype 6-*Trichoplusia Ni* ferritin | MDEKNSVSVDLPGGMTVLVSKEKDKDGKYSLEATVDKLELKGTSDKNNGSGTLEGEKTDKSKVKSTIADDLSQTKFEIFKEDGKTLVSKKVTLK<br>DKSSTEEKFNGKGETSEKTIVRANGTRLEYTDIKSDGSGKAKEVLKDFTLEGTLAADGKTTLKVTEGTVVLSKNILKSGEITAALDDSDTTRAT<br>KKTGKWDSKTSTLTISVNSQKTKNLVFTKEDTITVQRYDSAGTNLEGKAVEITTLKELKNALKGSTQCNVNPVQIPKDWITMHRSCRNSMRQQI<br>QMEVGASLQYLAMGAHFSKDVVNRPGFAQLFFDAASEEREHAMKLIEYLLMRGELTNDVSSLLQVRPPTRSSWKGGVEALEHALSMESDVTKSI<br>RNVIKACEDDSEFNDYHLVDYLTGDFLEEQYKGQRDLAGKASTLKKLMDRHEALGEFIFDKKLLGIDV | 50 |
| OspA Serotype 7-*Trichoplusia Ni* ferritin | MDEKNSVSVDLPGEMKVLVSKEKDKDGKYSLEATVDKLELKGTSDKNNGSGVLEGVKAAKSKAKLTIADDLSQTKFEIFKEDGKTLVSKKVTLK<br>DKSSTEEKFNDKGKLSEKVVTRANGTRLEYTEIQNDGSGKAKEVLKSLTLEGTLTADGETKLTVEAGTVTLSKNISESGEITVELKDTETTPAD<br>KKSGTWDSKTSTLTISKNSQKTKQLVFTKENTITVQKYNTAGTKLEGSPAEIKDLEALKAALKGSTQCNVNPVQIPKDWITMHRSCRNSMRQQI<br>QMEVGASLQYLAMGAHFSKDVVNRPGFAQLFFDAASEEREHAMKLIEYLLMRGELTNDVSSLLQVRPPTRSSWKGGVEALEHALSMESDVTKSI<br>RNVIKACEDDSEFNDYHLVDYLTGDFLEEQYKGQRDLAGKASTLKKLMDRHEALGEFIFDKKLLGIDV | 51 |
| Serotype 1 LFA-1 replacement RD2 OspA-ferritin | MDSKGSSQKGSRLLLLLVVSNLLLPQGVLAMDEKNSVSVDLPGEMKVLVSKEKNKDGKYDLIATVDKLELKGTSDKNNGSGVLEGVKADKSKVK<br>LTISDDLGQTTLEVFKEDGKTLVSKKVTSKDKSSTEEKFNEKGEVSEKIITRADGTRLEYTGIKSDGSGKAKEVLKG*YTLEGQLSD*EKTTLVVK<br>EGTVTLSKNISKSGEVSVELNDTDSSAATKKTAAWNSGTSTLTITVNSKKTKDLVFTKENTITVQQYDSNGTKLEGSAVEITKLDEIKNALKGS<br>*ESQVRQQF*SKDIEKLLNEQVNKEMQGSNLYMSMSSWSYTHSLDGAGLFLFDHAAEEYEHAKKLIIFLNENNVPVQLTSISAPEHKFEGLTQIFQ<br>KAYEHEQHISESINNIVDHAIKCKDHATFNFLQWYVAEQHEEEVLFKDILDKIELIGNENHGLYLADQYVKGIAKSRKS | 52 |
| Serotype 1 Non-glycosylated LFA-1 replacement RD2 OspA-ferritin | MDSKGSSQKGSRLLLLLVVSNLLLPQGVLAMDEKNSVSVDLPGEMKVLVSKEKNKDGKYDLIATVDKLELKGTSDKNQGSGVLEGVKADKSKVK<br>LTISDDLGQTTLEVFKEDGKTLVSKKVTSKDKSSTEEKFNEKGEVSEKIITRADGTRLEYTGIKSDGSGKAKEVLKG*YTLEGQLSD*EKTTLVVK<br>EGTVTLSKQISKSGEVSVELQDTDSSAATKKTAAWNSGTSTLTITVNSKKTKDLVFTKENTITVQQYDSQGTKLEGSAVEITKLDEIKNALKGS | 53 |

TABLE 1 -continued (Sequence Table): Description of sequences

| Description<br>("ferritin" refers to *H. pylori* ferritin optionally with one or more mutations unless otherwise indicated) | Sequences<br>Key for sequences 1-102:<br>Leader sequences are sometimes underlined<br>Modified LFA-1 site is Italicized and underlined (if present)<br>Mutations other than modified LFA-1 site are in BOLD and curvy underlined<br>Linker is double underlined<br>Bullfrog sequence is Italicized and curvy underlined (if present)<br>Human heavy chain ferritin sequence is in BOLD (if present)<br>Transmembrane domain is italicized (if present)<br>lipidation site is in Bold, italicized, and underlined (if present) | SEQ ID NO: |
|---|---|---|
| | *ESQVRQQF*SKDIEKLLNEQVNKEMQGSNLYMSMSSWSYTHSLDGAGLFLFDHAAEEYEHAKKLIIFLNENNVPVQLTSISAPEHKFEGLTQIFQ<br>KAYEHEQHISESINNIVDHAIKCKDHATFNFLQWYVAEQHEEEVLFKDILDKIELIGNENHGLYLADQYVKGIAKSRKS | |
| OspA-ferritin Serotype 1 with LFA-1 site replaced with Serotype 2 | MDSKGSSQKGSRLLLLLVVSNLLLPQGVLAMDEKNSVSVDLPGEMKVLVSKEKNKDGKYDLIATVDKLELKGTSDKNNGSGVLEGVKADKSKVK<br>LTISDDLGQTTLEVFKEDGKTLVSKKVTSKDKSSTEEKFNEKGEVSEKIITRADGTRLEYTGIKSDGSGKAKEVLKG*FTLEGKVAN*EKTTLVVK<br>EGTVTLSKNISKSGEVSVELNDTDSSAATKKTAAWNSGTSTLTITVNSKKTKDLVFTKENTITVQQYDSNGTKLEGSAVEITKLDEIKNALKGS<br>*ESQVRQQF*SKDIEKLLNEQVNKEMQGSNLYMSMSSWSYTHSLDGAGLFLFDHAAEEYEHAKKLIIFLNENNVPVQLTSISAPEHKFEGLTQIFQ<br>KAYEHEQHISESINNIVDHAIKCKDHATFNFLQWYVAEQHEEEVLFKDILDKIELIGNENHGLYLADQYVKGIAKSRKS | 54 |
| Non-glycosylated OspA-ferritin Serotype 1 with LFA-1 site replaced with Serotype 2 | MDSKGSSQKGSRLLLLLVVSNLLLPQGVLAMDEKNSVSVDLPGEMKVLVSKEKNKDGKYDLIATVDKLELKGTSDKNQGSGVLEGVKADKSKVK<br>LTISDDLGQTTLEVFKEDGKTLVSKKVTSKDKSSTEEKFNEKGEVSEKIITRADGTRLEYTGIKSDGSGKAKEVLKG*FTLEGKVAN*EKTTLVVK<br>EGTVTLSKQISKSGEVSVELQDTDSSAATKKTAAWNSGTSTLTITVNSKKTKDLVFTKENTITVQQYDSQGTKLEGSAVEITKLDEIKNALKGS<br>*ESQVRQQF*SKDIEKLLNEQVNKEMQGSNLYMSMSSWSYTHSLDGAGLFLFDHAAEEYEHAKKLIIFLNENNVPVQLTSISAPEHKFEGLTQIFQ<br>KAYEHEQHISESINNIVDHAIKCKDHATFNFLQWYVAEQHEEEVLFKDILDKIELIGNENHGLYLADQYVKGIAKSRKS | 55 |
| OspA-ferritin Serotype 1 with LFA-1 site replaced with Serotype 3 | MDSKGSSQKGSRLLLLLVVSNLLLPQGVLAMDEKNSVSVDLPGEMKVLVSKEKNKDGKYDLIATVDKLELKGTSDKNNGSGVLEGVKADKSKVK<br>LTISDDLGQTTLEVFKEDGKTLVSKKVTSKDKSSTEEKFNEKGEVSEKIITRADGTRLEYTGIKSDGSGKAKEVLKG*FALEGTLTD*EKTTLVVK<br>EGTVTLSKNISKSGEVSVELNDTDSSAATKKTAAWNSGTSTLTITVNSKKTKDLVFTKENTITVQQYDSNGTKLEGSAVEITKLDEIKNALKGS<br>*ESQVRQQF*SKDIEKLLNEQVNKEMQSSNLYMSMSSWSYTHSLDGAGLFLFDHAAEEYEHAKKLIIFLNENNVPVQLTSISAPEHKFEGLTQIFQ<br>KAYEHEQHISESINNIVDHAIKCKDHATFNFLQWYVAEQHEEEVLFKDILDKIELIGNENHGLYLADQYVKGIAKSRKS | 56 |
| Non-glycosylated OspA-ferritin Serotype 1 with LFA-1 site replaced with Serotype 3 | MDSKGSSQKGSRLLLLLVVSNLLLPQGVLAMDEKNSVSVDLPGEMKVLVSKEKNKDGKYDLIATVDKLELKGTSDKNQGSGVLEGVKADKSKVK<br>LTISDDLGQTTLEVFKEDGKTLVSKKVTSKDKSSTEEKFNEKGEVSEKIITRADGTRLEYTGIKSDGSGKAKEVLKG*FALEGTLTD*EKTTLVVK<br>EGTVTLSKQISKSGEVSVELQDTDSSAATKKTAAWNSGTSTLTITVNSKKTKDLVFTKENTITVQQYDSQGTKLEGSAVEITKLDEIKNALKGS | 57 |

TABLE 1 -continued (Sequence Table): Description of sequences

| Description ("ferritin" refers to *H. pylori* ferritin optionally with one or more mutations unless otherwise indicated) | Sequences<br>Key for sequences 1-102:<br>Leader sequences are sometimes underlined<br>Modified LFA-1 site is Italicized and underlined (if present)<br>Mutations other than modified LFA-1 site are in BOLD and curvy underlined<br>Linker is double underlined<br>Bullfrog sequence is Italicized and curvy underlined (if present)<br>Human heavy chain ferritin sequence is in BOLD (if present)<br>Transmembrane domain is italicized (if present)<br>lipidation site is in Bold, italicized, and underlined (if present) | SEQ ID NO: |
|---|---|---|
| | *ESQVRQQF*SKDIEKLLNEQVNKEMQSSNLYMSMSSWSYTHSLDGAGLFLFDHAAEEYEHAKKLIIFLNENNVPVQLTSISAPEHKFEGLTQIFQ<br><br>KAYEHEQHISESINNIVDHAIKCKDHATFNFLQWYVAEQHEEEVLFKDILDKIELIGNENHGLYLADQYVKGIAKSRKS | |
| OspA-ferritin Serotype 1 with LFA-1 site replaced with RD1 | MDSKGSSQKGSRLLLLLVVSNLLLPQGVLAMDEKNSVSVDLPGEMKVLVSKEKNKDGKYDLIATVDKLELKGTSDKNNGSGVLEGVKADKSKVK<br>LTISDDLGQTTLEVFKEDGKTLVSKKVTSKDKSSTEEKFNEKGEVSEKIITRADGTRLEYTGIKSDGSGKAKEVLKG*YDLKGELSS*EKTTLVVK<br>EGTVTLSKNISKSGEVSVELNDTDSSAATKKTAAWNSGTSTLTITVNSKKTKDLVFTKENTITVQQYDSNGTKLEGSAVEITKLDEIKNALKGS<br>ESQVRQQFSKDIEKLLNEQVNKEMQSSNLYMSMSSWSYTHSLDGAGLFLFDHAAEEYEHAKKLIIFLNENNVPVQLTSISAPEHKFEGLTQIFQ<br><br>KAYEHEQHISESINNIVDHAIKCKDHATFNFLQWYVAEQHEEEVLFKDILDKIELIGNENHGLYLADQYVKGIAKSRKS | 58 |
| Non-glycosylated OspA-ferritin Serotype 1 with LFA-1 site replaced with RD1 | MDSKGSSQKGSRLLLLLVVSNLLLPQGVLAMDEKNSVSVDLPGEMKVLVSKEKNKDGKYDLIATVDKLELKGTSDKNQGSGVLEGVKADKSKVK<br><br>LTISDDLGQTTLEVFKEDGKTLVSKKVTSKDKSSTEEKFNEKGEVSEKIITRADGTRLEYTGIKSDGSGKAKEVLKG*YDLKGELSS*EKTTLVVK<br>EGTVTLSKQISKSGEVSVELQDTDSSAATKKTAAWNSGTSTLTITVNSKKTKDLVFTKENTITVQQYDSQGTKLEGSAVEITKLDEIKNALKGS<br><br>*ESQVRQQF*SKDIEKLLNEQVNKEMQGSNLYMSMSSWSYTHSLDGAGLFLFDHAAEEYEHAKKLIIFLNENNVPVQLTSISAPEHKFEGLTQIFQ<br><br>KAYEHEQHISESINNIVDHAIKCKDHATFNFLQWYVAEQHEEEVLFKDILDKIELIGNENHGLYLADQYVKGIAKSRKS | 59 |
| Non-glycosylated, OspA-ferritin Serotype 1, LFA-1 replacement RD2, 1x GGGS linker (SEQ ID NO: 226) | MDSKGSSQKGSRLLLLLVVSNLLLPQGVLAMDEKNSVSVDLPGEMKVLVSKEKNKDGKYDLIATVDKLELKGTSDKNQGSGVLEGVKADKSKVK<br><br>LTISDDLGQTTLEVFKEDGKTLVSKKVTSKDKSSTEEKFNEKGEVSEKIITRADGTRLEYTGIKSDGSGKAKEVLKG*YTLEGQLSD*EKTTLVVK<br>EGTVTLSKQISKSGEVSVELQDTDSSAATKKTAAWNSGTSTLTITVNSKKTKDLVFTKENTITVQQYDSQGTKLEGSAVEITKLDEIKNALKGG<br><br>GS*ESQVRQQF*SKDIEKLLNEQVNKEMQSSNLYMSMSSWSYTHSLDGAGLFLFDHAAEEYEHAKKLIIFLNENNVPVQLTSISAPEHKFEGLTQI<br><br>FQKAYEHEQHISESINNIVDHAIKCKDHATFNFLQWYVAEQHEEEVLFKDILDKIELIGNENHGLYLADQYVKGIAKSRKS | 60 |
| Non-glycosylated,OspA-ferritin Serotype 1, LFA-1 replacement RD2, 2x GGGS linker (SEQ ID NO: 91) | MDSKGSSQKGSRLLLLLVVSNLLLPQGVLAMDEKNSVSVDLPGEMKVLVSKEKNKDGKYDLIATVDKLELKGTSDKNQGSGVLEGVKADKSKVK<br><br>LTISDDLGQTTLEVFKEDGKTLVSKKVTSKDKSSTEEKFNEKGEVSEKIITRADGTRLEYTGIKSDGSGKAKEVLKG*YTLEGQLSD*EKTTLVVK<br>EGTVTLSKQISKSGEVSVELQDTDSSAATKKTAAWNSGTSTLTITVNSKKTKDLVFTKENTITVQQYDSQGTKLEGSAVEITKLDEIKNALKGG | 61 |

TABLE 1-continued (Sequence Table): Description of sequences

```
Sequences
Key for sequences 1-102:
Leader sequences are sometimes underlined
Modified LFA-1 site is Italicized and underlined (if present)
Mutations other than modified LFA-1 site are in BOLD and curvy underlined
Linker is double underlined
Bullfrog sequence is Italicized and curvy underlined (if present)
Human heavy chain ferritin sequence is in BOLD (if present)
Transmembrane domain is italicized (if present)
lipidation site is Bold, italicized, and underlined (if present)
```

| Description ("ferritin" refers to H. pylori ferritin optionally with one or more mutations unless otherwise indicated) | Sequences | SEQ ID NO: |
|---|---|---|
| | GSGGGS*ESQVRQQFSKDIEKLLNEQVNKEMQSSNLYMSMSSWSYTHSLDGAGLFLFDHAAEEYEHAKKLIIFLNENNVPVQLTSISAPEHKFEG LTQIFQKAYEHEQHISESINNIVDHAIKCKDHATFNFLQWYVAEQHEEEVLFKDILDKIELIGNENHGLYLADQYVKGIAKSRKS* | 62 |
| Non-glycosylated, OspA-ferritin Serotype 1, LFA-1 replacement RD2, 5 x GGGS linker (SEQ ID NO: 92) | MD TABLE 1-continued (Sequence Table): Description of sequences Key for sequences 1-102:
Leader sequences are sometimes underlined
Modified LFA-1 site is Italicized and underlined (if present)
Mutations other than modified LFA-1 site are in BOLD and curvy underlined
Linker is double underlined
Bullfrog sequence is Italicized and curvy underlined (if present)
Human heavy chain ferritin sequence is in BOLD (if present)
Transmembrane domain is italicized (if present)
lipidation site is in Bold, italicized, and underlined (if present)

| Description ("ferritin" refers to H. pylori ferritin optionally with one or more mutations unless otherwise indicated) | Sequences | SEQ ID NO: |
|---|---|---|
| | ESQVRQQFSKDIEKLLNEQVNKEMQGSNLYMSMSSWSYTHSLDGAGLFLFDHAAEEYEHAKKLIIFLNENNVPVQLTSISAPEHKFEGLTQIFQ KAYEHEQHISESINNIVDHAIKCKDHATFNFLQMYVAEQHEEEVLFKDILDKIELIGNENHGLYLADQYVKGIAKSRKS | 66 |
| Non-glycosylated OspA-ferritin Serotype 2 | MDSKGSSQQKGSRLLLLLVVSNLLL TABLE 1-continued (Sequence Table): Description of sequences

| Description ("ferritin" refers to H. pylori ferritin optionally with one or more mutations unless otherwise indicated) | Sequences<br>Key for sequences 1-102:<br>Leader sequences are sometimes underlined<br>Modified LFA-1 site is Italicized and underlined (if present)<br>Mutations other than modified LFA-1 site are in BOLD and curvy underlined<br>Linker is double underlined<br>Bullfrog sequence is Italicized and curvy underlined (if present)<br>Human heavy chain ferritin sequence is in BOLD (if present)<br>Transmembrane domain is italicized (if present)<br>lipidation site is in Bold, italicized, and underlined (if present) | SEQ ID NO: |
|---|---|---|
| | *ESQVRQQFSKDIEKLLNEQVNKEMQSSNLYMSMSSWS*YTHSLDGAGLFLFDHAAEEYEHAKKLIIFLNENNVPVQLTSISAPEHKFEGLTQIFQ<br>KAYEHEQHISESINNIVDHAIKCKDHATFNFLQWYVAEQHEEEVLFKDILDKIELIGNENHGLYLADQYVKGIAKSRKS | 70 |
| Non-glycosylated OspA-ferritin Serotype 4 | <u>MDSKGSSSQQKGSRLLLLLVVSNLLLPQGVLAMDEKNSVSVDLPGEMKVLVSKEKDKDGKYSLMATVDKLELKGTSDKSQSGTLEGEKSDKSKAK</u><br>LTISEDLSKTTFEIFKEDGKTLVSKKVNSKDKSSIEEKFNAKGELSEKTILRAQGTRLEYTEIKSDGTGKAKEVLKDFALEGTLAADKTTLKVT<br>EGTVLSKKHIPNSGEITVELQDSQSTQATKKTGKWDSQTSTLTISVNSKKTKNIVFTKEDTITVQKYDSAGTNLEGNAVEIKTLDELKNALKGS<br>*SESQVRQQFSKDIEKLLNEQVNKEMQGSSNLYMSMSSWS*YTHSLDGAGLFLFDHAAEEYEHAKKLIIFLNENNVPVQLTSISAPEHKFEGLTQIFQ<br>KAYEHEQHISESINNIVDHAIKCKDHATFNFLQWYVAEQHEEEVLFKDILDKIELIGNENHGLYLADQYVKGIAKSRKS | 71 |
| OspA-ferritin Serotype 5 | <u>MDSKGSSSQQKGSRLLLLLVVSNLLLPQGVLAMDEKNSVSVDLPGGMKVLVSKEKDKDGKYSLMATVEKLELKGTSDKNNGSGTLEGEKTDKSKVK</u><br>LTIAEDLSKTTFEIFKEDGKTLVSKKVTLKDKSSTEEKFNEKGEISEKTIVRANGTRLEYTDIKSDGSGKAKEVLKDFTLEGTLAADGKTTLKV<br>TEGTVVLSKNILKSGEITVALDDSDTTQATKKTGKWDSKTSTLTISVNSQKTKNLVFTKEDTITVQKYDSAGTNLEGKAVEITTLEKLKDALKG<br>*SESQVRQQFSKDIEKLLNEQVNKEMQGSSNLYMSMSSWS*YTHSLDGAGLFLFDHAAEEYEHAKKLIIFLNENNVPVQLTSISAPEHKFEGLTQIF<br>QKAYEHEQHISESINNIVDHAIKCKDHATFNFLQWYVAEQHEEEVLFKDILDKIELIGNEHGLYLADQYVKGIAKSRKS | 72 |
| Serotype 5 Non-glycosylated OspA-ferritin | <u>MDSKGSSSQQKGSRLLLLLVVSNLLLPQGVLAMDEKNSVSVDLPGGMKVLVSKEKDKDGKYSLMATVEKLELKGTSDKNQSGTLEGEKTDKSKVK</u><br>LTIAEDLSKTTFEIFKEDGKTLVSKKVTLKDKSSTEEKFNEKGEISEKTIVRAQGTRLEYTDIKSDGSGKAKEVLKDFTLEGTLAADGKTTLKV<br>TEGTVVLSKNILKSGEITVALDDSDTTQATKKTGKWDSKTSTLTISVNSQKTKNLVFTKEDTITVQKYDSAGTNLEGKAVEITTLEKLKDALKG<br>*SESQVRQQFSKDIEKLLNEQVNKEMQGSSNLYMSMSSWS*YTHSLDGAGLFLFDHAAEEYEHAKKLIIFLNENNVPVQLTSISAPEHKFEGLTQIF<br>QKAYEHEQHISESINNIVDHAIKCKDHATFNFLQWYVAEQHEEEVLFKDILDKIELIGNEHGLYLADQYVKGIAKSRKS | 73 |
| Serotype 6 Non-glycosylated OspA-ferritin | <u>MDSKGSSSQQKGSRLLLLLVVSNLLLPQGVLAMDEKNSVSVDLPGGMTVLVSKEKDKDGKYSLEATVDKLELKGTSDKNQSGTLEGEKTDKSKVK</u><br>STIADDLSQTKFEIFKEDGKTLVSKKVTLKDKSSTEEKFNGKGETSEKTIVRAQGTRLEYTDIKSDGSGKAKEVLKDFTLEGTLAADGKTTLKV | |

TABLE 1 -continued (Sequence Table): Description of sequences

| Description ("ferritin" refers to H. pylori ferritin optionally with one or more mutations unless otherwise indicated) | Sequences<br>Key for sequences 1-102:<br>Leader sequences are sometimes underlined<br>Modified LFA-1 site is Italicized and underlined (if present)<br>Mutations other than modified LFA-1 site are in BOLD and curvy underlined<br>Linker is double underlined<br>Bullfrog sequence is Italicized and curvy underlined (if present)<br>Human heavy chain ferritin sequence is in BOLD (if present)<br>Transmembrane domain is italicized (if present)<br>lipidation site is in Bold, italicized, and underlined (if present) | SEQ ID NO: |
|---|---|---|
| Serotype 6 OspA-ferritin | TEGT TABLE 1 -continued (Sequence Table): Description of sequences

| Description ("ferritin" refers to H. pylori ferritin optionally with one or more mutations unless otherwise indicated) | Sequences<br>Key for sequences 1-102:<br>Leader sequences are sometimes underlined<br>Modified LFA-1 site is Italicized and underlined (if present)<br>Mutations other than modified LFA-1 site are in BOLD and curvy underlined<br>Linker is double underlined<br>Bullfrog sequence is Italicized and curvy underlined (if present)<br>Human heavy chain ferritin sequence is in BOLD (if present)<br>Transmembrane domain is italicized (if present)<br>lipidation site is in Bold, italicized, and underlined (if present) | SEQ ID NO: |
|---|---|---|
| S2 sequence from OspA serotype 2 | FTLE TABLE 1-continued (Sequence Table): Description of sequences Sequences
Key for sequences 1-102:
Leader sequences are sometimes underlined
Modified LFA-1 site is Italicized and underlined (if present)
Mutations other than modified LFA-1 site are in BOLD and curvy underlined
Linker is double underlined
Bullfrog sequence is Italicized and curvy underlined (if present)
Human heavy chain ferritin sequence is in BOLD (if present)
Transmembrane domain is italicized (if present)
lipidation site is in Bold, italicized, and underlined (if present)

| Description ("ferritin" refers to H. pylori ferritin optionally with one or more mutations unless otherwise indicated) | Sequences | SEQ ID NO: |
|---|---|---|
| Exemplary OspA serotype 6 (Str TABLE 1 -continued (Sequence Table): Description of sequences

| Description ("ferritin" refers to H. pylori ferritin optionally with one or more mutations unless otherwise indicated) | Sequences<br>Key for sequences 1-102:<br>Leader sequences are sometimes underlined<br>Modified LFA-1 site is Italicized and underlined (if present)<br>Mutations other than modified LFA-1 site are in BOLD and curvy underlined<br>Linker is double underlined<br>Bullfrog sequence is Italicized and curvy underlined (if present)<br>Human heavy chain ferritin sequence is in BOLD (if present)<br>Transmembrane domain is italicized (if present)<br>lipidation site is in Bold, italicized, and underlined (if present) | SEQ ID NO: |
|---|---|---|
| Serotype 1 Non-glycosylated LFA-1 replacement RD2 OspA | MDEKNSVSVDLPGEMKVLVSKEKNKDGKYDLIAT TABLE 1 -continued (Sequence Table): Description of sequences

| Description ("ferritin" refers to H. pylori ferritin optionally with one or more mutations unless otherwise indicated) | Sequences<br>Key for sequences 1-102:<br>Leader sequences are sometimes underlined<br>Modified LFA-1 site is Italicized and underlined (if present)<br>Mutations other than modified LFA-1 site are in BOLD and curvy underlined<br>Linker is double underlined<br>Bullfrog sequence is Italicized and curvy underlined (if present)<br>Human heavy chain ferritin sequence is in BOLD (if present)<br>Transmembrane domain is italicized (if present)<br>lipidation site is in Bold, italicized, and underlined (if present) | SEQ ID NO: |
|---|---|---|
| bfpFerritin-N19Q/C31S/S72C | ESQVRQQFSKDIEKLLNEQVNKEMQSSNLYMSMSSWSYTHSLDGAGLFLFDHAAEEYEHAKKLIIFLNENNVPVQLTCISAPEHKFEGLTQIFQ<br>KAYEHEQHISESINNIVDHAIKSKDHATFNFLQWYVAEQHEEEVLFKDILDKIELIGNENHGLYLADQYVKGIAKSRKS | 202 |
| bfpFerritin-N19Q/C31S/A75C | ESQVRQQFSKDIEKLLNEQVNKEMQSSNLYMSMSSWSYTHSLDGAGLFLFDHAAEEYEHAKKLIIFLNENNVPVQLTSISCPEHKFEGLTQIFQ<br>KAYEHEQHISESINNIVDHAIKSKDHATFNFLQWYVAEQHEEEVLFKDILDKIELIGNENHGLYLADQYVKGIAKSRKS | 203 |
| bfpFerritin-N19Q/C31S/K79C | ESQVRQQFSKDIEKLLNEQVNKEMQSSNLYMSMSSWSYTHSLDGAGLFLFDHAAEEYEHAKKLIIFLNENNVPVQLTSISAPEHCFEGLTQIFQ<br>KAYEHEQHISESINNIVDHAIKSKDHATFNFLQWYVAEQHEEEVLFKDILDKIELIGNENHGLYLADQYVKGIAKSRKS | 204 |
| bfpFerritin-N19Q/C31S/S100C | ESQVRQQFSKDIEKLLNEQVNKEMQSSNLYMSMSSWSYTHSLDGAGLFLFDHAAEEYEHAKKLIIFLNENNVPVQLTSISAPEHKFEGLTQIFQ<br>KAYEHEQHISECINNIVDHAIKSKDHATFNFLQWYVAEQHEEEVLFKDILDKIELIGNENHGLYLADQYVKGIAKSRKS | 205 |
| bfpFerritin-N19Q/C31S/S111C | ESQVRQQFSKDIEKLLNEQVNKEMQSSNLYMSMSSWSYTHSLDGAGLFLFDHAAEEYEHAKKLIIFLNENNVPVQLTSISAPEHKFEGLTQIFQ<br>KAYEHEQHISESINNIVDHAIKCKDHATFNFLQWYVAEQHEEEVLFKDILDKIELIGNENHGLYLADQYVKGIAKSRKS | 206 |
| bfpFerritin-N19Q/C31S/E12C | ESQVRQQFSKDIEKLLNCQVNKEMQSSNLYMSMSSWSYTHSLDGAGLFLFDHAAEEYEHAKKLIIFLNENNVPVQLTSISAPEHKFEGLTQIFQ<br>KAYEHEQHISESINNIVDHAIKSKDHATFNFLQWYVAEQHEEEVLFKDILDKIELIGNENHGLYLADQYVKGIAKSRKS | 207 |
| Exemplary H. pylori Ferritin with bullfrog linker | ESQVRQQFSKDIEKLLNEQVNKEMNSSNLYMSMSSWCYTHSLDGAGLFLFDHAAEEYEHAKKLIIFLNENNVPVQLTSISAPEHKFEGLTQIFQ<br>KAYEHEQHISESINNIVDHAIKSKDHATFNFLQWYVAEQHEEEVLFKDILDKIELIGNENHGLYLADQYVKGIAKSRKS | 208 |
| Exemplary wild-type H. pylori ferritin (GenBank Accession AAD06160.1) (without bullfrog linker or N-terminal Met) | LSKDIIIKLLNEQVNKEMNSSNLYMSMSSWCYTHSLDGAGLFLFDHAAEEYEHAKKLIIFLNENNVPVQLTSISAPEHKFEGLTQIFQKAYEHEQ<br>HISESINNIVDHAIKSKDHATFNFLQWVAEQHEEEVLFKDILDKIELIGNENHGLYLADQYVKGIAKSRKS | 209 |
| CpG (ISS-1018) | TGACTGTGAACGTTCGAGATGA | 210 |
| Trichoplusia ni heavy chain ferritin | TQCNVNPVQIPKDWITMHRSCRNSMRQOIQMEVGASLQYLAMGAHFSKDVVNRPGFAQLFFDAASEEREHAMKLIEYLLMRGELTNDVSSLLQV<br>RPPTRSSWKGGVEALEHALSMESDVTKSIRNVIKACEDDSEFNDYHLVDYLTGDFLEEQYKGQRDLAGKASTLKKLMDRHEALGEF<br>IPDKKLLGIDV | 211 |
| Trichoplusia ni light chain ferritin | ADTCYNDVALDCGITSNSLALPRCNAVYGEYGSHGNVATELQAYAKLHLERSYDYLLSAAYFNNYQTNRAGFSKLFKKLSDEAWSKTIDIIKHV<br>TKRGDKMNFDQHSTMKTERKNYTAENHLEEALAKALDTQKELAERAFYIHREATRNSQHLHDPEIAQYLEEEFIEDHAEKIRTLAGHTSDLKKF<br>ITANNGHDLSLALYVFDEYLQKTV | 212 |
| Pyrococcus furiosus ferritin | MLSERMLKALNDQLNRELYSAYLYFAMAAYFEDLGLEGFANWMKAQAEEEIGHALRFYNY<br>IYDRNGRVELDEIPKPPKEWESPLKAFRAAYEHEKFISKSIYELAALAEEEKDYSTRAFL<br>EWFINEQVEEEASVKKILDKLFKAPDSPQILFMLDKELSARAPKLPGLLMQGGE | 213 |

TABLE 1-continued (Sequence Table): Description of sequences

Sequences
Key for sequences 1-102:
Leader sequences are sometimes underlined
Modified LFA-1 site is Italicized and underlined (if present)
Mutations other than modified LFA-1 site are in BOLD and curvy underlined
Linker is double underlined
Bullfrog sequence is Italicized and curvy underlined (if present)
Human heavy chain ferritin sequence is in BOLD (if present)
Transmembrane domain is italicized (if present)
lipidation site is in Bold, italicized, and underlined (if present)

| Description ("ferritin" refers to H. pylori ferritin optionally with one or more mutations unless otherwise indicated) | Sequences | SEQ ID NO: |
|---|---|---|
| human heavy chain ferritin | MTTASTSQVRQNYHQDSEAAINRQINLELYASYVYLSMSYYFDRDDVALKNFAKYFLHQSHEREHAEKLMKLQNQRGGRIFLQDIKKPDCDDW ESGLNAMECALHLEKNVQQSLLELHKLATDKNDPHLCDFIETHYLNEQVKAIKELGDHVTNLRKMGAPESGLAEYLFDKHTLGDSDQES | 214 |
| human light chain ferritin (signal peptide is underlined) | MDSKGSSQKGSRLLLLVVSNLLLPQGVLASSQIRQNYSTDVEAAVNSLVNLYLQASYTYLSLGFYFDRDDVALEGVSHFFRELAEEKREGYER LLKMQNQRGGRALFQDIKKPAEDEWGKTPDAMKAAMALEKKLNQALLDLHALGSARTDPHLCDFLETHFLDEEVKLIKKMGDHLTNLHRLGGPE AGLGEYLFERLTLKHD | 215 |
| lumazine synthase from Aquifex aeolicus | MQIYEGKLTAEGLRFGIVASRFNHALVDRLVEGAIDCIVRHGGREEDITLVRVPGSWEIPVAAGELARKEDIDAVIAIGVLIRGATPHFDYIAS EVSKGLANLSLELRKPITFGVITADTLEQAIERAGTKHGNKGWEAALSAIEMANLFKSLR | 216 |
| bullfrog linker | ESQVRQQF | 217 |
| Cysteine-Thrombin-His Linker | CLVPRGSLEHHHHHH | 218 |
| E. coli 6,7-dimethyl-8-ribityl-lumazine synthase | MNIIEANVATPDARVAITIARFNNFINDSLLEGAIDALKRIGQVKDENITVVWVPGAYELPLAAGALAKTGKYDAVIALGTVIRGGTAHFEYVA GGASNGLAHVAQDSEIPVAFGVLTTESIEQAIERAGTKAGNKGAEAALTALEMINVLKAIKA | 219 |
| 16 amino acid linker | GGGGSGGGGSGGGGSG | 220 |
| 28 amino acid linker | GGSGSGNSSASSGASSGASGGSGGSG | 221 |
| 46 amino acid linker | GGGGSASSGASASGSSNGSGSGSGSNSSASSGASSGASGGSGASGGSGGSG | 222 |
| FR1 | GGSGSASAEAAAKEAAAKAGGSGGSG | 223 |
| FR2 | GGSGSASAEAAAKEAAAKEAAAKASGGSGGSG | 224 |
| 47 amino acid linker comprising a C for conjugation | SGGGSGSASSGASASGSCSGSGSGSGSSSASSGASSGGASGGGGSGGSG | 225 |

EXAMPLES

The following examples are provided to illustrate certain disclosed embodiments and are not to be construed as limiting the scope of this disclosure in any way.

1. Preparation of OspA-Ferritin Antigenic Polypeptides

Antigenic polypeptides comprising OspA and ferritin were generated.

OspA was synthesized by Genescript from the following sequences: *Borrelia burgdorferi* strain B31 (Serotype 1) NBCI sequence ID WP_010890378.1, *Borrelia afzelii* strain PKO (Serotype 2) NCBI sequence: WP_011703777.1, *Borrelia garinii* strain PBr (Serotype 3) GenBank: CAA56549.1, *Borrelia bavariensis* (Serotype 4) NCBI sequence WP_011187157.1, *Borrelia garinii* (Serotype 5) GenBank CAA59727.1, *Borrelia garinii* (serotype 6) GenBank: CAA45010.1, and *Borrelia garinii* (Serotype 7) GenBank CAA56547.1. The *H. pylori* ferritin with an inserted N-terminal bull frog ferritin sequence was synthesized by Genescript, in which the bull frog ferritin sequence is similar to that of a previous study (see Kanekiyo, M., et al., Cell 162(5):1090-100 (2015)). The pet21a vector was used to express both His-tagged OspA and OspA-ferritin nanoparticles in *E. coli*. A mammalian expression vector similar to that used previously was used for expression in Expi293 cells (see Xu, L., et al., Science 358(6359):85-90 (2017)).

OspA-ferritin nanoparticles were created by genetically fusing the ectodomain of OspA to the amino-terminus of ferritin to generate an antigenic polypeptide (FIG. 1A). OspA is a 31-kDa lipoprotein with an extended β-sheet structure made up of 21 consecutive antiparallel β-strands with only one carboxy-terminal α-helix (FIG. 1B) (see Kitahara, R., et al., Biophys J 102(4):916-26 (2012)). The carboxy-terminus of OspA also has an unusually large cavity (~200 Å) that represented a site compatible for linkage to ferritin using a glycine-serine sequence (FIG. 1B). The 24 subunits of ferritin assemble spontaneously into a hollow spherical nanoparticle (FIG. 1C). The ferritin used in this study contains the amino-terminal sequence of bullfrog ferritin fused to *Helicobacter pylori* ferritin to create a chimera minimally related to human ferritin (see Kanekiyo 2015). The amino-terminal bullfrog ferritin sequence projects radially from the nanoparticle core (see Trikha, J., et al. J Mol Biol 248(5):949-67 (1995)), facilitating the presentation of OspA evenly on the nanoparticle surface.

Three additional changes were made to the ferritin structure to improve its functionality: N19Q, C31S and S111C. The N19Q substitution removed a potential amino-terminal glycosylation site. The S111C substitution introduces a surface-exposed cysteine on the ferritin that can be used to conjugate adjuvants with, for example, click chemistry. Finally, cysteine 31 was modified to serine so that only one cysteine would be modified by conjugation. Display of OspA on the nanoparticle surface provides a 24-mer antigenic nanoparticle (FIG. 1D).

For purification from *E. coli*, we used BL21 Star (DE3) (Invitrogen Cat #C601003). We induced the protein with 100 μM IPTG overnight at 16° C. The cell pellet was lysed using sonication in Tris buffer pH 8, 50 mM NaCl. The filter sterilized supernatant was purified on an anion exchange column (HiTrap Q HP, GE), by collecting OspA-ferritin from the flow-through. Endotoxin was then removed by a 1% Triton X114 extraction that was repeated 6 times. The aqueous phase was then concentrated using an Amicon 100 MW cutoff filter (Millipore Cat #UFC910096) and nanoparticles were then further purified on a 120 ml Superose 6 preparatory SEC column at 4° C. For purification from mammalian cell culture, Expi293 cells were transfected with plasmid DNA using FectoPRO transfection Reagent (Polyplus, Cat #116-100) per manufacturer's instructions. Transfected cells were cultured on day 5 and the supernatant was collected and filtered. Endotoxin-free protocols were followed using endotoxin-free reagents and glassware. Q sepharose Fast flow beads (GE, Cat #17-0510-01) were prepared with 50 mM Tris pH7, 50 mM NaCl and applied to the filter-sterilized supernatant by gravity flow. The flow-through was collected and concentrated to 4 ml using Amicon 100 MW cutoff filter. Nanoparticles were then further purified on a 120 ml Superose 6 preparatory SEC column at room temperature.

For purification of $His_6$-tagged (SEQ ID NO: 227) OspA, serotype 1, 4, 5, and 7 OspA were purified from *E. coli* BL21 (DE3) (Invitrogen Cat #C600003), and serotype 2 and 3 were purified from Expi293 cells. These constructs lacked the transmembrane domain, comprised a C-terminal $His_6$-tag (SEQ ID NO: 227), and were otherwise wild-type. For *E. coli* purification, protein was induced at 500 μM IPTG for 5 hours and cells were pelleted and frozen at −20° C. Pellet was resuspended in 1% Triton in TBS buffer with Complete Protease Inhibitor (Sigma-Aldrich, Cat #11697498001) and sonicated to lyse cells. The supernatant was filter sterilized. For mammalian cell culture, the supernatant was collected at day 5 after transfection and filter sterilized. The supernatant was run on a GE HiTrap HP 5 ml column (Cat #17-5248-02) attached to an AKTA Pure FPLC. The column was washed and loaded and washed again with 20 mM imidizole in TBS. Final protein was eluted with 250 mM imidizole in TBS.

Figure 2A:
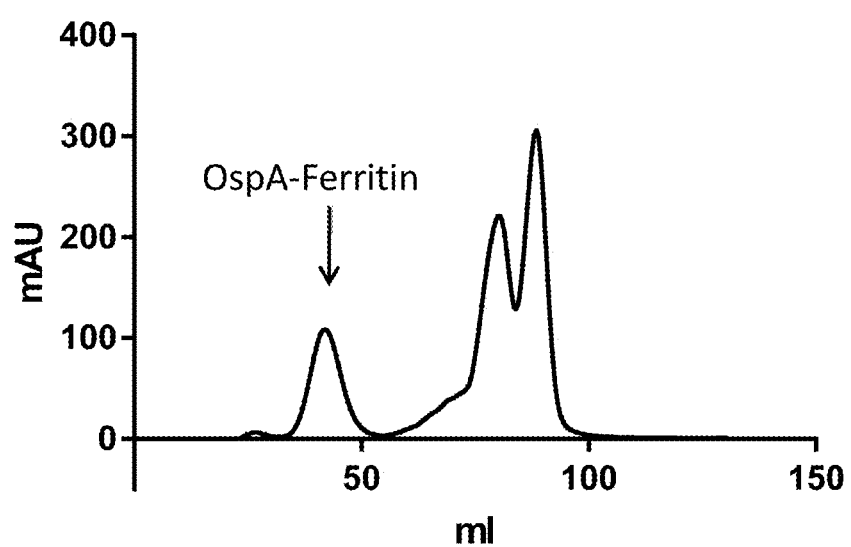
FIGS. 2A-2D show expression and purification of an exemplary OspA-Ferritin.
Figure 2B:
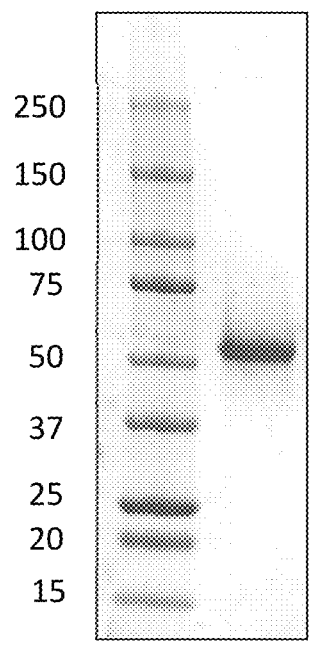

OspA serotype 1 was expressed from *B. burgdorferi* strain B31 fused to ferritin in a transformed human renal epithelial cell line, Expi293 (FIGS. 2A-2D; SEQ ID NO: 52). The formation of the nanoparticles and the purity of the protein were confirmed by size exclusion column chromatography (SEC) and SDS-PAGE (FIGS. 2A and 2B, respectively). SEC analysis revealed a single symmetrical peak of the expected retention time (FIG. 2A).

Figure 2C:
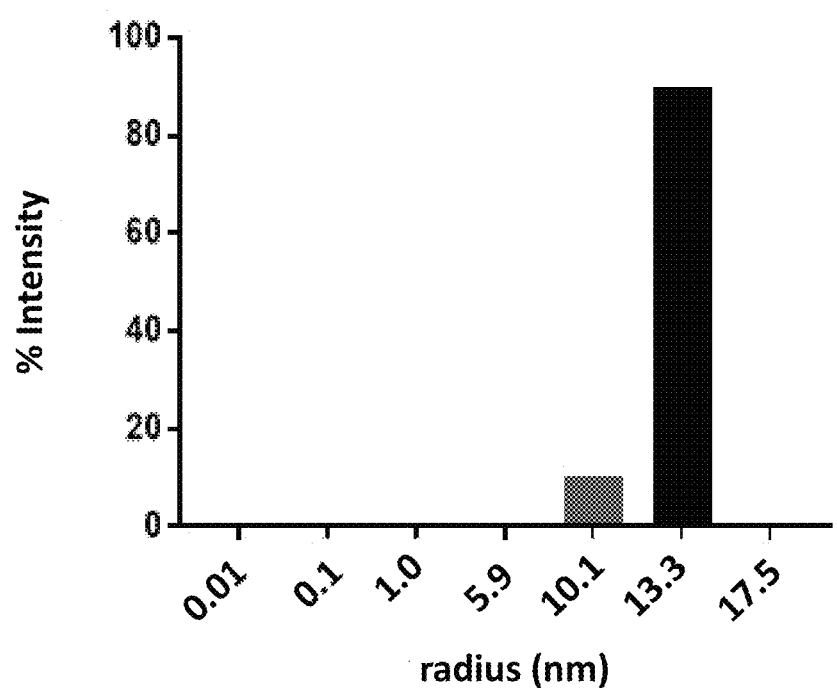

Dynamic light scattering (DLS) analysis was also performed. Purified nanoparticles were loaded into a black 384 well plate with a clear bottom (Corning, Cat #3540) at a concentration ~0.4 μg/ml. Samples were read with a DynaPro plater Reader II (Wyatt) at a control temperature of 25° C. DLS documented a particle size of 13 nm with low polydispersity (7.4%) that is pure and without aggregates (FIG. 2C). Elimination of the transmembrane domain of OspA (aa 1-25) that contains the lipidation site improved the ease of purification. The OspA sequence contains four potential amino-linked glycosylation sites, and OspA-ferritin purified from mammalian cells migrated at a higher molecular weight consistent with the addition of glycans (FIG. 2B).

Figure 2D:
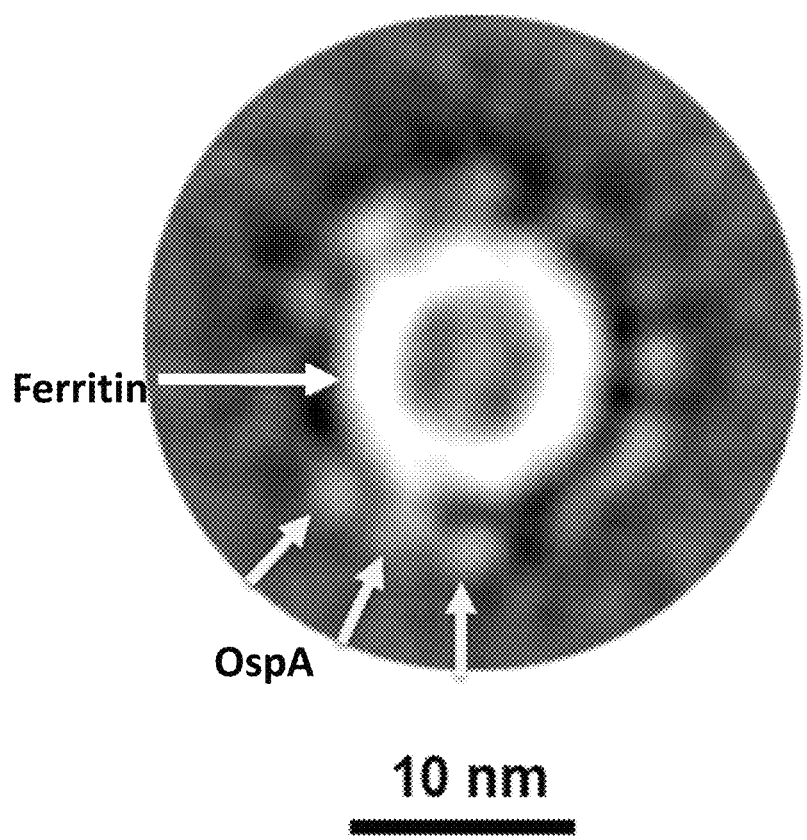

Transmission electron microscopy negative stain imaging and 2D class averaging analysis was performed on the OspA-ferritin nanoparticles (FIG. 2D). A sample of OspA-ferritin nanoparticles was diluted 300-fold in 1×TBS and imaged over a layer of continuous carbon supported by nitro-cellulose on a 400-mesh copper grid. The grids were prepared by applying 30 of sample suspension to a cleaned grid, blotting away with filter paper, and immediately stained with uranyl formate. Electron microscopy was performed using an FEI Tecnai T12 electron microscope equipped with an FEI Eagle 4k×4K CCD camera. High magnification images were acquired at magnification of 67,000 (0.16 nm/pixel). The images were acquired at a nominal underfocus of −1.9 μm to −0.8 μm and electron doses of ~30 e−/Å$^2$. Individual particles in the 67,000× high magnification images were selected using automated picking protocols (see Lander, G. C., et al., J Struct Biol, 166(1):95-102 (2009)). A reference-free alignment strategy was used based on the XMIPP processing package (see Sorzano, C. O., et al., J Struct Biol 148(2): p. 194-204 (2004)). Algorithms in this package align the selected particles and sort them into self-similar groups or classes.

The ferritin nanoparticle appeared as a strong circular density with a hollow center in the middle (FIG. 2D). Each nanoparticle was surrounded by numerous, short, uniform spikes of OspA that appear slightly oblong in shape. The particles have an overall diameter ranging from ~194-220 Å, with the ferritin core of 125 Å diameter. The spikes extended uniformly in size, shape and orientation from the particle surface up to 45 Å in length. The OspA spikes were ~30 Å in width and tapered to minimal density at the glycine-serine linker of ferritin.

Figure 5A:
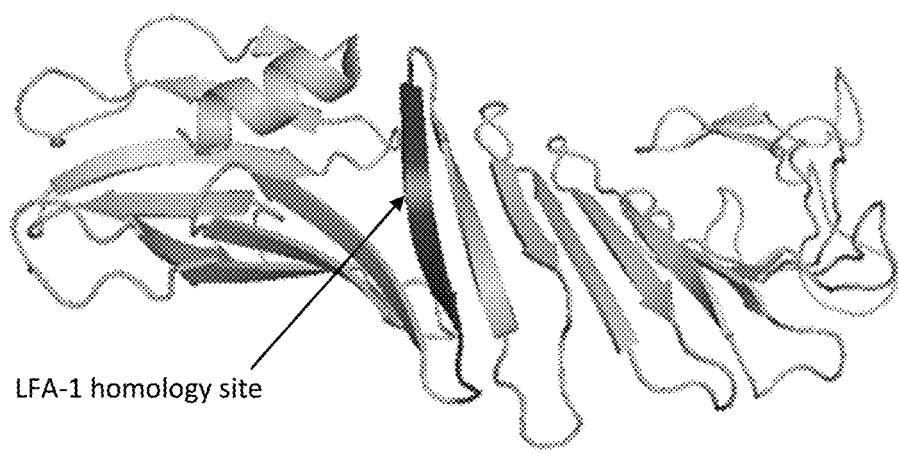
Figures 5C, 5D:
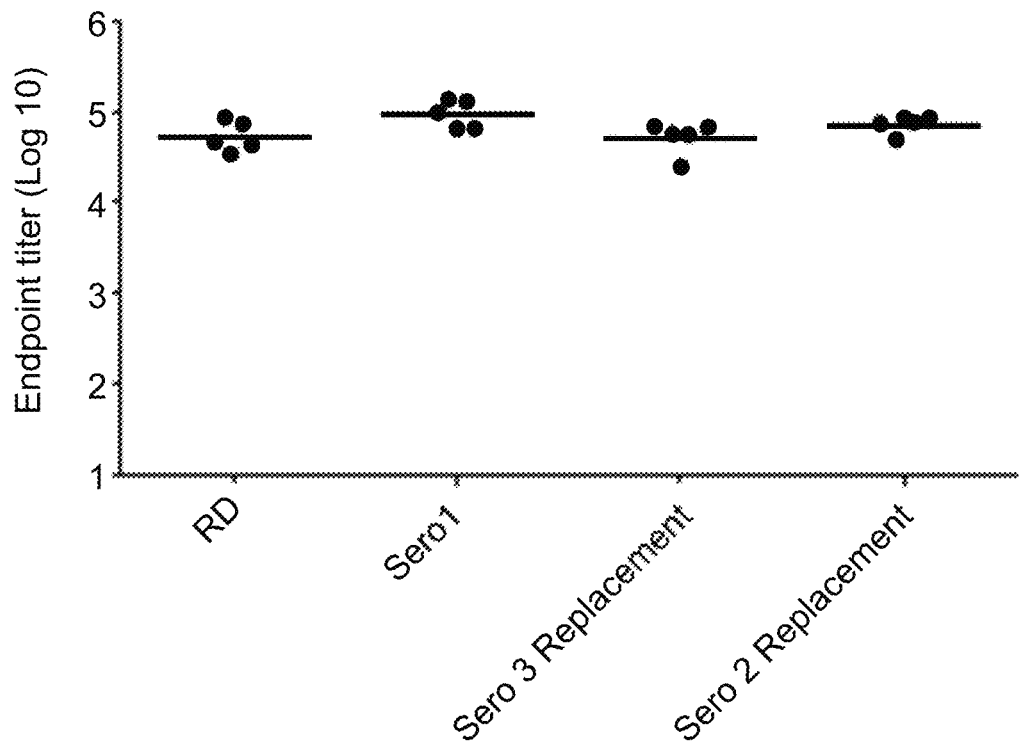

When the LYMErix™ vaccine was discontinued in 2002, the concern was raised that the vaccine contained an epitope (amino acids 165-173 of SEQ ID NO: 83) with homology to a nonapeptide segment (SEQ ID NO: 78) from the human leukocyte function-associated antigen-1 (hLFA-1, see Gross, D. M., et al., Science 281(5377): p. 703-6 (1998)) (FIG. 5A). Amino acids 165-173 of SEQ ID NO: 83 are referred to as the hLFA-1 homology site. OspA serotype 1 is the only serotype that contains this sequence homology (FIG. 5B). To avoid any potential concerns related to this sequence, the hLFA-1 homology site was replaced with either the corresponding OspA serotype 2 (SEQ ID NO: 79) or serotype 3 (SEQ ID NO: 80) nonapeptide sequences, or point substitutions were introduced that reduced similarity to hLFA-1 and were intended to prevent the generation of antibodies that bind to hLFA-1 (RD2, SEQ ID NO: 81) (FIG. 5C). For the point substitutions, surface-exposed amino acids were substituted to reduce similarity to hLFA-1 while avoiding or minimizing destabilization of the β-sheet structure.

The immunogenicity of the hLFA-1 nanoparticles with a modified hLFA-1 homology site was tested in mice to compare the immune response relative to an OspA-ferritin nanoparticle without such modification (FIG. 5D). The antibody titers elicited by the nanoparticles with a modified hLFA-1 homology site were robust and not significantly different from the nanoparticles with an unmodified hLFA-1 homology site.

2. Characterization of Immunogenicity of OspA-Ferritin Nanoparticles

To assess the immunogenicity of OspA-ferritin nanoparticles, C3H mice were immunized twice with serotype 1 OspA-ferritin nanoparticles in the presence of Ribi adjuvant or RECOMBITEK® Lyme (liquid suspension of purified Outer surface protein A (OspA) of *Borrelia burgdorferi*), a canine vaccine in which the OspA is full-length, lipidated, recombinant, and of serotype 1 (FIG. 4). C3H/HeN mice were vaccinated intramuscularly at week zero and week 4. ELISAs were run on serum from 2 weeks post $2^{nd}$ dose. Ribi (Sigma adjuvant system Cat #56322-1v1) was resuspended in 1 ml of PBS and vortexed for 1 minute and then added in equal volume to antigen prior to immunization.

The antibody response was determined using an enzyme-linked immunosorbent assay (ELISA) to recombinant OspA. Briefly, 96-well plates were coated with 1 μg/ml of OspA-His diluted in PBS and incubated overnight at 4° C. The OspA-His was removed and the plates were blocked with 5% skim milk dissolved in PBST. After removing the blocking reagent, the primary serum samples were added after being serially diluted in PBST. The primary samples were added in equal volume to blocking solution for a final 50% blocking solution concentration. After a 1-hour incubation, the plates were washed with PBST and incubated with Goat anti-mouse IgG, HRP-linked secondary antibody (1:5,000 dilution in blocking solution) for 1 hour at room temperature. The secondary antibody was aspirated and washed and the plates were incubated with Sure Blue TMB peroxidase substrate (KPL, Gaithersburg, Md.) followed by equal volume of stop solution (0.5 N sulfuric acid). Absorbance was measured at 450 nm.

Immunization with OspA-ferritin induced endpoint titers 4.4-fold higher than RECOMBITEK® Lyme at week six ($p<0.001$). The antibody titer at week 25 is also significantly higher than RECOMBITEK® Lyme ($p<0.005$) (FIG. 4).

3. Glycosylation Mutants; Evaluation of Efficacy

To evaluate the protective efficacy of this OspA-ferritin, a challenge model was used in which immunized or control mice were infected by ticks carrying *B. burgdorferi* (see Rosa, P. A., et al. Nat Rev Microbiol 3(2): p. 129-43 (2005)).

C3H/HeN mice were vaccinated intramuscularly with 1 μg of either OspA-ferritin nanoparticle mixed with AddaVax™ 1:1 or 1 μg of ferritin nanoparticle. Mice were vaccinated at week zero and week 4. A serotype 1 OspA-ferritin nanoparticle with rationally designed modifications to the hLFA-1 homology site and modifications to remove all potential N-glycosylation sites (SEQ ID NO: 53) was used to immunize mice since natural bacterially expressed OspA is not glycosylated at these positions. The sequence contained the following N>Q substitutions to prevent glycosylation: N71Q, N190Q, N202Q, and N251Q. Its immunogenicity was similar to the glycosylated nanoparticle (FIG. 13).

Glycosylation mutants of OspA-ferritin were also tested when the glycosylation site serine/threonines were mutated to an alanine (SEQ ID NO: 63). Both this construct and the N>Q construct discussed above gave a strong immune response as compared to the OspA-ferritin with wild-type glycosylation sites (SEQ ID NO: 52) and were superior to the RECOMBITEK® Lyme control (FIG. 14).

In a further experiment to evaluate the protective efficacy of OspA-ferritin nanoparticles in a tick challenge model, *Ixodes scapularis* tick larvae were obtained from National Tick Research and Education Center, Oklahoma State University (Stillwater, Okla.). *B. burgdorferi*-infected nymphs were generated by allowing uninfected larvae to feed to repletion on *B. burgdorferi* strain N40-infected SCID mice. The engorged larvae were collected and allowed to molt into nymphs in 4-6 weeks at room temperature and high relative humidity. Prevalence of *B. burgdorferi* infection in fed larvae was determined by culture of a portion of the recovered ticks from each batch.

Mice were immunized twice with 1 μg doses of OspA-ferritin (SEQ ID NO: 53) with AddaVax™ adjuvant or control ferritin at week 0 and week 4, and a comparison group was immunized in parallel with RECOMBITEK® Lyme. Mice were challenged at week 6 (i.e., 2 weeks after the second vaccination dose), by allowing 5 to 6 *B. burgdorferi* infected nymphal ticks to feed to repletion. The fed nymphs were collected and assayed for *B. burgdorferi* infection by culture in BSK media. Two weeks after challenge, the mice were sacrificed and assayed for *B. burgdorferi* infection by culture of the ear, ankle and heart culture. Presence of *B. burgdorferi* was determined by observing the cultures by dark field microscopy. A mouse was defined as infected with *B. burgdorferi* if one or more organ cultures were found positive by darkfield microscopy. Negative cultures were also tested by PCR specific to *B. burgdorferi*.

Mice were sacrificed two weeks later. Tissue samples from the heart, ankle and ear were cultured in BSK media with antibiotics for *B. burgdorferi* for 6 wks. Negative samples were tested by PCR for the presence of *B. burgdorferi*. All negative cultures were also PCR negative. Protection was calculated as a percentage of uninfected mice.

The composition comprising OspA-ferritin and AddaVax™ adjuvant showed no infection (0/4) in contrast to negative control ferritin, where 4 of 5 animals were infected (Table 2; p<0.01).

TABLE 2

Protective efficacy of OspA-ferritin nanoparticles

| Antigen | Mice/group | # mice infected | % Infected |
|---|---|---|---|
| Control particle | 5 | 4 | 80 |
| OspA-ferritin + AddaVax ™ | 4 | 0 | 0 |
| RECOMBITEK ® Lyme | 4 | 0 | 0 |

Figure 6A:
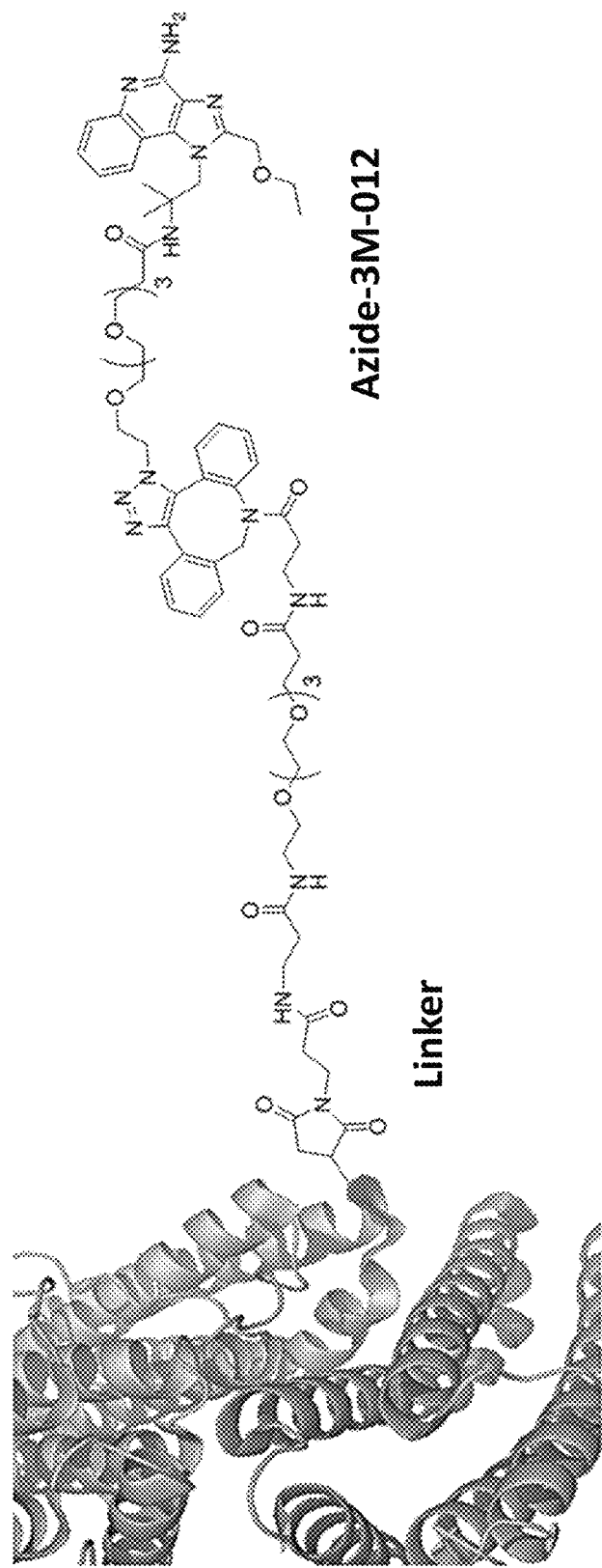
FIGS. 6A-6B present information regarding exemplary OspA-Ferritin nanoparticles conjugated to an exemplary immune-stimulatory moiety: TLR 7/8 agonist (3M-012).
Figure 7A:
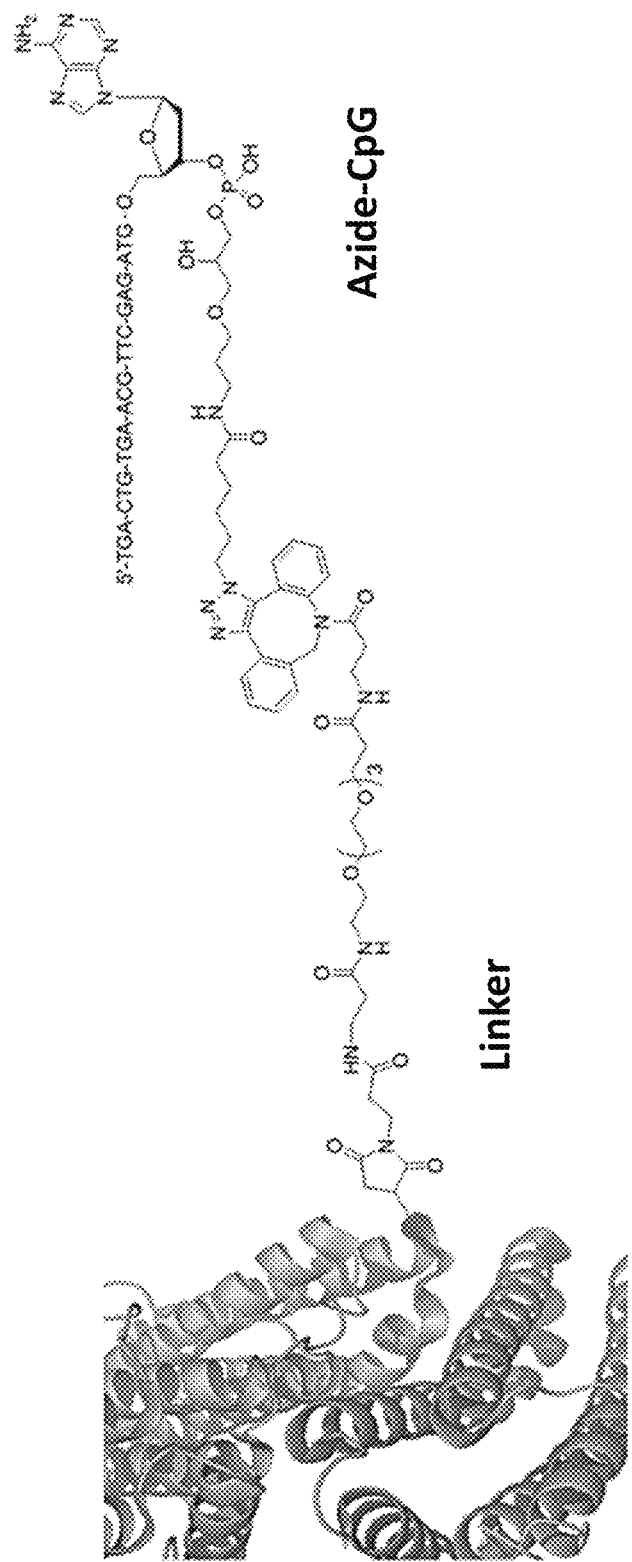
FIGS. 7A-7C present information regarding exemplary OspA-ferritin nanoparticles conjugated to an exemplary immune-stimulatory moiety: ISS-1018 CpG (SEQ ID NO: 210).

4. Evaluation of Efficacy of OspA-Ferritin Conjugated to Immune-Stimulatory Moieties A self-adjuvanting construct was generated by engineering a cysteine (S111C) on the surface of the ferritin nanoparticle that allows direct conjugation of immune-stimulatory moieties such as TLR agonists (FIG. 6A) or CpG (SEQ ID NO: 210; ISS-1018, FIG. 7A) through click chemistry. The procedure for direct conjugation was as follows: Mammalian produced material was reduced to remove cysteinylation with 10 mM TCEP (Amresco K831-10G) in 50 mM Tris pH8.5 for 1 hr. The protein was then dialyzed into 100 mM Tris pH 8, 50 mM NaCl to remove the TCEP. The *E. coli* produced material does not need to be reduced. A DBCO-PEG4-Malemide linker (Sigma-Aldrich cat #760676-5 mg) was resuspended at 5 mg/ml in DMSO. 2.5 mg of linker was added to 3 mg of protein in 10 ml volume (final DMSO concentration was 5%). Linker was incubated with the reduced protein for 30 minutes at room temperature. An Ambicon 100 MW cutoff filter concentrator was used to remove excess linker by buffer exchange (Millipore Cat #UFC910096). Azide-PEG4-3M-012 (synthesized in house) and Azide-CPG (ISS-1018 custom synthesized by IDT) were used for the final click chemistry step. 0.5 mg of adjuvant was added to 0.5 mg of protein for final conjugation step and incubated at 37° C. for 6 hours then 4° C. overnight. Excess adjuvant was removed by buffer exchange using an Ambicon 100 MW cutoff filter concentrator. Conjugation efficiency was confirmed by mass spectrometry for 3M-012 and SDS-PAGE analysis for CPG.

Figure 7B:
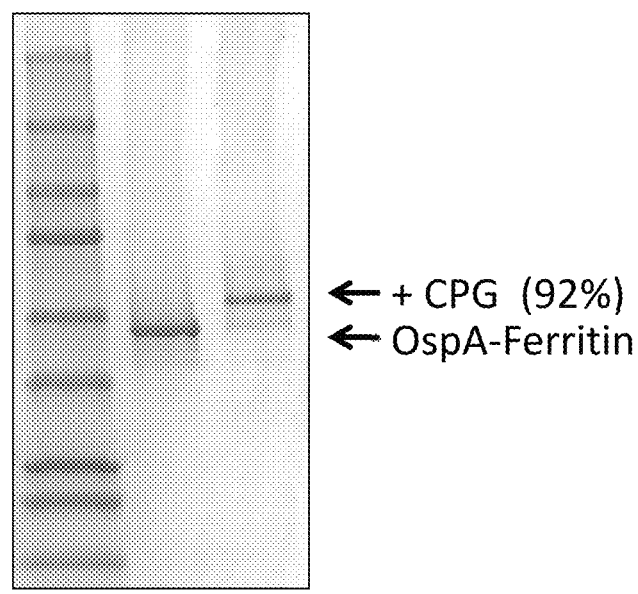
Figure 12:
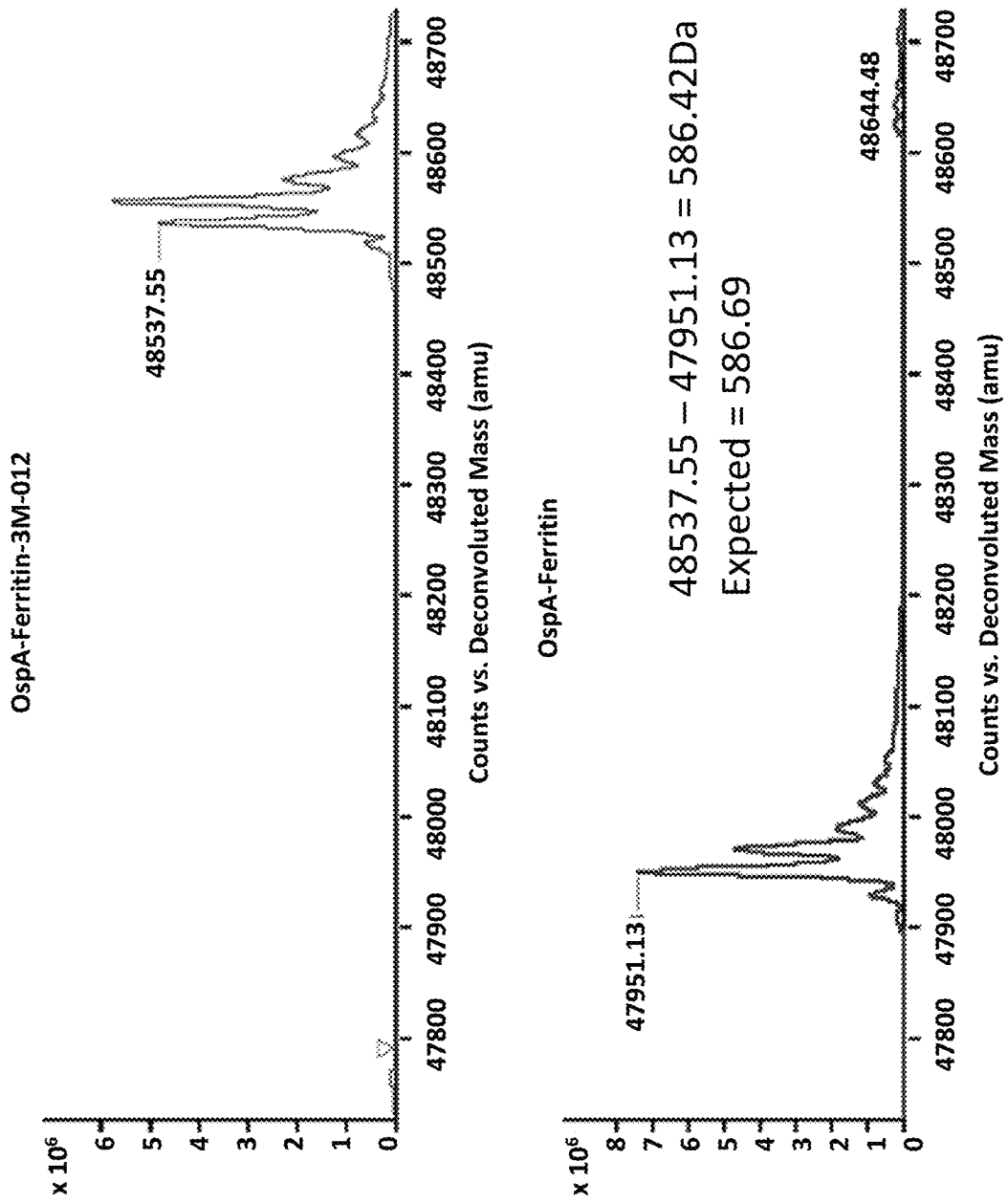
FIG. 12 shows confirmation of conjugation of OspA-ferritin nanoparticles to TLR 7/8 agonist 3M-012 by mass spectrometry. Top panel shows unconjugated, and bottom panel shows conjugated constructs. The data shows a mass shift of 586.69 Daltons, consistent with the addition of 3M-012.
Figure 13:
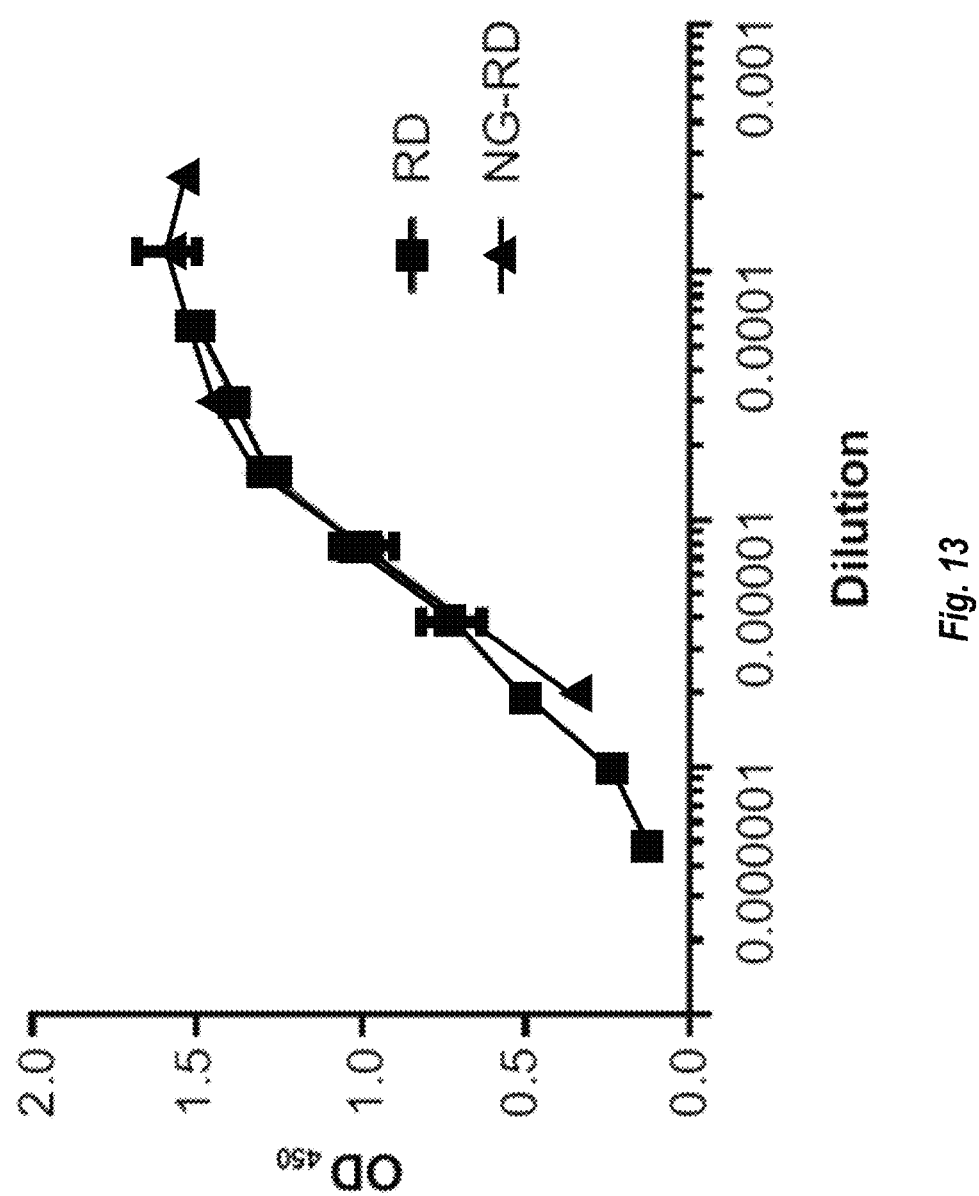
FIG. 13 shows antibody response in mice to non-glycosylated mutant OspA-ferritin (NG-RD) as compared to a glycosylated counterpart (RD) measured by ELISA across a dilution series as shown. RD=SEQ ID NO: 52. NG-RD=SEQ ID NO: 53. Mice were vaccinated with 1 μg doses at week zero and week 4.

The TLR 7/8 agonist 3M-012, which has previously been shown to increase antibody responses when directly conjugated to the HIV Gag protein (see Wille-Reece, U., et al., Proc Natl Acad Sci USA 102(42): p. 15190-4 (2005)), was used. A two-step, click chemistry approach was used to attach 3M-012 to the nanoparticle of SEQ ID NO: 53. First, the DBCO-PEG4-maleimide linker was connected to the cysteine and then a modified 3M-012 with a PEG4-Azide linker was then added through copper-free azide-alkyne cycloadditions (FIG. 6A). >99% conjugation efficiency was confirmed by mass spectrometry with a mass shift of 587 Daltons (FIG. 12). In addition to azide-3M-012, azide-CPG was also successfully added (FIG. 7A), for which conjugation could be confirmed by gel shift (FIG. 7B).

Nearly complete conjugation of ferritin was observed, suggesting that most nanoparticles carried 24 molecules of agonists. The immunogenicity of the conjugated OspA ferritin nanoparticles was then assessed in mice. C3H/HeN mice were vaccinated intramuscularly at week zero and week 4. ELISAs were run on serum from 2 weeks post $2^{nd}$ dose. Alum (Alyhydrogel '85 2%; Brenntag—Cat #21645-51-2) was added in equal volume to antigen prior to immunization. Ribi (Sigma adjuvant system Cat #56322-1v1) was resuspended in 1 ml of PBS and vortexed for 1 minute and then added in equal volume to antigen prior to immunization.

Figure 6B:
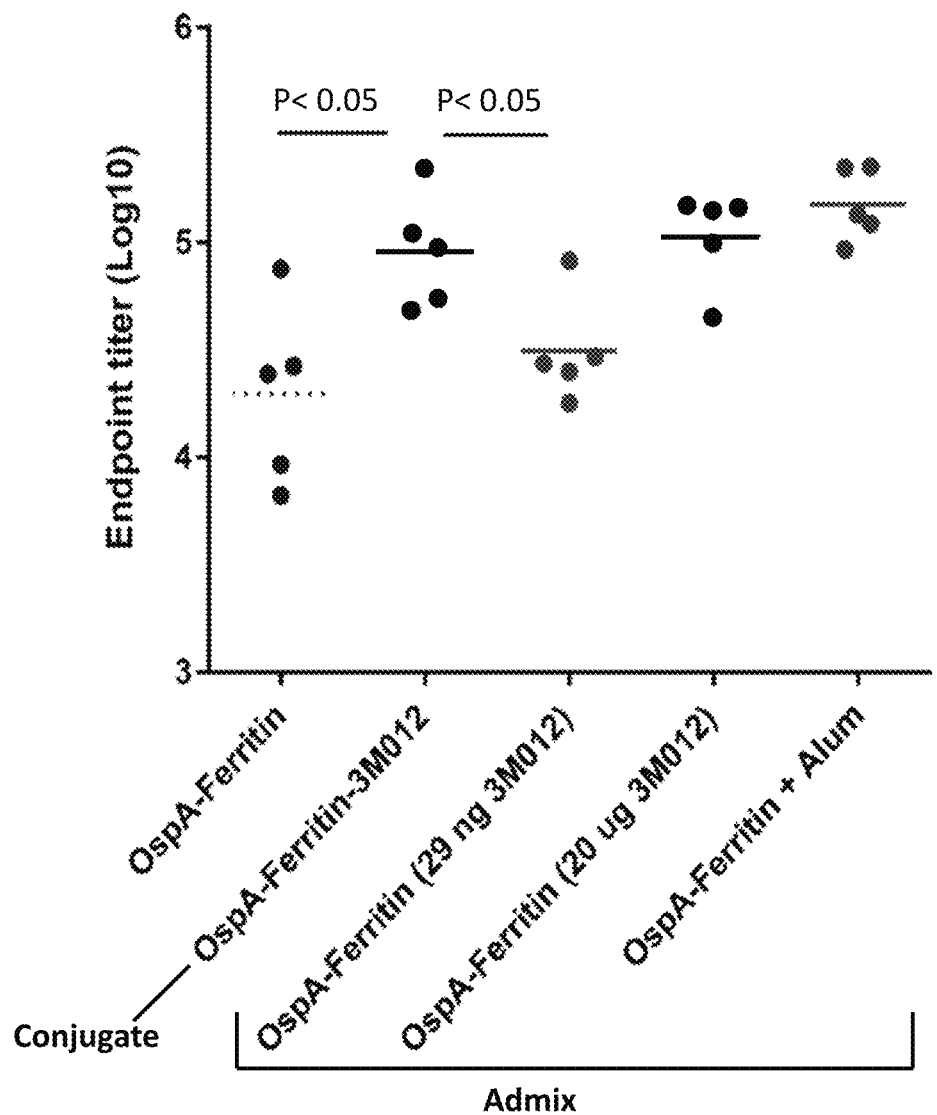

Mice immunized with 3M-012 conjugated particles produced 4.5-fold higher OspA antibody responses than the unconjugated material (FIG. 6B, p<0.05). The antibody responses elicited by 3M-012 conjugated particles were higher than the particles mixed with molar equivalent amount of 3M-012 (29 ng) and comparable to particles mixed with 1,000-fold higher dose (20 µg) of 3M-012 or a standard Alum (Alyhydrogel '85 2%; Brenntag—Cat #21645-51-2) adjuvant.

Figure 7C:
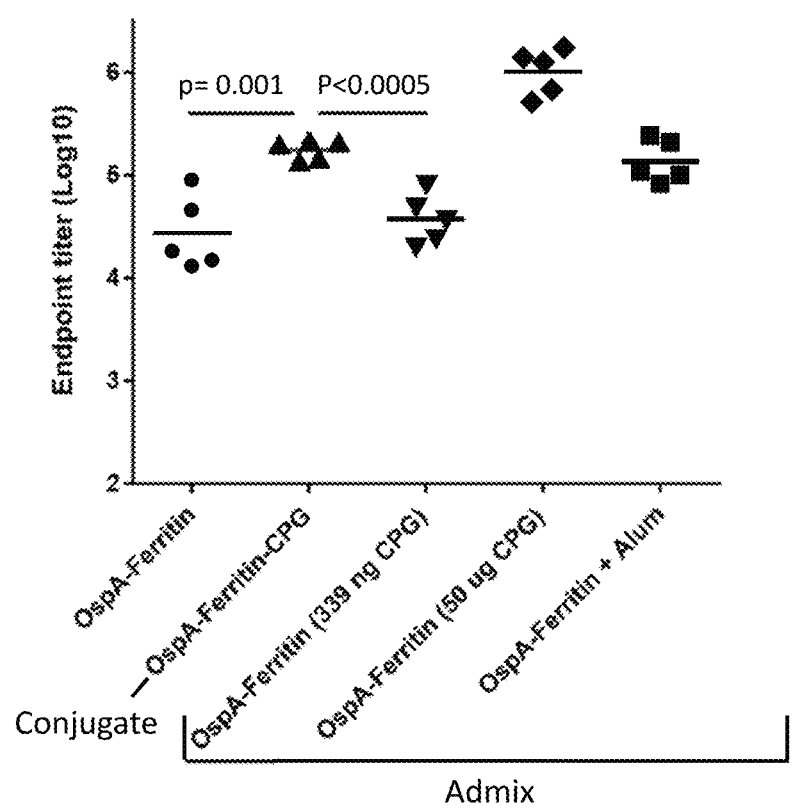
Figure 8A:
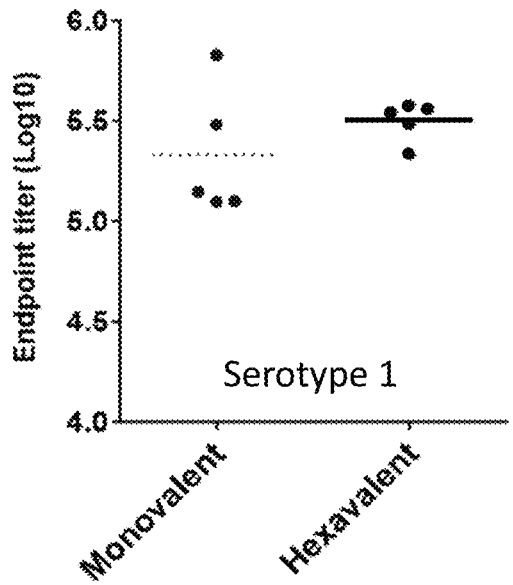
FIGS. 8A-8F compare antibody responses to serotype 1 (FIG. 8A), serotype 2 (FIG. 8B), serotype 3 (FIG. 8C), serotype 4 (FIG. 8D), serotype 5 (FIG. 8E), and serotype 7 (FIG. 8F) following administration of monovalent serotype-matched OspA-ferritin (1 μg per dose) ("Monovalent") with Alum adjuvant or a hexavalent composition comprising each of serotype 1 OspA-ferritin, serotype 2 OspA-ferritin, serotype 3 OspA-ferritin, serotype 4 OspA-ferritin, serotype 5 OspA-ferritin, and serotype 7 OspA-ferritin at 1 μg each per dose with Alum adjuvant ("Hexavalent"). C3H mice (n=5) were immunized intramuscularly at weeks 0 and 4, and antibody response was assessed via endpoint titer measured by ELISA 2 weeks later. ELISA plates were coated with the specified serotype of OspA.
Figure 8B:
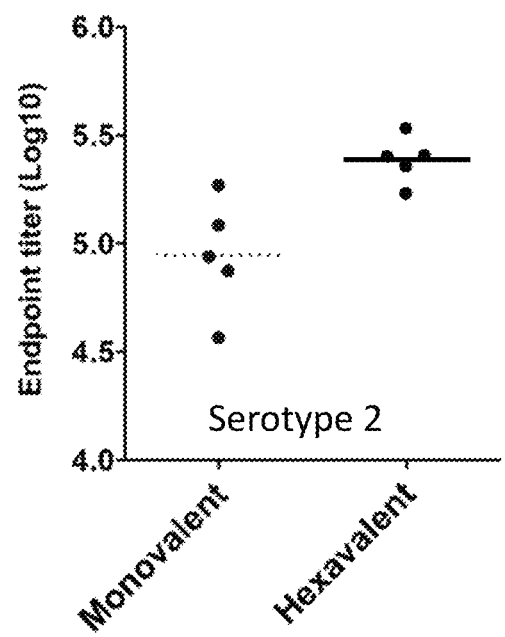
Figure 8C:
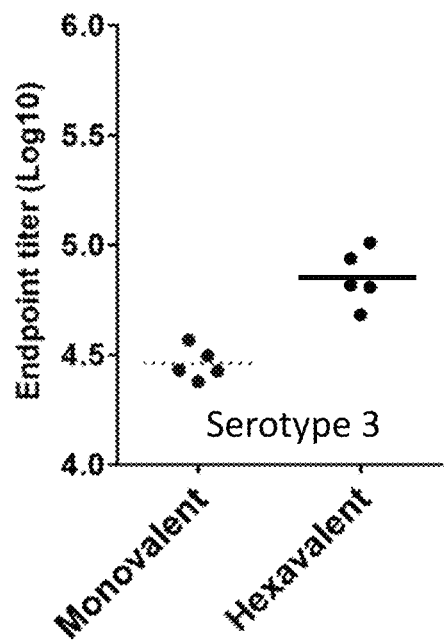
Figure 8D:
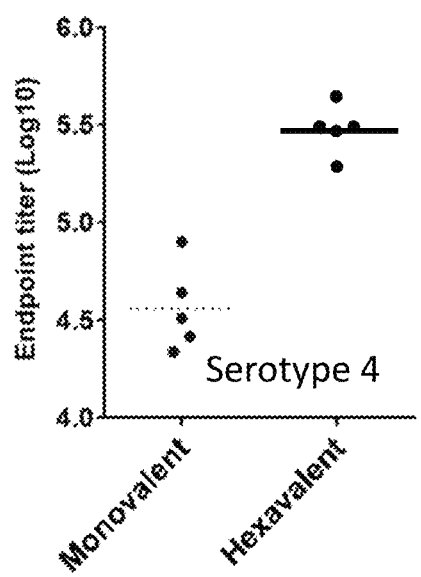
Figure 8E:
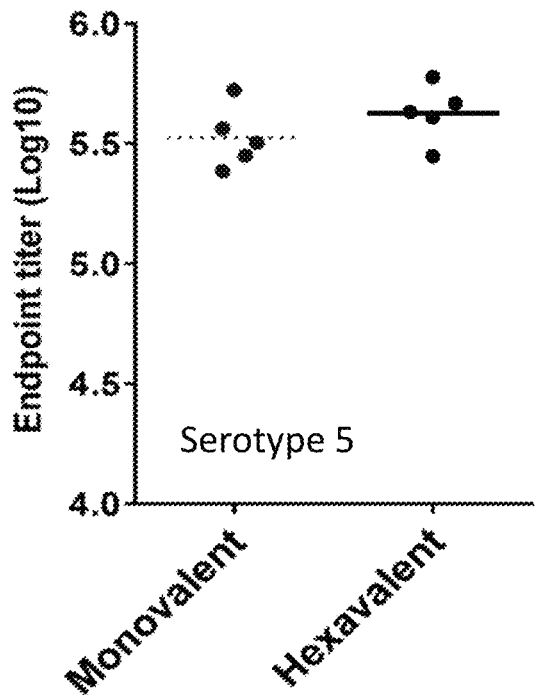
Figure 8F:
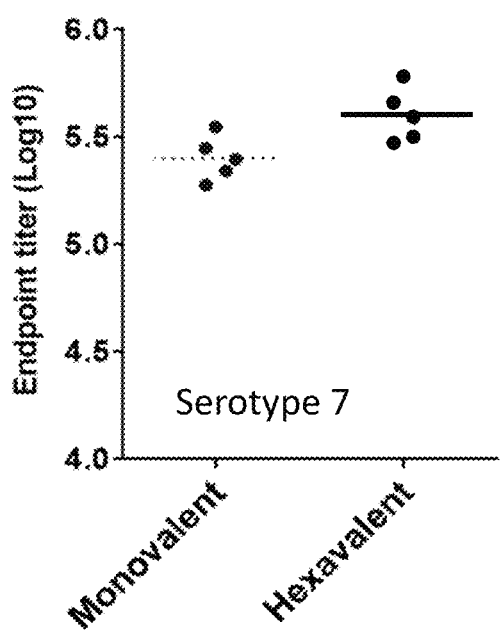
Figure 9A:
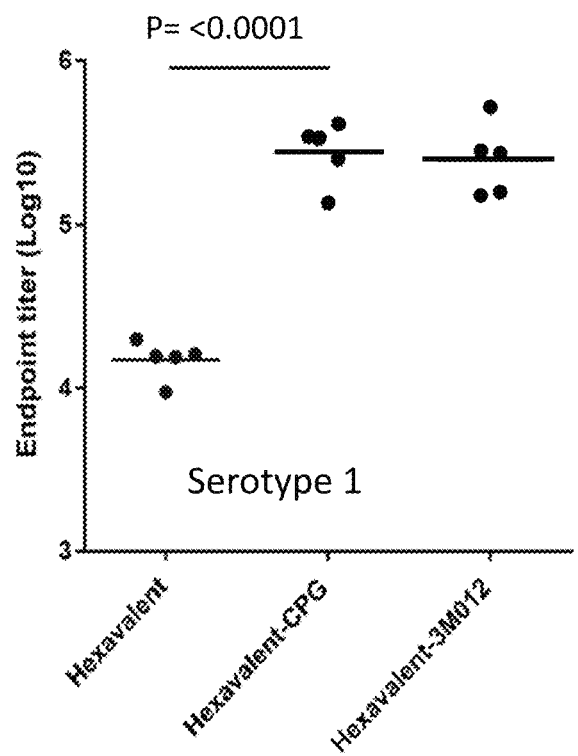
FIGS. 9A-9G show antibody responses in mice to serotype 1 (FIG. 9A), serotype 2 (FIG. 9B), serotype 3 (FIG. 9C), serotype 4 (FIG. 9D), serotype 5 (FIG. 9E), serotype 6 (FIG. 9F), and serotype 7 (FIG. 9G) observed in mice following administration of conjugated and non-conjugated hexavalent OspA-ferritin nanoparticle compositions. Hexavalent compositions comprised each of serotype 1 OspA-ferritin, serotype 2 OspA-ferritin, serotype 3 OspA-ferritin, serotype 4 OspA-ferritin, serotype 5 OspA-ferritin, and serotype 7 OspA-ferritin as described for FIGS. 8A-F except that "Hexavalent-CPG" and "Hexavalent-3M-012" indicate that nanoparticles were chemically conjugated to CPG and 3M-012 (see FIGS. 7A and 6A and accompanying description). Antibody response was assessed via endpoint titer measured by ELISA 2 weeks later. ELISA plates were coated with the specified serotype of OspA.
Figure 9B:
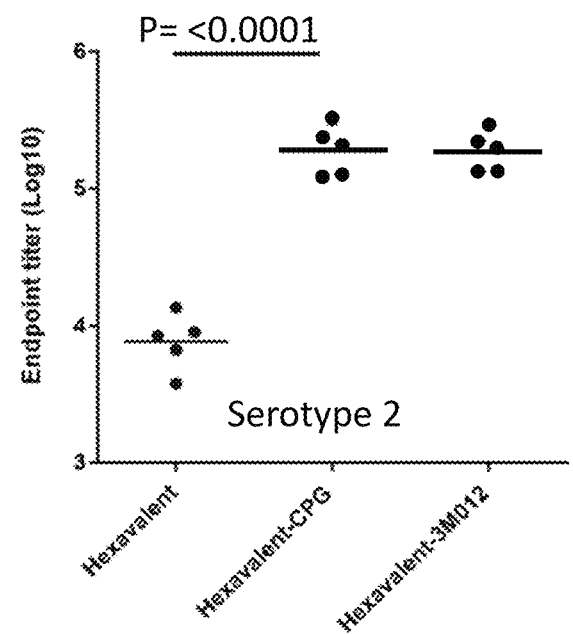
Figure 9C:
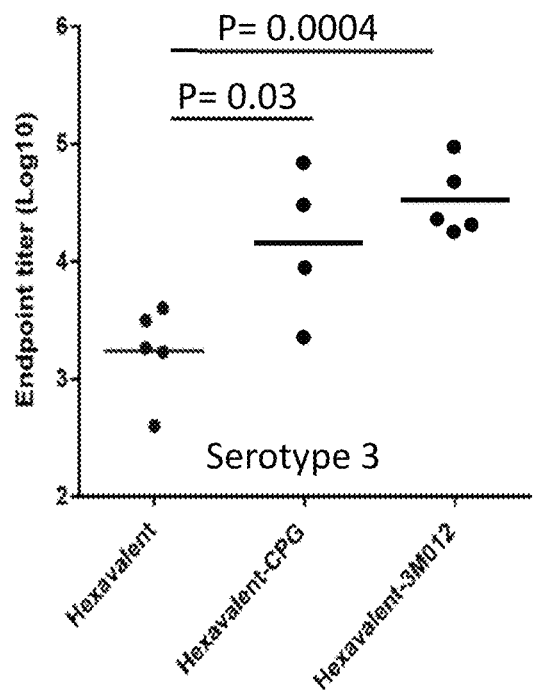
Figure 9D:
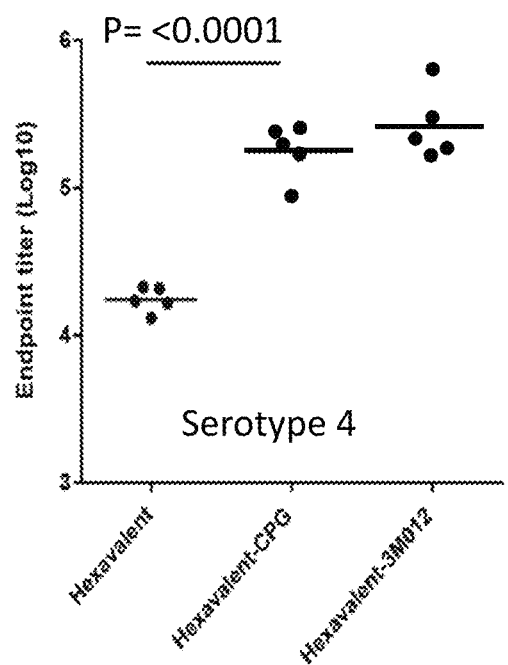
Figure 9E:
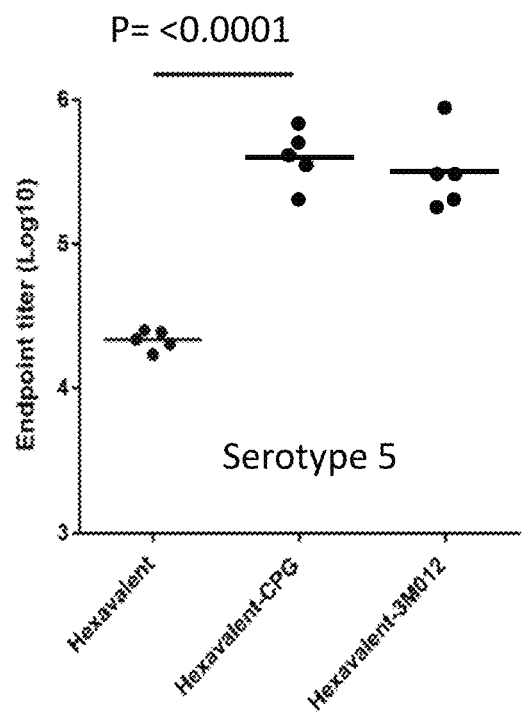
Figure 9F:
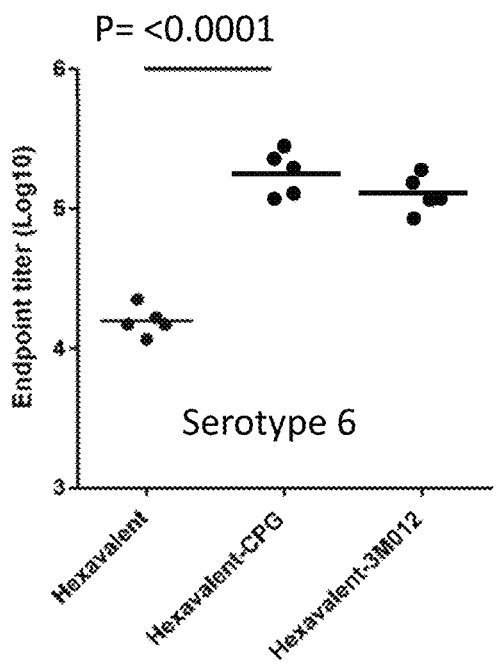
Figure 9G:
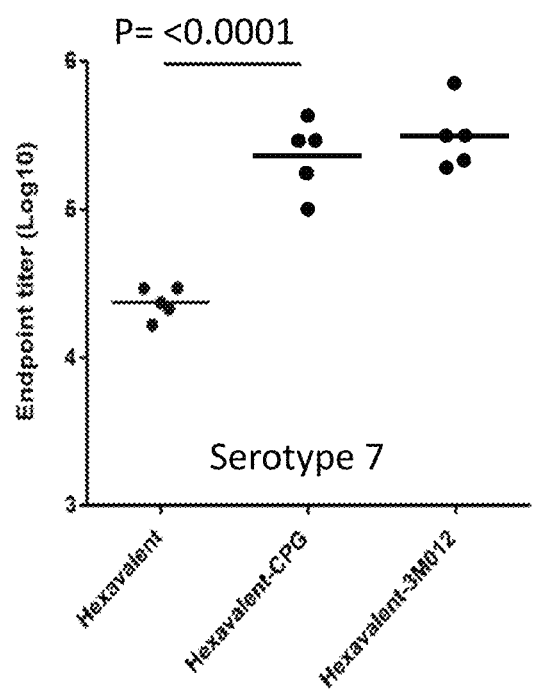
Figure 10F:
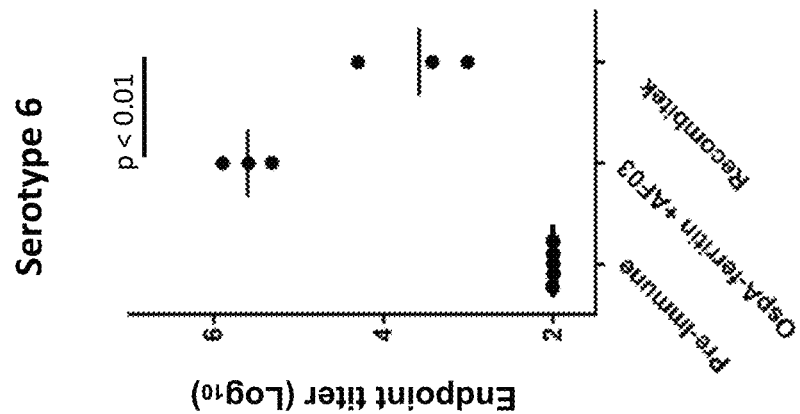
Figure 10E:
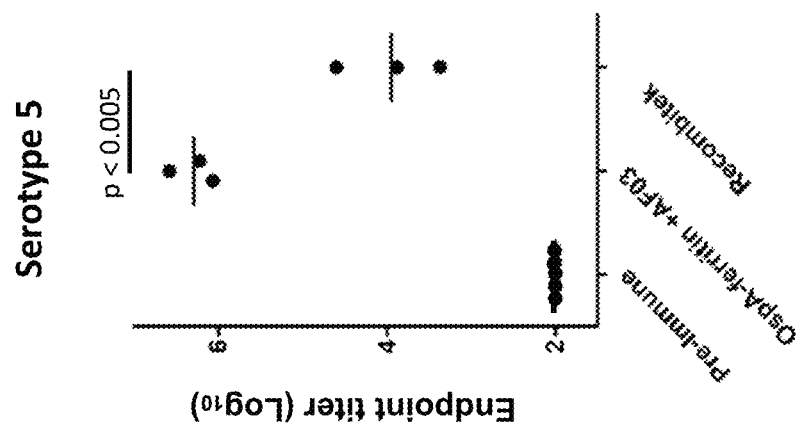
Figure 10D:
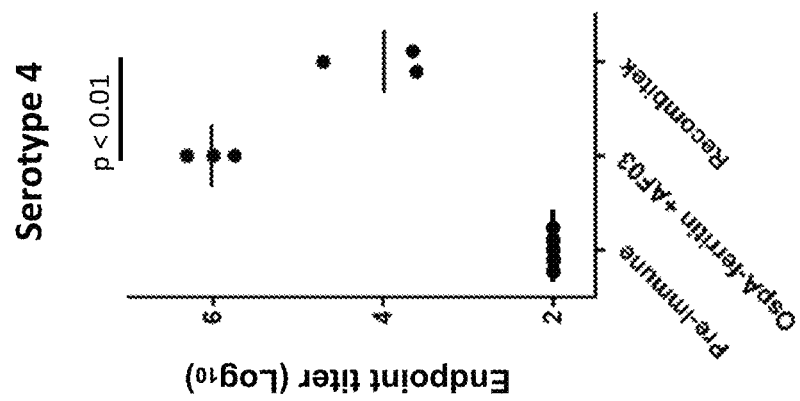
Figure 10I:
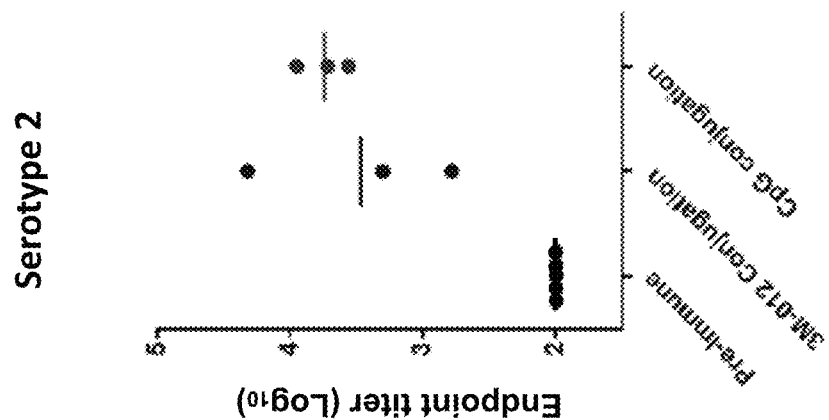
FIGS. 10H-10N show antibody responses to serotypes 1-7, respectively, in Rhesus monkeys (n=3 per group) to hexavalent OspA-ferritin nanoparticle compositions, which were as described for FIGS. 10A-G except that no AF03 adjuvant was used and nanoparticles were instead conjugated to 3M-012 or CpG (see FIGS. 6A and 7A and accompanying description). Doses were 60 μg total (10 μg each serotype). Monkeys were immunized intramuscularly at week 0 and week 6. Antibody response was analyzed 2 weeks after immunization via endpoint titer measured by ELISA. For all experiments, an ELISA plate was coated with the OspA serotype indicated in each panel.
Figure 10H:
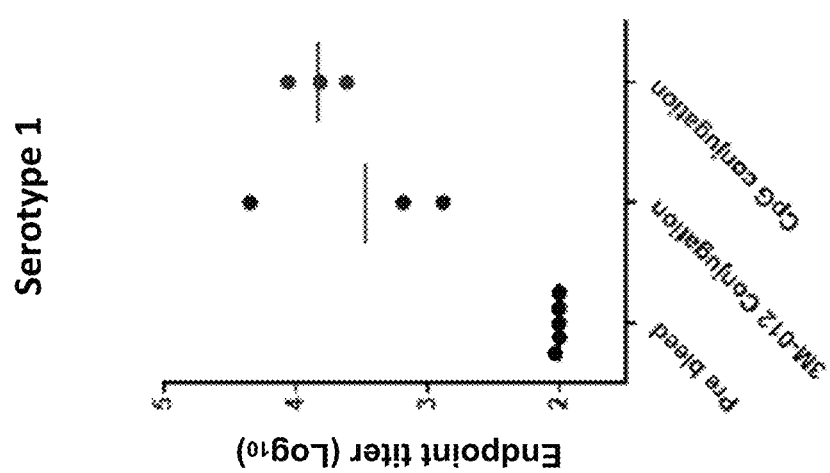
Figure 10G:
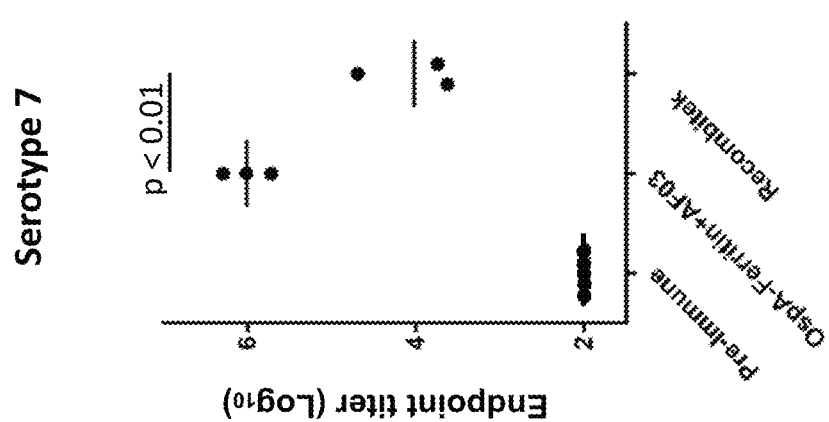
Figures 10J, 10K, 10L:
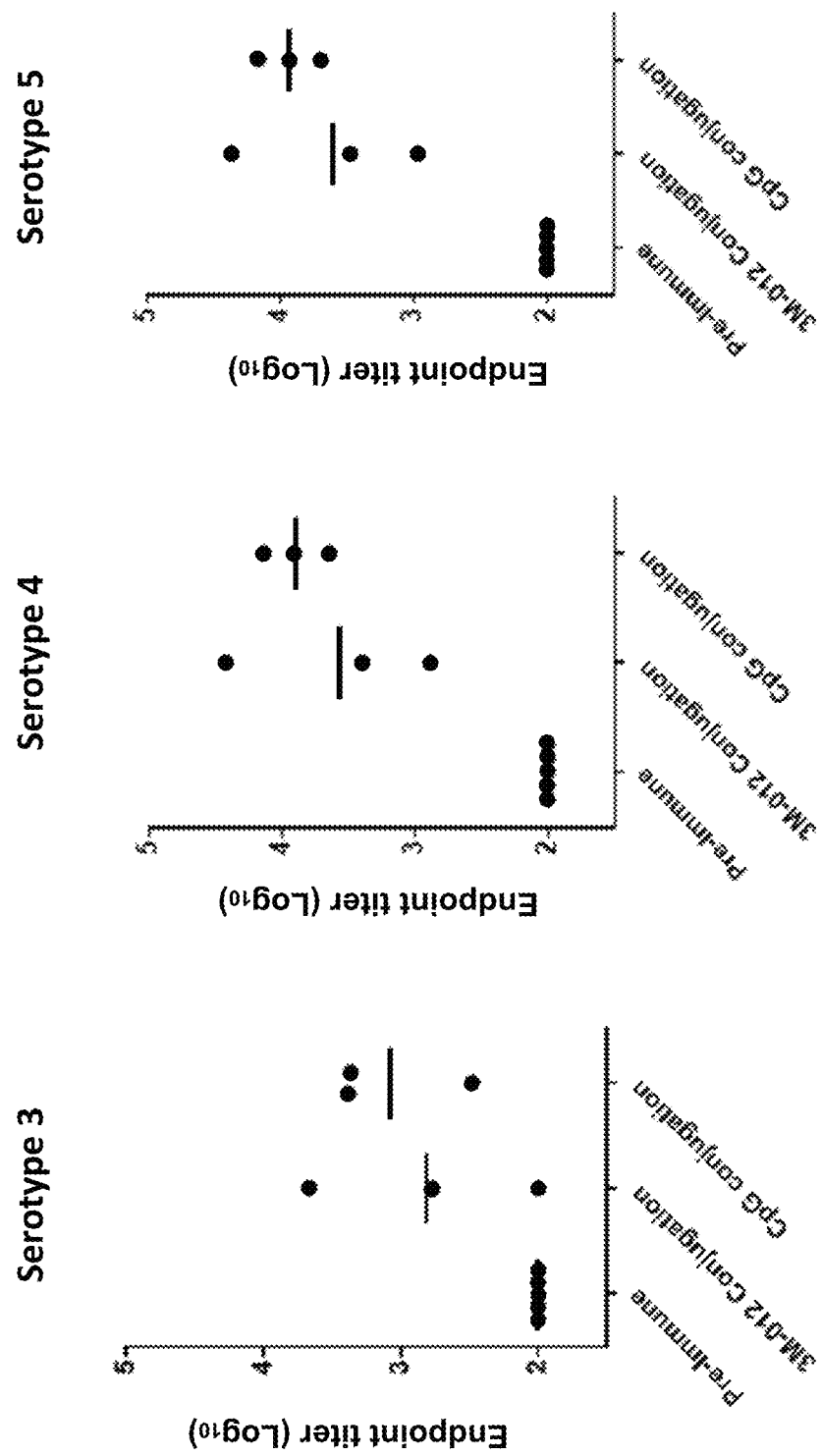
Figure 10N:
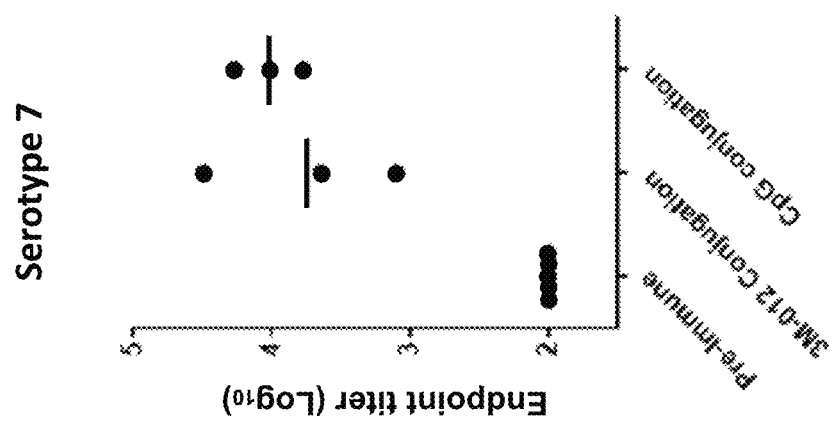
Figure 10M:
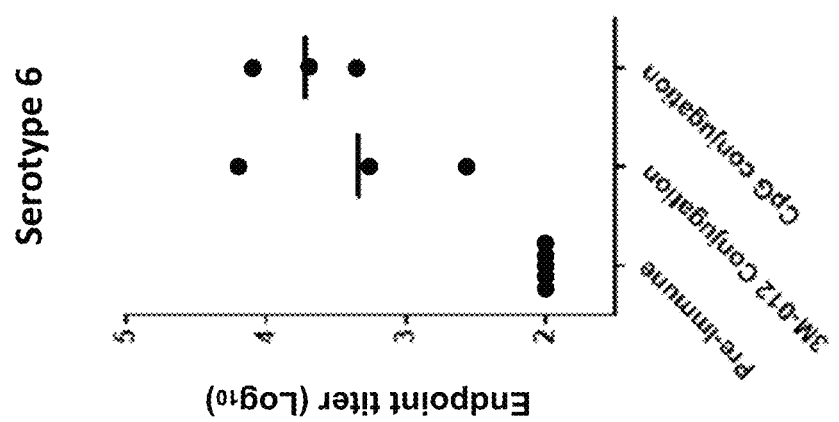

A similar enhancement of antibody production was observed with CPG-conjugated OspA-ferritin nanoparticle (SEQ ID NO: 53) with a 6.3-fold increase in the immune response compared to unconjugated particles, and a 4.7-fold increase relative to an equivalent amount of unconjugated CPG mixed with nanoparticle (FIG. 7C).

Thus, targeted delivery of adjuvant conjugated to a OspA-ferritin nanoparticle allows substantial reduction in the amount of adjuvant while stimulating an effective and specific antibody response.

Figure 3A:
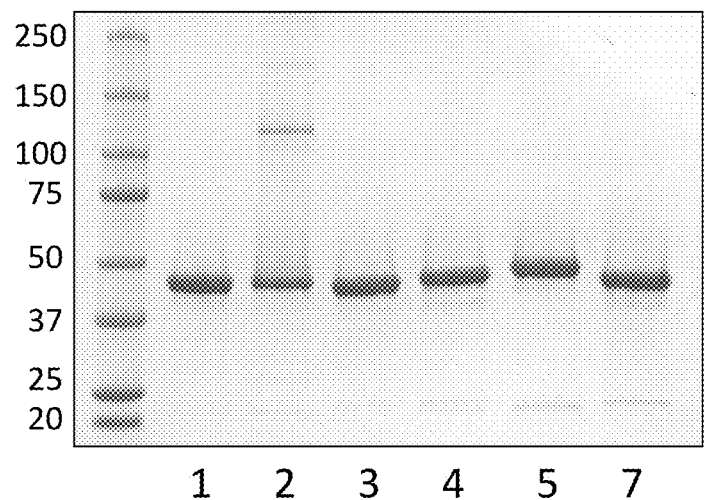
FIGS. 3A-3B show generation of alternative serotype OspA nanoparticles in *E. coli*.
Figure 3B:
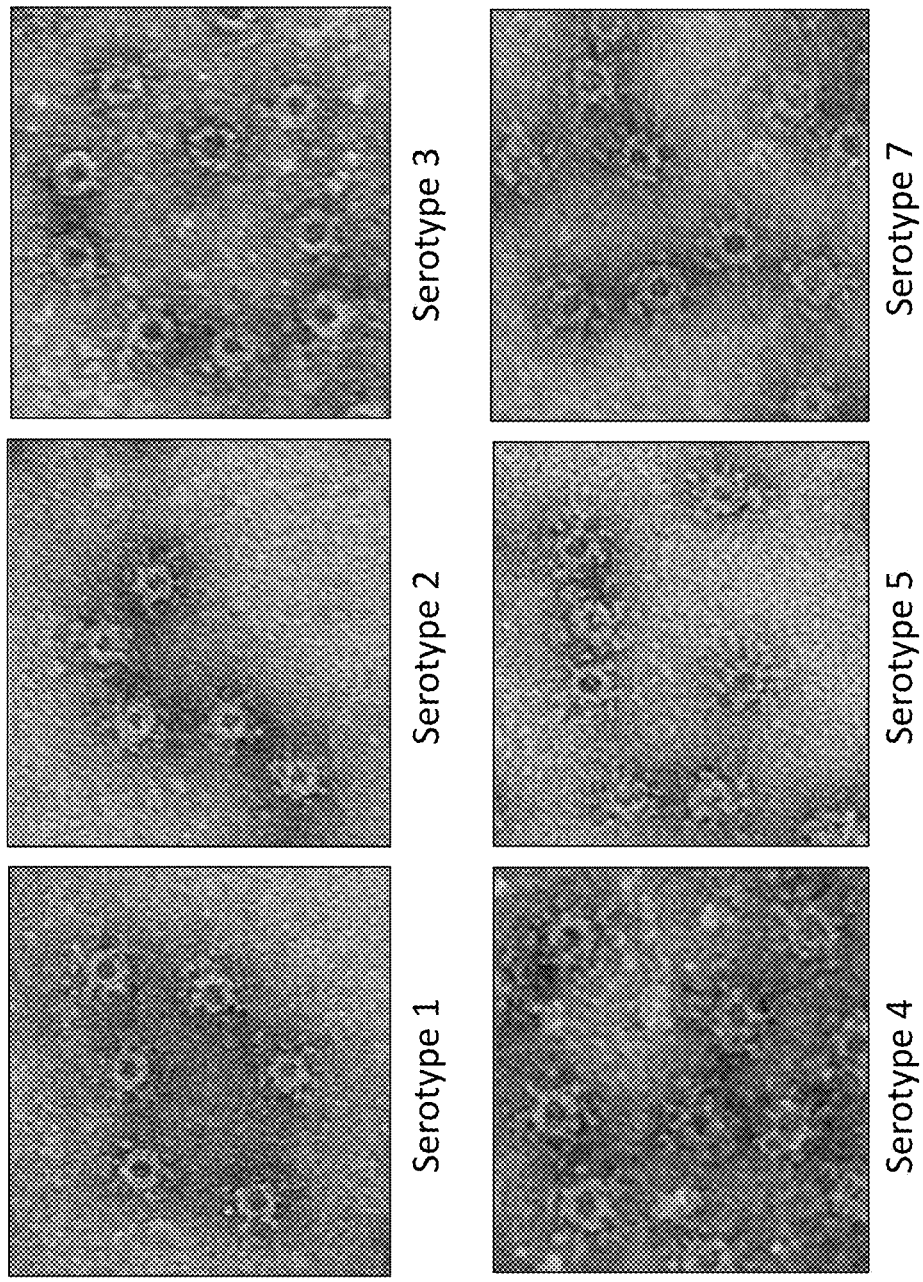
Figure 4:
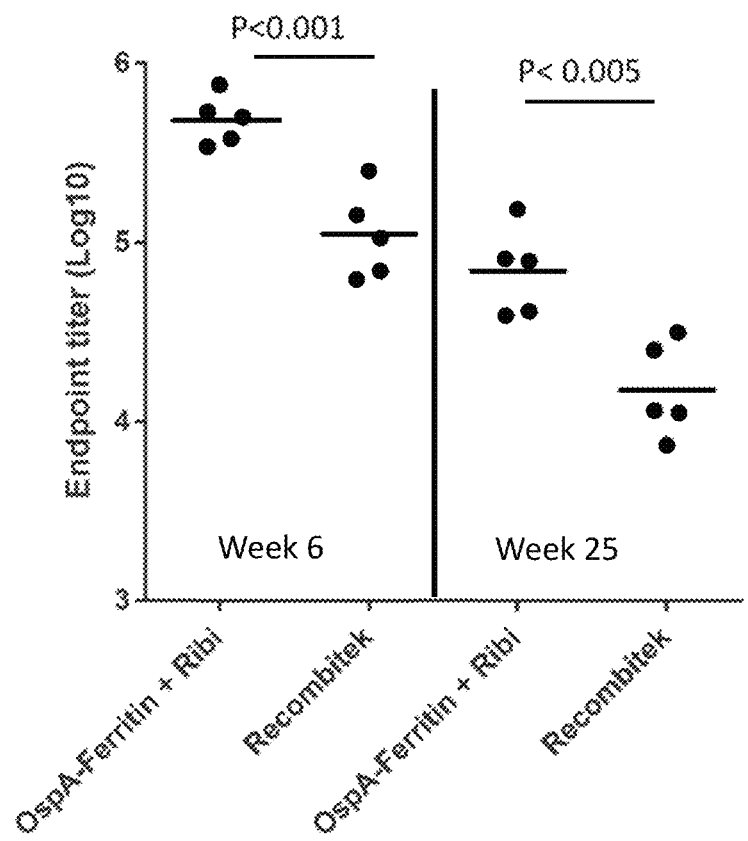
FIG. 4 shows comparison of immunogenicity and duration of exemplary Serotype 1 OspA-Ferritin nanoparticles to RECOMBITEK® Lyme (liquid suspension of purified Outer surface protein A (OspA) of *Borrelia burgdorferi*). C3H mice (n=5) were immunized intramuscularly with 1 μg of the OspA-Ferritin+Ribi adjuvant (Sigma adjuvant system Cat #S6322-1v1) or RECOMBITEK® Lyme at week 0 and week 4. Antibody response was assessed by measuring endpoint titers via ELISA 2 weeks after the 2nd immunization (week 6) and 21 weeks after $2^{nd}$ immunization (week 25) with each composition.

5. Evaluation of Immunogenicity of OspA-Ferritin Nanoparticles Comprising Different Serotypes While the serotype 1 OspA strain *B. burgdorferi* causes disease in the United States, *B. afzelii* (serotype 2), *B. garinii* (serotype 3, 5, 6, 7), and *B. bavariensis* (serotype 4) cause disease in Europe, Asia, and elsewhere. To generate a broadly cross-protective composition, OspA-ferritin nanoparticles were designed for serotypes 1, 2, 3, 4, 5, and 7. (SEQ ID NOS: 1, 5, 6, 7, 8, and 10). These particles were expressed and purified from *E. coli* using anion exchange and size exclusion chromatography (FIG. 3A). All OspA-ferritin antigenic polypeptides have the expected molecular weight of 47 kDa and DLS analysis and transmission electron microscopy also confirmed the formation of all six OspA nanoparticles (FIG. 3B).

A six-component composition was generated by combining each of serotypes 1-5 and 7 of OspA-ferritin in equimolar proportions.

The immunogenicity of this six-component composition (i.e., hexavalent) with Alum was compared in mice to the single-serotype particles (i.e., monovalent) with the same adjuvant (FIGS. 8A-8F). The monovalent composition was given at 1 µg dose, and the hexavalent composition was given at 1 µg for each serotype (total of 6 µg dose). Alum (Alyhydrogel '85 2%; Brenntag—Cat #21645-51-2) was added in equal volume to antigen prior to immunization. The six-component composition induced a robust antibody response against all six of OspA serotypes 1-5 and 7. Moreover, the response to a single serotype control was similar to the mixture, indicating a lack of interference among the six-serotype combination. An improved immune response was seen against serotype 4 with the hexavalent composition relative to the single component composition (see FIG. 8D, serotype 4).

Having established that the hexavalent composition was immunogenic, and in some cases superior to the monovalent composition, 3M-012 and CpG conjugates of each of the six OspA-ferritin nanoparticles were prepared. Two six-component conjugated compositions were created by combining the six OspA-ferritin nanoparticles conjugated to 3M-012 and, separately, by combining the six OspA-ferritin nanoparticles conjugated to CpG. The CpG-conjugated and 3M-012-conjugated hexavalent compositions showed a significant increase in antibody response in mice over the unconjugated hexavalent composition for all seven serotypes of OspA found world-wide (FIG. 9A-9G), indicating that the hexavalent formulation also conferred protection against serotype 6 even though no OspA serotype 6 polypeptide was in the composition.

Figure 25:
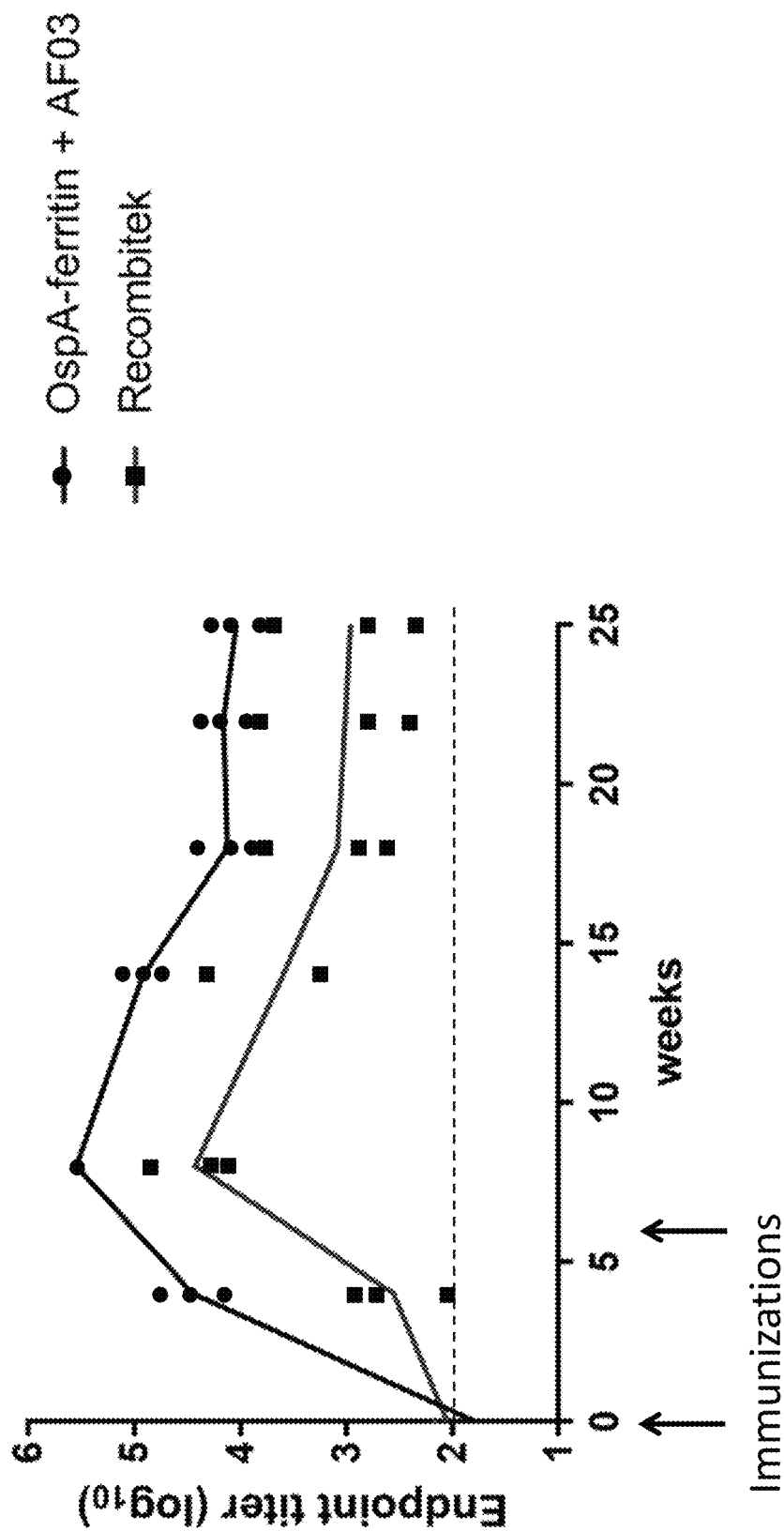
FIG. 25 shows a time course of endpoint antibody titer in Rhesus monkeys. Monkeys were immunized intramuscularly at week 0 and week 6 with either hexavalent OspA-ferritin vaccine (containing OspA of serotypes 1, 2, 3, 4, 5, and 7 in separate nanoparticles) with AF03 adjuvant or RECOMBITEK®. ELISA plate was coated with OspA serotype 1.

When tested in non-human primates (NHP [Rhesus monkeys]), the hexavalent nanoparticle composition (unconjugated) with AF03 adjuvant outperformed the RECOMBITEK® Lyme control 11 to 200-fold higher Ab titer against all seven circulating *Borrelia* serotypes (FIGS. 10A-10G). Similar to mice, hexavalent composition elicited high titer Ab response in the presence of adjuvant. The 3M-012 and CpG-conjugated compositions induced a similar response as RECOMBITEK® Lyme control in NHP (compare FIGS. 10A-G with 10H-N, respectively). Antibody titers for the hexavalent vaccine in NHP were robust out to 19 weeks after the boost dose and retained an advantage over the RECOMBITEK® Lyme control (FIG. 25).

Conjugated compositions were also tested in a tick challenge model. Mice were vaccinated with 1 μg dose of antigens at week 0 and week 4. The monovalent composition contained 1 μg of OspA-ferritin serotype 1 conjugated to 3M-012. The hexavalent composition included OspA from serotypes 1, 2, 3, 4, 5, and 7 at 1 μg each conjugated to 3M-012. Mice were challenged with 5-6 ticks infected with *Borrelia burgdorferi* N40 strain (serotype 1) for 5 days two weeks after the second immunization and sacrificed two weeks later. Tissue samples from the heart, ankle and ear were cultured in BSK media with antibiotics for *B. burgdorferi* for 6 weeks. Negative samples were tested by PCR for the presence of *B. burgdorferi*. Positive samples were positive for either culture or PCR (FIG. 11).

We additionally tested a heptavalent vaccine containing all seven serotypes in mice. Mice were immunized intramuscularly at week 0 and week 4 with heptavalent OspA-ferritin nanoparticle compositions of 1 ug each of OspA-ferritin nanoparticles corresponding to OspA serotypes 1-7 (total 7 ug) adjuvanted with either alum or AF03, or with RECOMBITEK® Lyme (1 μg dose). Antibody response was analyzed 2 weeks after immunization via endpoint titer measured by ELISA. A robust immune response was demonstrated as compared to RECOMBITEK® (FIG. 24A-G).

Thus, OspA-ferritin nanoparticles elicited high titer antibody responses to the seven major serotypes. Further, a seven-component Lyme vaccine candidate offers the potential to control the global spread of Lyme disease.

6. Characterization of OspA-Ferritin Constructs with Different Flexible Linkers

Several different linkers were tested to provide flexibility between OspA and ferritin. The constructs ranged from one to five -GGGS (SEQ ID NO: 226)-sequences. The various linker constructs were purified and formed nanoparticles of uniform size.

Figure 15A:
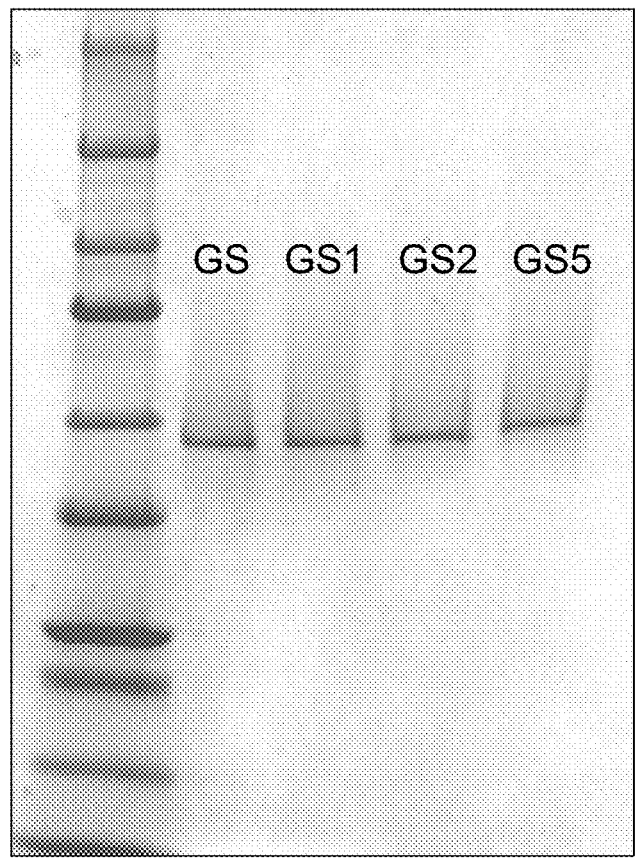
FIGS. 15A-15E show purification and characterization of OspA constructs comprising different linkers (GS, Gly-Ser linker; GS1, Gly-Gly-Gly-Ser linker (SEQ ID NO: 226); GS2, SEQ ID NO: 91 linker; GS5, SEQ ID NO: 92 linker; construct sequences were SEQ ID NOs: 53 and 60-62, respectively).
Figure 15B:
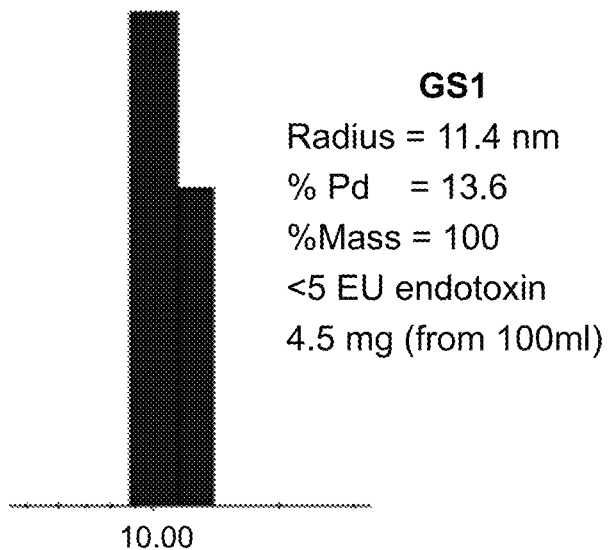
Figure 15C:
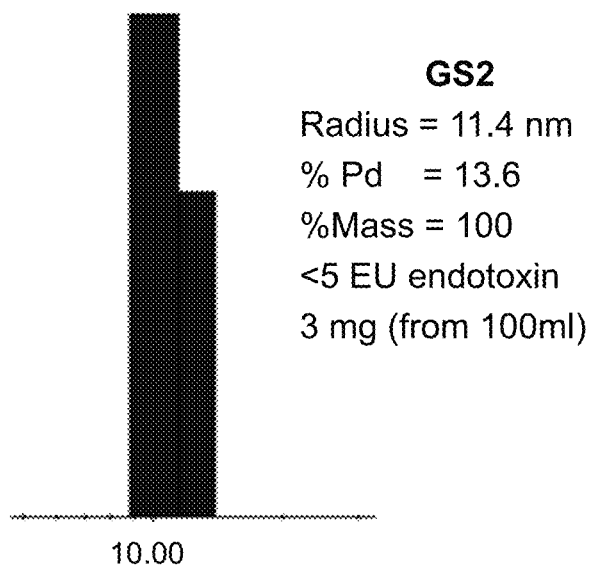
Figure 15D:
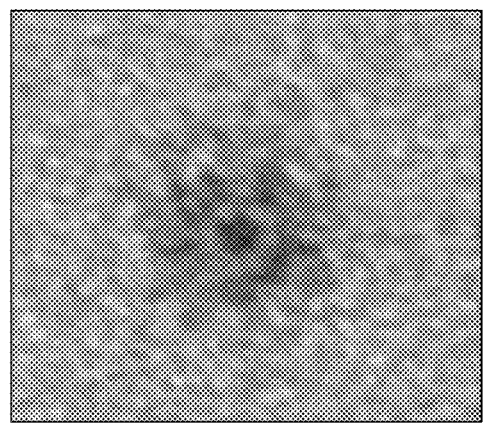
Figure 15E:
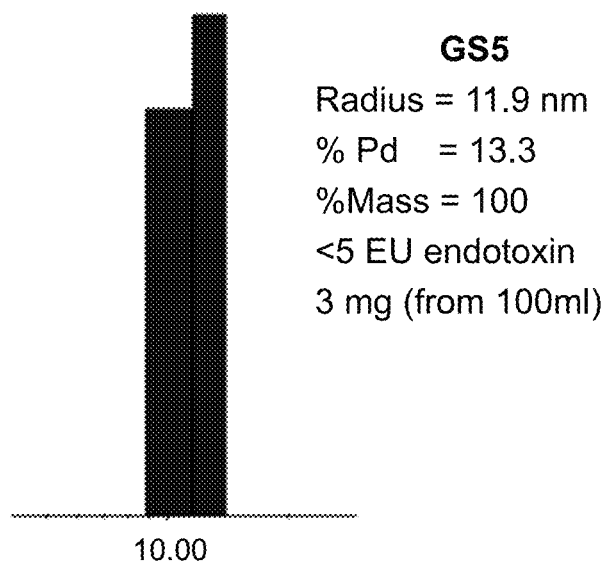

OspA-linker-ferritin constructs comprising GS1 (GGGS (SEQ ID NO: 226)), GS2 (SEQ ID NO: 91), or GS5 (SEQ ID NO: 92) linkers could all be expressed (FIG. 15A) and showed consistent DLS (FIGS. 15B, 15C, and 15E) and EM (FIG. 15D) profiles.

Figure 16:
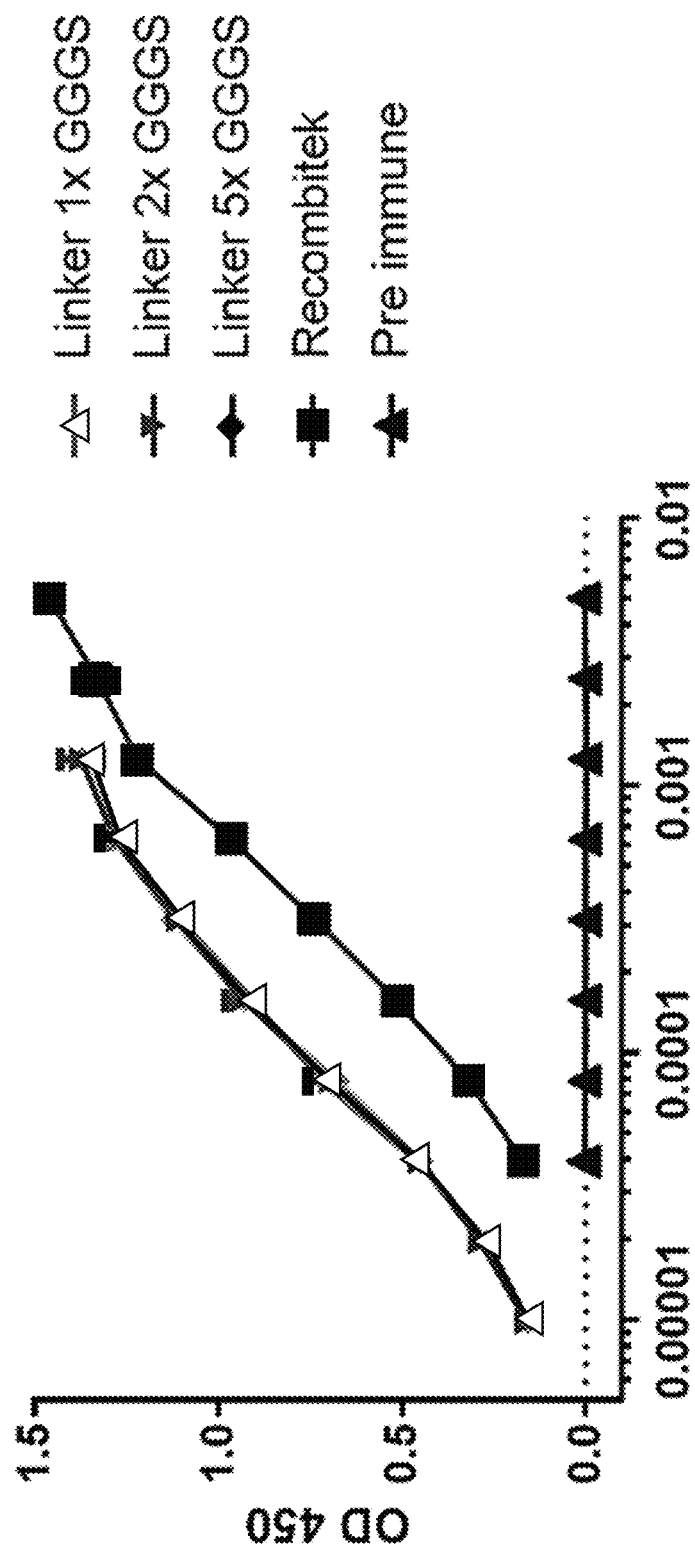
FIG. 16 shows antibody response in mice to OspA-ferritin constructs comprising different linkers (Linker 1× GGGS (SEQ ID NO: 226) construct, SEQ ID NO: 60; Linker 2× GGGS (SEQ ID NO: 91) construct, SEQ ID NO: 61; Linker 5× GGGS (SEQ ID NO: 92) construct, SEQ ID NO: 62) compared to RECOMBITEK® Lyme and negative (Pre-immune) controls, measured by ELISA across a dilution series as shown.

Further, the different -GGGS (SEQ ID NO: 226)-linker constructs (Linker 1× GGGS (SEQ ID NO: 226) [SEQ ID NO: 60], Linker 2× GGGS (SEQ ID NO: 91) [SEQ ID NO: 61], and Linker 5× GGGS (SEQ ID NO: 92) [SEQ ID NO: 62]) all showed strong immune responses in C3H mice (FIG. 16).

7. Characterization of Lumazine Synthase OspA Nanoparticles

Figures 17A, 17C:
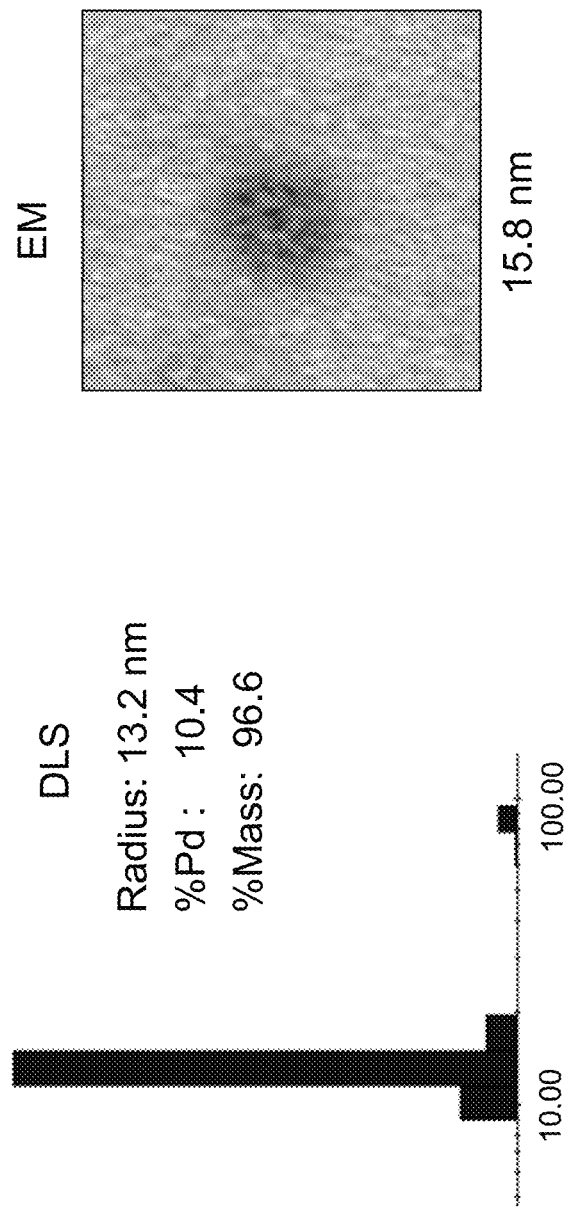
FIGS. 17A-17C show characterization of a lumazine synthase OspA serotype 4 construct (SEQ ID NO: 18).
Figure 17B:
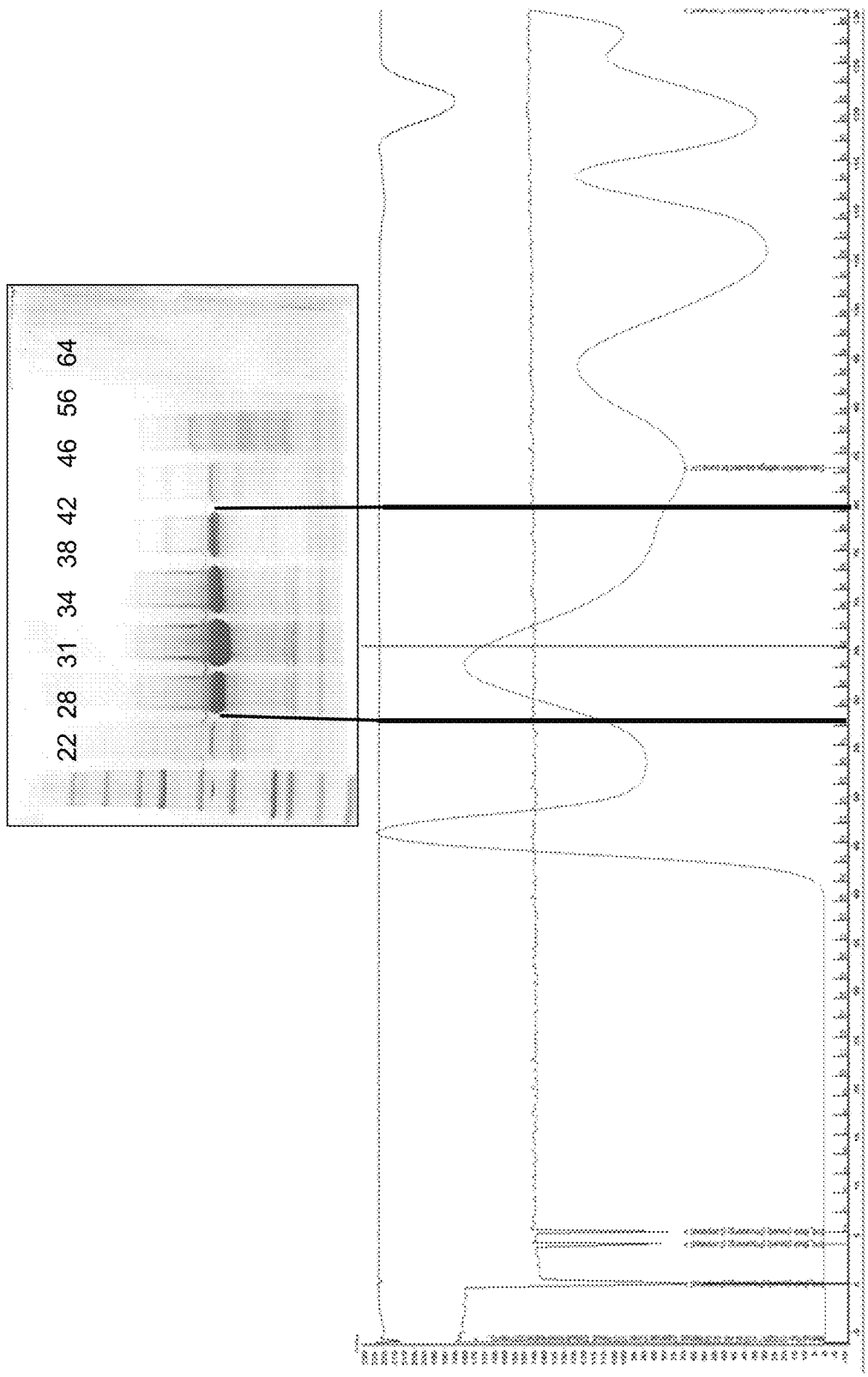
Figure 19C:
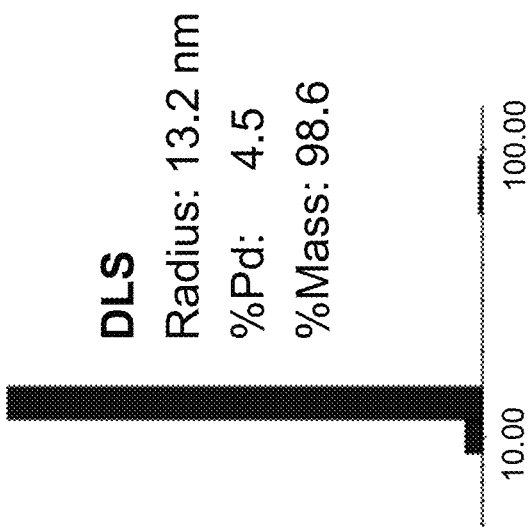
FIGS. 19A-19C show characterization of a OspA serotype 1-lumazine synthase construct (SEQ ID NO: 12).
Figure 19A:
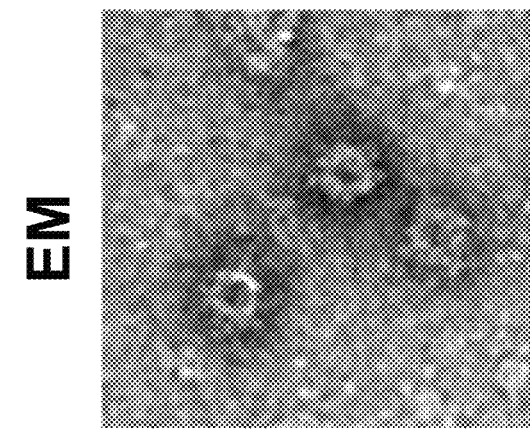
Figure 19B:
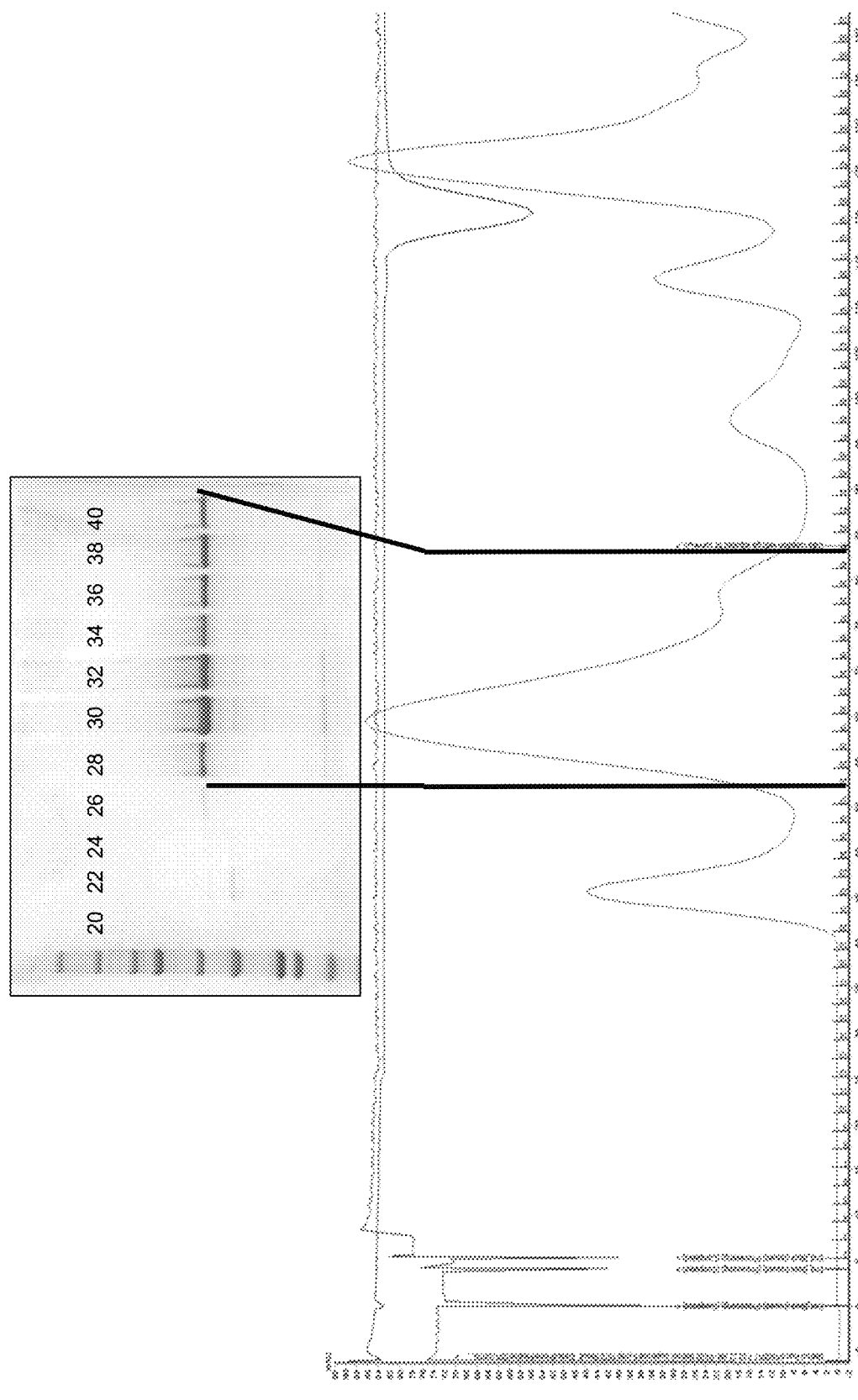
Figure 20B:
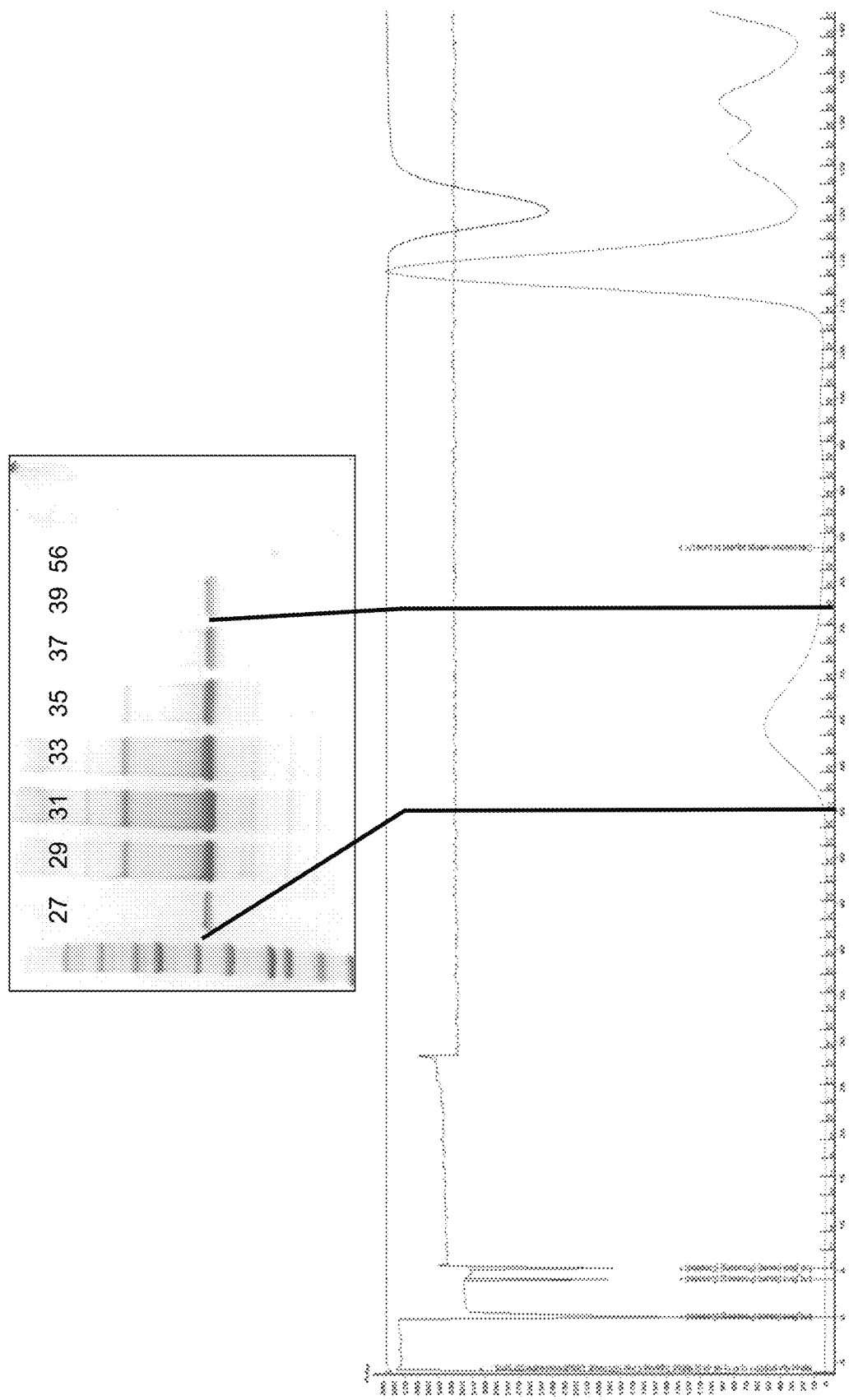
Figure 21A:
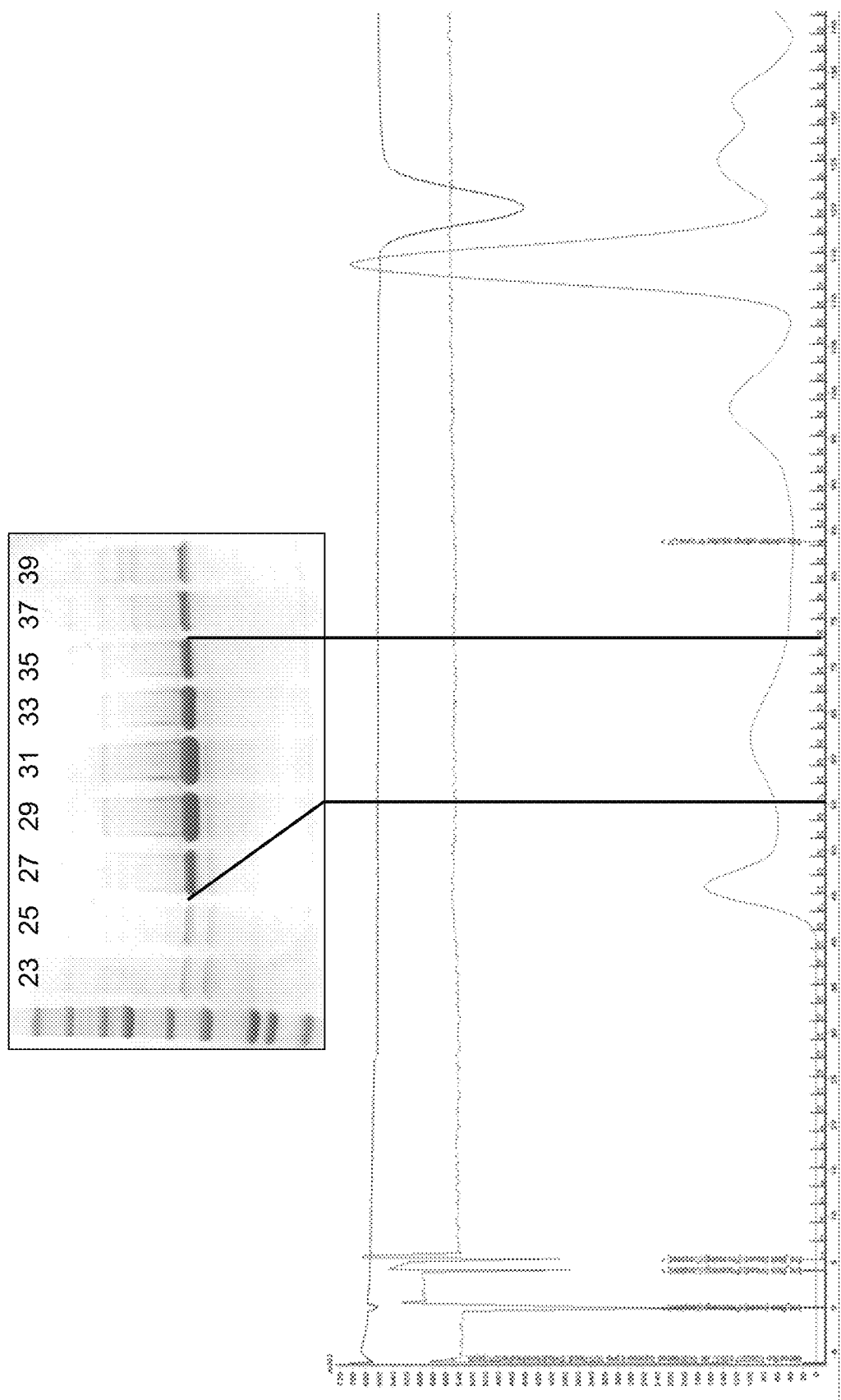
Figures 21B, 22A:
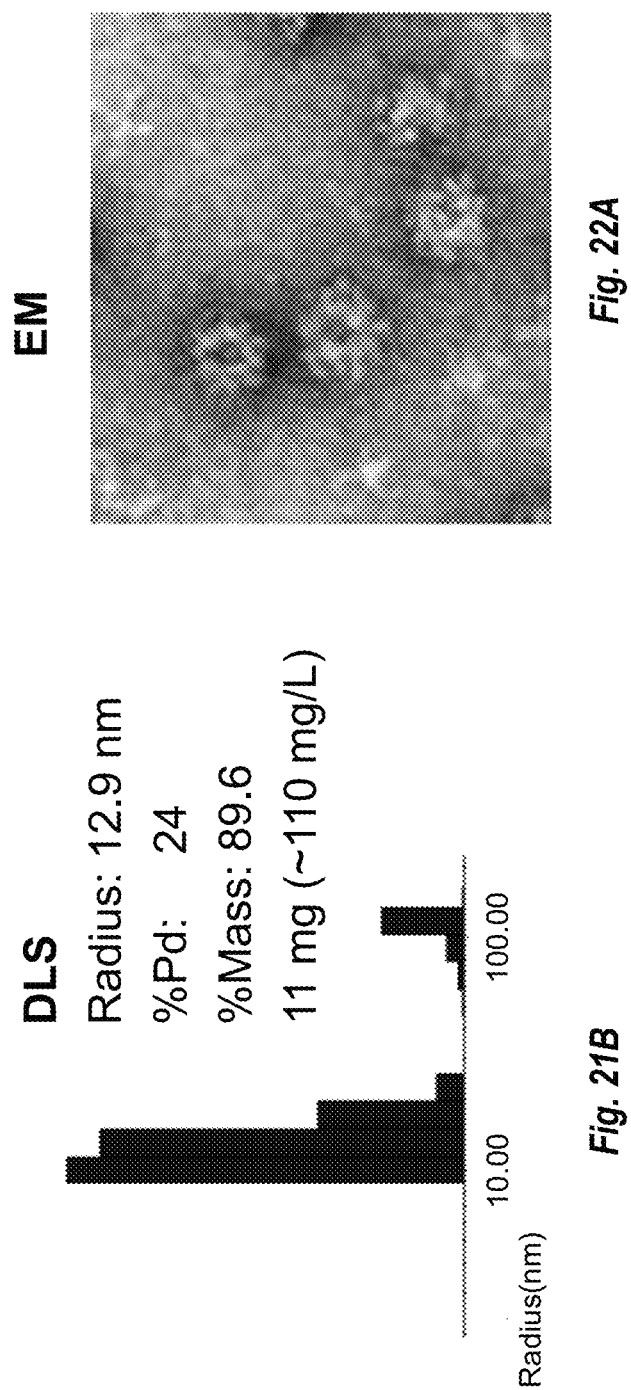
Figure 22B:
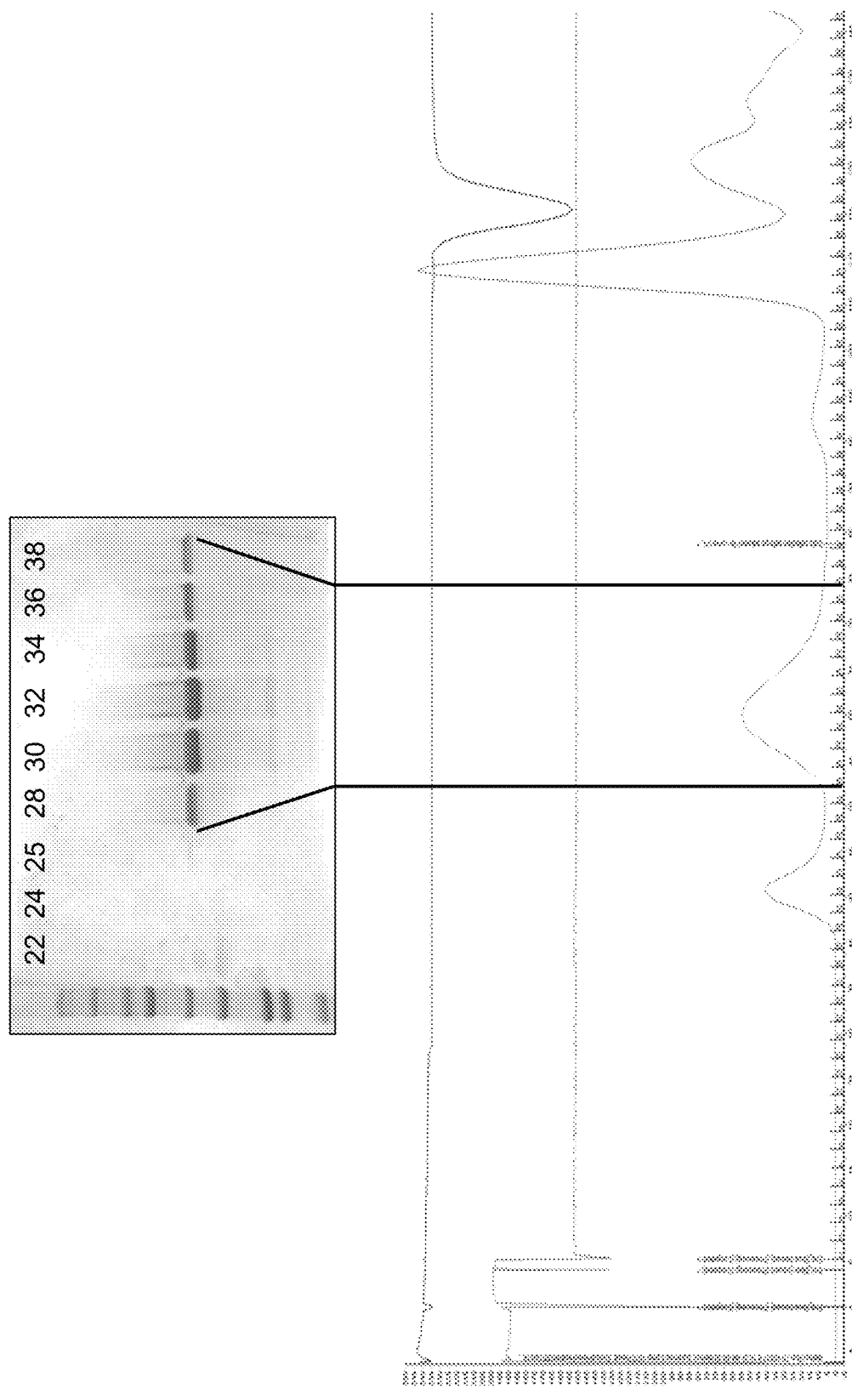
Figure 23B:
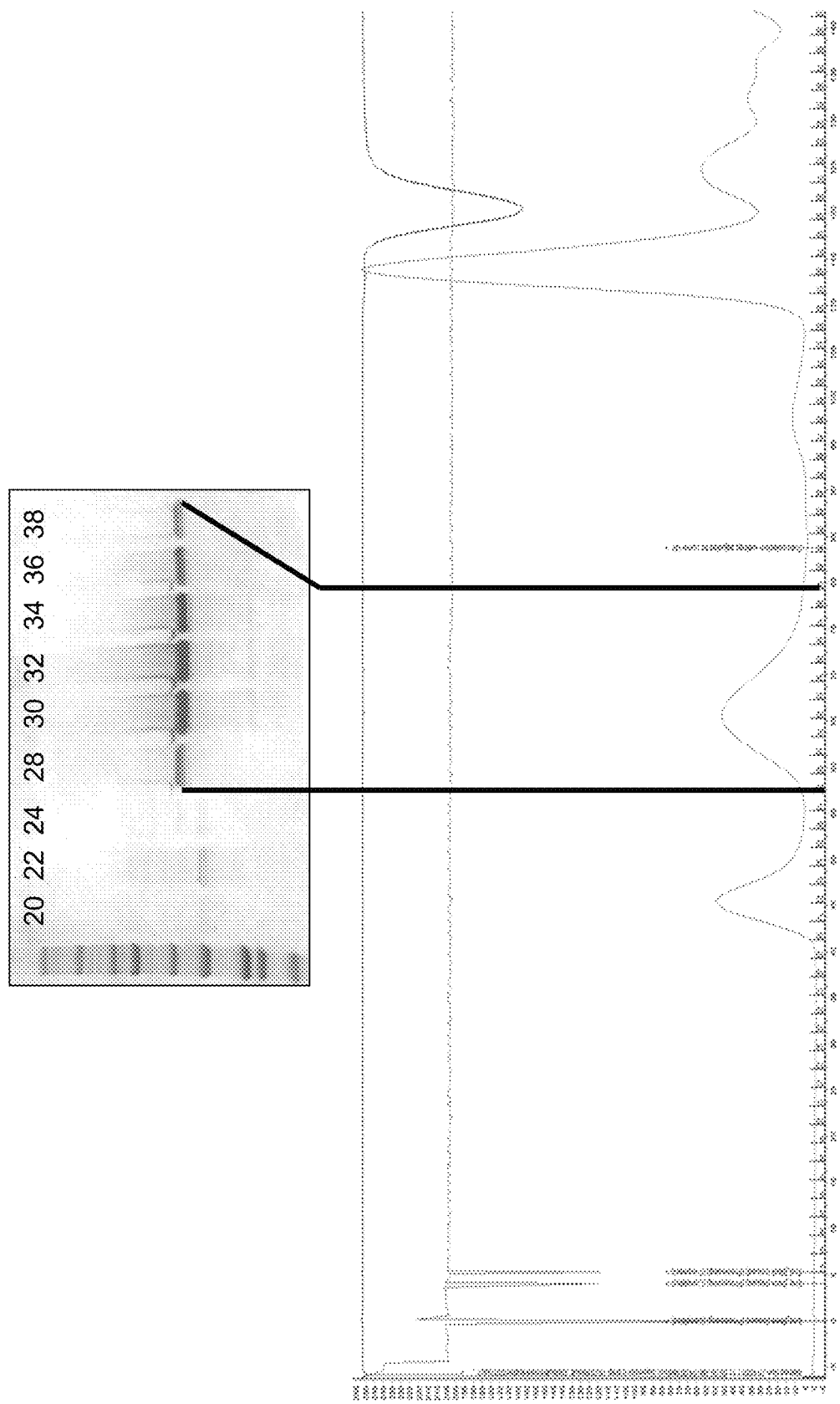
Figure 23C:
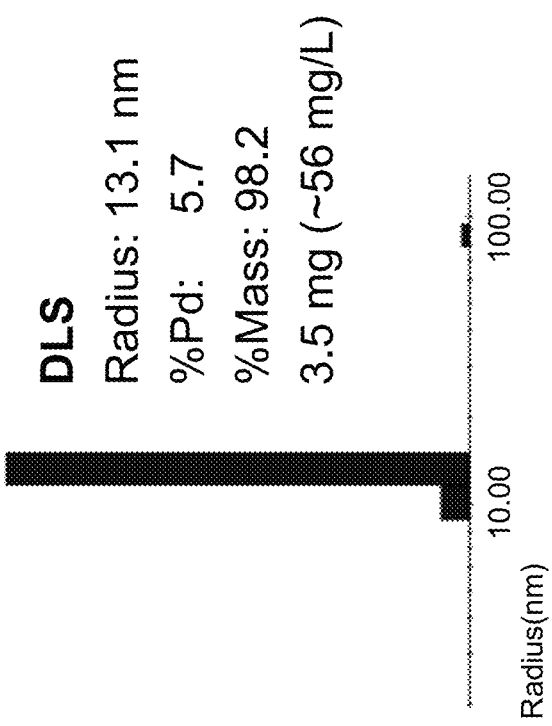
Figures 24A, 24B:
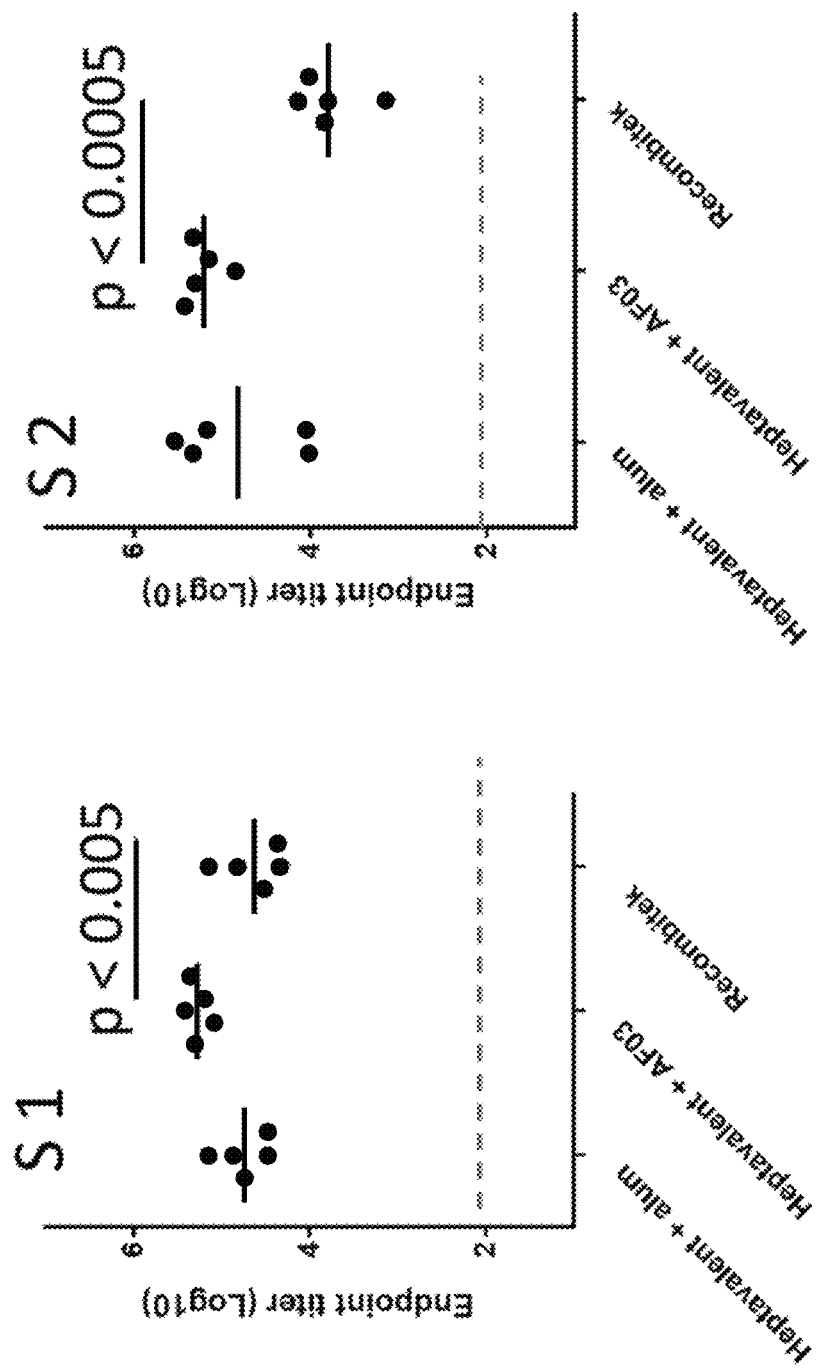
FIG. 24A-24G show antibody responses to serotypes 1-7, respectively, in C3H mice (n=5 per group) to heptavalent OspA-ferritin nanoparticle compositions of 1 ug each of OspA-ferritin nanoparticles corresponding to OspA serotypes 1-7 (total 7 ug) adjuvanted with either alum or AF03, or to RECOMBITEK® Lyme. For all experiments, an ELISA plate was coated with the OspA serotype indicated in each panel as "S X" where X is the serotype number.
Figures 24C, 24D:
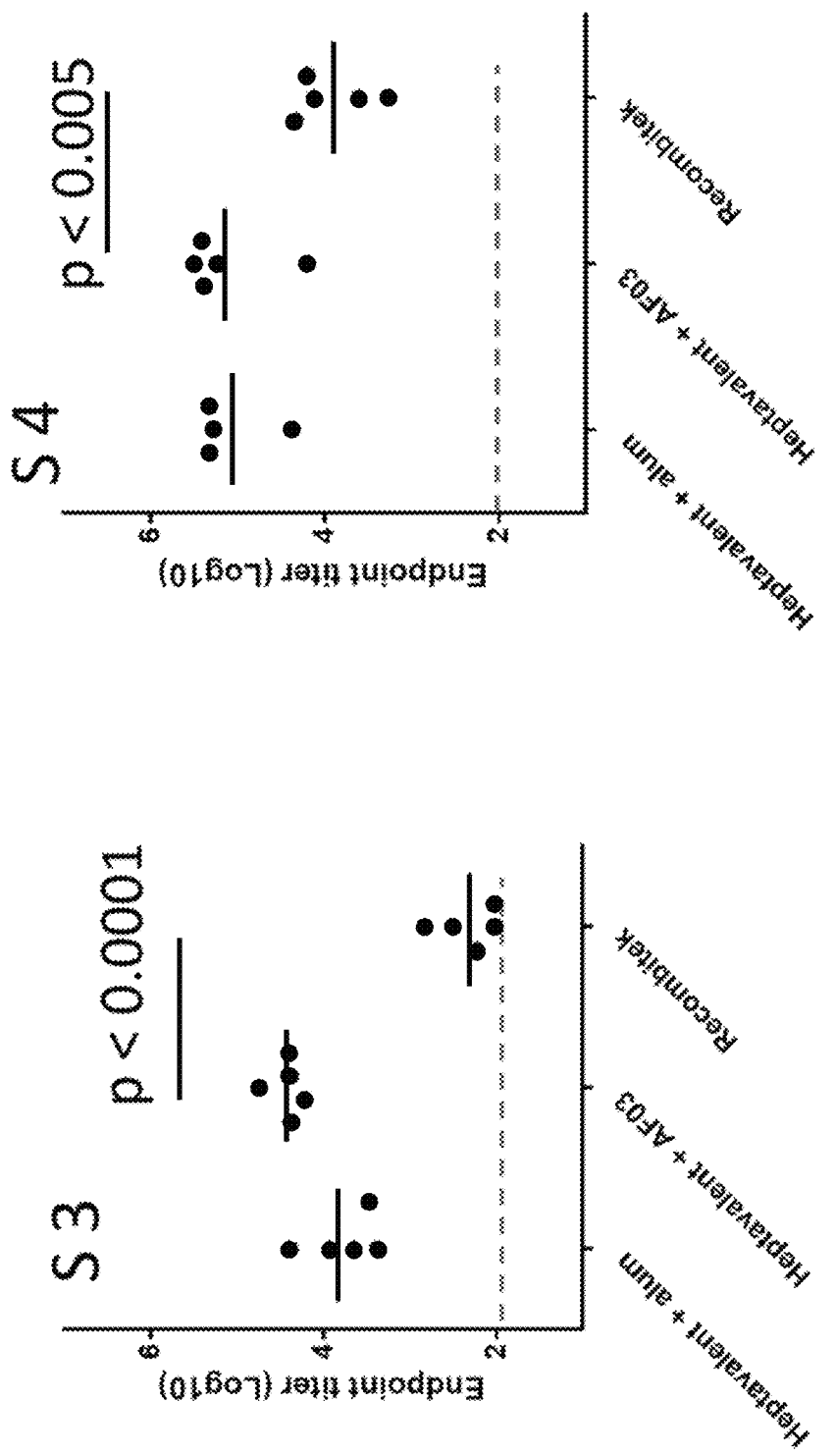
Figures 24E, 24F:
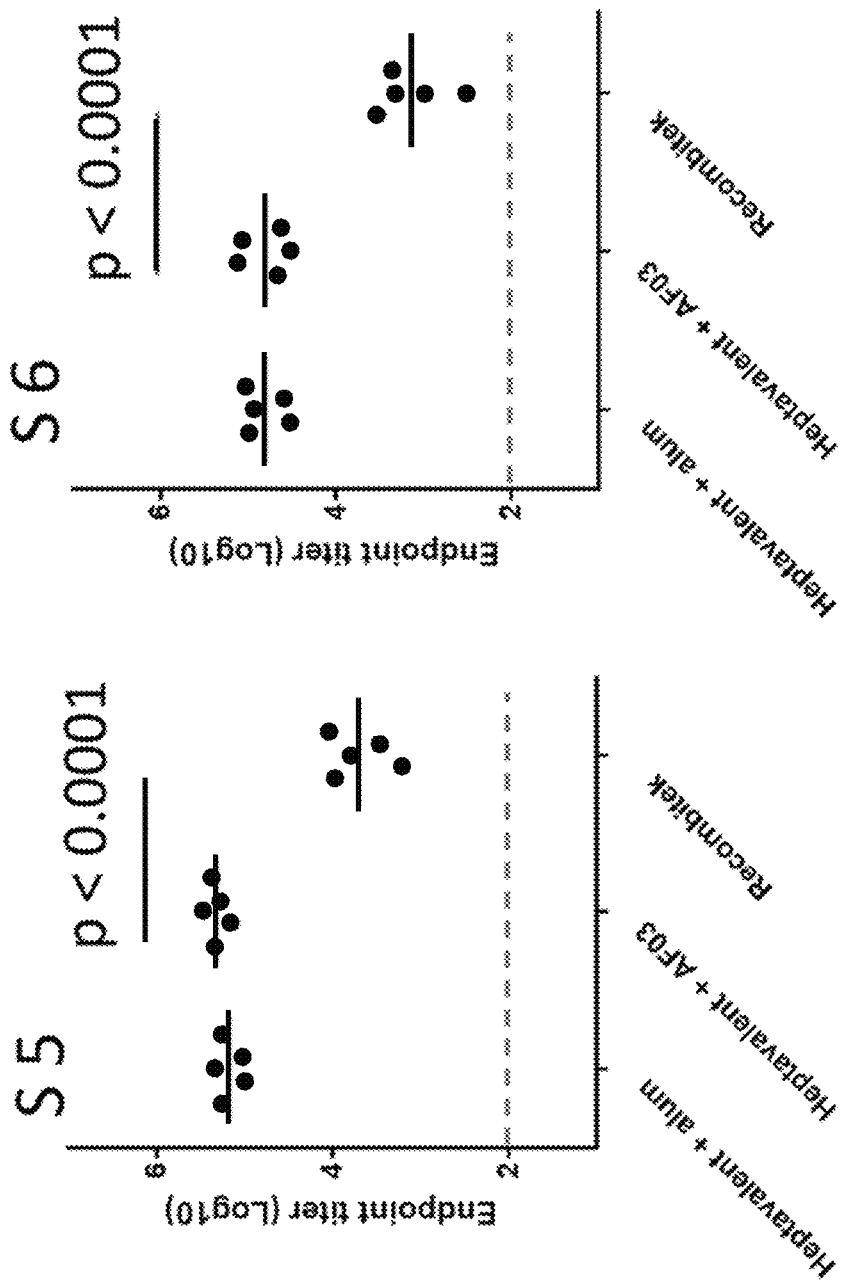
Figure 24G:
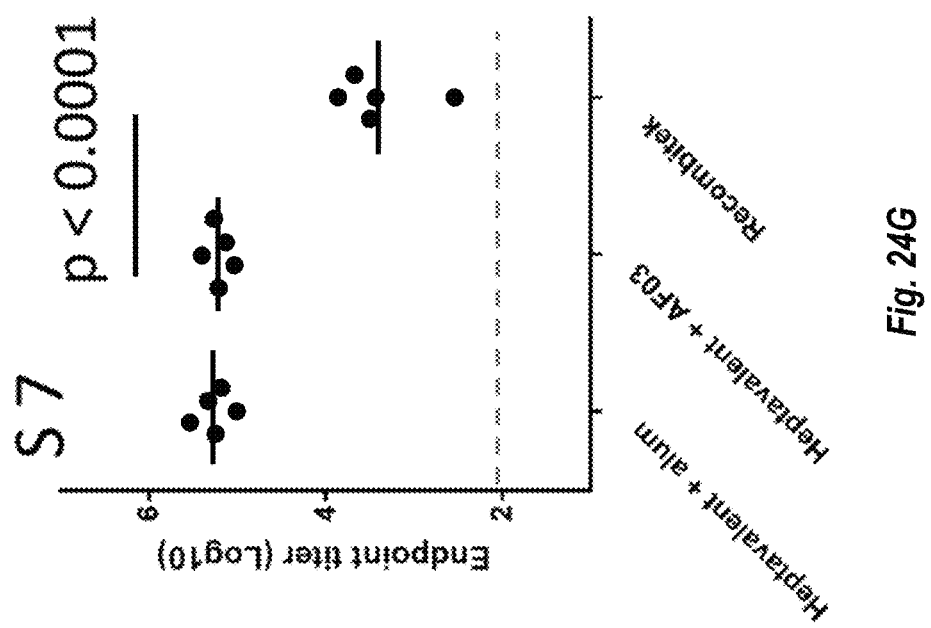

Another nanoparticle, lumazine synthase from *Aquifex aeolicus*, was investigated for antigenic display of OspA. OspA-lumazine synthase particles comprising different serotypes were purified easily from *E. coli* cells by anion exchange and size exclusion chromatography. Constructs were generated and characterized that comprised OspA serotype 1 (SEQ ID NO: 12, FIGS. 19A-19C); OspA serotype 2 (SEQ ID NO: 16, FIGS. 20A-20C); OspA serotype 3 (SEQ ID NO: 17, FIGS. 21A-21B); OspA serotype 4 (SEQ ID NO: 18, FIGS. 17A-17C); OspA serotype 5 (SEQ ID NO: 19, FIGS. 22A-22C); and OspA serotype 7 (SEQ ID NO: 21, FIGS. 23A-23C). The OspA-lumazine synthase particles formed a 15.8 nm particle by EM and were uniform in size by DLS.

Figure 18:
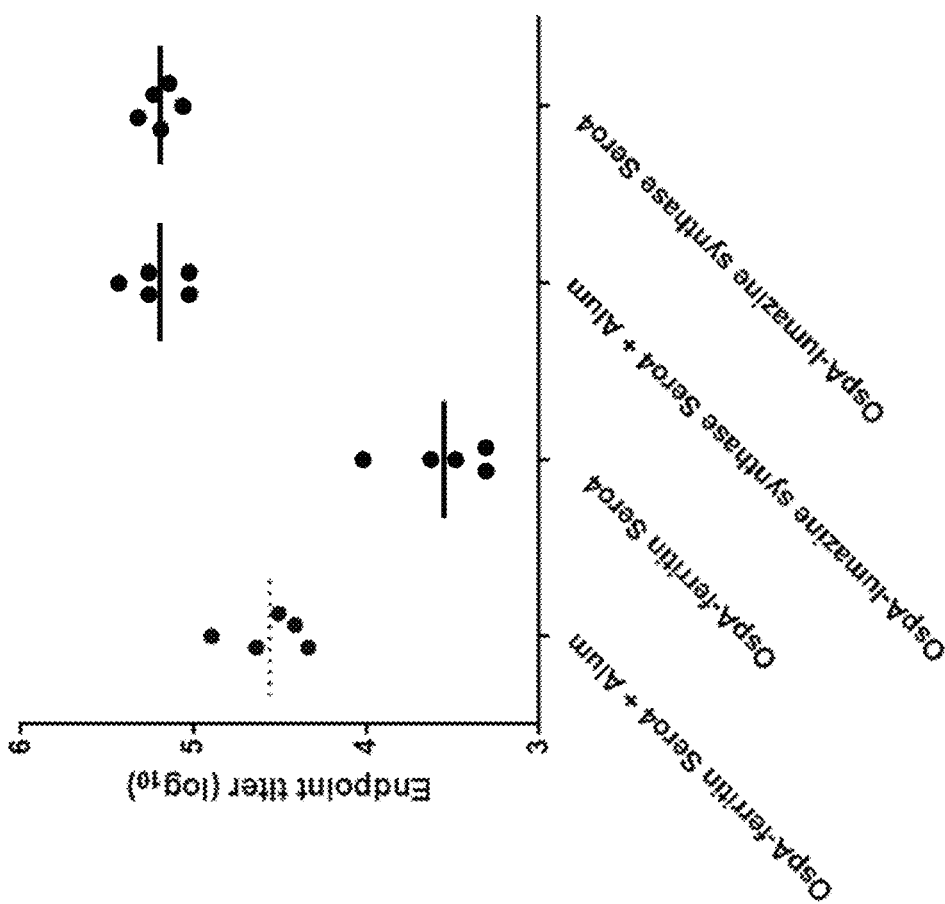
FIG. 18 shows antibody response in mice to a OspA serotype 4-ferritin construct (SEQ ID NO: 4) and an OspA serotype 4-lumazine synthase construct (SEQ ID NO: 18), with or without Alum.

OspA serotype 4 lumazine synthase particles (SEQ ID NO: 18) were tested in mice for immunogenicity (FIG. 18). The OspA lumazine synthase particles with and without Alum gave a strong immune response that appeared at least as robust as that of a similar OspA serotype 4 ferritin nanoparticle (SEQ ID NO: 7).

Thus, antigenic polypeptides comprising lumazine synthase and an OspA polypeptide can also be used to elicit anti-OspA antibody responses.

---

SEQUENCE LISTING

<160> NUMBER OF SEQ ID NOS: 228

<210> SEQ ID NO 1
<211> LENGTH: 425
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Asp Glu Lys Asn Ser Val Ser Val Asp Leu Pro Gly Glu Met Lys
1               5                   10                  15

-continued

```
Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Asp Lys Ser Lys Val Lys
    50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
        115                 120                 125

Ser Asp Gly Ser Gly Lys Ala Lys Glu Val Leu Lys Gly Tyr Thr Leu
    130                 135                 140

Glu Gly Gln Leu Ser Asp Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
        195                 200                 205

Thr Lys Asp Leu Val Phe Thr Lys Glu Asn Thr Ile Thr Val Gln Gln
    210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Ser Glu Ser Gln Val
                245                 250                 255

Arg Gln Gln Phe Ser Lys Asp Ile Glu Lys Leu Leu Asn Glu Gln Val
            260                 265                 270

Asn Lys Glu Met Gln Ser Ser Asn Leu Tyr Met Ser Met Ser Ser Trp
        275                 280                 285

Ser Tyr Thr His Ser Leu Asp Gly Ala Gly Leu Phe Leu Phe Asp His
    290                 295                 300

Ala Ala Glu Glu Tyr Glu His Ala Lys Lys Leu Ile Ile Phe Leu Asn
305                 310                 315                 320

Glu Asn Asn Val Pro Val Gln Leu Thr Ser Ile Ser Ala Pro Glu His
                325                 330                 335

Lys Phe Glu Gly Leu Thr Gln Ile Phe Gln Lys Ala Tyr Glu His Glu
            340                 345                 350

Gln His Ile Ser Glu Ser Ile Asn Asn Ile Val Asp His Ala Ile Lys
        355                 360                 365

Cys Lys Asp His Ala Thr Phe Asn Phe Leu Gln Trp Tyr Val Ala Glu
    370                 375                 380

Gln His Glu Glu Glu Val Leu Phe Lys Asp Ile Leu Asp Lys Ile Glu
385                 390                 395                 400

Leu Ile Gly Asn Glu Asn His Gly Leu Tyr Leu Ala Asp Gln Tyr Val
                405                 410                 415

Lys Gly Ile Ala Lys Ser Arg Lys Ser
            420                 425
```

```
<210> SEQ ID NO 2
<211> LENGTH: 425
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Asp Lys Ser Lys Val Lys
    50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
        115                 120                 125

Ser Asp Gly Ser Gly Lys Ala Lys Glu Val Leu Lys Gly Tyr Asp Leu
    130                 135                 140

Lys Gly Glu Leu Ser Ser Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
        195                 200                 205

Thr Lys Asp Leu Val Phe Thr Lys Glu Asn Thr Ile Thr Val Gln Gln
    210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Ser Glu Ser Gln Val
                245                 250                 255

Arg Gln Gln Phe Ser Lys Asp Ile Glu Lys Leu Leu Asn Glu Gln Val
            260                 265                 270

Asn Lys Glu Met Gln Ser Asn Leu Tyr Met Ser Met Ser Ser Trp
        275                 280                 285

Ser Tyr Thr His Ser Leu Asp Gly Ala Gly Leu Phe Leu Phe Asp His
    290                 295                 300

Ala Ala Glu Glu Tyr Glu His Ala Lys Lys Leu Ile Ile Phe Leu Asn
305                 310                 315                 320

Glu Asn Asn Val Pro Val Gln Leu Thr Ser Ile Ser Ala Pro Glu His
                325                 330                 335

Lys Phe Glu Gly Leu Thr Gln Ile Phe Gln Lys Ala Tyr Glu His Glu
            340                 345                 350

Gln His Ile Ser Glu Ser Ile Asn Asn Ile Val Asp His Ala Ile Lys
        355                 360                 365
```

-continued

```
Cys Lys Asp His Ala Thr Phe Asn Phe Leu Gln Trp Tyr Val Ala Glu
370                 375                 380

Gln His Glu Glu Val Leu Phe Lys Asp Ile Leu Asp Lys Ile Glu
385                 390                 395                 400

Leu Ile Gly Asn Glu Asn His Gly Leu Tyr Leu Ala Asp Gln Tyr Val
                405                 410                 415

Lys Gly Ile Ala Lys Ser Arg Lys Ser
                420                 425

<210> SEQ ID NO 3
<211> LENGTH: 425
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
                20                  25                  30

Ala Thr Val Asp Lys Leu Glu Leu Lys Gly Thr Ser Asp Lys Asn Asn
            35                  40                  45

Gly Ser Gly Val Leu Glu Gly Val Lys Ala Asp Lys Ser Lys Val Lys
    50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
                100                 105                 110

Ile Ile Thr Arg Ala Asp Gly Thr Arg Leu Glu Tyr Thr Gly Ile Lys
            115                 120                 125

Ser Asp Gly Ser Gly Lys Ala Lys Glu Val Leu Lys Gly Phe Thr Leu
    130                 135                 140

Glu Gly Lys Val Ala Asn Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
    195                 200                 205

Thr Lys Asp Leu Val Phe Thr Lys Glu Asn Thr Ile Thr Val Gln Gln
210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Ser Glu Ser Gln Val
                245                 250                 255

Arg Gln Gln Phe Ser Lys Asp Ile Glu Lys Leu Leu Asn Glu Gln Val
            260                 265                 270

Asn Lys Glu Met Gln Ser Ser Asn Leu Tyr Met Ser Met Ser Ser Trp
    275                 280                 285
```

Ser Tyr Thr His Ser Leu Asp Gly Ala Gly Leu Phe Leu Phe Asp His
    290                 295                 300

Ala Ala Glu Glu Tyr Glu His Ala Lys Lys Leu Ile Ile Phe Leu Asn
305                 310                 315                 320

Glu Asn Asn Val Pro Val Gln Leu Thr Ser Ile Ser Ala Pro Glu His
                325                 330                 335

Lys Phe Glu Gly Leu Thr Gln Ile Phe Gln Lys Ala Tyr Glu His Glu
            340                 345                 350

Gln His Ile Ser Glu Ser Ile Asn Asn Ile Val Asp His Ala Ile Lys
        355                 360                 365

Cys Lys Asp His Ala Thr Phe Asn Phe Leu Gln Trp Tyr Val Ala Glu
370                 375                 380

Gln His Glu Glu Val Leu Phe Lys Asp Ile Leu Asp Lys Ile Glu
385                 390                 395                 400

Leu Ile Gly Asn Glu Asn His Gly Leu Tyr Leu Ala Asp Gln Tyr Val
                405                 410                 415

Lys Gly Ile Ala Lys Ser Arg Lys Ser
            420                 425

<210> SEQ ID NO 4
<211> LENGTH: 425
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
                20                  25                  30

Ala Thr Val Asp Lys Leu Glu Leu Lys Gly Thr Ser Asp Lys Asn Asn
            35                  40                  45

Gly Ser Gly Val Leu Glu Gly Val Lys Ala Asp Lys Ser Lys Val Lys
50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
        115                 120                 125

Ser Asp Gly Ser Gly Lys Ala Lys Glu Val Leu Lys Gly Phe Ala Leu
130                 135                 140

Glu Gly Thr Leu Thr Asp Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
        195                 200                 205

Thr Lys Asp Leu Val Phe Thr Lys Glu Asn Thr Ile Thr Val Gln Gln

```
                210                 215                 220
Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Ser Glu Ser Gln Val
                245                 250                 255

Arg Gln Gln Phe Ser Lys Asp Ile Glu Lys Leu Leu Asn Glu Gln Val
                260                 265                 270

Asn Lys Glu Met Gln Ser Ser Asn Leu Tyr Met Ser Met Ser Ser Trp
            275                 280                 285

Ser Tyr Thr His Ser Leu Asp Gly Ala Gly Leu Phe Leu Phe Asp His
            290                 295                 300

Ala Ala Glu Glu Tyr Glu His Ala Lys Lys Leu Ile Ile Phe Leu Asn
305                 310                 315                 320

Glu Asn Asn Val Pro Val Gln Leu Thr Ser Ile Ser Ala Pro Glu His
                325                 330                 335

Lys Phe Glu Gly Leu Thr Gln Ile Phe Gln Lys Ala Tyr Glu His Glu
                340                 345                 350

Gln His Ile Ser Glu Ser Ile Asn Asn Ile Val Asp His Ala Ile Lys
            355                 360                 365

Cys Lys Asp His Ala Thr Phe Asn Phe Leu Gln Trp Tyr Val Ala Glu
            370                 375                 380

Gln His Glu Glu Val Leu Phe Lys Asp Ile Leu Asp Lys Ile Glu
385                 390                 395                 400

Leu Ile Gly Asn Glu Asn His Gly Leu Tyr Leu Ala Asp Gln Tyr Val
                405                 410                 415

Lys Gly Ile Ala Lys Ser Arg Lys Ser
                420                 425

<210> SEQ ID NO 5
<211> LENGTH: 425
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Met Asp Glu Lys Asn Ser Ala Ser Val Asp Leu Pro Gly Glu Met Lys
1               5                   10                  15

Val Leu Val Ser Lys Glu Lys Asp Lys Asp Gly Lys Tyr Ser Leu Lys
                20                  25                  30

Ala Thr Val Asp Lys Ile Glu Leu Lys Gly Thr Ser Asp Lys Asp Asn
            35                  40                  45

Gly Ser Gly Val Leu Glu Gly Thr Lys Asp Asp Lys Ser Lys Ala Lys
        50                  55                  60

Leu Thr Ile Ala Asp Asp Leu Ser Lys Thr Thr Phe Glu Leu Phe Lys
65                  70                  75                  80

Glu Asp Gly Lys Thr Leu Val Ser Arg Lys Val Ser Ser Lys Asp Lys
                85                  90                  95

Thr Ser Thr Asp Glu Met Phe Asn Glu Lys Gly Glu Leu Ser Ala Lys
                100                 105                 110

Thr Met Thr Arg Glu Asn Gly Thr Lys Leu Glu Tyr Thr Glu Met Lys
            115                 120                 125

Ser Asp Gly Thr Gly Lys Ala Lys Glu Val Leu Lys Asn Phe Thr Leu
        130                 135                 140
```

Glu Gly Lys Val Ala Asn Asp Lys Val Thr Leu Glu Val Lys Glu Gly
145                 150                 155                 160

Thr Val Thr Leu Ser Lys Glu Ile Ala Lys Ser Gly Glu Val Thr Val
                165                 170                 175

Ala Leu Asn Asp Thr Asn Thr Thr Gln Ala Thr Lys Lys Thr Gly Ala
                180                 185                 190

Trp Asp Ser Lys Thr Ser Thr Leu Thr Ile Ser Val Asn Ser Lys Lys
                195                 200                 205

Thr Thr Gln Leu Val Phe Thr Lys Gln Asp Thr Ile Thr Val Gln Lys
            210                 215                 220

Tyr Asp Ser Ala Gly Thr Asn Leu Glu Gly Thr Ala Val Glu Ile Lys
225                 230                 235                 240

Thr Leu Asp Glu Leu Lys Asn Ala Leu Lys Gly Ser Glu Ser Gln Val
                245                 250                 255

Arg Gln Gln Phe Ser Lys Asp Ile Glu Lys Leu Leu Asn Glu Gln Val
                260                 265                 270

Asn Lys Glu Met Gln Ser Ser Asn Leu Tyr Met Ser Met Ser Ser Trp
            275                 280                 285

Ser Tyr Thr His Ser Leu Asp Gly Ala Gly Leu Phe Leu Phe Asp His
            290                 295                 300

Ala Ala Glu Glu Tyr Glu His Ala Lys Lys Leu Ile Ile Phe Leu Asn
305                 310                 315                 320

Glu Asn Asn Val Pro Val Gln Leu Thr Ser Ile Ser Ala Pro Glu His
                325                 330                 335

Lys Phe Glu Gly Leu Thr Gln Ile Phe Gln Lys Ala Tyr Glu His Glu
                340                 345                 350

Gln His Ile Ser Glu Ser Ile Asn Asn Ile Val Asp His Ala Ile Lys
            355                 360                 365

Cys Lys Asp His Ala Thr Phe Asn Phe Leu Gln Trp Tyr Val Ala Glu
            370                 375                 380

Gln His Glu Glu Glu Val Leu Phe Lys Asp Ile Leu Asp Lys Ile Glu
385                 390                 395                 400

Leu Ile Gly Asn Glu Asn His Gly Leu Tyr Leu Ala Asp Gln Tyr Val
                405                 410                 415

Lys Gly Ile Ala Lys Ser Arg Lys Ser
                420                 425

<210> SEQ ID NO 6
<211> LENGTH: 426
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 6

Met Asp Glu Lys Asn Ser Val Ser Val Asp Leu Pro Gly Gly Met Lys
1               5                   10                  15

Val Leu Val Ser Lys Glu Lys Asp Lys Asp Gly Lys Tyr Ser Leu Met
                20                  25                  30

Ala Thr Val Glu Lys Leu Glu Leu Lys Gly Thr Ser Asp Lys Ser Asn
            35                  40                  45

Gly Ser Gly Val Leu Glu Gly Glu Lys Ala Asp Lys Ser Lys Ala Lys
        50                  55                  60

```
Leu Thr Ile Ser Gln Asp Leu Asn Gln Thr Thr Phe Glu Ile Phe Lys
 65                  70                  75                  80

Glu Asp Gly Lys Thr Leu Val Ser Arg Lys Val Asn Ser Lys Asp Lys
                 85                  90                  95

Ser Ser Thr Glu Glu Lys Phe Asn Asp Lys Gly Lys Leu Ser Glu Lys
            100                 105                 110

Val Val Thr Arg Ala Asn Gly Thr Arg Leu Glu Tyr Thr Glu Ile Lys
        115                 120                 125

Asn Asp Gly Ser Gly Lys Ala Lys Glu Val Leu Lys Gly Phe Ala Leu
130                 135                 140

Glu Gly Thr Leu Thr Asp Gly Glu Thr Lys Leu Thr Val Thr Glu
145                 150                 155                 160

Gly Thr Val Thr Leu Ser Lys Asn Ile Ser Lys Ser Gly Glu Ile Thr
                165                 170                 175

Val Ala Leu Asn Asp Thr Glu Thr Thr Pro Ala Asp Lys Lys Thr Gly
            180                 185                 190

Glu Trp Lys Ser Asp Thr Ser Thr Leu Thr Ile Ser Lys Asn Ser Gln
                195                 200                 205

Lys Pro Lys Gln Leu Val Phe Thr Lys Glu Asn Thr Ile Thr Val Gln
210                 215                 220

Asn Tyr Asn Arg Ala Gly Asn Ala Leu Glu Gly Ser Pro Ala Glu Ile
225                 230                 235                 240

Lys Asp Leu Ala Glu Leu Lys Ala Ala Leu Lys Gly Ser Glu Ser Gln
                245                 250                 255

Val Arg Gln Gln Phe Ser Lys Asp Ile Glu Lys Leu Leu Asn Glu Gln
            260                 265                 270

Val Asn Lys Glu Met Gln Ser Ser Asn Leu Tyr Met Ser Met Ser Ser
            275                 280                 285

Trp Ser Tyr Thr His Ser Leu Asp Gly Ala Gly Leu Phe Leu Phe Asp
            290                 295                 300

His Ala Glu Glu Tyr Glu His Ala Lys Lys Leu Ile Ile Phe Leu
305                 310                 315                 320

Asn Glu Asn Asn Val Pro Val Gln Leu Thr Ser Ile Ser Ala Pro Glu
                325                 330                 335

His Lys Phe Glu Gly Leu Thr Gln Ile Phe Gln Lys Ala Tyr Glu His
            340                 345                 350

Glu Gln His Ile Ser Glu Ser Ile Asn Asn Ile Val Asp His Ala Ile
                355                 360                 365

Lys Cys Lys Asp His Ala Thr Phe Asn Phe Leu Gln Trp Tyr Val Ala
370                 375                 380

Glu Gln His Glu Glu Val Leu Phe Lys Asp Ile Leu Asp Lys Ile
385                 390                 395                 400

Glu Leu Ile Gly Asn Glu Asn His Gly Leu Tyr Leu Ala Asp Gln Tyr
                405                 410                 415

Val Lys Gly Ile Ala Lys Ser Arg Lys Ser
            420                 425

<210> SEQ ID NO 7
<211> LENGTH: 425
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

```
<400> SEQUENCE: 7

Met Asp Glu Lys Asn Ser Val Ser Val Asp Leu Pro Gly Glu Met Lys
1               5                   10                  15

Val Leu Val Ser Lys Glu Lys Asp Lys Asp Gly Lys Tyr Ser Leu Met
            20                  25                  30

Ala Thr Val Asp Lys Leu Glu Leu Lys Gly Thr Ser Asp Lys Ser Asn
        35                  40                  45

Gly Ser Gly Thr Leu Glu Gly Glu Lys Ser Asp Lys Ser Lys Ala Lys
    50                  55                  60

Leu Thr Ile Ser Glu Asp Leu Ser Lys Thr Thr Phe Glu Ile Phe Lys
65                  70                  75                  80

Glu Asp Gly Lys Thr Leu Val Ser Lys Val Asn Ser Lys Asp Lys
                85                  90                  95

Ser Ser Ile Glu Glu Lys Phe Asn Ala Lys Gly Glu Leu Ser Glu Lys
                100                 105                 110

Thr Ile Leu Arg Ala Asn Gly Thr Arg Leu Glu Tyr Thr Glu Ile Lys
            115                 120                 125

Ser Asp Gly Thr Gly Lys Ala Lys Glu Val Leu Lys Asp Phe Ala Leu
    130                 135                 140

Glu Gly Thr Leu Ala Ala Asp Lys Thr Thr Leu Lys Val Thr Glu Gly
145                 150                 155                 160

Thr Val Leu Ser Lys His Ile Pro Asn Ser Gly Glu Ile Thr Val
                165                 170                 175

Glu Leu Asn Asp Ser Asn Ser Thr Gln Ala Thr Lys Lys Thr Gly Lys
            180                 185                 190

Trp Asp Ser Asn Thr Ser Thr Leu Thr Ile Ser Val Asn Ser Lys Lys
    195                 200                 205

Thr Lys Asn Ile Val Phe Thr Lys Glu Asp Thr Ile Thr Val Gln Lys
    210                 215                 220

Tyr Asp Ser Ala Gly Thr Asn Leu Glu Gly Asn Ala Val Glu Ile Lys
225                 230                 235                 240

Thr Leu Asp Glu Leu Lys Asn Ala Leu Lys Gly Ser Glu Ser Gln Val
                245                 250                 255

Arg Gln Gln Phe Ser Lys Asp Ile Glu Lys Leu Leu Asn Glu Gln Val
                260                 265                 270

Asn Lys Glu Met Gln Ser Ser Asn Leu Tyr Met Ser Met Ser Ser Trp
            275                 280                 285

Ser Tyr Thr His Ser Leu Asp Gly Ala Gly Leu Phe Leu Phe Asp His
    290                 295                 300

Ala Ala Glu Glu Tyr Glu His Ala Lys Lys Leu Ile Ile Phe Leu Asn
305                 310                 315                 320

Glu Asn Asn Val Pro Val Gln Leu Thr Ser Ile Ser Ala Pro Glu His
                325                 330                 335

Lys Phe Glu Gly Leu Thr Gln Ile Phe Gln Lys Ala Tyr Glu His Glu
            340                 345                 350

Gln His Ile Ser Glu Ser Ile Asn Asn Ile Val Asp His Ala Ile Lys
    355                 360                 365

Cys Lys Asp His Ala Thr Phe Asn Phe Leu Gln Trp Tyr Val Ala Glu
    370                 375                 380

Gln His Glu Glu Val Leu Phe Lys Asp Ile Leu Asp Lys Ile Glu
385                 390                 395                 400

Leu Ile Gly Asn Glu Asn His Gly Leu Tyr Leu Ala Asp Gln Tyr Val
                405                 410                 415
```

```
Lys Gly Ile Ala Lys Ser Arg Lys Ser
            420             425

<210> SEQ ID NO 8
<211> LENGTH: 426
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Met Asp Glu Lys Asn Ser Val Ser Val Asp Leu Pro Gly Gly Met Lys
1               5                   10                  15

Val Leu Val Ser Lys Glu Lys Asp Lys Asp Gly Lys Tyr Ser Leu Met
            20                  25                  30

Ala Thr Val Glu Lys Leu Glu Leu Lys Gly Thr Ser Asp Lys Asn Asn
        35                  40                  45

Gly Ser Gly Thr Leu Glu Gly Glu Lys Thr Asp Lys Ser Lys Val Lys
    50                  55                  60

Leu Thr Ile Ala Glu Asp Leu Ser Lys Thr Thr Phe Glu Ile Phe Lys
65                  70                  75                  80

Glu Asp Gly Lys Thr Leu Val Ser Lys Val Thr Leu Lys Asp Lys
                85                  90                  95

Ser Ser Thr Glu Glu Lys Phe Asn Glu Lys Gly Glu Ile Ser Glu Lys
                100                 105                 110

Thr Ile Val Arg Ala Asn Gly Thr Arg Leu Glu Tyr Thr Asp Ile Lys
            115                 120                 125

Ser Asp Gly Ser Gly Lys Ala Lys Glu Val Leu Lys Asp Phe Thr Leu
    130                 135                 140

Glu Gly Thr Leu Ala Ala Asp Gly Lys Thr Thr Leu Lys Val Thr Glu
145                 150                 155                 160

Gly Thr Val Val Leu Ser Lys Asn Ile Leu Lys Ser Gly Glu Ile Thr
                165                 170                 175

Val Ala Leu Asp Asp Ser Asp Thr Thr Gln Ala Thr Lys Lys Thr Gly
            180                 185                 190

Lys Trp Asp Ser Lys Thr Ser Thr Leu Thr Ile Ser Val Asn Ser Gln
            195                 200                 205

Lys Thr Lys Asn Leu Val Phe Thr Lys Glu Asp Thr Ile Thr Val Gln
    210                 215                 220

Lys Tyr Asp Ser Ala Gly Thr Asn Leu Glu Gly Lys Ala Val Glu Ile
225                 230                 235                 240

Thr Thr Leu Glu Lys Leu Lys Asp Ala Leu Lys Gly Ser Glu Ser Gln
                245                 250                 255

Val Arg Gln Gln Phe Ser Lys Asp Ile Glu Lys Leu Leu Asn Glu Gln
            260                 265                 270

Val Asn Lys Glu Met Gln Ser Ser Asn Leu Tyr Met Ser Met Ser Ser
        275                 280                 285

Trp Ser Tyr Thr His Ser Leu Asp Gly Ala Gly Leu Phe Leu Phe Asp
    290                 295                 300

His Ala Ala Glu Glu Tyr Glu His Ala Lys Lys Leu Ile Ile Phe Leu
305                 310                 315                 320

Asn Glu Asn Asn Val Pro Val Gln Leu Thr Ser Ile Ser Ala Pro Glu
                325                 330                 335
```

```
His Lys Phe Glu Gly Leu Thr Gln Ile Phe Gln Lys Ala Tyr Glu His
                340                 345                 350

Glu Gln His Ile Ser Glu Ser Ile Asn Asn Ile Val Asp His Ala Ile
            355                 360                 365

Lys Cys Lys Asp His Ala Thr Phe Asn Phe Leu Gln Trp Tyr Val Ala
370                 375                 380

Glu Gln His Glu Glu Val Leu Phe Lys Asp Ile Leu Asp Lys Ile
385                 390                 395                 400

Glu Leu Ile Gly Asn Glu Asn His Gly Leu Tyr Leu Ala Asp Gln Tyr
                405                 410                 415

Val Lys Gly Ile Ala Lys Ser Arg Lys Ser
                420                 425

<210> SEQ ID NO 9
<211> LENGTH: 426
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Met Asp Glu Lys Asn Ser Val Ser Val Asp Leu Pro Gly Gly Met Thr
1               5                   10                  15

Val Leu Val Ser Lys Glu Lys Asp Lys Asp Gly Lys Tyr Ser Leu Glu
                20                  25                  30

Ala Thr Val Asp Lys Leu Glu Leu Lys Gly Thr Ser Asp Lys Asn Asn
            35                  40                  45

Gly Ser Gly Thr Leu Glu Gly Glu Lys Thr Asp Lys Ser Lys Val Lys
        50                  55                  60

Ser Thr Ile Ala Asp Asp Leu Ser Gln Thr Lys Phe Glu Ile Phe Lys
65                  70                  75                  80

Glu Asp Gly Lys Thr Leu Val Ser Lys Lys Val Thr Leu Lys Asp Lys
                85                  90                  95

Ser Ser Thr Glu Glu Lys Phe Asn Gly Lys Gly Glu Thr Ser Glu Lys
            100                 105                 110

Thr Ile Val Arg Ala Asn Gly Thr Arg Leu Glu Tyr Thr Asp Ile Lys
        115                 120                 125

Ser Asp Gly Ser Gly Lys Ala Lys Glu Val Leu Lys Asp Phe Thr Leu
    130                 135                 140

Glu Gly Thr Leu Ala Ala Asp Gly Lys Thr Thr Leu Lys Val Thr Glu
145                 150                 155                 160

Gly Thr Val Val Leu Ser Lys Asn Ile Leu Lys Ser Gly Glu Ile Thr
                165                 170                 175

Ala Ala Leu Asp Asp Ser Asp Thr Thr Arg Ala Thr Lys Lys Thr Gly
            180                 185                 190

Lys Trp Asp Ser Lys Thr Ser Thr Leu Thr Ile Ser Val Asn Ser Gln
        195                 200                 205

Lys Thr Lys Asn Leu Val Phe Thr Lys Glu Asp Thr Ile Thr Val Gln
    210                 215                 220

Arg Tyr Asp Ser Ala Gly Thr Asn Leu Glu Gly Lys Ala Val Glu Ile
225                 230                 235                 240

Thr Thr Leu Lys Glu Leu Lys Asn Ala Leu Lys Gly Ser Glu Ser Gln
                245                 250                 255

Val Arg Gln Gln Phe Ser Lys Asp Ile Glu Lys Leu Leu Asn Glu Gln
```

```
                    260                 265                 270
Val Asn Lys Glu Met Gln Ser Ser Asn Leu Tyr Met Ser Met Ser Ser
                275                 280                 285

Trp Ser Tyr Thr His Ser Leu Asp Gly Ala Gly Leu Phe Leu Phe Asp
            290                 295                 300

His Ala Ala Glu Glu Tyr Glu His Ala Lys Lys Leu Ile Ile Phe Leu
305                 310                 315                 320

Asn Glu Asn Asn Val Pro Val Gln Leu Thr Ser Ile Ser Ala Pro Glu
                325                 330                 335

His Lys Phe Glu Gly Leu Thr Gln Ile Phe Gln Lys Ala Tyr Glu His
            340                 345                 350

Glu Gln His Ile Ser Glu Ser Ile Asn Asn Ile Val Asp His Ala Ile
        355                 360                 365

Lys Cys Lys Asp His Ala Thr Phe Asn Phe Leu Gln Trp Tyr Val Ala
370                 375                 380

Glu Gln His Glu Glu Val Leu Phe Lys Asp Ile Leu Asp Lys Ile
385                 390                 395                 400

Glu Leu Ile Gly Asn Glu Asn His Gly Leu Tyr Leu Ala Asp Gln Tyr
                405                 410                 415

Val Lys Gly Ile Ala Lys Ser Arg Lys Ser
            420                 425

<210> SEQ ID NO 10
<211> LENGTH: 426
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Met Asp Glu Lys Asn Ser Val Ser Val Asp Leu Pro Gly Glu Met Lys
1               5                   10                  15

Val Leu Val Ser Lys Glu Lys Asp Lys Asp Gly Lys Tyr Ser Leu Glu
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Ala Lys Ser Lys Ala Lys
    50                  55                  60

Leu Thr Ile Ala Asp Asp Leu Ser Gln Thr Lys Phe Glu Ile Phe Lys
65                  70                  75                  80

Glu Asp Gly Lys Thr Leu Val Ser Lys Val Thr Leu Lys Asp Lys
                85                  90                  95

Ser Ser Thr Glu Glu Lys Phe Asn Asp Lys Gly Lys Leu Ser Glu Lys
            100                 105                 110

Val Val Thr Arg Ala Asn Gly Thr Arg Leu Glu Tyr Thr Glu Ile Gln
        115                 120                 125

Asn Asp Gly Ser Gly Lys Ala Lys Glu Val Leu Lys Ser Leu Thr Leu
    130                 135                 140

Glu Gly Thr Leu Thr Ala Asp Gly Glu Thr Lys Leu Thr Val Glu Ala
145                 150                 155                 160

Gly Thr Val Thr Leu Ser Lys Asn Ile Ser Glu Ser Gly Glu Ile Thr
                165                 170                 175

Val Glu Leu Lys Asp Thr Glu Thr Thr Pro Ala Asp Lys Lys Ser Gly
            180                 185                 190
```

-continued

```
Thr Trp Asp Ser Lys Thr Ser Thr Leu Thr Ile Ser Lys Asn Ser Gln
            195                 200                 205
Lys Thr Lys Gln Leu Val Phe Thr Lys Glu Asn Thr Ile Thr Val Gln
        210                 215                 220
Lys Tyr Asn Thr Ala Gly Thr Lys Leu Glu Gly Ser Pro Ala Glu Ile
225                 230                 235                 240
Lys Asp Leu Glu Ala Leu Lys Ala Leu Lys Gly Ser Glu Ser Gln
                245                 250                 255
Val Arg Gln Gln Phe Ser Lys Asp Ile Glu Lys Leu Leu Asn Glu Gln
            260                 265                 270
Val Asn Lys Glu Met Gln Ser Ser Asn Leu Tyr Met Ser Met Ser Ser
        275                 280                 285
Trp Ser Tyr Thr His Ser Leu Asp Gly Ala Gly Leu Phe Leu Phe Asp
    290                 295                 300
His Ala Ala Glu Glu Tyr Glu His Ala Lys Lys Leu Ile Ile Phe Leu
305                 310                 315                 320
Asn Glu Asn Asn Val Pro Val Gln Leu Thr Ser Ile Ser Ala Pro Glu
                325                 330                 335
His Lys Phe Glu Gly Leu Thr Gln Ile Phe Gln Lys Ala Tyr Glu His
            340                 345                 350
Glu Gln His Ile Ser Glu Ser Ile Asn Asn Ile Val Asp His Ala Ile
        355                 360                 365
Lys Cys Lys Asp His Ala Thr Phe Asn Phe Leu Gln Trp Tyr Val Ala
370                 375                 380
Glu Gln His Glu Glu Val Leu Phe Lys Asp Ile Leu Asp Lys Ile
385                 390                 395                 400
Glu Leu Ile Gly Asn Glu Asn His Gly Leu Tyr Leu Ala Asp Gln Tyr
                405                 410                 415
Val Lys Gly Ile Ala Lys Ser Arg Lys Ser
            420                 425
```

<210> SEQ ID NO 11
<211> LENGTH: 265
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

```
Met Asp Glu Lys Asn Ser Val Ser Val Asp Leu Pro Gly Glu Met Lys
1               5                   10                  15
Val Leu Val Ser Lys Glu Lys Asp Lys Asp Gly Lys Tyr Ser Leu Met
            20                  25                  30
Ala Thr Val Asp Lys Leu Glu Leu Lys Gly Thr Ser Asp Lys Ser Asn
        35                  40                  45
Gly Ser Gly Thr Leu Glu Gly Glu Lys Ser Asp Lys Ser Lys Ala Lys
    50                  55                  60
Leu Thr Ile Ser Glu Asp Leu Ser Lys Thr Thr Phe Glu Ile Phe Lys
65                  70                  75                  80
Glu Asp Gly Lys Thr Leu Val Ser Lys Val Asn Ser Lys Asp Lys
                85                  90                  95
Ser Ser Ile Glu Glu Lys Phe Asn Ala Lys Gly Glu Leu Ser Glu Lys
            100                 105                 110
```

```
Thr Ile Leu Arg Ala Asn Gly Thr Arg Leu Glu Tyr Thr Glu Ile Lys
            115                 120                 125

Ser Asp Gly Thr Gly Lys Ala Lys Glu Val Leu Lys Asp Phe Ala Leu
        130                 135                 140

Glu Gly Thr Leu Ala Ala Asp Lys Thr Thr Leu Lys Val Thr Glu Gly
145                 150                 155                 160

Thr Val Val Leu Ser Lys His Ile Pro Asn Ser Gly Glu Ile Thr Val
                165                 170                 175

Glu Leu Asn Asp Ser Asn Ser Thr Gln Ala Thr Lys Lys Thr Gly Lys
            180                 185                 190

Trp Asp Ser Asn Thr Ser Thr Leu Thr Ile Ser Val Asn Ser Lys Lys
        195                 200                 205

Thr Lys Asn Ile Val Phe Thr Lys Glu Asp Thr Ile Thr Val Gln Lys
    210                 215                 220

Tyr Asp Ser Ala Gly Thr Asn Leu Glu Gly Asn Ala Val Glu Ile Lys
225                 230                 235                 240

Thr Leu Asp Glu Leu Lys Asn Ala Leu Lys Cys Leu Val Pro Arg Gly
                245                 250                 255

Ser Leu Glu His His His His His His
            260                 265

<210> SEQ ID NO 12
<211> LENGTH: 408
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Asp Lys Ser Lys Val Lys
    50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
        115                 120                 125

Ser Asp Gly Ser Gly Lys Ala Lys Glu Val Leu Lys Gly Tyr Thr Leu
    130                 135                 140

Glu Gly Gln Leu Ser Asp Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
```

```
                195                 200                 205
Thr Lys Asp Leu Val Phe Thr Lys Glu Asn Thr Ile Thr Val Gln Gln
210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Gly Gly Ser Met Gln
                245                 250                 255

Ile Tyr Glu Gly Lys Leu Thr Ala Glu Gly Leu Arg Phe Gly Ile Val
                260                 265                 270

Ala Ser Arg Phe Asn His Ala Leu Val Asp Arg Leu Val Glu Gly Ala
            275                 280                 285

Ile Asp Cys Ile Val Arg His Gly Gly Arg Glu Glu Asp Ile Thr Leu
290                 295                 300

Val Arg Val Pro Gly Ser Trp Glu Ile Pro Val Ala Ala Gly Glu Leu
305                 310                 315                 320

Ala Arg Lys Glu Asp Ile Asp Ala Val Ile Ala Ile Gly Val Leu Ile
                325                 330                 335

Arg Gly Ala Thr Pro His Phe Asp Tyr Ile Ala Ser Glu Val Ser Lys
                340                 345                 350

Gly Leu Ala Asn Leu Ser Leu Glu Leu Arg Lys Pro Ile Thr Phe Gly
            355                 360                 365

Val Ile Thr Ala Asp Thr Leu Glu Gln Ala Ile Glu Arg Ala Gly Thr
370                 375                 380

Lys His Gly Asn Lys Gly Trp Glu Ala Ala Leu Ser Ala Ile Glu Met
385                 390                 395                 400

Ala Asn Leu Phe Lys Ser Leu Arg
                405

<210> SEQ ID NO 13
<211> LENGTH: 408
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
                20                  25                  30

Ala Thr Val Asp Lys Leu Glu Leu Lys Gly Thr Ser Asp Lys Asn Asn
            35                  40                  45

Gly Ser Gly Val Leu Glu Gly Val Lys Ala Asp Lys Ser Lys Val Lys
        50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Val Thr Ser Lys Asp Lys
                85                  90                  95

Ser Ser Thr Glu Glu Lys Phe Asn Glu Lys Gly Glu Val Ser Glu Lys
                100                 105                 110

Ile Ile Thr Arg Ala Asp Gly Thr Arg Leu Glu Tyr Thr Gly Ile Lys
            115                 120                 125

Ser Asp Gly Ser Gly Lys Ala Lys Glu Val Leu Lys Gly Tyr Asp Leu
        130                 135                 140
```

```
Lys Gly Glu Leu Ser Ser Glu Lys Thr Thr Leu Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
        195                 200                 205

Thr Lys Asp Leu Val Phe Thr Lys Glu Asn Thr Ile Thr Val Gln Gln
    210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Gly Gly Ser Met Gln
                245                 250                 255

Ile Tyr Glu Gly Lys Leu Thr Ala Glu Gly Leu Arg Phe Gly Ile Val
            260                 265                 270

Ala Ser Arg Phe Asn His Ala Leu Val Asp Arg Leu Val Glu Gly Ala
        275                 280                 285

Ile Asp Cys Ile Val Arg His Gly Gly Arg Glu Glu Asp Ile Thr Leu
    290                 295                 300

Val Arg Val Pro Gly Ser Trp Glu Ile Pro Val Ala Ala Gly Glu Leu
305                 310                 315                 320

Ala Arg Lys Glu Asp Ile Asp Ala Val Ile Ala Ile Gly Val Leu Ile
                325                 330                 335

Arg Gly Ala Thr Pro His Phe Asp Tyr Ile Ala Ser Glu Val Ser Lys
            340                 345                 350

Gly Leu Ala Asn Leu Ser Leu Glu Leu Arg Lys Pro Ile Thr Phe Gly
        355                 360                 365

Val Ile Thr Ala Asp Thr Leu Glu Gln Ala Ile Glu Arg Ala Gly Thr
    370                 375                 380

Lys His Gly Asn Lys Gly Trp Glu Ala Ala Leu Ser Ala Ile Glu Met
385                 390                 395                 400

Ala Asn Leu Phe Lys Ser Leu Arg
                405

<210> SEQ ID NO 14
<211> LENGTH: 408
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
                20                  25                  30

Ala Thr Val Asp Lys Leu Glu Leu Lys Gly Thr Ser Asp Lys Asn Asn
            35                  40                  45

Gly Ser Gly Val Leu Glu Gly Val Lys Ala Asp Lys Ser Lys Val Lys
        50                  55                  60

Leu Thr Ile Ser Asp Asp Leu Gly Gln Thr Thr Leu Glu Val Phe Lys
65                  70                  75                  80
```

```
Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
            115                 120                 125

Ser Asp Gly Ser Gly Lys Ala Lys Glu Val Leu Lys Gly Phe Thr Leu
            130                 135                 140

Glu Gly Lys Val Ala Asn Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
            195                 200                 205

Thr Lys Asp Leu Val Phe Thr Lys Glu Asn Thr Ile Thr Val Gln Gln
            210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Gly Ser Met Gln
                245                 250                 255

Ile Tyr Glu Gly Lys Leu Thr Ala Glu Gly Leu Arg Phe Gly Ile Val
            260                 265                 270

Ala Ser Arg Phe Asn His Ala Leu Val Asp Arg Leu Val Glu Gly Ala
            275                 280                 285

Ile Asp Cys Ile Val Arg His Gly Gly Arg Glu Glu Asp Ile Thr Leu
            290                 295                 300

Val Arg Val Pro Gly Ser Trp Glu Ile Pro Val Ala Ala Gly Glu Leu
305                 310                 315                 320

Ala Arg Lys Glu Asp Ile Asp Ala Val Ile Ala Ile Gly Val Leu Ile
            325                 330                 335

Arg Gly Ala Thr Pro His Phe Asp Tyr Ile Ala Ser Glu Val Ser Lys
            340                 345                 350

Gly Leu Ala Asn Leu Ser Leu Glu Leu Arg Lys Pro Ile Thr Phe Gly
            355                 360                 365

Val Ile Thr Ala Asp Thr Leu Glu Gln Ala Ile Glu Arg Ala Gly Thr
            370                 375                 380

Lys His Gly Asn Lys Gly Trp Glu Ala Ala Leu Ser Ala Ile Glu Met
385                 390                 395                 400

Ala Asn Leu Phe Lys Ser Leu Arg
                405

<210> SEQ ID NO 15
<211> LENGTH: 408
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
```

```
            20                  25                  30
Ala Thr Val Asp Lys Leu Glu Leu Lys Gly Thr Ser Asp Lys Asn Asn
            35                  40                  45

Gly Ser Gly Val Leu Glu Gly Val Lys Ala Asp Lys Ser Lys Val Lys
     50                  55                  60

Leu Thr Ile Ser Asp Asp Leu Gly Gln Thr Thr Leu Glu Val Phe Lys
 65                  70                  75                  80

Glu Asp Gly Lys Thr Leu Val Ser Lys Val Thr Ser Lys Asp Lys
                 85                  90                  95

Ser Ser Thr Glu Glu Lys Phe Asn Glu Lys Gly Glu Val Ser Glu Lys
             100                 105                 110

Ile Ile Thr Arg Ala Asp Gly Thr Arg Leu Glu Tyr Thr Gly Ile Lys
             115                 120                 125

Ser Asp Gly Ser Gly Lys Ala Lys Glu Val Leu Lys Gly Phe Ala Leu
             130                 135                 140

Glu Gly Thr Leu Thr Asp Glu Lys Thr Thr Leu Val Val Lys Glu Gly
145                 150                 155                 160

Thr Val Thr Leu Ser Lys Asn Ile Ser Lys Ser Gly Glu Val Ser Val
                 165                 170                 175

Glu Leu Asn Asp Thr Asp Ser Ser Ala Ala Thr Lys Lys Thr Ala Ala
             180                 185                 190

Trp Asn Ser Gly Thr Ser Thr Leu Thr Ile Thr Val Asn Ser Lys Lys
             195                 200                 205

Thr Lys Asp Leu Val Phe Thr Lys Glu Asn Thr Ile Thr Val Gln Gln
             210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Gly Gly Ser Met Gln
                 245                 250                 255

Ile Tyr Glu Gly Lys Leu Thr Ala Glu Gly Leu Arg Phe Gly Ile Val
             260                 265                 270

Ala Ser Arg Phe Asn His Ala Leu Val Asp Arg Leu Val Glu Gly Ala
             275                 280                 285

Ile Asp Cys Ile Val Arg His Gly Gly Arg Glu Glu Asp Ile Thr Leu
             290                 295                 300

Val Arg Val Pro Gly Ser Trp Glu Ile Pro Val Ala Ala Gly Glu Leu
305                 310                 315                 320

Ala Arg Lys Glu Asp Ile Asp Ala Val Ile Ala Ile Gly Val Leu Ile
                 325                 330                 335

Arg Gly Ala Thr Pro His Phe Asp Tyr Ile Ala Ser Glu Val Ser Lys
             340                 345                 350

Gly Leu Ala Asn Leu Ser Leu Glu Leu Arg Lys Pro Ile Thr Phe Gly
             355                 360                 365

Val Ile Thr Ala Asp Thr Leu Glu Gln Ala Ile Glu Arg Ala Gly Thr
             370                 375                 380

Lys His Gly Asn Lys Gly Trp Glu Ala Ala Leu Ser Ala Ile Glu Met
385                 390                 395                 400

Ala Asn Leu Phe Lys Ser Leu Arg
                 405

<210> SEQ ID NO 16
<211> LENGTH: 408
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 16

Met Asp Glu Lys Asn Ser Ala Ser Val Asp Leu Pro Gly Met Lys
1               5                   10                  15

Val Leu Val Ser Lys Glu Lys Asp Gly Lys Tyr Ser Leu Lys
            20                  25                  30

Ala Thr Val Asp Lys Ile Glu Leu Lys Gly Thr Ser Asp Lys Asp Asn
            35                  40                  45

Gly Ser Gly Val Leu Glu Gly Thr Lys Asp Lys Ser Lys Ala Lys
50                  55                  60

Leu Thr Ile Ala Asp Asp Leu Ser Lys Thr Thr Phe Glu Leu Phe Lys
65                  70                  75                  80

Glu Asp Gly Lys Thr Leu Val Ser Arg Lys Val Ser Ser Lys Asp Lys
                85                  90                  95

Thr Ser Thr Asp Glu Met Phe Asn Glu Lys Gly Glu Leu Ser Ala Lys
                100                 105                 110

Thr Met Thr Arg Glu Asn Gly Thr Lys Leu Glu Tyr Thr Glu Met Lys
            115                 120                 125

Ser Asp Gly Thr Gly Lys Ala Lys Glu Val Leu Lys Asn Phe Thr Leu
130                 135                 140

Glu Gly Lys Val Ala Asn Asp Lys Val Thr Leu Glu Val Lys Glu Gly
145                 150                 155                 160

Thr Val Thr Leu Ser Lys Glu Ile Ala Lys Ser Gly Glu Val Thr Val
                165                 170                 175

Ala Leu Asn Asp Thr Asn Thr Thr Gln Ala Thr Lys Lys Thr Gly Ala
                180                 185                 190

Trp Asp Ser Lys Thr Ser Thr Leu Thr Ile Ser Val Asn Ser Lys Lys
                195                 200                 205

Thr Thr Gln Leu Val Phe Thr Lys Gln Asp Thr Ile Thr Val Gln Lys
210                 215                 220

Tyr Asp Ser Ala Gly Thr Asn Leu Glu Gly Thr Ala Val Glu Ile Lys
225                 230                 235                 240

Thr Leu Asp Glu Leu Lys Asn Ala Leu Lys Gly Gly Ser Met Gln
                245                 250                 255

Ile Tyr Glu Gly Lys Leu Thr Ala Glu Gly Leu Arg Phe Gly Ile Val
                260                 265                 270

Ala Ser Arg Phe Asn His Ala Leu Val Asp Arg Leu Val Glu Gly Ala
            275                 280                 285

Ile Asp Cys Ile Val Arg His Gly Gly Arg Glu Glu Asp Ile Thr Leu
290                 295                 300

Val Arg Val Pro Gly Ser Trp Glu Ile Pro Val Ala Ala Gly Glu Leu
305                 310                 315                 320

Ala Arg Lys Glu Asp Ile Asp Ala Val Ile Ala Ile Gly Val Leu Ile
                325                 330                 335

Arg Gly Ala Thr Pro His Phe Asp Tyr Ile Ala Ser Glu Val Ser Lys
                340                 345                 350

Gly Leu Ala Asn Leu Ser Leu Glu Leu Arg Lys Pro Ile Thr Phe Gly
            355                 360                 365

Val Ile Thr Ala Asp Thr Leu Glu Gln Ala Ile Glu Arg Ala Gly Thr
370                 375                 380
```

Lys His Gly Asn Lys Gly Trp Glu Ala Ala Leu Ser Ala Ile Glu Met
385                 390                 395                 400

Ala Asn Leu Phe Lys Ser Leu Arg
                405

<210> SEQ ID NO 17
<211> LENGTH: 409
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Met Asp Glu Lys Asn Ser Val Ser Val Asp Leu Pro Gly Gly Met Lys
1               5                   10                  15

Val Leu Val Ser Lys Glu Lys Asp Lys Asp Gly Lys Tyr Ser Leu Met
                20                  25                  30

Ala Thr Val Glu Lys Leu Glu Leu Lys Gly Thr Ser Asp Lys Ser Asn
            35                  40                  45

Gly Ser Gly Val Leu Glu Gly Glu Lys Ala Asp Lys Ser Lys Ala Lys
50                  55                  60

Leu Thr Ile Ser Gln Asp Leu Asn Gln Thr Thr Phe Glu Ile Phe Lys
65                  70                  75                  80

Glu Asp Gly Lys Thr Leu Val Ser Arg Lys Val Asn Ser Lys Asp Lys
                85                  90                  95

Ser Ser Thr Glu Glu Lys Phe Asn Asp Lys Gly Lys Leu Ser Glu Lys
            100                 105                 110

Val Val Thr Arg Ala Asn Gly Thr Arg Leu Glu Tyr Thr Glu Ile Lys
        115                 120                 125

Asn Asp Gly Ser Gly Lys Ala Lys Glu Val Leu Lys Gly Phe Ala Leu
130                 135                 140

Glu Gly Thr Leu Thr Asp Gly Glu Thr Lys Leu Thr Val Thr Glu
145                 150                 155                 160

Gly Thr Val Thr Leu Ser Lys Asn Ile Ser Lys Ser Gly Glu Ile Thr
                165                 170                 175

Val Ala Leu Asn Asp Thr Glu Thr Thr Pro Ala Asp Lys Lys Thr Gly
            180                 185                 190

Glu Trp Lys Ser Asp Thr Ser Thr Leu Thr Ile Ser Lys Asn Ser Gln
        195                 200                 205

Lys Pro Lys Gln Leu Val Phe Thr Lys Glu Asn Thr Ile Thr Val Gln
210                 215                 220

Asn Tyr Asn Arg Ala Gly Asn Ala Leu Glu Gly Ser Pro Ala Glu Ile
225                 230                 235                 240

Lys Asp Leu Ala Glu Leu Lys Ala Ala Leu Lys Gly Gly Gly Ser Met
                245                 250                 255

Gln Ile Tyr Glu Gly Lys Leu Thr Ala Glu Gly Leu Arg Phe Gly Ile
            260                 265                 270

Val Ala Ser Arg Phe Asn His Ala Leu Val Asp Arg Leu Val Glu Gly
        275                 280                 285

Ala Ile Asp Cys Ile Val Arg His Gly Gly Arg Glu Glu Asp Ile Thr
290                 295                 300

Leu Val Arg Val Pro Gly Ser Trp Glu Ile Pro Val Ala Ala Gly Glu
305                 310                 315                 320

Leu Ala Arg Lys Glu Asp Ile Asp Ala Val Ile Ala Ile Gly Val Leu

```
                    325                 330                 335
Ile Arg Gly Ala Thr Pro His Phe Asp Tyr Ile Ala Ser Glu Val Ser
                340                 345                 350

Lys Gly Leu Ala Asn Leu Ser Leu Glu Leu Arg Lys Pro Ile Thr Phe
            355                 360                 365

Gly Val Ile Thr Ala Asp Thr Leu Glu Gln Ala Ile Glu Arg Ala Gly
        370                 375                 380

Thr Lys His Gly Asn Lys Gly Trp Glu Ala Ala Leu Ser Ala Ile Glu
385                 390                 395                 400

Met Ala Asn Leu Phe Lys Ser Leu Arg
                405

<210> SEQ ID NO 18
<211> LENGTH: 408
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Asp Glu Lys Asn Ser Val Ser Val Asp Leu Pro Gly Glu Met Lys
1               5                   10                  15

Val Leu Val Ser Lys Glu Lys Asp Lys Asp Gly Lys Tyr Ser Leu Met
            20                  25                  30

Ala Thr Val Asp Lys Leu Glu Leu Lys Gly Thr Ser Asp Lys Ser Asn
        35                  40                  45

Gly Ser Gly Thr Leu Glu Gly Glu Lys Ser Asp Lys Ser Lys Ala Lys
    50                  55                  60

Leu Thr Ile Ser Glu Asp Leu Ser Lys Thr Thr Phe Glu Ile Phe Lys
65                  70                  75                  80

Glu Asp Gly Lys Thr Leu Val Ser Lys Val Asn Ser Lys Asp Lys
                85                  90                  95

Ser Ser Ile Glu Glu Lys Phe Asn Ala Lys Gly Glu Leu Ser Glu Lys
            100                 105                 110

Thr Ile Leu Arg Ala Asn Gly Thr Arg Leu Glu Tyr Thr Glu Ile Lys
        115                 120                 125

Ser Asp Gly Thr Gly Lys Ala Lys Glu Val Leu Lys Asp Phe Ala Leu
    130                 135                 140

Glu Gly Thr Leu Ala Ala Asp Lys Thr Thr Leu Lys Val Thr Glu Gly
145                 150                 155                 160

Thr Val Val Leu Ser Lys His Ile Pro Asn Ser Gly Glu Ile Thr Val
                165                 170                 175

Glu Leu Asn Asp Ser Asn Ser Thr Gln Ala Thr Lys Lys Thr Gly Lys
            180                 185                 190

Trp Asp Ser Asn Thr Ser Thr Leu Thr Ile Ser Val Asn Ser Lys Lys
        195                 200                 205

Thr Lys Asn Ile Val Phe Thr Lys Glu Asp Thr Ile Thr Val Gln Lys
    210                 215                 220

Tyr Asp Ser Ala Gly Thr Asn Leu Glu Gly Asn Ala Val Glu Ile Lys
225                 230                 235                 240

Thr Leu Asp Glu Leu Lys Asn Ala Leu Lys Gly Gly Ser Met Gln
                245                 250                 255

Ile Tyr Glu Gly Lys Leu Thr Ala Glu Gly Leu Arg Phe Gly Ile Val
            260                 265                 270
```

```
Ala Ser Arg Phe Asn His Ala Leu Val Asp Arg Leu Val Glu Gly Ala
        275                 280                 285

Ile Asp Cys Ile Val Arg His Gly Gly Arg Glu Glu Asp Ile Thr Leu
290                 295                 300

Val Arg Val Pro Gly Ser Trp Glu Ile Pro Val Ala Ala Gly Glu Leu
305                 310                 315                 320

Ala Arg Lys Glu Asp Ile Asp Ala Val Ile Ala Ile Gly Val Leu Ile
                325                 330                 335

Arg Gly Ala Thr Pro His Phe Asp Tyr Ile Ala Ser Glu Val Ser Lys
                340                 345                 350

Gly Leu Ala Asn Leu Ser Leu Glu Leu Arg Lys Pro Ile Thr Phe Gly
        355                 360                 365

Val Ile Thr Ala Asp Thr Leu Glu Gln Ala Ile Glu Arg Ala Gly Thr
370                 375                 380

Lys His Gly Asn Lys Gly Trp Glu Ala Ala Leu Ser Ala Ile Glu Met
385                 390                 395                 400

Ala Asn Leu Phe Lys Ser Leu Arg
                405

<210> SEQ ID NO 19
<211> LENGTH: 409
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Met Asp Glu Lys Asn Ser Val Ser Val Asp Leu Pro Gly Gly Met Lys
1               5                   10                  15

Val Leu Val Ser Lys Glu Lys Asp Lys Asp Gly Lys Tyr Ser Leu Met
                20                  25                  30

Ala Thr Val Glu Lys Leu Glu Leu Lys Gly Thr Ser Asp Lys Asn Asn
            35                  40                  45

Gly Ser Gly Thr Leu Glu Gly Glu Lys Thr Asp Lys Ser Lys Val Lys
        50                  55                  60

Leu Thr Ile Ala Glu Asp Leu Ser Lys Thr Thr Phe Glu Ile Phe Lys
65                  70                  75                  80

Glu Asp Gly Lys Thr Leu Val Ser Lys Val Thr Leu Lys Asp Lys
                85                  90                  95

Ser Ser Thr Glu Glu Lys Phe Asn Glu Lys Gly Glu Ile Ser Glu Lys
                100                 105                 110

Thr Ile Val Arg Ala Asn Gly Thr Arg Leu Glu Tyr Thr Asp Ile Lys
            115                 120                 125

Ser Asp Gly Ser Gly Lys Ala Lys Glu Val Leu Lys Asp Phe Thr Leu
        130                 135                 140

Glu Gly Thr Leu Ala Ala Asp Gly Lys Thr Thr Leu Lys Val Thr Glu
145                 150                 155                 160

Gly Thr Val Val Leu Ser Lys Asn Ile Leu Lys Ser Gly Glu Ile Thr
                165                 170                 175

Val Ala Leu Asp Asp Ser Asp Thr Thr Gln Ala Thr Lys Lys Thr Gly
                180                 185                 190

Lys Trp Asp Ser Lys Thr Ser Thr Leu Thr Ile Ser Val Asn Ser Gln
            195                 200                 205
```

```
Lys Thr Lys Asn Leu Val Phe Thr Lys Glu Asp Thr Ile Thr Val Gln
        210                 215                 220

Lys Tyr Asp Ser Ala Gly Thr Asn Leu Glu Gly Lys Ala Val Glu Ile
225                 230                 235                 240

Thr Thr Leu Glu Lys Leu Lys Asp Ala Leu Lys Gly Gly Ser Met
                245                 250                 255

Gln Ile Tyr Glu Gly Lys Leu Thr Ala Glu Gly Leu Arg Phe Gly Ile
                260                 265                 270

Val Ala Ser Arg Phe Asn His Ala Leu Val Asp Arg Leu Val Glu Gly
            275                 280                 285

Ala Ile Asp Cys Ile Val Arg His Gly Gly Arg Glu Glu Asp Ile Thr
        290                 295                 300

Leu Val Arg Val Pro Gly Ser Trp Glu Ile Pro Val Ala Ala Gly Glu
305                 310                 315                 320

Leu Ala Arg Lys Glu Asp Ile Asp Ala Val Ile Ala Ile Gly Val Leu
                325                 330                 335

Ile Arg Gly Ala Thr Pro His Phe Asp Tyr Ile Ala Ser Glu Val Ser
                340                 345                 350

Lys Gly Leu Ala Asn Leu Ser Leu Glu Leu Arg Lys Pro Ile Thr Phe
            355                 360                 365

Gly Val Ile Thr Ala Asp Thr Leu Glu Gln Ala Ile Glu Arg Ala Gly
370                 375                 380

Thr Lys His Gly Asn Lys Gly Trp Glu Ala Ala Leu Ser Ala Ile Glu
385                 390                 395                 400

Met Ala Asn Leu Phe Lys Ser Leu Arg
                405

<210> SEQ ID NO 20
<211> LENGTH: 409
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Met Asp Glu Lys Asn Ser Val Ser Val Asp Leu Pro Gly Gly Met Thr
1               5                   10                  15

Val Leu Val Ser Lys Glu Lys Asp Asp Gly Lys Tyr Ser Leu Glu
                20                  25                  30

Ala Thr Val Asp Lys Leu Glu Leu Lys Gly Thr Ser Asp Lys Asn Asn
            35                  40                  45

Gly Ser Gly Thr Leu Glu Gly Glu Lys Thr Asp Lys Ser Lys Val Lys
50                  55                  60

Ser Thr Ile Ala Asp Asp Leu Ser Gln Thr Lys Phe Glu Ile Phe Lys
65                  70                  75                  80

Glu Asp Gly Lys Thr Leu Val Ser Lys Lys Val Thr Leu Lys Asp Lys
                85                  90                  95

Ser Ser Thr Glu Glu Lys Phe Asn Gly Lys Gly Glu Thr Ser Glu Lys
                100                 105                 110

Thr Ile Val Arg Ala Asn Gly Thr Arg Leu Glu Tyr Thr Asp Ile Lys
            115                 120                 125

Ser Asp Gly Ser Gly Lys Ala Lys Glu Val Leu Lys Asp Phe Thr Leu
130                 135                 140

Glu Gly Thr Leu Ala Ala Asp Gly Lys Thr Thr Leu Lys Val Thr Glu
```

```
                145                 150                 155                 160
Gly Thr Val Val Leu Ser Lys Asn Ile Leu Lys Ser Gly Glu Ile Thr
                165                 170                 175

Ala Ala Leu Asp Asp Ser Asp Thr Thr Arg Ala Thr Lys Lys Thr Gly
                180                 185                 190

Lys Trp Asp Ser Lys Thr Ser Thr Leu Thr Ile Ser Val Asn Ser Gln
                195                 200                 205

Lys Thr Lys Asn Leu Val Phe Thr Lys Glu Asp Thr Ile Thr Val Gln
                210                 215                 220

Arg Tyr Asp Ser Ala Gly Thr Asn Leu Glu Gly Lys Ala Val Glu Ile
225                 230                 235                 240

Thr Thr Leu Lys Glu Leu Lys Asn Ala Leu Lys Gly Gly Gly Ser Met
                245                 250                 255

Gln Ile Tyr Glu Gly Lys Leu Thr Ala Glu Gly Leu Arg Phe Gly Ile
                260                 265                 270

Val Ala Ser Arg Phe Asn His Ala Leu Val Asp Arg Leu Val Glu Gly
                275                 280                 285

Ala Ile Asp Cys Ile Val Arg His Gly Gly Arg Glu Glu Asp Ile Thr
                290                 295                 300

Leu Val Arg Val Pro Gly Ser Trp Glu Ile Pro Val Ala Ala Gly Glu
305                 310                 315                 320

Leu Ala Arg Lys Glu Asp Ile Asp Ala Val Ile Ala Ile Gly Val Leu
                325                 330                 335

Ile Arg Gly Ala Thr Pro His Phe Asp Tyr Ile Ala Ser Glu Val Ser
                340                 345                 350

Lys Gly Leu Ala Asn Leu Ser Leu Glu Leu Arg Lys Pro Ile Thr Phe
                355                 360                 365

Gly Val Ile Thr Ala Asp Thr Leu Glu Gln Ala Ile Glu Arg Ala Gly
                370                 375                 380

Thr Lys His Gly Asn Lys Gly Trp Glu Ala Ala Leu Ser Ala Ile Glu
385                 390                 395                 400

Met Ala Asn Leu Phe Lys Ser Leu Arg
                405

<210> SEQ ID NO 21
<211> LENGTH: 409
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Met Asp Glu Lys Asn Ser Val Ser Val Asp Leu Pro Gly Glu Met Lys
1               5                   10                  15

Val Leu Val Ser Lys Glu Lys Asp Lys Asp Gly Lys Tyr Ser Leu Glu
                20                  25                  30

Ala Thr Val Asp Lys Leu Glu Leu Lys Gly Thr Ser Asp Lys Asn Asn
                35                  40                  45

Gly Ser Gly Val Leu Glu Gly Val Lys Ala Ala Lys Ser Lys Ala Lys
                50                  55                  60

Leu Thr Ile Ala Asp Asp Leu Ser Gln Thr Lys Phe Glu Ile Phe Lys
65                  70                  75                  80

Glu Asp Gly Lys Thr Leu Val Ser Lys Lys Val Thr Leu Lys Asp Lys
                85                  90                  95
```

```
Ser Ser Thr Glu Glu Lys Phe Asn Asp Lys Gly Lys Leu Ser Glu Lys
            100                 105                 110

Val Val Thr Arg Ala Asn Gly Thr Arg Leu Glu Tyr Thr Glu Ile Gln
            115                 120                 125

Asn Asp Gly Ser Gly Lys Ala Lys Glu Val Leu Lys Ser Leu Thr Leu
        130                 135                 140

Glu Gly Thr Leu Thr Ala Asp Gly Glu Thr Lys Leu Thr Val Glu Ala
145                 150                 155                 160

Gly Thr Val Thr Leu Ser Lys Asn Ile Ser Glu Ser Gly Glu Ile Thr
                165                 170                 175

Val Glu Leu Lys Asp Thr Glu Thr Thr Pro Ala Asp Lys Lys Ser Gly
            180                 185                 190

Thr Trp Asp Ser Lys Thr Ser Thr Leu Thr Ile Ser Lys Asn Ser Gln
            195                 200                 205

Lys Thr Lys Gln Leu Val Phe Thr Lys Glu Asn Thr Ile Thr Val Gln
        210                 215                 220

Lys Tyr Asn Thr Ala Gly Thr Lys Leu Glu Gly Ser Pro Ala Glu Ile
225                 230                 235                 240

Lys Asp Leu Glu Ala Leu Lys Ala Ala Leu Lys Gly Gly Gly Ser Met
                245                 250                 255

Gln Ile Tyr Glu Gly Lys Leu Thr Ala Glu Gly Leu Arg Phe Gly Ile
            260                 265                 270

Val Ala Ser Arg Phe Asn His Ala Leu Val Asp Arg Leu Val Glu Gly
            275                 280                 285

Ala Ile Asp Cys Ile Val Arg His Gly Gly Arg Glu Glu Asp Ile Thr
        290                 295                 300

Leu Val Arg Val Pro Gly Ser Trp Glu Ile Pro Val Ala Ala Gly Glu
305                 310                 315                 320

Leu Ala Arg Lys Glu Asp Ile Asp Ala Val Ile Ala Ile Gly Val Leu
                325                 330                 335

Ile Arg Gly Ala Thr Pro His Phe Asp Tyr Ile Ala Ser Glu Val Ser
            340                 345                 350

Lys Gly Leu Ala Asn Leu Ser Leu Glu Leu Arg Lys Pro Ile Thr Phe
            355                 360                 365

Gly Val Ile Thr Ala Asp Thr Leu Glu Gln Ala Ile Glu Arg Ala Gly
        370                 375                 380

Thr Lys His Gly Asn Lys Gly Trp Glu Ala Ala Leu Ser Ala Ile Glu
385                 390                 395                 400

Met Ala Asn Leu Phe Lys Ser Leu Arg
                405

<210> SEQ ID NO 22
<211> LENGTH: 435
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
                20                  25                  30
```

```
Ala Thr Val Asp Lys Leu Glu Leu Lys Gly Thr Ser Asp Lys Asn Asn
            35                  40                  45

Gly Ser Gly Val Leu Glu Gly Val Lys Ala Asp Lys Ser Lys Val Lys
 50                  55                  60

Leu Thr Ile Ser Asp Asp Leu Gly Gln Thr Thr Leu Glu Val Phe Lys
 65                  70                  75                  80

Glu Asp Gly Lys Thr Leu Val Ser Lys Val Thr Ser Lys Asp Lys
                 85                  90                  95

Ser Ser Thr Glu Glu Lys Phe Asn Glu Lys Gly Glu Val Ser Glu Lys
             100                 105                 110

Ile Ile Thr Arg Ala Asp Gly Thr Arg Leu Glu Tyr Thr Gly Ile Lys
             115                 120                 125

Ser Asp Gly Ser Gly Lys Ala Lys Glu Val Leu Lys Gly Tyr Thr Leu
         130                 135                 140

Glu Gly Gln Leu Ser Asp Glu Lys Thr Thr Leu Val Val Lys Glu Gly
145                 150                 155                 160

Thr Val Thr Leu Ser Lys Asn Ile Ser Lys Ser Gly Glu Val Ser Val
                 165                 170                 175

Glu Leu Asn Asp Thr Asp Ser Ser Ala Ala Thr Lys Lys Thr Ala Ala
             180                 185                 190

Trp Asn Ser Gly Thr Ser Thr Leu Thr Ile Thr Val Asn Ser Lys Lys
         195                 200                 205

Thr Lys Asp Leu Val Phe Thr Lys Glu Asn Thr Ile Thr Val Gln Gln
             210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Ser Met Thr Thr Ala
                 245                 250                 255

Ser Thr Ser Gln Val Arg Gln Asn Tyr His Gln Asp Ser Glu Ala Ala
             260                 265                 270

Ile Asn Arg Gln Ile Asn Leu Glu Leu Tyr Ala Ser Tyr Val Tyr Leu
         275                 280                 285

Ser Met Ser Tyr Tyr Phe Asp Arg Asp Asp Val Ala Leu Lys Asn Phe
         290                 295                 300

Ala Lys Tyr Phe Leu His Gln Ser His Glu Glu Arg Glu His Ala Glu
305                 310                 315                 320

Lys Leu Met Lys Leu Gln Asn Gln Arg Gly Gly Arg Ile Phe Leu Gln
                 325                 330                 335

Asp Ile Lys Lys Pro Asp Cys Asp Asp Trp Glu Ser Gly Leu Asn Ala
             340                 345                 350

Met Glu Cys Ala Leu His Leu Glu Lys Asn Val Asn Gln Ser Leu Leu
         355                 360                 365

Glu Leu His Lys Leu Ala Thr Asp Lys Asn Asp Pro His Leu Cys Asp
         370                 375                 380

Phe Ile Glu Thr His Tyr Leu Asn Glu Gln Val Lys Ala Ile Lys Glu
385                 390                 395                 400

Leu Gly Asp His Val Thr Asn Leu Arg Lys Met Gly Ala Pro Glu Ser
                 405                 410                 415

Gly Leu Ala Glu Tyr Leu Phe Asp Lys His Thr Leu Gly Asp Ser Asp
             420                 425                 430

Asn Glu Ser
         435
```

```
<210> SEQ ID NO 23
<211> LENGTH: 435
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23
```

Met Asp Glu Lys Asn Ser Val Ser Val Asp Leu Pro Gly Met Lys
1               5                   10                  15

Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Asp Lys Ser Lys Val Lys
50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
        115                 120                 125

Ser Asp Gly Ser Gly Lys Ala Lys Glu Val Leu Lys Gly Tyr Asp Leu
130                 135                 140

Lys Gly Glu Leu Ser Ser Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
        195                 200                 205

Thr Lys Asp Leu Val Phe Thr Lys Glu Asn Thr Ile Thr Val Gln Gln
210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Ser Met Thr Thr Ala
                245                 250                 255

Ser Thr Ser Gln Val Arg Gln Asn Tyr His Gln Asp Ser Glu Ala Ala
            260                 265                 270

Ile Asn Arg Gln Ile Asn Leu Glu Leu Tyr Ala Ser Tyr Val Tyr Leu
        275                 280                 285

Ser Met Ser Tyr Tyr Phe Asp Arg Asp Asp Val Ala Leu Lys Asn Phe
290                 295                 300

Ala Lys Tyr Phe Leu His Gln Ser His Glu Glu Arg Glu His Ala Glu
305                 310                 315                 320

Lys Leu Met Lys Leu Gln Asn Gln Arg Gly Gly Arg Ile Phe Leu Gln
                325                 330                 335

Asp Ile Lys Lys Pro Asp Cys Asp Asp Trp Glu Ser Gly Leu Asn Ala
            340                 345                 350

Met Glu Cys Ala Leu His Leu Glu Lys Asn Val Asn Gln Ser Leu Leu
        355                 360                 365

```
Glu Leu His Lys Leu Ala Thr Asp Lys Asn Asp Pro His Leu Cys Asp
        370                 375                 380

Phe Ile Glu Thr His Tyr Leu Asn Glu Gln Val Lys Ala Ile Lys Glu
385                 390                 395                 400

Leu Gly Asp His Val Thr Asn Leu Arg Lys Met Gly Ala Pro Glu Ser
                405                 410                 415

Gly Leu Ala Glu Tyr Leu Phe Asp Lys His Thr Leu Gly Asp Ser Asp
                420                 425                 430

Asn Glu Ser
        435

<210> SEQ ID NO 24
<211> LENGTH: 435
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
                20                  25                  30

Ala Thr Val Asp Lys Leu Glu Leu Lys Gly Thr Ser Asp Lys Asn Asn
            35                  40                  45

Gly Ser Gly Val Leu Glu Gly Val Lys Ala Asp Lys Ser Lys Val Lys
        50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
                100                 105                 110

Ile Ile Thr Arg Ala Asp Gly Thr Arg Leu Glu Tyr Thr Gly Ile Lys
            115                 120                 125

Ser Asp Gly Ser Gly Lys Ala Lys Glu Val Leu Lys Gly Phe Thr Leu
        130                 135                 140

Glu Gly Lys Val Ala Asn Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
                180                 185                 190

Trp Asn Ser Gly Thr Ser Thr Leu Thr Ile Thr Val Asn Ser Lys Lys
            195                 200                 205

Thr Lys Asp Leu Val Phe Thr Lys Glu Asn Thr Ile Thr Val Gln Gln
        210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Ser Met Thr Thr Ala
                245                 250                 255

Ser Thr Ser Gln Val Arg Gln Asn Tyr His Gln Asp Ser Glu Ala Ala
                260                 265                 270
```

```
Ile Asn Arg Gln Ile Asn Leu Glu Leu Tyr Ala Ser Tyr Val Tyr Leu
            275                 280                 285

Ser Met Ser Tyr Tyr Phe Asp Arg Asp Val Ala Leu Lys Asn Phe
    290                 295                 300

Ala Lys Tyr Phe Leu His Gln Ser His Glu Glu Arg Glu His Ala Glu
305                 310                 315                 320

Lys Leu Met Lys Leu Gln Asn Gln Arg Gly Gly Arg Ile Phe Leu Gln
                325                 330                 335

Asp Ile Lys Lys Pro Asp Cys Asp Asp Trp Glu Ser Gly Leu Asn Ala
            340                 345                 350

Met Glu Cys Ala Leu His Leu Glu Lys Asn Val Asn Gln Ser Leu Leu
    355                 360                 365

Glu Leu His Lys Leu Ala Thr Asp Lys Asn Asp Pro His Leu Cys Asp
370                 375                 380

Phe Ile Glu Thr His Tyr Leu Asn Glu Gln Val Lys Ala Ile Lys Glu
385                 390                 395                 400

Leu Gly Asp His Val Thr Asn Leu Arg Lys Met Gly Ala Pro Glu Ser
                405                 410                 415

Gly Leu Ala Glu Tyr Leu Phe Asp Lys His Thr Leu Gly Asp Ser Asp
            420                 425                 430

Asn Glu Ser
        435

<210> SEQ ID NO 25
<211> LENGTH: 435
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Asp Lys Ser Lys Val Lys
    50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Val Thr Ser Lys Asp Lys
                85                  90                  95

Ser Ser Thr Glu Glu Lys Phe Asn Glu Lys Gly Glu Val Ser Glu Lys
                100                 105                 110

Ile Ile Thr Arg Ala Asp Gly Thr Arg Leu Glu Tyr Thr Gly Ile Lys
            115                 120                 125

Ser Asp Gly Ser Gly Lys Ala Lys Glu Val Leu Lys Gly Phe Ala Leu
        130                 135                 140

Glu Gly Thr Leu Thr Asp Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
```

```
                    180                 185                 190
Trp Asn Ser Gly Thr Ser Thr Leu Thr Ile Thr Val Asn Ser Lys Lys
            195                 200                 205

Thr Lys Asp Leu Val Phe Thr Lys Glu Asn Thr Ile Thr Val Gln Gln
        210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Ser Met Thr Thr Ala
                245                 250                 255

Ser Thr Ser Gln Val Arg Gln Asn Tyr His Gln Asp Ser Glu Ala Ala
            260                 265                 270

Ile Asn Arg Gln Ile Asn Leu Glu Leu Tyr Ala Ser Tyr Val Tyr Leu
        275                 280                 285

Ser Met Ser Tyr Tyr Phe Asp Arg Asp Val Ala Leu Lys Asn Phe
290                 295                 300

Ala Lys Tyr Phe Leu His Gln Ser His Glu Glu Arg Glu His Ala Glu
305                 310                 315                 320

Lys Leu Met Lys Leu Gln Asn Gln Arg Gly Gly Arg Ile Phe Leu Gln
                325                 330                 335

Asp Ile Lys Lys Pro Asp Cys Asp Asp Trp Glu Ser Gly Leu Asn Ala
            340                 345                 350

Met Glu Cys Ala Leu His Leu Glu Lys Asn Val Asn Gln Ser Leu Leu
        355                 360                 365

Glu Leu His Lys Leu Ala Thr Asp Lys Asn Asp Pro His Leu Cys Asp
    370                 375                 380

Phe Ile Glu Thr His Tyr Leu Asn Glu Gln Val Lys Ala Ile Lys Glu
385                 390                 395                 400

Leu Gly Asp His Val Thr Asn Leu Arg Lys Met Gly Ala Pro Glu Ser
                405                 410                 415

Gly Leu Ala Glu Tyr Leu Phe Asp Lys His Thr Leu Gly Asp Ser Asp
            420                 425                 430

Asn Glu Ser
        435

<210> SEQ ID NO 26
<211> LENGTH: 435
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Met Asp Glu Lys Asn Ser Ala Ser Val Asp Leu Pro Gly Glu Met Lys
1               5                   10                  15

Val Leu Val Ser Lys Glu Lys Asp Lys Asp Gly Lys Tyr Ser Leu Lys
            20                  25                  30

Ala Thr Val Asp Lys Ile Glu Leu Lys Gly Thr Ser Asp Lys Asp Asn
        35                  40                  45

Gly Ser Gly Val Leu Glu Gly Thr Lys Asp Lys Ser Lys Ala Lys
    50                  55                  60

Leu Thr Ile Ala Asp Asp Leu Ser Lys Thr Thr Phe Glu Leu Phe Lys
65                  70                  75                  80

Glu Asp Gly Lys Thr Leu Val Ser Arg Lys Val Ser Ser Lys Asp Lys
                85                  90                  95
```

Thr Ser Thr Asp Glu Met Phe Asn Glu Lys Gly Glu Leu Ser Ala Lys
            100                 105                 110

Thr Met Thr Arg Glu Asn Gly Thr Lys Leu Glu Tyr Thr Glu Met Lys
            115                 120                 125

Ser Asp Gly Thr Gly Lys Ala Lys Glu Val Leu Lys Asn Phe Thr Leu
        130                 135                 140

Glu Gly Lys Val Ala Asn Asp Lys Val Thr Leu Glu Val Lys Glu Gly
145                 150                 155                 160

Thr Val Thr Leu Ser Lys Glu Ile Ala Lys Ser Gly Glu Val Thr Val
                165                 170                 175

Ala Leu Asn Asp Thr Asn Thr Thr Gln Ala Thr Lys Lys Thr Gly Ala
            180                 185                 190

Trp Asp Ser Lys Thr Ser Thr Leu Thr Ile Ser Val Asn Ser Lys Lys
            195                 200                 205

Thr Thr Gln Leu Val Phe Thr Lys Gln Asp Thr Ile Thr Val Gln Lys
        210                 215                 220

Tyr Asp Ser Ala Gly Thr Asn Leu Glu Gly Thr Ala Val Glu Ile Lys
225                 230                 235                 240

Thr Leu Asp Glu Leu Lys Asn Ala Leu Lys Gly Ser Met Thr Thr Ala
                245                 250                 255

Ser Thr Ser Gln Val Arg Gln Asn Tyr His Gln Asp Ser Glu Ala Ala
            260                 265                 270

Ile Asn Arg Gln Ile Asn Leu Glu Leu Tyr Ala Ser Tyr Val Tyr Leu
        275                 280                 285

Ser Met Ser Tyr Tyr Phe Asp Arg Asp Asp Val Ala Leu Lys Asn Phe
290                 295                 300

Ala Lys Tyr Phe Leu His Gln Ser His Glu Glu Arg Glu His Ala Glu
305                 310                 315                 320

Lys Leu Met Lys Leu Gln Asn Gln Arg Gly Gly Arg Ile Phe Leu Gln
                325                 330                 335

Asp Ile Lys Lys Pro Asp Cys Asp Asp Trp Glu Ser Gly Leu Asn Ala
            340                 345                 350

Met Glu Cys Ala Leu His Leu Glu Lys Asn Val Asn Gln Ser Leu Leu
        355                 360                 365

Glu Leu His Lys Leu Ala Thr Asp Lys Asn Asp Pro His Leu Cys Asp
370                 375                 380

Phe Ile Glu Thr His Tyr Leu Asn Glu Gln Val Lys Ala Ile Lys Glu
385                 390                 395                 400

Leu Gly Asp His Val Thr Asn Leu Arg Lys Met Gly Ala Pro Glu Ser
                405                 410                 415

Gly Leu Ala Glu Tyr Leu Phe Asp Lys His Thr Leu Gly Asp Ser Asp
            420                 425                 430

Asn Glu Ser
        435

<210> SEQ ID NO 27
<211> LENGTH: 436
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Met Asp Glu Lys Asn Ser Val Ser Val Asp Leu Pro Gly Gly Met Lys
1               5                   10                  15

Val Leu Val Ser Lys Glu Lys Asp Lys Asp Gly Lys Tyr Ser Leu Met
            20                  25                  30

Ala Thr Val Glu Lys Leu Glu Leu Lys Gly Thr Ser Asp Lys Ser Asn
        35                  40                  45

Gly Ser Gly Val Leu Glu Gly Glu Lys Ala Asp Lys Ser Lys Ala Lys
    50                  55                  60

Leu Thr Ile Ser Gln Asp Leu Asn Gln Thr Thr Phe Glu Ile Phe Lys
65                  70                  75                  80

Glu Asp Gly Lys Thr Leu Val Ser Arg Lys Val Asn Ser Lys Asp Lys
                85                  90                  95

Ser Ser Thr Glu Glu Lys Phe Asn Asp Lys Gly Lys Leu Ser Glu Lys
            100                 105                 110

Val Val Thr Arg Ala Asn Gly Thr Arg Leu Glu Tyr Thr Glu Ile Lys
        115                 120                 125

Asn Asp Gly Ser Gly Lys Ala Lys Glu Val Leu Lys Gly Phe Ala Leu
    130                 135                 140

Glu Gly Thr Leu Thr Asp Gly Gly Glu Thr Lys Leu Thr Val Thr Glu
145                 150                 155                 160

Gly Thr Val Thr Leu Ser Lys Asn Ile Ser Lys Ser Gly Glu Ile Thr
                165                 170                 175

Val Ala Leu Asn Asp Thr Glu Thr Thr Pro Ala Asp Lys Lys Thr Gly
            180                 185                 190

Glu Trp Lys Ser Asp Thr Ser Thr Leu Thr Ile Ser Lys Asn Ser Gln
        195                 200                 205

Lys Pro Lys Gln Leu Val Phe Thr Lys Glu Asn Thr Ile Thr Val Gln
    210                 215                 220

Asn Tyr Asn Arg Ala Gly Asn Ala Leu Glu Gly Ser Pro Ala Glu Ile
225                 230                 235                 240

Lys Asp Leu Ala Glu Leu Lys Ala Leu Lys Gly Ser Met Thr Thr
                245                 250                 255

Ala Ser Thr Ser Gln Val Arg Gln Asn Tyr His Gln Asp Ser Glu Ala
            260                 265                 270

Ala Ile Asn Arg Gln Ile Asn Leu Glu Leu Tyr Ala Ser Tyr Val Tyr
        275                 280                 285

Leu Ser Met Ser Tyr Tyr Phe Asp Arg Asp Asp Val Ala Leu Lys Asn
    290                 295                 300

Phe Ala Lys Tyr Phe Leu His Gln Ser His Glu Glu Arg Glu His Ala
305                 310                 315                 320

Glu Lys Leu Met Lys Leu Gln Asn Gln Arg Gly Gly Arg Ile Phe Leu
                325                 330                 335

Gln Asp Ile Lys Lys Pro Asp Cys Asp Asp Trp Glu Ser Gly Leu Asn
            340                 345                 350

Ala Met Glu Cys Ala Leu His Leu Glu Lys Asn Val Asn Gln Ser Leu
        355                 360                 365

Leu Glu Leu His Lys Leu Ala Thr Asp Lys Asn Asp Pro His Leu Cys
    370                 375                 380

Asp Phe Ile Glu Thr His Tyr Leu Asn Glu Gln Val Lys Ala Ile Lys
385                 390                 395                 400

Glu Leu Gly Asp His Val Thr Asn Leu Arg Lys Met Gly Ala Pro Glu
                405                 410                 415

Ser Gly Leu Ala Glu Tyr Leu Phe Asp Lys His Thr Leu Gly Asp Ser

```
                    420                 425                 430
Asp Asn Glu Ser
        435

<210> SEQ ID NO 28
<211> LENGTH: 435
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Met Asp Glu Lys Asn Ser Val Ser Val Asp Leu Pro Gly Glu Met Lys
1               5                   10                  15

Val Leu Val Ser Lys Glu Lys Asp Lys Asp Gly Lys Tyr Ser Leu Met
            20                  25                  30

Ala Thr Val Asp Lys Leu Glu Leu Lys Gly Thr Ser Asp Lys Ser Asn
        35                  40                  45

Gly Ser Gly Thr Leu Glu Gly Glu Lys Ser Lys Ser Lys Ala Lys
    50                  55                  60

Leu Thr Ile Ser Glu Asp Leu Ser Lys Thr Thr Phe Glu Ile Phe Lys
65                  70                  75                  80

Glu Asp Gly Lys Thr Leu Val Ser Lys Val Asn Ser Lys Asp Lys
                85                  90                  95

Ser Ser Ile Glu Glu Lys Phe Asn Ala Lys Gly Glu Leu Ser Glu Lys
                100                 105                 110

Thr Ile Leu Arg Ala Asn Gly Thr Arg Leu Glu Tyr Thr Glu Ile Lys
            115                 120                 125

Ser Asp Gly Thr Gly Lys Ala Lys Glu Val Leu Lys Asp Phe Ala Leu
        130                 135                 140

Glu Gly Thr Leu Ala Ala Asp Lys Thr Thr Leu Lys Val Thr Glu Gly
145                 150                 155                 160

Thr Val Val Leu Ser Lys His Ile Pro Asn Ser Gly Glu Ile Thr Val
                165                 170                 175

Glu Leu Asn Asp Ser Asn Ser Thr Gln Ala Thr Lys Lys Thr Gly Lys
            180                 185                 190

Trp Asp Ser Asn Thr Ser Thr Leu Thr Ile Ser Val Asn Ser Lys Lys
        195                 200                 205

Thr Lys Asn Ile Val Phe Thr Lys Glu Asp Thr Ile Thr Val Gln Lys
    210                 215                 220

Tyr Asp Ser Ala Gly Thr Asn Leu Glu Gly Asn Ala Val Glu Ile Lys
225                 230                 235                 240

Thr Leu Asp Glu Leu Lys Asn Ala Leu Lys Gly Ser Met Thr Thr Ala
                245                 250                 255

Ser Thr Ser Gln Val Arg Gln Asn Tyr His Gln Asp Ser Glu Ala Ala
            260                 265                 270

Ile Asn Arg Gln Ile Asn Leu Glu Leu Tyr Ala Ser Tyr Val Tyr Leu
        275                 280                 285

Ser Met Ser Tyr Tyr Phe Asp Arg Asp Asp Val Ala Leu Lys Asn Phe
    290                 295                 300

Ala Lys Tyr Phe Leu His Gln Ser His Glu Glu Arg Glu His Ala Glu
305                 310                 315                 320

Lys Leu Met Lys Leu Gln Asn Gln Arg Gly Gly Arg Ile Phe Leu Gln
                325                 330                 335
```

```
Asp Ile Lys Lys Pro Asp Cys Asp Asp Trp Glu Ser Gly Leu Asn Ala
            340                 345                 350

Met Glu Cys Ala Leu His Leu Glu Lys Asn Val Asn Gln Ser Leu Leu
            355                 360                 365

Glu Leu His Lys Leu Ala Thr Asp Lys Asn Asp Pro His Leu Cys Asp
370                 375                 380

Phe Ile Glu Thr His Tyr Leu Asn Glu Gln Val Lys Ala Ile Lys Glu
385                 390                 395                 400

Leu Gly Asp His Val Thr Asn Leu Arg Lys Met Gly Ala Pro Glu Ser
            405                 410                 415

Gly Leu Ala Glu Tyr Leu Phe Asp Lys His Thr Leu Gly Asp Ser Asp
            420                 425                 430

Asn Glu Ser
    435

<210> SEQ ID NO 29
<211> LENGTH: 436
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Met Asp Glu Lys Asn Ser Val Ser Val Asp Leu Pro Gly Gly Met Lys
1               5                   10                  15

Val Leu Val Ser Lys Glu Lys Asp Lys Asp Gly Lys Tyr Ser Leu Met
            20                  25                  30

Ala Thr Val Glu Lys Leu Glu Leu Lys Gly Thr Ser Asp Lys Asn Asn
            35                  40                  45

Gly Ser Gly Thr Leu Glu Gly Glu Lys Thr Asp Lys Ser Lys Val Lys
    50                  55                  60

Leu Thr Ile Ala Glu Asp Leu Ser Lys Thr Thr Phe Glu Ile Phe Lys
65                  70                  75                  80

Glu Asp Gly Lys Thr Leu Val Ser Lys Lys Val Thr Leu Lys Asp Lys
            85                  90                  95

Ser Ser Thr Glu Glu Lys Phe Asn Glu Lys Gly Glu Ile Ser Glu Lys
            100                 105                 110

Thr Ile Val Arg Ala Asn Gly Thr Arg Leu Glu Tyr Thr Asp Ile Lys
            115                 120                 125

Ser Asp Gly Ser Gly Lys Ala Lys Glu Val Leu Lys Asp Phe Thr Leu
    130                 135                 140

Glu Gly Thr Leu Ala Ala Asp Gly Lys Thr Thr Leu Lys Val Thr Glu
145                 150                 155                 160

Gly Thr Val Val Leu Ser Lys Asn Ile Leu Lys Ser Gly Glu Ile Thr
            165                 170                 175

Val Ala Leu Asp Asp Ser Asp Thr Thr Gln Ala Thr Lys Lys Thr Gly
            180                 185                 190

Lys Trp Asp Ser Lys Thr Ser Thr Leu Thr Ile Ser Val Asn Ser Gln
            195                 200                 205

Lys Thr Lys Asn Leu Val Phe Thr Lys Glu Asp Thr Ile Thr Val Gln
    210                 215                 220

Lys Tyr Asp Ser Ala Gly Thr Asn Leu Glu Gly Lys Ala Val Glu Ile
225                 230                 235                 240
```

```
Thr Thr Leu Glu Lys Leu Lys Asp Ala Leu Lys Gly Ser Met Thr Thr
                245                 250                 255

Ala Ser Thr Ser Gln Val Arg Gln Asn Tyr His Gln Asp Ser Glu Ala
            260                 265                 270

Ala Ile Asn Arg Gln Ile Asn Leu Glu Leu Tyr Ala Ser Tyr Val Tyr
        275                 280                 285

Leu Ser Met Ser Tyr Tyr Phe Asp Arg Asp Asp Val Ala Leu Lys Asn
    290                 295                 300

Phe Ala Lys Tyr Phe Leu His Gln Ser His Glu Glu Arg Glu His Ala
305                 310                 315                 320

Glu Lys Leu Met Lys Leu Gln Asn Gln Arg Gly Gly Arg Ile Phe Leu
                325                 330                 335

Gln Asp Ile Lys Lys Pro Asp Cys Asp Asp Trp Glu Ser Gly Leu Asn
            340                 345                 350

Ala Met Glu Cys Ala Leu His Leu Glu Lys Asn Val Asn Gln Ser Leu
        355                 360                 365

Leu Glu Leu His Lys Leu Ala Thr Asp Lys Asn Asp Pro His Leu Cys
    370                 375                 380

Asp Phe Ile Glu Thr His Tyr Leu Asn Glu Gln Val Lys Ala Ile Lys
385                 390                 395                 400

Glu Leu Gly Asp His Val Thr Asn Leu Arg Lys Met Gly Ala Pro Glu
                405                 410                 415

Ser Gly Leu Ala Glu Tyr Leu Phe Asp Lys His Thr Leu Gly Asp Ser
            420                 425                 430

Asp Asn Glu Ser
        435

<210> SEQ ID NO 30
<211> LENGTH: 436
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Met Asp Glu Lys Asn Ser Val Ser Val Asp Leu Pro Gly Gly Met Thr
1               5                   10                  15

Val Leu Val Ser Lys Glu Lys Asp Lys Asp Gly Lys Tyr Ser Leu Glu
                20                  25                  30

Ala Thr Val Asp Lys Leu Glu Leu Lys Gly Thr Ser Asp Lys Asn Asn
            35                  40                  45

Gly Ser Gly Thr Leu Glu Gly Glu Lys Thr Asp Lys Ser Lys Val Lys
        50                  55                  60

Ser Thr Ile Ala Asp Asp Leu Ser Gln Thr Lys Phe Glu Ile Phe Lys
65                  70                  75                  80

Glu Asp Gly Lys Thr Leu Val Ser Lys Lys Val Thr Leu Lys Asp Lys
                85                  90                  95

Ser Ser Thr Glu Glu Lys Phe Asn Gly Lys Gly Glu Thr Ser Glu Lys
            100                 105                 110

Thr Ile Val Arg Ala Asn Gly Thr Arg Leu Glu Tyr Thr Asp Ile Lys
        115                 120                 125

Ser Asp Gly Ser Gly Lys Ala Lys Glu Val Leu Lys Asp Phe Thr Leu
    130                 135                 140

Glu Gly Thr Leu Ala Ala Asp Gly Lys Thr Thr Leu Lys Val Thr Glu
```

```
145                 150                 155                 160
Gly Thr Val Val Leu Ser Lys Asn Ile Leu Lys Ser Gly Glu Ile Thr
                165                 170                 175

Ala Ala Leu Asp Asp Ser Asp Thr Thr Arg Ala Thr Lys Lys Thr Gly
            180                 185                 190

Lys Trp Asp Ser Lys Thr Ser Thr Leu Thr Ile Ser Val Asn Ser Gln
        195                 200                 205

Lys Thr Lys Asn Leu Val Phe Thr Lys Glu Asp Thr Ile Thr Val Gln
    210                 215                 220

Arg Tyr Asp Ser Ala Gly Thr Asn Leu Glu Gly Lys Ala Val Glu Ile
225                 230                 235                 240

Thr Thr Leu Lys Glu Leu Lys Asn Ala Leu Lys Gly Ser Met Thr Thr
                245                 250                 255

Ala Ser Thr Ser Gln Val Arg Gln Asn Tyr His Gln Asp Ser Glu Ala
            260                 265                 270

Ala Ile Asn Arg Gln Ile Asn Leu Glu Leu Tyr Ala Ser Tyr Val Tyr
        275                 280                 285

Leu Ser Met Ser Tyr Tyr Phe Asp Arg Asp Asp Val Ala Leu Lys Asn
    290                 295                 300

Phe Ala Lys Tyr Phe Leu His Gln Ser His Glu Glu Arg Glu His Ala
305                 310                 315                 320

Glu Lys Leu Met Lys Leu Gln Asn Gln Arg Gly Gly Arg Ile Phe Leu
                325                 330                 335

Gln Asp Ile Lys Lys Pro Asp Cys Asp Asp Trp Glu Ser Gly Leu Asn
            340                 345                 350

Ala Met Glu Cys Ala Leu His Leu Glu Lys Asn Val Asn Gln Ser Leu
        355                 360                 365

Leu Glu Leu His Lys Leu Ala Thr Asp Lys Asn Asp Pro His Leu Cys
    370                 375                 380

Asp Phe Ile Glu Thr His Tyr Leu Asn Glu Gln Val Lys Ala Ile Lys
385                 390                 395                 400

Glu Leu Gly Asp His Val Thr Asn Leu Arg Lys Met Gly Ala Pro Glu
                405                 410                 415

Ser Gly Leu Ala Glu Tyr Leu Phe Asp Lys His Thr Leu Gly Asp Ser
            420                 425                 430

Asp Asn Glu Ser
        435

<210> SEQ ID NO 31
<211> LENGTH: 436
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Met Asp Glu Lys Asn Ser Val Ser Val Asp Leu Pro Gly Glu Met Lys
1               5                   10                  15

Val Leu Val Ser Lys Glu Lys Asp Lys Asp Gly Lys Tyr Ser Leu Glu
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Ala Lys Ser Lys Ala Lys
    50                  55                  60
```

```
Leu Thr Ile Ala Asp Asp Leu Ser Gln Thr Lys Phe Glu Ile Phe Lys
 65                  70                  75                  80

Glu Asp Gly Lys Thr Leu Val Ser Lys Lys Val Thr Leu Lys Asp Lys
                 85                  90                  95

Ser Ser Thr Glu Glu Lys Phe Asn Asp Lys Gly Lys Leu Ser Glu Lys
            100                 105                 110

Val Val Thr Arg Ala Asn Gly Thr Arg Leu Glu Tyr Thr Glu Ile Gln
            115                 120                 125

Asn Asp Gly Ser Gly Lys Ala Lys Glu Val Leu Lys Ser Leu Thr Leu
130                 135                 140

Glu Gly Thr Leu Thr Ala Asp Gly Glu Thr Lys Leu Thr Val Glu Ala
145                 150                 155                 160

Gly Thr Val Thr Leu Ser Lys Asn Ile Ser Glu Ser Gly Glu Ile Thr
                165                 170                 175

Val Glu Leu Lys Asp Thr Glu Thr Thr Pro Ala Asp Lys Lys Ser Gly
            180                 185                 190

Thr Trp Asp Ser Lys Thr Ser Thr Leu Thr Ile Ser Lys Asn Ser Gln
            195                 200                 205

Lys Thr Lys Gln Leu Val Phe Thr Lys Glu Asn Thr Ile Thr Val Gln
210                 215                 220

Lys Tyr Asn Thr Ala Gly Thr Lys Leu Glu Gly Ser Pro Ala Glu Ile
225                 230                 235                 240

Lys Asp Leu Glu Ala Leu Lys Ala Ala Leu Lys Gly Ser Met Thr Thr
                245                 250                 255

Ala Ser Thr Ser Gln Val Arg Gln Asn Tyr His Gln Asp Ser Glu Ala
            260                 265                 270

Ala Ile Asn Arg Gln Ile Asn Leu Glu Leu Tyr Ala Ser Tyr Val Tyr
            275                 280                 285

Leu Ser Met Ser Tyr Tyr Phe Asp Arg Asp Asp Val Ala Leu Lys Asn
290                 295                 300

Phe Ala Lys Tyr Phe Leu His Gln Ser His Glu Glu Arg Glu His Ala
305                 310                 315                 320

Glu Lys Leu Met Lys Leu Gln Asn Gln Arg Gly Gly Arg Ile Phe Leu
                325                 330                 335

Gln Asp Ile Lys Lys Pro Asp Cys Asp Asp Trp Glu Ser Gly Leu Asn
            340                 345                 350

Ala Met Glu Cys Ala Leu His Leu Glu Lys Asn Val Asn Gln Ser Leu
            355                 360                 365

Leu Glu Leu His Lys Leu Ala Thr Asp Lys Asn Asp Pro His Leu Cys
370                 375                 380

Asp Phe Ile Glu Thr His Tyr Leu Asn Glu Gln Val Lys Ala Ile Lys
385                 390                 395                 400

Glu Leu Gly Asp His Val Thr Asn Leu Arg Lys Met Gly Ala Pro Glu
                405                 410                 415

Ser Gly Leu Ala Glu Tyr Leu Phe Asp Lys His Thr Leu Gly Asp Ser
            420                 425                 430

Asp Asn Glu Ser
        435

<210> SEQ ID NO 32
<211> LENGTH: 426
<212> TYPE: PRT
<213> ORGANISM: Artificial Sequence
<220> FEATURE:
```

<221> NAME/KEY: source
<223> OTHER INFORMATION: /note="Description of Artificial Sequence: Synthetic polypeptide"

<400> SEQUENCE: 32

```
Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Asp Lys Ser Lys Val Lys
50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
        115                 120                 125

Ser Asp Gly Ser Gly Lys Ala Lys Glu Val Leu Lys Gly Tyr Thr Leu
130                 135                 140

Glu Gly Gln Leu Ser Asp Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
        195                 200                 205

Thr Lys Asp Leu Val Phe Thr Lys Glu Asn Thr Ile Thr Val Gln Gln
    210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Ser Met Leu Ser Glu
                245                 250                 255

Arg Met Leu Lys Ala Leu Asn Asp Gln Leu Asn Arg Glu Leu Tyr Ser
            260                 265                 270

Ala Tyr Leu Tyr Phe Ala Met Ala Ala Tyr Phe Glu Asp Leu Gly Leu
        275                 280                 285

Glu Gly Phe Ala Asn Trp Met Lys Ala Gln Ala Glu Glu Ile Gly
290                 295                 300

His Ala Leu Arg Phe Tyr Asn Tyr Ile Tyr Asp Arg Asn Gly Arg Val
305                 310                 315                 320

Glu Leu Asp Glu Ile Pro Lys Pro Pro Lys Trp Glu Ser Pro Leu
                325                 330                 335

Lys Ala Phe Glu Ala Ala Tyr Glu His Glu Lys Phe Ile Ser Lys Ser
            340                 345                 350

Ile Tyr Glu Leu Ala Ala Leu Ala Glu Glu Glu Lys Asp Tyr Ser Thr
        355                 360                 365

Arg Ala Phe Leu Glu Trp Phe Ile Asn Glu Gln Val Glu Glu Glu Ala
    370                 375                 380

Ser Val Lys Lys Ile Leu Asp Lys Leu Lys Phe Ala Lys Asp Ser Pro
```

```
385                 390                 395                 400
Gln Ile Leu Phe Met Leu Asp Lys Glu Leu Ser Ala Arg Ala Pro Lys
                405                 410                 415

Leu Pro Gly Leu Leu Met Gln Gly Gly Glu
                420                 425

<210> SEQ ID NO 33
<211> LENGTH: 426
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
                20                  25                  30

Ala Thr Val Asp Lys Leu Glu Leu Lys Gly Thr Ser Asp Lys Asn Asn
            35                  40                  45

Gly Ser Gly Val Leu Glu Gly Val Lys Ala Asp Lys Ser Lys Val Lys
        50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Val Thr Ser Lys Asp Lys
                85                  90                  95

Ser Ser Thr Glu Glu Lys Phe Asn Glu Lys Gly Glu Val Ser Glu Lys
                100                 105                 110

Ile Ile Thr Arg Ala Asp Gly Thr Arg Leu Glu Tyr Thr Gly Ile Lys
            115                 120                 125

Ser Asp Gly Ser Gly Lys Ala Lys Glu Val Leu Lys Gly Tyr Asp Leu
        130                 135                 140

Lys Gly Glu Leu Ser Ser Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
                180                 185                 190

Trp Asn Ser Gly Thr Ser Thr Leu Thr Ile Thr Val Asn Ser Lys Lys
                195                 200                 205

Thr Lys Asp Leu Val Phe Thr Lys Glu Asn Thr Ile Thr Val Gln Gln
            210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Ser Met Leu Ser Glu
                245                 250                 255

Arg Met Leu Lys Ala Leu Asn Asp Gln Leu Asn Arg Glu Leu Tyr Ser
                260                 265                 270

Ala Tyr Leu Tyr Phe Ala Met Ala Ala Tyr Phe Glu Asp Leu Gly Leu
            275                 280                 285

Glu Gly Phe Ala Asn Trp Met Lys Ala Gln Ala Glu Glu Ile Gly
        290                 295                 300

His Ala Leu Arg Phe Tyr Asn Tyr Ile Tyr Asp Arg Asn Gly Arg Val
305                 310                 315                 320
```

```
Glu Leu Asp Glu Ile Pro Lys Pro Lys Glu Trp Glu Ser Pro Leu
                325                 330                 335

Lys Ala Phe Glu Ala Ala Tyr Glu His Glu Lys Phe Ile Ser Lys Ser
            340                 345                 350

Ile Tyr Glu Leu Ala Ala Leu Ala Glu Glu Lys Asp Tyr Ser Thr
        355                 360                 365

Arg Ala Phe Leu Glu Trp Phe Ile Asn Glu Gln Val Glu Glu Glu Ala
        370                 375                 380

Ser Val Lys Lys Ile Leu Asp Lys Leu Lys Phe Ala Lys Asp Ser Pro
385                 390                 395                 400

Gln Ile Leu Phe Met Leu Asp Lys Glu Leu Ser Arg Ala Pro Lys
                405                 410                 415

Leu Pro Gly Leu Leu Met Gln Gly Gly Glu
                420                 425

<210> SEQ ID NO 34
<211> LENGTH: 426
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
                20                  25                  30

Ala Thr Val Asp Lys Leu Glu Leu Lys Gly Thr Ser Asp Lys Asn Asn
            35                  40                  45

Gly Ser Gly Val Leu Glu Gly Val Lys Ala Asp Lys Ser Lys Val Lys
        50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
                100                 105                 110

Ile Ile Thr Arg Ala Asp Gly Thr Arg Leu Glu Tyr Thr Gly Ile Lys
            115                 120                 125

Ser Asp Gly Ser Gly Lys Ala Lys Glu Val Leu Lys Gly Phe Thr Leu
        130                 135                 140

Glu Gly Lys Val Ala Asn Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
        195                 200                 205

Thr Lys Asp Leu Val Phe Thr Lys Glu Asn Thr Ile Thr Val Gln Gln
    210                 215                 220

Tyr Asp Ser Asn Gly Thr Lys Leu Glu Gly Ser Ala Val Glu Ile Thr
225                 230                 235                 240
```

Lys Leu Asp Glu Ile Lys Asn Ala Leu Lys Gly Ser Met Leu Ser Glu
                    245                 250                 255

Arg Met Leu Lys Ala Leu Asn Asp Gln Leu Asn Arg Glu Leu Tyr Ser
            260                 265                 270

Ala Tyr Leu Tyr Phe Ala Met Ala Ala Tyr Phe Glu Asp Leu Gly Leu
        275                 280                 285

Glu Gly Phe Ala Asn Trp Met Lys Ala Gln Ala Glu Glu Ile Gly
    290                 295                 300

His Ala Leu Arg Phe Tyr Asn Tyr Ile Tyr Asp Arg Asn Gly Arg Val
305                 310                 315                 320

Glu Leu Asp Glu Ile Pro Lys Pro Lys Glu Trp Glu Ser Pro Leu
                325                 330                 335

Lys Ala Phe Glu Ala Ala Tyr Glu His Glu Lys Phe Ile Ser Lys Ser
                340                 345                 350

Ile Tyr Glu Leu Ala Ala Leu Ala Glu Glu Lys Asp Tyr Ser Thr
        355                 360                 365

Arg Ala Phe Leu Glu Trp Phe Ile Asn Glu Gln Val Glu Glu Glu Ala
    370                 375                 380

Ser Val Lys Lys Ile Leu Asp Lys Leu Lys Phe Ala Lys Asp Ser Pro
385                 390                 395                 400

Gln Ile Leu Phe Met Leu Asp Lys Glu Leu Ser Ala Arg Ala Pro Lys
                405                 410                 415

Leu Pro Gly Leu Leu Met Gln Gly Gly Glu
            420                 425

<210> SEQ ID NO 35
<211> LENGTH: 426
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Asp Lys Ser Lys Val Lys
    50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Val Thr Ser Lys Asp Lys
                85                  90                  95

Ser Ser Thr Glu Glu Lys Phe Asn Glu Lys Gly Glu Val Ser Glu Lys
                100                 105                 110

Ile Ile Thr Arg Ala Asp Gly Thr Arg Leu Glu Tyr Thr Gly Ile Lys
            115                 120                 125

Ser Asp Gly Ser Gly Lys Ala Lys Glu Val Leu Lys Gly Phe Ala Leu
        130                 135                 140

Glu Gly Thr Leu Thr Asp Glu Lys Thr Thr Leu Val Val Lys Glu Gly
145                 150                 155                 160

Thr Val Thr Leu Ser Lys Asn Ile Ser Lys Ser Gly Glu Val Ser Val 165                 170                 175
Glu Leu Asn Asp Thr Asp Ser Ser Ala Ala Thr Lys Thr Ala Ala
            180                 185                 190

Trp Asn Ser Gly Thr Ser Thr Leu Thr Ile Thr Val Asn Ser Lys Lys
            195                 200                 205

Thr Lys Asp Leu Val Phe Thr Lys Glu Asn Thr Ile Thr Val Gln Gln
            210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Ser Met Leu Ser Glu
                245                 250                 255

Arg Met Leu Lys Ala Leu Asn Asp Gln Leu Asn Arg Glu Leu Tyr Ser
            260                 265                 270

Ala Tyr Leu Tyr Phe Ala Met Ala Ala Tyr Phe Glu Asp Leu Gly Leu
            275                 280                 285

Glu Gly Phe Ala Asn Trp Met Lys Ala Gln Ala Glu Glu Ile Gly
            290                 295                 300

His Ala Leu Arg Phe Tyr Asn Tyr Ile Tyr Asp Arg Asn Gly Arg Val
305                 310                 315                 320

Glu Leu Asp Glu Ile Pro Lys Pro Lys Glu Trp Glu Ser Pro Leu
                325                 330                 335

Lys Ala Phe Glu Ala Ala Tyr Glu His Glu Lys Phe Ile Ser Lys Ser
            340                 345                 350

Ile Tyr Glu Leu Ala Ala Leu Ala Glu Glu Lys Asp Tyr Ser Thr
            355                 360                 365

Arg Ala Phe Leu Glu Trp Phe Ile Asn Glu Gln Val Glu Glu Glu Ala
            370                 375                 380

Ser Val Lys Lys Ile Leu Asp Lys Leu Lys Phe Ala Lys Asp Ser Pro
385                 390                 395                 400

Gln Ile Leu Phe Met Leu Asp Lys Glu Leu Ser Ala Arg Ala Pro Lys
                405                 410                 415

Leu Pro Gly Leu Leu Met Gln Gly Gly Glu
            420                 425

<210> SEQ ID NO 36
<211> LENGTH: 426
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Met Asp Glu Lys Asn Ser Ala Ser Val Asp Leu Pro Gly Glu Met Lys
1               5                   10                  15

Val Leu Val Ser Lys Glu Lys Asp Lys Asp Gly Lys Tyr Ser Leu Lys
                20                  25                  30

Ala Thr Val Asp Lys Ile Glu Leu Lys Gly Thr Ser Asp Lys Asp Asn
            35                  40                  45

Gly Ser Gly Val Leu Glu Gly Thr Lys Asp Lys Ser Lys Ala Lys
            50                  55                  60

Leu Thr Ile Ala Asp Asp Leu Ser Lys Thr Thr Phe Glu Leu Phe Lys
65              70                  75                  80

Glu Asp Gly Lys Thr Leu Val Ser Arg Lys Val Ser Ser Lys Asp Lys
                85                  90                  95

```
Thr Ser Thr Asp Glu Met Phe Asn Glu Lys Gly Glu Leu Ser Ala Lys
            100                 105                 110
Thr Met Thr Arg Glu Asn Gly Thr Lys Leu Glu Tyr Thr Glu Met Lys
            115                 120                 125
Ser Asp Gly Thr Gly Lys Ala Lys Glu Val Leu Lys Asn Phe Thr Leu
            130                 135                 140
Glu Gly Lys Val Ala Asn Asp Lys Val Thr Leu Glu Val Lys Glu Gly
145                 150                 155                 160
Thr Val Thr Leu Ser Lys Glu Ile Ala Lys Ser Gly Glu Val Thr Val
                165                 170                 175
Ala Leu Asn Asp Thr Asn Thr Thr Gln Ala Thr Lys Lys Thr Gly Ala
            180                 185                 190
Trp Asp Ser Lys Thr Ser Thr Leu Thr Ile Ser Val Asn Ser Lys Lys
            195                 200                 205
Thr Thr Gln Leu Val Phe Thr Lys Gln Asp Thr Ile Thr Val Gln Lys
            210                 215                 220
Tyr Asp Ser Ala Gly Thr Asn Leu Glu Gly Thr Ala Val Glu Ile Lys
225                 230                 235                 240
Thr Leu Asp Glu Leu Lys Asn Ala Leu Lys Gly Ser Met Leu Ser Glu
                245                 250                 255
Arg Met Leu Lys Ala Leu Asn Asp Gln Leu Asn Arg Glu Leu Tyr Ser
            260                 265                 270
Ala Tyr Leu Tyr Phe Ala Met Ala Ala Tyr Phe Glu Asp Leu Gly Leu
            275                 280                 285
Glu Gly Phe Ala Asn Trp Met Lys Ala Gln Ala Glu Glu Ile Gly
            290                 295                 300
His Ala Leu Arg Phe Tyr Asn Tyr Ile Tyr Asp Arg Asn Gly Arg Val
305                 310                 315                 320
Glu Leu Asp Glu Ile Pro Lys Pro Lys Glu Trp Glu Ser Pro Leu
                325                 330                 335
Lys Ala Phe Glu Ala Ala Tyr Glu His Glu Lys Phe Ile Ser Lys Ser
            340                 345                 350
Ile Tyr Glu Leu Ala Ala Leu Ala Glu Glu Lys Asp Tyr Ser Thr
            355                 360                 365
Arg Ala Phe Leu Glu Trp Phe Ile Asn Glu Gln Val Glu Glu Ala
370                 375                 380
Ser Val Lys Lys Ile Leu Asp Lys Leu Lys Phe Ala Lys Asp Ser Pro
385                 390                 395                 400
Gln Ile Leu Phe Met Leu Asp Lys Glu Leu Ser Ala Arg Ala Pro Lys
            405                 410                 415
Leu Pro Gly Leu Leu Met Gln Gly Gly Glu
            420                 425

<210> SEQ ID NO 37
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Met Asp Glu Lys Asn Ser Val Ser Val Asp Leu Pro Gly Gly Met Lys
1               5                   10                  15
```

```
Val Leu Val Ser Lys Glu Lys Asp Lys Asp Gly Lys Tyr Ser Leu Met
            20                  25                  30

Ala Thr Val Glu Lys Leu Glu Leu Lys Gly Thr Ser Asp Lys Ser Asn
            35                  40                  45

Gly Ser Gly Val Leu Glu Gly Glu Lys Ala Asp Lys Ser Lys Ala Lys
            50                  55                  60

Leu Thr Ile Ser Gln Asp Leu Asn Gln Thr Thr Phe Glu Ile Phe Lys
65                      70                  75                  80

Glu Asp Gly Lys Thr Leu Val Ser Arg Lys Val Asn Ser Lys Asp Lys
                    85                  90                  95

Ser Ser Thr Glu Glu Lys Phe Asn Asp Lys Gly Lys Leu Ser Glu Lys
                100                 105                 110

Val Val Thr Arg Ala Asn Gly Thr Arg Leu Glu Tyr Thr Glu Ile Lys
                115                 120                 125

Asn Asp Gly Ser Gly Lys Ala Lys Glu Val Leu Lys Gly Phe Ala Leu
            130                 135                 140

Glu Gly Thr Leu Thr Asp Gly Glu Thr Lys Leu Thr Val Thr Glu
145                 150                 155                 160

Gly Thr Val Thr Leu Ser Lys Asn Ile Ser Lys Ser Gly Glu Ile Thr
                165                 170                 175

Val Ala Leu Asn Asp Thr Glu Thr Thr Pro Ala Asp Lys Lys Thr Gly
            180                 185                 190

Glu Trp Lys Ser Asp Thr Ser Thr Leu Thr Ile Ser Lys Asn Ser Gln
            195                 200                 205

Lys Pro Lys Gln Leu Val Phe Thr Lys Glu Asn Thr Ile Thr Val Gln
210                 215                 220

Asn Tyr Asn Arg Ala Gly Asn Ala Leu Glu Gly Ser Pro Ala Glu Ile
225                 230                 235                 240

Lys Asp Leu Ala Glu Leu Lys Ala Ala Leu Lys Gly Ser Met Leu Ser
                245                 250                 255

Glu Arg Met Leu Lys Ala Leu Asn Asp Gln Leu Asn Arg Glu Leu Tyr
            260                 265                 270

Ser Ala Tyr Leu Tyr Phe Ala Met Ala Ala Tyr Phe Glu Asp Leu Gly
            275                 280                 285

Leu Glu Gly Phe Ala Asn Trp Met Lys Ala Gln Ala Glu Glu Glu Ile
            290                 295                 300

Gly His Ala Leu Arg Phe Tyr Asn Tyr Ile Tyr Asp Arg Asn Gly Arg
305                 310                 315                 320

Val Glu Leu Asp Glu Ile Pro Lys Pro Pro Lys Glu Trp Glu Ser Pro
                325                 330                 335

Leu Lys Ala Phe Glu Ala Ala Tyr Glu His Glu Lys Phe Ile Ser Lys
            340                 345                 350

Ser Ile Tyr Glu Leu Ala Ala Leu Ala Glu Glu Lys Asp Tyr Ser
            355                 360                 365

Thr Arg Ala Phe Leu Glu Trp Phe Ile Asn Glu Gln Val Glu Glu Glu
            370                 375                 380

Ala Ser Val Lys Lys Ile Leu Asp Lys Leu Lys Phe Ala Lys Asp Ser
385                 390                 395                 400

Pro Gln Ile Leu Phe Met Leu Asp Lys Glu Leu Ser Ala Arg Ala Pro
                405                 410                 415

Lys Leu Pro Gly Leu Leu Met Gln Gly Gly Glu
            420                 425
```

```
<210> SEQ ID NO 38
<211> LENGTH: 426
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38
```

| | | | | | | | | | | | | | | | |
|---|---|---|---|---|---|---|---|---|---|---|---|---|---|---|---|
| Met | Asp | Glu | Lys | Asn | Ser | Val | Ser | Val | Asp | Leu | Pro | Gly | Glu | Met | Lys |
| 1 | | | | 5 | | | | | 10 | | | | | 15 | |
| Val | Leu | Val | Ser | Lys | Glu | Lys | Asp | Lys | Asp | Gly | Lys | Tyr | Ser | Leu | Met |
| | | | 20 | | | | | 25 | | | | | 30 | | |
| Ala | Thr | Val | Asp | Lys | Leu | Glu | Leu | Lys | Gly | Thr | Ser | Asp | Lys | Ser | Asn |
| | | | 35 | | | | | 40 | | | | | 45 | | |
| Gly | Ser | Gly | Thr | Leu | Glu | Gly | Glu | Lys | Ser | Asp | Lys | Ser | Lys | Ala | Lys |
| | 50 | | | | | 55 | | | | | 60 | | | | |
| Leu | Thr | Ile | Ser | Glu | Asp | Leu | Ser | Lys | Thr | Thr | Phe | Glu | Ile | Phe | Lys |
| 65 | | | | | 70 | | | | | 75 | | | | | 80 |
| Glu | Asp | Gly | Lys | Thr | Leu | Val | Ser | Lys | Val | Asn | Ser | Lys | Asp | Lys |
| | | | | 85 | | | | | 90 | | | | | 95 | |
| Ser | Ser | Ile | Glu | Glu | Lys | Phe | Asn | Ala | Lys | Gly | Glu | Leu | Ser | Glu | Lys |
| | | | 100 | | | | | 105 | | | | | 110 | | |
| Thr | Ile | Leu | Arg | Ala | Asn | Gly | Thr | Arg | Leu | Glu | Tyr | Thr | Glu | Ile | Lys |
| | | | 115 | | | | | 120 | | | | | 125 | | |
| Ser | Asp | Gly | Thr | Gly | Lys | Ala | Lys | Glu | Val | Leu | Lys | Asp | Phe | Ala | Leu |
| | 130 | | | | | 135 | | | | | 140 | | | | |
| Glu | Gly | Thr | Leu | Ala | Ala | Asp | Lys | Thr | Thr | Leu | Lys | Val | Thr | Glu | Gly |
| 145 | | | | | 150 | | | | | 155 | | | | | 160 |
| Thr | Val | Val | Leu | Ser | Lys | His | Ile | Pro | Asn | Ser | Gly | Glu | Ile | Thr | Val |
| | | | | 165 | | | | | 170 | | | | | 175 | |
| Glu | Leu | Asn | Asp | Ser | Asn | Ser | Thr | Gln | Ala | Thr | Lys | Lys | Thr | Gly | Lys |
| | | | 180 | | | | | 185 | | | | | 190 | | |
| Trp | Asp | Ser | Asn | Thr | Ser | Thr | Leu | Thr | Ile | Ser | Val | Asn | Ser | Lys | Lys |
| | | | 195 | | | | | 200 | | | | | 205 | | |
| Thr | Lys | Asn | Ile | Val | Phe | Thr | Lys | Glu | Asp | Thr | Ile | Thr | Val | Gln | Lys |
| | 210 | | | | | 215 | | | | | 220 | | | | |
| Tyr | Asp | Ser | Ala | Gly | Thr | Asn | Leu | Glu | Gly | Asn | Ala | Val | Glu | Ile | Lys |
| 225 | | | | | 230 | | | | | 235 | | | | | 240 |
| Thr | Leu | Asp | Glu | Leu | Lys | Asn | Ala | Leu | Lys | Gly | Ser | Met | Leu | Ser | Glu |
| | | | | 245 | | | | | 250 | | | | | 255 | |
| Arg | Met | Leu | Lys | Ala | Leu | Asn | Asp | Gln | Leu | Asn | Arg | Glu | Leu | Tyr | Ser |
| | | | 260 | | | | | 265 | | | | | 270 | | |
| Ala | Tyr | Leu | Tyr | Phe | Ala | Met | Ala | Tyr | Phe | Glu | Asp | Leu | Gly | Leu |
| | | | 275 | | | | | 280 | | | | | 285 | | |
| Glu | Gly | Phe | Ala | Asn | Trp | Met | Lys | Ala | Gln | Ala | Glu | Glu | Ile | Gly |
| | 290 | | | | | 295 | | | | | 300 | | | | |
| His | Ala | Leu | Arg | Phe | Tyr | Asn | Tyr | Ile | Tyr | Asp | Arg | Asn | Gly | Arg | Val |
| 305 | | | | | 310 | | | | | 315 | | | | | 320 |
| Glu | Leu | Asp | Glu | Ile | Pro | Lys | Pro | Pro | Lys | Glu | Trp | Glu | Ser | Pro | Leu |
| | | | | 325 | | | | | 330 | | | | | 335 | |
| Lys | Ala | Phe | Glu | Ala | Ala | Tyr | Glu | His | Glu | Lys | Phe | Ile | Ser | Lys | Ser |
| | | | 340 | | | | | 345 | | | | | 350 | | |
| Ile | Tyr | Glu | Leu | Ala | Ala | Leu | Ala | Glu | Glu | Glu | Lys | Asp | Tyr | Ser | Thr |
| | | | 355 | | | | | 360 | | | | | 365 | | |

```
Arg Ala Phe Leu Glu Trp Phe Ile Asn Glu Gln Val Glu Glu Ala
        370                 375                 380

Ser Val Lys Lys Ile Leu Asp Lys Leu Lys Phe Ala Lys Asp Ser Pro
385                 390                 395                 400

Gln Ile Leu Phe Met Leu Asp Lys Glu Leu Ser Ala Arg Ala Pro Lys
                405                 410                 415

Leu Pro Gly Leu Leu Met Gln Gly Gly Glu
                420                 425

<210> SEQ ID NO 39
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Met Asp Glu Lys Asn Ser Val Ser Val Asp Leu Pro Gly Gly Met Lys
1               5                   10                  15

Val Leu Val Ser Lys Glu Lys Asp Lys Asp Gly Lys Tyr Ser Leu Met
                20                  25                  30

Ala Thr Val Glu Lys Leu Glu Leu Lys Gly Thr Ser Asp Lys Asn Asn
            35                  40                  45

Gly Ser Gly Thr Leu Glu Gly Glu Lys Thr Lys Ser Lys Val Lys
        50                  55                  60

Leu Thr Ile Ala Glu Asp Leu Ser Lys Thr Thr Phe Glu Ile Phe Lys
65                  70                  75                  80

Glu Asp Gly Lys Thr Leu Val Ser Lys Val Thr Leu Lys Asp Lys
                85                  90                  95

Ser Ser Thr Glu Glu Lys Phe Asn Glu Lys Gly Glu Ile Ser Glu Lys
                100                 105                 110

Thr Ile Val Arg Ala Asn Gly Thr Arg Leu Glu Tyr Thr Asp Ile Lys
            115                 120                 125

Ser Asp Gly Ser Gly Lys Ala Lys Glu Val Leu Lys Asp Phe Thr Leu
    130                 135                 140

Glu Gly Thr Leu Ala Ala Asp Gly Lys Thr Thr Leu Lys Val Thr Glu
145                 150                 155                 160

Gly Thr Val Val Leu Ser Lys Asn Ile Leu Lys Ser Gly Glu Ile Thr
                165                 170                 175

Val Ala Leu Asp Asp Ser Asp Thr Thr Gln Ala Thr Lys Lys Thr Gly
                180                 185                 190

Lys Trp Asp Ser Lys Thr Ser Thr Leu Thr Ile Ser Val Asn Ser Gln
            195                 200                 205

Lys Thr Lys Asn Leu Val Phe Thr Lys Glu Asp Thr Ile Thr Val Gln
    210                 215                 220

Lys Tyr Asp Ser Ala Gly Thr Asn Leu Glu Gly Lys Ala Val Glu Ile
225                 230                 235                 240

Thr Thr Leu Glu Lys Leu Lys Asp Ala Leu Lys Gly Ser Met Leu Ser
                245                 250                 255

Glu Arg Met Leu Lys Ala Leu Asn Asp Gln Leu Asn Arg Glu Leu Tyr
                260                 265                 270

Ser Ala Tyr Leu Tyr Phe Ala Met Ala Ala Tyr Phe Glu Asp Leu Gly
            275                 280                 285
```

```
Leu Glu Gly Phe Ala Asn Trp Met Lys Ala Gln Ala Glu Glu Ile
    290                 295                 300

Gly His Ala Leu Arg Phe Tyr Asn Tyr Ile Tyr Asp Arg Asn Gly Arg
305                 310                 315                 320

Val Glu Leu Asp Glu Ile Pro Lys Pro Pro Lys Glu Trp Glu Ser Pro
                325                 330                 335

Leu Lys Ala Phe Glu Ala Ala Tyr Glu His Glu Lys Phe Ile Ser Lys
                340                 345                 350

Ser Ile Tyr Glu Leu Ala Ala Leu Ala Glu Glu Lys Asp Tyr Ser
                355                 360                 365

Thr Arg Ala Phe Leu Glu Trp Phe Ile Asn Glu Gln Val Glu Glu Glu
370                 375                 380

Ala Ser Val Lys Lys Ile Leu Asp Lys Leu Lys Phe Ala Lys Asp Ser
385                 390                 395                 400

Pro Gln Ile Leu Phe Met Leu Asp Lys Glu Leu Ser Ala Arg Ala Pro
                405                 410                 415

Lys Leu Pro Gly Leu Leu Met Gln Gly Gly Glu
                420                 425

<210> SEQ ID NO 40
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Met Asp Glu Lys Asn Ser Val Ser Val Asp Leu Pro Gly Gly Met Thr
1               5                   10                  15

Val Leu Val Ser Lys Glu Lys Asp Lys Asp Gly Lys Tyr Ser Leu Glu
                20                  25                  30

Ala Thr Val Asp Lys Leu Glu Leu Lys Gly Thr Ser Asp Lys Asn Asn
                35                  40                  45

Gly Ser Gly Thr Leu Glu Gly Glu Lys Thr Asp Lys Ser Lys Val Lys
50                  55                  60

Ser Thr Ile Ala Asp Asp Leu Ser Gln Thr Lys Phe Glu Ile Phe Lys
65                  70                  75                  80

Glu Asp Gly Lys Thr Leu Val Ser Lys Lys Val Thr Leu Lys Asp Lys
                85                  90                  95

Ser Ser Thr Glu Glu Lys Phe Asn Gly Lys Gly Glu Thr Ser Glu Lys
                100                 105                 110

Thr Ile Val Arg Ala Asn Gly Thr Arg Leu Glu Tyr Thr Asp Ile Lys
                115                 120                 125

Ser Asp Gly Ser Gly Lys Ala Lys Glu Val Leu Lys Asp Phe Thr Leu
130                 135                 140

Glu Gly Thr Leu Ala Ala Asp Gly Lys Thr Thr Leu Lys Val Thr Glu
145                 150                 155                 160

Gly Thr Val Val Leu Ser Lys Asn Ile Leu Lys Ser Gly Glu Ile Thr
                165                 170                 175

Ala Ala Leu Asp Asp Ser Asp Thr Thr Arg Ala Thr Lys Lys Thr Gly
                180                 185                 190

Lys Trp Asp Ser Lys Thr Ser Thr Leu Thr Ile Ser Val Asn Ser Gln
                195                 200                 205

Lys Thr Lys Asn Leu Val Phe Thr Lys Glu Asp Thr Ile Thr Val Gln
```

210                 215                 220
Arg Tyr Asp Ser Ala Gly Thr Asn Leu Glu Gly Lys Ala Val Glu Ile
225                 230                 235                 240

Thr Thr Leu Lys Glu Leu Lys Asn Ala Leu Lys Gly Ser Met Leu Ser
                245                 250                 255

Glu Arg Met Leu Lys Ala Leu Asn Asp Gln Leu Asn Arg Glu Leu Tyr
            260                 265                 270

Ser Ala Tyr Leu Tyr Phe Ala Met Ala Tyr Phe Glu Asp Leu Gly
        275                 280                 285

Leu Glu Gly Phe Ala Asn Trp Met Lys Ala Gln Ala Glu Glu Ile
    290                 295                 300

Gly His Ala Leu Arg Phe Tyr Asn Tyr Ile Tyr Asp Arg Asn Gly Arg
305                 310                 315                 320

Val Glu Leu Asp Glu Ile Pro Lys Pro Lys Glu Trp Glu Ser Pro
                325                 330                 335

Leu Lys Ala Phe Glu Ala Ala Tyr Glu His Glu Lys Phe Ile Ser Lys
                340                 345                 350

Ser Ile Tyr Glu Leu Ala Ala Leu Ala Glu Glu Lys Asp Tyr Ser
        355                 360                 365

Thr Arg Ala Phe Leu Glu Trp Phe Ile Asn Glu Gln Val Glu Glu Glu
370                 375                 380

Ala Ser Val Lys Lys Ile Leu Asp Lys Leu Lys Phe Ala Lys Asp Ser
385                 390                 395                 400

Pro Gln Ile Leu Phe Met Leu Asp Lys Glu Leu Ser Ala Arg Ala Pro
                405                 410                 415

Lys Leu Pro Gly Leu Leu Met Gln Gly Gly Glu
                420                 425

<210> SEQ ID NO 41
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Met Asp Glu Lys Asn Ser Val Ser Val Asp Leu Pro Gly Glu Met Lys
1               5                   10                  15

Val Leu Val Ser Lys Glu Lys Asp Lys Asp Gly Lys Tyr Ser Leu Glu
                20                  25                  30

Ala Thr Val Asp Lys Leu Glu Leu Lys Gly Thr Ser Asp Lys Asn Asn
            35                  40                  45

Gly Ser Gly Val Leu Glu Gly Val Lys Ala Ala Lys Ser Lys Ala Lys
        50                  55                  60

Leu Thr Ile Ala Asp Asp Leu Ser Gln Thr Lys Phe Glu Ile Phe Lys
65                  70                  75                  80

Glu Asp Gly Lys Thr Leu Val Ser Lys Val Thr Leu Lys Asp Lys
                85                  90                  95

Ser Ser Thr Glu Glu Lys Phe Asn Asp Lys Gly Lys Leu Ser Glu Lys
            100                 105                 110

Val Val Thr Arg Ala Asn Gly Thr Arg Leu Glu Tyr Thr Glu Ile Gln
        115                 120                 125

Asn Asp Gly Ser Gly Lys Ala Lys Glu Val Leu Lys Ser Leu Thr Leu
    130                 135                 140

```
Glu Gly Thr Leu Thr Ala Asp Gly Glu Thr Lys Leu Thr Val Glu Ala
145                 150                 155                 160

Gly Thr Val Thr Leu Ser Lys Asn Ile Ser Glu Ser Gly Glu Ile Thr
            165                 170                 175

Val Glu Leu Lys Asp Thr Glu Thr Thr Pro Ala Asp Lys Lys Ser Gly
        180                 185                 190

Thr Trp Asp Ser Lys Thr Ser Thr Leu Thr Ile Ser Lys Asn Ser Gln
            195                 200                 205

Lys Thr Lys Gln Leu Val Phe Thr Lys Glu Asn Thr Ile Thr Val Gln
210                 215                 220

Lys Tyr Asn Thr Ala Gly Thr Lys Leu Glu Gly Ser Pro Ala Glu Ile
225                 230                 235                 240

Lys Asp Leu Glu Ala Leu Lys Ala Ala Leu Lys Gly Ser Met Leu Ser
                245                 250                 255

Glu Arg Met Leu Lys Ala Leu Asn Asp Gln Leu Asn Arg Glu Leu Tyr
            260                 265                 270

Ser Ala Tyr Leu Tyr Phe Ala Met Ala Ala Tyr Phe Glu Asp Leu Gly
        275                 280                 285

Leu Glu Gly Phe Ala Asn Trp Met Lys Ala Gln Ala Glu Glu Glu Ile
290                 295                 300

Gly His Ala Leu Arg Phe Tyr Asn Tyr Ile Tyr Asp Arg Asn Gly Arg
305                 310                 315                 320

Val Glu Leu Asp Glu Ile Pro Lys Pro Pro Lys Glu Trp Glu Ser Pro
                325                 330                 335

Leu Lys Ala Phe Glu Ala Ala Tyr Glu His Glu Lys Phe Ile Ser Lys
            340                 345                 350

Ser Ile Tyr Glu Leu Ala Ala Leu Ala Glu Glu Lys Asp Tyr Ser
        355                 360                 365

Thr Arg Ala Phe Leu Glu Trp Phe Ile Asn Glu Gln Val Glu Glu Glu
            370                 375                 380

Ala Ser Val Lys Lys Ile Leu Asp Lys Leu Lys Phe Ala Lys Asp Ser
385                 390                 395                 400

Pro Gln Ile Leu Phe Met Leu Asp Lys Glu Leu Ser Ala Arg Ala Pro
                405                 410                 415

Lys Leu Pro Gly Leu Leu Met Gln Gly Gly Glu
            420                 425

<210> SEQ ID NO 42
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Asp Lys Ser Lys Val Lys
    50                  55                  60
```

```
Leu Thr Ile Ser Asp Asp Leu Gly Gln Thr Thr Leu Glu Val Phe Lys
 65                  70                  75                  80

Glu Asp Gly Lys Thr Leu Val Ser Lys Lys Val Thr Ser Lys Asp Lys
                 85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
        115                 120                 125

Ser Asp Gly Ser Gly Lys Ala Lys Glu Val Leu Lys Gly Tyr Thr Leu
130                 135                 140

Glu Gly Gln Leu Ser Asp Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
        195                 200                 205

Thr Lys Asp Leu Val Phe Thr Lys Glu Asn Thr Ile Thr Val Gln Gln
210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Ser Thr Gln Cys Asn
                245                 250                 255

Val Asn Pro Val Gln Ile Pro Lys Asp Trp Ile Thr Met His Arg Ser
            260                 265                 270

Cys Arg Asn Ser Met Arg Gln Gln Ile Gln Met Glu Val Gly Ala Ser
        275                 280                 285

Leu Gln Tyr Leu Ala Met Gly Ala His Phe Ser Lys Asp Val Val Asn
290                 295                 300

Arg Pro Gly Phe Ala Gln Leu Phe Phe Asp Ala Ala Ser Glu Glu Arg
305                 310                 315                 320

Glu His Ala Met Lys Leu Ile Glu Tyr Leu Leu Met Arg Gly Glu Leu
                325                 330                 335

Thr Asn Asp Val Ser Ser Leu Leu Gln Val Arg Pro Pro Thr Arg Ser
            340                 345                 350

Ser Trp Lys Gly Gly Val Glu Ala Leu Glu His Ala Leu Ser Met Glu
        355                 360                 365

Ser Asp Val Thr Lys Ser Ile Arg Asn Val Ile Lys Ala Cys Glu Asp
370                 375                 380

Asp Ser Glu Phe Asn Asp Tyr His Leu Val Asp Tyr Leu Thr Gly Asp
385                 390                 395                 400

Phe Leu Glu Glu Gln Tyr Lys Gly Gln Arg Asp Leu Ala Gly Lys Ala
                405                 410                 415

Ser Thr Leu Lys Lys Leu Met Asp Arg His Glu Ala Leu Gly Glu Phe
            420                 425                 430

Ile Phe Asp Lys Lys Leu Leu Gly Ile Asp Val
        435                 440
```

<210> SEQ ID NO 43
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 43

```
Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Asp Lys Ser Lys Val Lys
    50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
        115                 120                 125

Ser Asp Gly Ser Gly Lys Ala Lys Glu Val Leu Lys Gly Tyr Asp Leu
    130                 135                 140

Lys Gly Glu Leu Ser Ser Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
        195                 200                 205

Thr Lys Asp Leu Val Phe Thr Lys Glu Asn Thr Ile Thr Val Gln Gln
    210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Ser Thr Gln Cys Asn
                245                 250                 255

Val Asn Pro Val Gln Ile Pro Lys Asp Trp Ile Thr Met His Arg Ser
            260                 265                 270

Cys Arg Asn Ser Met Arg Gln Gln Ile Gln Met Glu Val Gly Ala Ser
        275                 280                 285

Leu Gln Tyr Leu Ala Met Gly Ala His Phe Ser Lys Asp Val Val Asn
    290                 295                 300

Arg Pro Gly Phe Ala Gln Leu Phe Phe Asp Ala Ala Ser Glu Glu Arg
305                 310                 315                 320

Glu His Ala Met Lys Leu Ile Glu Tyr Leu Leu Met Arg Gly Glu Leu
                325                 330                 335

Thr Asn Asp Val Ser Ser Leu Leu Gln Val Arg Pro Pro Thr Arg Ser
            340                 345                 350

Ser Trp Lys Gly Gly Val Glu Ala Leu Glu His Ala Leu Ser Met Glu
        355                 360                 365

Ser Asp Val Thr Lys Ser Ile Arg Asn Val Ile Lys Ala Cys Glu Asp
    370                 375                 380

Asp Ser Glu Phe Asn Asp Tyr His Leu Val Asp Tyr Leu Thr Gly Asp
385                 390                 395                 400
```

-continued

```
Phe Leu Glu Glu Gln Tyr Lys Gly Gln Arg Asp Leu Ala Gly Lys Ala
                405                 410                 415

Ser Thr Leu Lys Lys Leu Met Asp Arg His Glu Ala Leu Gly Glu Phe
            420                 425                 430

Ile Phe Asp Lys Lys Leu Leu Gly Ile Asp Val
        435                 440

<210> SEQ ID NO 44
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
                20                  25                  30

Ala Thr Val Asp Lys Leu Glu Leu Lys Gly Thr Ser Asp Lys Asn Asn
            35                  40                  45

Gly Ser Gly Val Leu Glu Gly Val Lys Ala Asp Lys Ser Lys Val Lys
    50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
        115                 120                 125

Ser Asp Gly Ser Gly Lys Ala Lys Glu Val Leu Lys Gly Phe Thr Leu
    130                 135                 140

Glu Gly Lys Val Ala Asn Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
        195                 200                 205

Thr Lys Asp Leu Val Phe Thr Lys Glu Asn Thr Ile Thr Val Gln Gln
    210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Ser Thr Gln Cys Asn
                245                 250                 255

Val Asn Pro Val Gln Ile Pro Lys Asp Trp Ile Thr Met His Arg Ser
            260                 265                 270

Cys Arg Asn Ser Met Arg Gln Gln Ile Gln Met Glu Val Gly Ala Ser
        275                 280                 285

Leu Gln Tyr Leu Ala Met Gly Ala His Phe Ser Lys Asp Val Val Asn
    290                 295                 300
```

```
Arg Pro Gly Phe Ala Gln Leu Phe Phe Asp Ala Ser Glu Glu Arg
305                 310                 315                 320

Glu His Ala Met Lys Leu Ile Glu Tyr Leu Leu Met Arg Gly Glu Leu
                325                 330                 335

Thr Asn Asp Val Ser Ser Leu Leu Gln Val Arg Pro Pro Thr Arg Ser
                340                 345                 350

Ser Trp Lys Gly Gly Val Glu Ala Leu Glu His Ala Leu Ser Met Glu
                355                 360                 365

Ser Asp Val Thr Lys Ser Ile Arg Asn Val Ile Lys Ala Cys Glu Asp
            370                 375                 380

Asp Ser Glu Phe Asn Asp Tyr His Leu Val Asp Tyr Leu Thr Gly Asp
385                 390                 395                 400

Phe Leu Glu Glu Gln Tyr Lys Gly Gln Arg Asp Leu Ala Gly Lys Ala
                405                 410                 415

Ser Thr Leu Lys Lys Leu Met Asp Arg His Glu Ala Leu Gly Glu Phe
                420                 425                 430

Ile Phe Asp Lys Lys Leu Leu Gly Ile Asp Val
                435                 440

<210> SEQ ID NO 45
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
                20                  25                  30

Ala Thr Val Asp Lys Leu Glu Leu Lys Gly Thr Ser Asp Lys Asn Asn
            35                  40                  45

Gly Ser Gly Val Leu Glu Gly Val Lys Ala Asp Lys Ser Lys Val Lys
50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
                100                 105                 110

Ile Ile Thr Arg Ala Asp Gly Thr Arg Leu Glu Tyr Thr Gly Ile Lys
            115                 120                 125

Ser Asp Gly Ser Gly Lys Ala Lys Glu Val Leu Lys Gly Phe Ala Leu
130                 135                 140

Glu Gly Thr Leu Thr Asp Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
                180                 185                 190

Trp Asn Ser Gly Thr Ser Thr Leu Thr Ile Thr Val Asn Ser Lys Lys
            195                 200                 205

Thr Lys Asp Leu Val Phe Thr Lys Glu Asn Thr Ile Thr Val Gln Gln
```

```
                    210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys Gly Ser Thr Gln Cys Asn
                    245                 250                 255

Val Asn Pro Val Gln Ile Pro Lys Asp Trp Ile Thr Met His Arg Ser
                260                 265                 270

Cys Arg Asn Ser Met Arg Gln Gln Ile Gln Met Glu Val Gly Ala Ser
            275                 280                 285

Leu Gln Tyr Leu Ala Met Gly Ala His Phe Ser Lys Asp Val Val Asn
        290                 295                 300

Arg Pro Gly Phe Ala Gln Leu Phe Phe Asp Ala Ala Ser Glu Glu Arg
305                 310                 315                 320

Glu His Ala Met Lys Leu Ile Glu Tyr Leu Leu Met Arg Gly Glu Leu
                    325                 330                 335

Thr Asn Asp Val Ser Ser Leu Leu Gln Val Arg Pro Pro Thr Arg Ser
                340                 345                 350

Ser Trp Lys Gly Gly Val Glu Ala Leu Glu His Ala Leu Ser Met Glu
            355                 360                 365

Ser Asp Val Thr Lys Ser Ile Arg Asn Val Ile Lys Ala Cys Glu Asp
        370                 375                 380

Asp Ser Glu Phe Asn Asp Tyr His Leu Val Asp Tyr Leu Thr Gly Asp
385                 390                 395                 400

Phe Leu Glu Glu Gln Tyr Lys Gly Gln Arg Asp Leu Ala Gly Lys Ala
                    405                 410                 415

Ser Thr Leu Lys Lys Leu Met Asp Arg His Glu Ala Leu Gly Glu Phe
                420                 425                 430

Ile Phe Asp Lys Lys Leu Leu Gly Ile Asp Val
            435                 440

<210> SEQ ID NO 46
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Met Asp Glu Lys Asn Ser Ala Ser Val Asp Leu Pro Gly Glu Met Lys
1               5                   10                  15

Val Leu Val Ser Lys Glu Lys Asp Lys Asp Gly Lys Tyr Ser Leu Lys
                20                  25                  30

Ala Thr Val Asp Lys Ile Glu Leu Lys Gly Thr Ser Asp Lys Asp Asn
            35                  40                  45

Gly Ser Gly Val Leu Glu Gly Thr Lys Asp Asp Lys Ser Lys Ala Lys
        50                  55                  60

Leu Thr Ile Ala Asp Asp Leu Ser Lys Thr Thr Phe Glu Leu Phe Lys
65                  70                  75                  80

Glu Asp Gly Lys Thr Leu Val Ser Arg Lys Val Ser Ser Lys Asp Lys
                85                  90                  95

Thr Ser Thr Asp Glu Met Phe Asn Glu Lys Gly Glu Leu Ser Ala Lys
            100                 105                 110

Thr Met Thr Arg Glu Asn Gly Thr Lys Leu Glu Tyr Thr Glu Met Lys
        115                 120                 125
```

```
Ser Asp Gly Thr Gly Lys Ala Lys Glu Val Leu Lys Asn Phe Thr Leu
        130                 135                 140

Glu Gly Lys Val Ala Asn Asp Lys Val Thr Leu Glu Val Lys Glu Gly
145                 150                 155                 160

Thr Val Thr Leu Ser Lys Glu Ile Ala Lys Ser Gly Glu Val Thr Val
                165                 170                 175

Ala Leu Asn Asp Thr Asn Thr Thr Gln Ala Thr Lys Lys Thr Gly Ala
            180                 185                 190

Trp Asp Ser Lys Thr Ser Thr Leu Thr Ile Ser Val Asn Ser Lys Lys
        195                 200                 205

Thr Thr Gln Leu Val Phe Thr Lys Gln Asp Thr Ile Thr Val Gln Lys
210                 215                 220

Tyr Asp Ser Ala Gly Thr Asn Leu Glu Gly Thr Ala Val Glu Ile Lys
225                 230                 235                 240

Thr Leu Asp Glu Leu Lys Asn Ala Leu Lys Gly Ser Thr Gln Cys Asn
                245                 250                 255

Val Asn Pro Val Gln Ile Pro Lys Asp Trp Ile Thr Met His Arg Ser
            260                 265                 270

Cys Arg Asn Ser Met Arg Gln Gln Ile Gln Met Glu Val Gly Ala Ser
        275                 280                 285

Leu Gln Tyr Leu Ala Met Gly Ala His Phe Ser Lys Asp Val Val Asn
290                 295                 300

Arg Pro Gly Phe Ala Gln Leu Phe Phe Asp Ala Ala Ser Glu Glu Arg
305                 310                 315                 320

Glu His Ala Met Lys Leu Ile Glu Tyr Leu Leu Met Arg Gly Glu Leu
                325                 330                 335

Thr Asn Asp Val Ser Ser Leu Leu Gln Val Arg Pro Pro Thr Arg Ser
            340                 345                 350

Ser Trp Lys Gly Gly Val Glu Ala Leu Glu His Ala Leu Ser Met Glu
        355                 360                 365

Ser Asp Val Thr Lys Ser Ile Arg Asn Val Ile Lys Ala Cys Glu Asp
370                 375                 380

Asp Ser Glu Phe Asn Asp Tyr His Leu Val Asp Tyr Leu Thr Gly Asp
385                 390                 395                 400

Phe Leu Glu Glu Gln Tyr Lys Gly Gln Arg Asp Leu Ala Gly Lys Ala
                405                 410                 415

Ser Thr Leu Lys Lys Leu Met Asp Arg His Glu Ala Leu Gly Glu Phe
            420                 425                 430

Ile Phe Asp Lys Lys Leu Leu Gly Ile Asp Val
        435                 440
```

<210> SEQ ID NO 47
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

```
Met Asp Glu Lys Asn Ser Val Ser Val Asp Leu Pro Gly Gly Met Lys
1               5                   10                  15

Val Leu Val Ser Lys Glu Lys Asp Lys Asp Gly Lys Tyr Ser Leu Met
            20                  25                  30
```

-continued

```
Ala Thr Val Glu Lys Leu Glu Leu Lys Gly Thr Ser Asp Lys Ser Asn
            35                  40                  45

Gly Ser Gly Val Leu Glu Gly Lys Ala Asp Lys Ser Lys Ala Lys
 50                  55                  60

Leu Thr Ile Ser Gln Asp Leu Asn Gln Thr Thr Phe Glu Ile Phe Lys
 65                  70                  75                  80

Glu Asp Gly Lys Thr Leu Val Ser Arg Lys Val Asn Ser Lys Asp Lys
                 85                  90                  95

Ser Ser Thr Glu Glu Lys Phe Asn Asp Lys Gly Lys Leu Ser Glu Lys
             100                 105                 110

Val Val Thr Arg Ala Asn Gly Thr Arg Leu Glu Tyr Thr Glu Ile Lys
             115                 120                 125

Asn Asp Gly Ser Gly Lys Ala Lys Glu Val Leu Lys Gly Phe Ala Leu
             130                 135                 140

Glu Gly Thr Leu Thr Asp Gly Gly Glu Thr Lys Leu Thr Val Thr Glu
145                 150                 155                 160

Gly Thr Val Thr Leu Ser Lys Asn Ile Ser Lys Ser Gly Glu Ile Thr
                 165                 170                 175

Val Ala Leu Asn Asp Thr Glu Thr Thr Pro Ala Asp Lys Lys Thr Gly
             180                 185                 190

Glu Trp Lys Ser Asp Thr Ser Thr Leu Thr Ile Ser Lys Asn Ser Gln
             195                 200                 205

Lys Pro Lys Gln Leu Val Phe Thr Lys Glu Asn Thr Ile Thr Val Gln
             210                 215                 220

Asn Tyr Asn Arg Ala Gly Asn Ala Leu Glu Gly Ser Pro Ala Glu Ile
225                 230                 235                 240

Lys Asp Leu Ala Glu Leu Lys Ala Ala Leu Lys Gly Ser Thr Gln Cys
                 245                 250                 255

Asn Val Asn Pro Val Gln Ile Pro Lys Asp Trp Ile Thr Met His Arg
             260                 265                 270

Ser Cys Arg Asn Ser Met Arg Gln Gln Ile Gln Met Glu Val Gly Ala
             275                 280                 285

Ser Leu Gln Tyr Leu Ala Met Gly Ala His Phe Ser Lys Asp Val Val
             290                 295                 300

Asn Arg Pro Gly Phe Ala Gln Leu Phe Phe Asp Ala Ala Ser Glu Glu
305                 310                 315                 320

Arg Glu His Ala Met Lys Leu Ile Glu Tyr Leu Leu Met Arg Gly Glu
                 325                 330                 335

Leu Thr Asn Asp Val Ser Ser Leu Leu Gln Val Arg Pro Pro Thr Arg
             340                 345                 350

Ser Ser Trp Lys Gly Gly Val Glu Ala Leu Glu His Ala Leu Ser Met
             355                 360                 365

Glu Ser Asp Val Thr Lys Ser Ile Arg Asn Val Ile Lys Ala Cys Glu
370                 375                 380

Asp Asp Ser Glu Phe Asn Asp Tyr His Leu Val Asp Tyr Leu Thr Gly
385                 390                 395                 400

Asp Phe Leu Glu Glu Gln Tyr Lys Gly Gln Arg Asp Leu Ala Gly Lys
                 405                 410                 415

Ala Ser Thr Leu Lys Lys Leu Met Asp Arg His Glu Ala Leu Gly Glu
             420                 425                 430

Phe Ile Phe Asp Lys Lys Leu Leu Gly Ile Asp Val
             435                 440
```

```
<210> SEQ ID NO 48
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Met Asp Glu Lys Asn Ser Val Ser Val Asp Leu Pro Gly Glu Met Lys
1               5                   10                  15

Val Leu Val Ser Lys Glu Lys Asp Lys Asp Gly Lys Tyr Ser Leu Met
            20                  25                  30

Ala Thr Val Asp Lys Leu Glu Leu Lys Gly Thr Ser Asp Lys Ser Asn
        35                  40                  45

Gly Ser Gly Thr Leu Glu Gly Glu Lys Ser Asp Lys Ser Lys Ala Lys
    50                  55                  60

Leu Thr Ile Ser Glu Asp Leu Ser Lys Thr Thr Phe Glu Ile Phe Lys
65                  70                  75                  80

Glu Asp Gly Lys Thr Leu Val Ser Lys Val Asn Ser Lys Asp Lys
                85                  90                  95

Ser Ser Ile Glu Glu Lys Phe Asn Ala Lys Gly Glu Leu Ser Glu Lys
                100                 105                 110

Thr Ile Leu Arg Ala Asn Gly Thr Arg Leu Glu Tyr Thr Glu Ile Lys
            115                 120                 125

Ser Asp Gly Thr Gly Lys Ala Lys Glu Val Leu Lys Asp Phe Ala Leu
        130                 135                 140

Glu Gly Thr Leu Ala Ala Asp Lys Thr Thr Leu Lys Val Thr Glu Gly
145                 150                 155                 160

Thr Val Val Leu Ser Lys His Ile Pro Asn Ser Gly Glu Ile Thr Val
                165                 170                 175

Glu Leu Asn Asp Ser Asn Ser Thr Gln Ala Thr Lys Lys Thr Gly Lys
            180                 185                 190

Trp Asp Ser Asn Thr Ser Thr Leu Thr Ile Ser Val Asn Ser Lys Lys
        195                 200                 205

Thr Lys Asn Ile Val Phe Thr Lys Glu Asp Thr Ile Thr Val Gln Lys
    210                 215                 220

Tyr Asp Ser Ala Gly Thr Asn Leu Glu Gly Asn Ala Val Glu Ile Lys
225                 230                 235                 240

Thr Leu Asp Glu Leu Lys Asn Ala Leu Lys Gly Ser Thr Gln Cys Asn
                245                 250                 255

Val Asn Pro Val Gln Ile Pro Lys Asp Trp Ile Thr Met His Arg Ser
            260                 265                 270

Cys Arg Asn Ser Met Arg Gln Gln Ile Gln Met Glu Val Gly Ala Ser
        275                 280                 285

Leu Gln Tyr Leu Ala Met Gly Ala His Phe Ser Lys Asp Val Val Asn
    290                 295                 300

Arg Pro Gly Phe Ala Gln Leu Phe Phe Asp Ala Ala Ser Glu Glu Arg
305                 310                 315                 320

Glu His Ala Met Lys Leu Ile Glu Tyr Leu Leu Met Arg Gly Glu Leu
                325                 330                 335

Thr Asn Asp Val Ser Ser Leu Leu Gln Val Arg Pro Pro Thr Arg Ser
            340                 345                 350

Ser Trp Lys Gly Gly Val Glu Ala Leu Glu His Ala Leu Ser Met Glu
        355                 360                 365
```

```
Ser Asp Val Thr Lys Ser Ile Arg Asn Val Ile Lys Ala Cys Glu Asp
        370                 375                 380

Asp Ser Glu Phe Asn Asp Tyr His Leu Val Asp Tyr Leu Thr Gly Asp
385                 390                 395                 400

Phe Leu Glu Glu Gln Tyr Lys Gly Gln Arg Asp Leu Ala Gly Lys Ala
                405                 410                 415

Ser Thr Leu Lys Lys Leu Met Asp Arg His Glu Ala Leu Gly Glu Phe
                420                 425                 430

Ile Phe Asp Lys Lys Leu Leu Gly Ile Asp Val
        435                 440

<210> SEQ ID NO 49
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Met Asp Glu Lys Asn Ser Val Ser Val Asp Leu Pro Gly Gly Met Lys
1               5                   10                  15

Val Leu Val Ser Lys Glu Lys Asp Lys Asp Gly Lys Tyr Ser Leu Met
                20                  25                  30

Ala Thr Val Glu Lys Leu Glu Leu Lys Gly Thr Ser Asp Lys Asn Asn
            35                  40                  45

Gly Ser Gly Thr Leu Glu Gly Glu Lys Thr Asp Lys Ser Lys Val Lys
    50                  55                  60

Leu Thr Ile Ala Glu Asp Leu Ser Lys Thr Thr Phe Glu Ile Phe Lys
65                  70                  75                  80

Glu Asp Gly Lys Thr Leu Val Ser Lys Val Thr Leu Lys Asp Lys
                85                  90                  95

Ser Ser Thr Glu Glu Lys Phe Asn Glu Lys Gly Glu Ile Ser Glu Lys
                100                 105                 110

Thr Ile Val Arg Ala Asn Gly Thr Arg Leu Glu Tyr Thr Asp Ile Lys
            115                 120                 125

Ser Asp Gly Ser Gly Lys Ala Lys Glu Val Leu Lys Asp Phe Thr Leu
    130                 135                 140

Glu Gly Thr Leu Ala Ala Asp Gly Lys Thr Thr Leu Lys Val Thr Glu
145                 150                 155                 160

Gly Thr Val Val Leu Ser Lys Asn Ile Leu Lys Ser Gly Glu Ile Thr
                165                 170                 175

Val Ala Leu Asp Asp Ser Asp Thr Thr Gln Ala Thr Lys Lys Thr Gly
                180                 185                 190

Lys Trp Asp Ser Lys Thr Ser Thr Leu Thr Ile Ser Val Asn Ser Gln
            195                 200                 205

Lys Thr Lys Asn Leu Val Phe Thr Lys Glu Asp Thr Ile Thr Val Gln
    210                 215                 220

Lys Tyr Asp Ser Ala Gly Thr Asn Leu Glu Gly Lys Ala Val Glu Ile
225                 230                 235                 240

Thr Thr Leu Glu Lys Leu Lys Asp Ala Leu Lys Gly Ser Thr Gln Cys
                245                 250                 255

Asn Val Asn Pro Val Gln Ile Pro Lys Asp Trp Ile Thr Met His Arg
                260                 265                 270
```

```
Ser Cys Arg Asn Ser Met Arg Gln Gln Ile Gln Met Glu Val Gly Ala
        275                 280                 285

Ser Leu Gln Tyr Leu Ala Met Gly Ala His Phe Ser Lys Asp Val Val
    290                 295                 300

Asn Arg Pro Gly Phe Ala Gln Leu Phe Phe Asp Ala Ala Ser Glu Glu
305                 310                 315                 320

Arg Glu His Ala Met Lys Leu Ile Glu Tyr Leu Leu Met Arg Gly Glu
                325                 330                 335

Leu Thr Asn Asp Val Ser Ser Leu Leu Gln Val Arg Pro Pro Thr Arg
                340                 345                 350

Ser Ser Trp Lys Gly Gly Val Glu Ala Leu Glu His Ala Leu Ser Met
        355                 360                 365

Glu Ser Asp Val Thr Lys Ser Ile Arg Asn Val Ile Lys Ala Cys Glu
    370                 375                 380

Asp Asp Ser Glu Phe Asn Asp Tyr His Leu Val Asp Tyr Leu Thr Gly
385                 390                 395                 400

Asp Phe Leu Glu Glu Gln Tyr Lys Gly Gln Arg Asp Leu Ala Gly Lys
                405                 410                 415

Ala Ser Thr Leu Lys Lys Leu Met Asp Arg His Glu Ala Leu Gly Glu
                420                 425                 430

Phe Ile Phe Asp Lys Lys Leu Leu Gly Ile Asp Val
        435                 440

<210> SEQ ID NO 50
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Met Asp Glu Lys Asn Ser Val Ser Val Asp Leu Pro Gly Gly Met Thr
1               5                   10                  15

Val Leu Val Ser Lys Glu Lys Asp Lys Asp Gly Lys Tyr Ser Leu Glu
                20                  25                  30

Ala Thr Val Asp Lys Leu Glu Leu Lys Gly Thr Ser Asp Lys Asn Asn
            35                  40                  45

Gly Ser Gly Thr Leu Glu Gly Glu Lys Thr Asp Lys Ser Lys Val Lys
        50                  55                  60

Ser Thr Ile Ala Asp Asp Leu Ser Gln Thr Lys Phe Glu Ile Phe Lys
65                  70                  75                  80

Glu Asp Gly Lys Thr Leu Val Ser Lys Lys Val Thr Leu Lys Asp Lys
                85                  90                  95

Ser Ser Thr Glu Glu Lys Phe Asn Gly Lys Gly Thr Ser Glu Lys
            100                 105                 110

Thr Ile Val Arg Ala Asn Gly Thr Arg Leu Glu Tyr Thr Asp Ile Lys
            115                 120                 125

Ser Asp Gly Ser Gly Lys Ala Lys Glu Val Leu Lys Asp Phe Thr Leu
        130                 135                 140

Glu Gly Thr Leu Ala Ala Asp Gly Lys Thr Thr Leu Lys Val Thr Glu
145                 150                 155                 160

Gly Thr Val Val Leu Ser Lys Asn Ile Leu Lys Ser Gly Glu Ile Thr
                165                 170                 175

Ala Ala Leu Asp Asp Ser Asp Thr Thr Arg Ala Thr Lys Lys Thr Gly
```

```
                  180                 185                 190
Lys Trp Asp Ser Lys Thr Ser Thr Leu Thr Ile Ser Val Asn Ser Gln
                195                 200                 205

Lys Thr Lys Asn Leu Val Phe Thr Lys Glu Asp Thr Ile Thr Val Gln
        210                 215                 220

Arg Tyr Asp Ser Ala Gly Thr Asn Leu Glu Gly Lys Ala Val Glu Ile
225                 230                 235                 240

Thr Thr Leu Lys Glu Leu Lys Asn Ala Leu Lys Gly Ser Thr Gln Cys
                245                 250                 255

Asn Val Asn Pro Val Gln Ile Pro Lys Asp Trp Ile Thr Met His Arg
            260                 265                 270

Ser Cys Arg Asn Ser Met Arg Gln Gln Ile Gln Met Glu Val Gly Ala
        275                 280                 285

Ser Leu Gln Tyr Leu Ala Met Gly Ala His Phe Ser Lys Asp Val Val
            290                 295                 300

Asn Arg Pro Gly Phe Ala Gln Leu Phe Phe Asp Ala Ala Ser Glu Glu
305                 310                 315                 320

Arg Glu His Ala Met Lys Leu Ile Glu Tyr Leu Leu Met Arg Gly Glu
                325                 330                 335

Leu Thr Asn Asp Val Ser Ser Leu Leu Gln Val Arg Pro Pro Thr Arg
            340                 345                 350

Ser Ser Trp Lys Gly Gly Val Glu Ala Leu Glu His Ala Leu Ser Met
        355                 360                 365

Glu Ser Asp Val Thr Lys Ser Ile Arg Asn Val Ile Lys Ala Cys Glu
    370                 375                 380

Asp Asp Ser Glu Phe Asn Asp Tyr His Leu Val Asp Tyr Leu Thr Gly
385                 390                 395                 400

Asp Phe Leu Glu Glu Gln Tyr Lys Gly Gln Arg Asp Leu Ala Gly Lys
                405                 410                 415

Ala Ser Thr Leu Lys Lys Leu Met Asp Arg His Glu Ala Leu Gly Glu
            420                 425                 430

Phe Ile Phe Asp Lys Lys Leu Leu Gly Ile Asp Val
        435                 440

<210> SEQ ID NO 51
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Met Asp Glu Lys Asn Ser Val Ser Val Asp Leu Pro Gly Glu Met Lys
1               5                   10                  15

Val Leu Val Ser Lys Glu Lys Asp Lys Asp Gly Lys Tyr Ser Leu Glu
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Ala Lys Ser Lys Ala Lys
    50                  55                  60

Leu Thr Ile Ala Asp Asp Leu Ser Gln Thr Lys Phe Glu Ile Phe Lys
65                  70                  75                  80

Glu Asp Gly Lys Thr Leu Val Ser Lys Lys Val Thr Leu Lys Asp Lys
                85                  90                  95
```

```
Ser Ser Thr Glu Glu Lys Phe Asn Asp Lys Gly Lys Leu Ser Glu Lys
            100                 105                 110

Val Val Thr Arg Ala Asn Gly Thr Arg Leu Glu Tyr Thr Glu Ile Gln
            115                 120                 125

Asn Asp Gly Ser Gly Lys Ala Lys Glu Val Leu Lys Ser Leu Thr Leu
        130                 135                 140

Glu Gly Thr Leu Thr Ala Asp Gly Glu Thr Lys Leu Thr Val Glu Ala
145                 150                 155                 160

Gly Thr Val Thr Leu Ser Lys Asn Ile Ser Glu Ser Gly Glu Ile Thr
                165                 170                 175

Val Glu Leu Lys Asp Thr Glu Thr Thr Pro Ala Asp Lys Lys Ser Gly
            180                 185                 190

Thr Trp Asp Ser Lys Thr Ser Thr Leu Thr Ile Ser Lys Asn Ser Gln
        195                 200                 205

Lys Thr Lys Gln Leu Val Phe Thr Lys Glu Asn Thr Ile Thr Val Gln
    210                 215                 220

Lys Tyr Asn Thr Ala Gly Thr Lys Leu Glu Gly Ser Pro Ala Glu Ile
225                 230                 235                 240

Lys Asp Leu Glu Ala Leu Lys Ala Ala Leu Lys Gly Ser Thr Gln Cys
                245                 250                 255

Asn Val Asn Pro Val Gln Ile Pro Lys Asp Trp Ile Thr Met His Arg
            260                 265                 270

Ser Cys Arg Asn Ser Met Arg Gln Gln Ile Gln Met Glu Val Gly Ala
        275                 280                 285

Ser Leu Gln Tyr Leu Ala Met Gly Ala His Phe Ser Lys Asp Val Val
    290                 295                 300

Asn Arg Pro Gly Phe Ala Gln Leu Phe Phe Asp Ala Ala Ser Glu Glu
305                 310                 315                 320

Arg Glu His Ala Met Lys Leu Ile Glu Tyr Leu Leu Met Arg Gly Glu
                325                 330                 335

Leu Thr Asn Asp Val Ser Ser Leu Leu Gln Val Arg Pro Pro Thr Arg
            340                 345                 350

Ser Ser Trp Lys Gly Gly Val Glu Ala Leu Glu His Ala Leu Ser Met
        355                 360                 365

Glu Ser Asp Val Thr Lys Ser Ile Arg Asn Val Ile Lys Ala Cys Glu
    370                 375                 380

Asp Asp Ser Glu Phe Asn Asp Tyr His Leu Val Asp Tyr Leu Thr Gly
385                 390                 395                 400

Asp Phe Leu Glu Glu Gln Tyr Lys Gly Gln Arg Asp Leu Ala Gly Lys
                405                 410                 415

Ala Ser Thr Leu Lys Lys Leu Met Asp Arg His Glu Ala Leu Gly Glu
            420                 425                 430

Phe Ile Phe Asp Lys Lys Leu Leu Gly Ile Asp Val
        435                 440
```

<210> SEQ ID NO 52
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

```
Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Met Asp
            20                  25                  30

Glu Lys Asn Ser Val Ser Val Asp Leu Pro Gly Glu Met Lys Val Leu
                35                  40                  45

Val Ser Lys Glu Lys Asn Lys Asp Gly Lys Tyr Asp Leu Ile Ala Thr
50                  55                  60

Val Asp Lys Leu Glu Leu Lys Gly Thr Ser Asp Lys Asn Asn Gly Ser
65                  70                  75                  80

Gly Val Leu Glu Gly Val Lys Ala Asp Lys Ser Lys Val Lys Leu Thr
                85                  90                  95

Ile Ser Asp Asp Leu Gly Gln Thr Thr Leu Glu Val Phe Lys Glu Asp
                100                 105                 110

Gly Lys Thr Leu Val Ser Lys Lys Val Thr Ser Lys Asp Lys Ser Ser
            115                 120                 125

Thr Glu Glu Lys Phe Asn Glu Lys Gly Glu Val Ser Glu Lys Ile Ile
        130                 135                 140

Thr Arg Ala Asp Gly Thr Arg Leu Glu Tyr Thr Gly Ile Lys Ser Asp
145                 150                 155                 160

Gly Ser Gly Lys Ala Lys Glu Val Leu Lys Gly Tyr Thr Leu Glu Gly
                165                 170                 175

Gln Leu Ser Asp Glu Lys Thr Thr Leu Val Val Lys Glu Gly Thr Val
                180                 185                 190

Thr Leu Ser Lys Asn Ile Ser Lys Ser Gly Glu Val Ser Val Glu Leu
            195                 200                 205

Asn Asp Thr Asp Ser Ser Ala Ala Thr Lys Lys Thr Ala Ala Trp Asn
    210                 215                 220

Ser Gly Thr Ser Thr Leu Thr Ile Thr Val Asn Ser Lys Lys Thr Lys
225                 230                 235                 240

Asp Leu Val Phe Thr Lys Glu Asn Thr Ile Thr Val Gln Gln Tyr Asp
                245                 250                 255

Ser Asn Gly Thr Lys Leu Glu Gly Ser Ala Val Glu Ile Thr Lys Leu
                260                 265                 270

Asp Glu Ile Lys Asn Ala Leu Lys Gly Ser Glu Ser Gln Val Arg Gln
            275                 280                 285

Gln Phe Ser Lys Asp Ile Glu Lys Leu Leu Asn Glu Gln Val Asn Lys
        290                 295                 300

Glu Met Gln Ser Ser Asn Leu Tyr Met Ser Met Ser Ser Trp Ser Tyr
305                 310                 315                 320

Thr His Ser Leu Asp Gly Ala Gly Leu Phe Leu Phe Asp His Ala Ala
                325                 330                 335

Glu Glu Tyr Glu His Ala Lys Lys Leu Ile Ile Phe Leu Asn Glu Asn
                340                 345                 350

Asn Val Pro Val Gln Leu Thr Ser Ile Ser Ala Pro Glu His Lys Phe
            355                 360                 365

Glu Gly Leu Thr Gln Ile Phe Gln Lys Ala Tyr Glu His Glu Gln His
        370                 375                 380

Ile Ser Glu Ser Ile Asn Asn Ile Val Asp His Ala Ile Lys Cys Lys
385                 390                 395                 400

Asp His Ala Thr Phe Asn Phe Leu Gln Trp Tyr Val Ala Glu Gln His
                405                 410                 415

Glu Glu Glu Val Leu Phe Lys Asp Ile Leu Asp Lys Ile Glu Leu Ile
```

```
                 420                 425                 430

Gly Asn Glu Asn His Gly Leu Tyr Leu Ala Asp Gln Tyr Val Lys Gly
            435                 440                 445

Ile Ala Lys Ser Arg Lys Ser
    450                 455

<210> SEQ ID NO 53
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Met Asp
            20                  25                  30

Glu Lys Asn Ser Val Ser Val Asp Leu Pro Gly Glu Met Lys Val Leu
        35                  40                  45

Val Ser Lys Glu Lys Asn Lys Asp Gly Lys Tyr Asp Leu Ile Ala Thr
    50                  55                  60

Val Asp Lys Leu Glu Leu Lys Gly Thr Ser Asp Lys Asn Gln Gly Ser
65                  70                  75                  80

Gly Val Leu Glu Gly Val Lys Ala Asp Lys Ser Lys Val Lys Leu Thr
                85                  90                  95

Ile Ser Asp Asp Leu Gly Gln Thr Thr Leu Glu Val Phe Lys Glu Asp
            100                 105                 110

Gly Lys Thr Leu Val Ser Lys Lys Val Thr Ser Lys Asp Lys Ser Ser
        115                 120                 125

Thr Glu Glu Lys Phe Asn Glu Lys Gly Glu Val Ser Glu Lys Ile Ile
    130                 135                 140

Thr Arg Ala Asp Gly Thr Arg Leu Glu Tyr Thr Gly Ile Lys Ser Asp
145                 150                 155                 160

Gly Ser Gly Lys Ala Lys Glu Val Leu Lys Gly Tyr Thr Leu Glu Gly
                165                 170                 175

Gln Leu Ser Asp Glu Lys Thr Thr Leu Val Val Lys Glu Gly Thr Val
            180                 185                 190

Thr Leu Ser Lys Gln Ile Ser Lys Ser Gly Glu Val Ser Val Glu Leu
        195                 200                 205

Gln Asp Thr Asp Ser Ser Ala Ala Thr Lys Lys Thr Ala Ala Trp Asn
    210                 215                 220

Ser Gly Thr Ser Thr Leu Thr Ile Thr Val Asn Ser Lys Lys Thr Lys
225                 230                 235                 240

Asp Leu Val Phe Thr Lys Glu Asn Thr Ile Thr Val Gln Gln Tyr Asp
                245                 250                 255

Ser Gln Gly Thr Lys Leu Glu Gly Ser Ala Val Glu Ile Thr Lys Leu
            260                 265                 270

Asp Glu Ile Lys Asn Ala Leu Lys Gly Ser Glu Ser Gln Val Arg Gln
        275                 280                 285

Gln Phe Ser Lys Asp Ile Glu Lys Leu Leu Asn Glu Gln Val Asn Lys
    290                 295                 300

Glu Met Gln Ser Ser Asn Leu Tyr Met Ser Met Ser Ser Trp Ser Tyr
305                 310                 315                 320
```

-continued

```
Thr His Ser Leu Asp Gly Ala Gly Leu Phe Leu Phe Asp His Ala Ala
            325                 330                 335

Glu Glu Tyr Glu His Ala Lys Lys Leu Ile Ile Phe Leu Asn Glu Asn
        340                 345                 350

Asn Val Pro Val Gln Leu Thr Ser Ile Ser Ala Pro Glu His Lys Phe
            355                 360                 365

Glu Gly Leu Thr Gln Ile Phe Gln Lys Ala Tyr Glu His Glu Gln His
    370                 375                 380

Ile Ser Glu Ser Ile Asn Asn Ile Val Asp His Ala Ile Lys Cys Lys
385                 390                 395                 400

Asp His Ala Thr Phe Asn Phe Leu Gln Trp Tyr Val Ala Glu Gln His
                405                 410                 415

Glu Glu Glu Val Leu Phe Lys Asp Ile Leu Asp Lys Ile Glu Leu Ile
            420                 425                 430

Gly Asn Glu Asn His Gly Leu Tyr Leu Ala Asp Gln Tyr Val Lys Gly
        435                 440                 445

Ile Ala Lys Ser Arg Lys Ser
    450                 455
```

<210> SEQ ID NO 54
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 54

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Met Asp
            20                  25                  30

Glu Lys Asn Ser Val Ser Val Asp Leu Pro Gly Glu Met Lys Val Leu
        35                  40                  45

Val Ser Lys Glu Lys Asn Lys Asp Gly Lys Tyr Asp Leu Ile Ala Thr
    50                  55                  60

Val Asp Lys Leu Glu Leu Lys Gly Thr Ser Asp Lys Asn Asn Gly Ser
65                  70                  75                  80

Gly Val Leu Glu Gly Val Lys Ala Asp Lys Ser Lys Val Lys Leu Thr
                85                  90                  95

Ile Ser Asp Asp Leu Gly Gln Thr Thr Leu Glu Val Phe Lys Glu Asp
            100                 105                 110

Gly Lys Thr Leu Val Ser Lys Lys Val Thr Ser Lys Asp Lys Ser Ser
        115                 120                 125

Thr Glu Glu Lys Phe Asn Glu Lys Gly Glu Val Ser Glu Lys Ile Ile
    130                 135                 140

Thr Arg Ala Asp Gly Thr Arg Leu Glu Tyr Thr Gly Ile Lys Ser Asp
145                 150                 155                 160

Gly Ser Gly Lys Ala Lys Glu Val Leu Lys Gly Phe Thr Leu Glu Gly
                165                 170                 175

Lys Val Ala Asn Glu Lys Thr Thr Leu Val Val Lys Glu Gly Thr Val
            180                 185                 190

Thr Leu Ser Lys Asn Ile Ser Lys Ser Gly Glu Val Ser Val Glu Leu
        195                 200                 205
```

Asn Asp Thr Asp Ser Ser Ala Ala Thr Lys Lys Thr Ala Ala Trp Asn
210                 215                 220

Ser Gly Thr Ser Thr Leu Thr Ile Thr Val Asn Ser Lys Lys Thr Lys
225                 230                 235                 240

Asp Leu Val Phe Thr Lys Glu Asn Thr Ile Thr Val Gln Gln Tyr Asp
            245                 250                 255

Ser Asn Gly Thr Lys Leu Glu Gly Ser Ala Val Glu Ile Thr Lys Leu
            260                 265                 270

Asp Glu Ile Lys Asn Ala Leu Lys Gly Ser Glu Ser Gln Val Arg Gln
            275                 280                 285

Gln Phe Ser Lys Asp Ile Glu Lys Leu Leu Asn Glu Gln Val Asn Lys
290                 295                 300

Glu Met Gln Ser Ser Asn Leu Tyr Met Ser Met Ser Ser Trp Ser Tyr
305                 310                 315                 320

Thr His Ser Leu Asp Gly Ala Gly Leu Phe Leu Phe Asp His Ala Ala
            325                 330                 335

Glu Glu Tyr Glu His Ala Lys Lys Leu Ile Ile Phe Leu Asn Glu Asn
            340                 345                 350

Asn Val Pro Val Gln Leu Thr Ser Ile Ser Ala Pro Glu His Lys Phe
            355                 360                 365

Glu Gly Leu Thr Gln Ile Phe Gln Lys Ala Tyr Glu His Glu Gln His
            370                 375                 380

Ile Ser Glu Ser Ile Asn Asn Ile Val Asp His Ala Ile Lys Cys Lys
385                 390                 395                 400

Asp His Ala Thr Phe Asn Phe Leu Gln Trp Tyr Val Ala Glu Gln His
            405                 410                 415

Glu Glu Glu Val Leu Phe Lys Asp Ile Leu Asp Lys Ile Glu Leu Ile
            420                 425                 430

Gly Asn Glu Asn His Gly Leu Tyr Leu Ala Asp Gln Tyr Val Lys Gly
            435                 440                 445

Ile Ala Lys Ser Arg Lys Ser
        450                 455

<210> SEQ ID NO 55
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Met Asp
            20                  25                  30

Glu Lys Asn Ser Val Ser Val Asp Leu Pro Gly Glu Met Lys Val Leu
        35                  40                  45

Val Ser Lys Glu Lys Asn Lys Asp Gly Lys Tyr Asp Leu Ile Ala Thr
50                  55                  60

Val Asp Lys Leu Glu Leu Lys Gly Thr Ser Asp Lys Asn Gln Gly Ser
65                  70                  75                  80

Gly Val Leu Glu Gly Val Lys Ala Asp Lys Ser Lys Val Lys Leu Thr
            85                  90                  95

Ile Ser Asp Asp Leu Gly Gln Thr Thr Leu Glu Val Phe Lys Glu Asp

Gly Lys Thr Leu Val Ser Lys Val Thr Ser Lys Asp Lys Ser Ser
            100                 105                 110

Thr Glu Glu Lys Phe Asn Glu Lys Gly Glu Val Ser Glu Lys Ile Ile
    115                 120                 125

Thr Arg Ala Asp Gly Thr Arg Leu Glu Tyr Thr Gly Ile Lys Ser Asp
130                 135                 140                 145

Gly Ser Gly Lys Ala Lys Glu Val Leu Lys Gly Phe Thr Leu Glu Gly
        150                 155                 160

Lys Val Ala Asn Glu Lys Thr Thr Leu Val Val Lys Glu Gly Thr Val
    165                 170                 175

Thr Leu Ser Lys Gln Ile Ser Lys Ser Gly Glu Val Ser Val Glu Leu
180                 185                 190                 195

Gln Asp Thr Asp Ser Ser Ala Ala Thr Lys Lys Thr Ala Ala Trp Asn
        200                 205                 210

Ser Gly Thr Ser Thr Leu Thr Ile Thr Val Asn Ser Lys Lys Thr Lys
    215                 220                 225

Asp Leu Val Phe Thr Lys Glu Asn Thr Ile Thr Val Gln Gln Tyr Asp
230                 235                 240                 245

Ser Gln Gly Thr Lys Leu Glu Gly Ser Ala Val Glu Ile Thr Lys Leu
        250                 255                 260

Asp Glu Ile Lys Asn Ala Leu Lys Gly Ser Glu Ser Gln Val Arg Gln
    265                 270                 275

Gln Phe Ser Lys Asp Ile Glu Lys Leu Leu Asn Glu Gln Val Asn Lys
280                 285                 290                 295

Glu Met Gln Ser Ser Asn Leu Tyr Met Ser Met Ser Ser Trp Ser Tyr
        300                 305                 310

Thr His Ser Leu Asp Gly Ala Gly Leu Phe Leu Phe Asp His Ala Ala
    315                 320                 325

Glu Glu Tyr Glu His Ala Lys Lys Leu Ile Ile Phe Leu Asn Glu Asn
330                 335                 340                 345

Asn Val Pro Val Gln Leu Thr Ser Ile Ser Ala Pro Glu His Lys Phe
        350                 355                 360

Glu Gly Leu Thr Gln Ile Phe Gln Lys Ala Tyr Glu His Glu Gln His
    365                 370                 375

Ile Ser Glu Ser Ile Asn Asn Ile Val Asp His Ala Ile Lys Cys Lys
380                 385                 390                 395

Asp His Ala Thr Phe Asn Phe Leu Gln Trp Tyr Val Ala Glu Gln His
        400                 405                 410

Glu Glu Glu Val Leu Phe Lys Asp Ile Leu Asp Lys Ile Glu Leu Ile
    415                 420                 425

Gly Asn Glu Asn His Gly Leu Tyr Leu Ala Asp Gln Tyr Val Lys Gly
430                 435                 440                 445

Ile Ala Lys Ser Arg Lys Ser
        450                 455

<210> SEQ ID NO 56
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

-continued

```
Met Asp Ser Lys Gly Ser Ser Gln Lys Gly Ser Arg Leu Leu Leu Leu
1               5                   10                  15
Leu Val Val Ser Asn Leu Leu Pro Gln Gly Val Leu Ala Met Asp
            20                  25                  30
Glu Lys Asn Ser Val Ser Val Asp Leu Pro Gly Glu Met Lys Val Leu
            35                  40                  45
Val Ser Lys Glu Lys Asn Lys Asp Gly Lys Tyr Asp Leu Ile Ala Thr
50                  55                  60
Val Asp Lys Leu Glu Leu Lys Gly Thr Ser Asp Lys Asn Asn Gly Ser
65                  70                  75                  80
Gly Val Leu Glu Gly Val Lys Ala Asp Lys Ser Lys Val Lys Leu Thr
                85                  90                  95
Ile Ser Asp Asp Leu Gly Gln Thr Thr Leu Glu Val Phe Lys Glu Asp
                100                 105                 110
Gly Lys Thr Leu Val Ser Lys Lys Val Thr Ser Lys Asp Lys Ser Ser
            115                 120                 125
Thr Glu Glu Lys Phe Asn Glu Lys Gly Glu Val Ser Glu Lys Ile Ile
            130                 135                 140
Thr Arg Ala Asp Gly Thr Arg Leu Glu Tyr Thr Gly Ile Lys Ser Asp
145                 150                 155                 160
Gly Ser Gly Lys Ala Lys Glu Val Leu Lys Gly Phe Ala Leu Glu Gly
                165                 170                 175
Thr Leu Thr Asp Glu Lys Thr Thr Leu Val Val Lys Glu Gly Thr Val
                180                 185                 190
Thr Leu Ser Lys Asn Ile Ser Lys Ser Gly Glu Val Ser Val Glu Leu
            195                 200                 205
Asn Asp Thr Asp Ser Ser Ala Ala Thr Lys Lys Thr Ala Ala Trp Asn
            210                 215                 220
Ser Gly Thr Ser Thr Leu Thr Ile Thr Val Asn Ser Lys Lys Thr Lys
225                 230                 235                 240
Asp Leu Val Phe Thr Lys Glu Asn Thr Ile Thr Val Gln Gln Tyr Asp
                245                 250                 255
Ser Asn Gly Thr Lys Leu Glu Gly Ser Ala Val Glu Ile Thr Lys Leu
                260                 265                 270
Asp Glu Ile Lys Asn Ala Leu Lys Gly Ser Glu Ser Gln Val Arg Gln
            275                 280                 285
Gln Phe Ser Lys Asp Ile Glu Lys Leu Leu Asn Glu Gln Val Asn Lys
            290                 295                 300
Glu Met Gln Ser Ser Asn Leu Tyr Met Ser Met Ser Ser Trp Ser Tyr
305                 310                 315                 320
Thr His Ser Leu Asp Gly Ala Gly Leu Phe Leu Phe Asp His Ala Ala
                325                 330                 335
Glu Glu Tyr Glu His Ala Lys Lys Leu Ile Ile Phe Leu Asn Glu Asn
                340                 345                 350
Asn Val Pro Val Gln Leu Thr Ser Ile Ser Ala Pro Glu His Lys Phe
            355                 360                 365
Glu Gly Leu Thr Gln Ile Phe Gln Lys Ala Tyr Glu His Glu Gln His
            370                 375                 380
Ile Ser Glu Ser Ile Asn Asn Ile Val Asp His Ala Ile Lys Cys Lys
385                 390                 395                 400
Asp His Ala Thr Phe Asn Phe Leu Gln Trp Tyr Val Ala Glu Gln His
                405                 410                 415
```

```
Glu Glu Glu Val Leu Phe Lys Asp Ile Leu Asp Lys Ile Glu Leu Ile
                420                 425                 430

Gly Asn Glu Asn His Gly Leu Tyr Leu Ala Asp Gln Tyr Val Lys Gly
            435                 440                 445

Ile Ala Lys Ser Arg Lys Ser
    450                 455

<210> SEQ ID NO 57
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Met Asp
                20                  25                  30

Glu Lys Asn Ser Val Ser Val Asp Leu Pro Gly Glu Met Lys Val Leu
            35                  40                  45

Val Ser Lys Glu Lys Asn Lys Asp Gly Lys Tyr Asp Leu Ile Ala Thr
    50                  55                  60

Val Asp Lys Leu Glu Leu Lys Gly Thr Ser Asp Lys Asn Gln Gly Ser
65                  70                  75                  80

Gly Val Leu Glu Gly Val Lys Ala Asp Lys Ser Lys Val Lys Leu Thr
                85                  90                  95

Ile Ser Asp Asp Leu Gly Gln Thr Thr Leu Glu Val Phe Lys Glu Asp
                100                 105                 110

Gly Lys Thr Leu Val Ser Lys Lys Val Thr Ser Lys Asp Lys Ser Ser
            115                 120                 125

Thr Glu Glu Lys Phe Asn Glu Lys Gly Glu Val Ser Glu Lys Ile Ile
    130                 135                 140

Thr Arg Ala Asp Gly Thr Arg Leu Glu Tyr Thr Gly Ile Lys Ser Asp
145                 150                 155                 160

Gly Ser Gly Lys Ala Lys Glu Val Leu Lys Gly Phe Ala Leu Glu Gly
                165                 170                 175

Thr Leu Thr Asp Glu Lys Thr Thr Leu Val Val Lys Glu Gly Thr Val
                180                 185                 190

Thr Leu Ser Lys Gln Ile Ser Lys Ser Gly Glu Val Ser Val Glu Leu
            195                 200                 205

Gln Asp Thr Asp Ser Ser Ala Ala Thr Lys Lys Thr Ala Ala Trp Asn
    210                 215                 220

Ser Gly Thr Ser Thr Leu Thr Ile Thr Val Asn Ser Lys Lys Thr Lys
225                 230                 235                 240

Asp Leu Val Phe Thr Lys Glu Asn Thr Ile Thr Val Gln Gln Tyr Asp
                245                 250                 255

Ser Gln Gly Thr Lys Leu Glu Gly Ser Ala Val Glu Ile Thr Lys Leu
                260                 265                 270

Asp Glu Ile Lys Asn Ala Leu Lys Gly Ser Glu Ser Gln Val Arg Gln
            275                 280                 285

Gln Phe Ser Lys Asp Ile Glu Lys Leu Leu Asn Glu Gln Val Asn Lys
    290                 295                 300

Glu Met Gln Ser Ser Asn Leu Tyr Met Ser Met Ser Ser Trp Ser Tyr
```

```
              305                 310                 315                 320
      Thr His Ser Leu Asp Gly Ala Gly Leu Phe Leu Phe Asp His Ala Ala
                      325                 330                 335

Glu Glu Tyr Glu His Ala Lys Lys Leu Ile Ile Phe Leu Asn Glu Asn
                      340                 345                 350

Asn Val Pro Val Gln Leu Thr Ser Ile Ser Ala Pro Glu His Lys Phe
                      355                 360                 365

Glu Gly Leu Thr Gln Ile Phe Gln Lys Ala Tyr Glu His Glu Gln His
                      370                 375                 380

Ile Ser Glu Ser Ile Asn Asn Ile Val Asp His Ala Ile Lys Cys Lys
      385                 390                 395                 400

Asp His Ala Thr Phe Asn Phe Leu Gln Trp Tyr Val Ala Glu Gln His
                      405                 410                 415

Glu Glu Glu Val Leu Phe Lys Asp Ile Leu Asp Lys Ile Glu Leu Ile
                      420                 425                 430

Gly Asn Glu Asn His Gly Leu Tyr Leu Ala Asp Gln Tyr Val Lys Gly
                      435                 440                 445

Ile Ala Lys Ser Arg Lys Ser
          450                 455

<210> SEQ ID NO 58
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Met Asp Ser Lys Gly Ser Ser Gln Lys Gly Ser Arg Leu Leu Leu Leu
      1               5                   10                  15

Leu Val Val Ser Asn Leu Leu Leu Pro Gln Gly Val Leu Ala Met Asp
                      20                  25                  30

Glu Lys Asn Ser Val Ser Val Asp Leu Pro Gly Glu Met Lys Val Leu
                      35                  40                  45

Val Ser Lys Glu Lys Asn Lys Asp Gly Lys Tyr Asp Leu Ile Ala Thr
                      50                  55                  60

Val Asp Lys Leu Glu Leu Lys Gly Thr Ser Asp Lys Asn Asn Gly Ser
      65                  70                  75                  80

Gly Val Leu Glu Gly Val Lys Ala Asp Lys Ser Lys Val Lys Leu Thr
                      85                  90                  95

Ile Ser Asp Asp Leu Gly Gln Thr Thr Leu Glu Val Phe Lys Glu Asp
                      100                 105                 110

Gly Lys Thr Leu Val Ser Lys Lys Val Thr Ser Lys Asp Lys Ser Ser
                      115                 120                 125

Thr Glu Glu Lys Phe Asn Glu Lys Gly Glu Val Ser Glu Lys Ile Ile
                      130                 135                 140

Thr Arg Ala Asp Gly Thr Arg Leu Glu Tyr Thr Gly Ile Lys Ser Asp
      145                 150                 155                 160

Gly Ser Gly Lys Ala Lys Glu Val Leu Lys Gly Tyr Asp Leu Lys Gly
                      165                 170                 175

Glu Leu Ser Ser Glu Lys Thr Thr Leu Val Val Lys Glu Gly Thr Val
                      180                 185                 190

Thr Leu Ser Lys Asn Ile Ser Lys Ser Gly Glu Val Ser Val Glu Leu
                      195                 200                 205
```

```
Asn Asp Thr Asp Ser Ser Ala Ala Thr Lys Lys Thr Ala Ala Trp Asn
            210                 215                 220

Ser Gly Thr Ser Thr Leu Thr Ile Thr Val Asn Ser Lys Lys Thr Lys
225                 230                 235                 240

Asp Leu Val Phe Thr Lys Glu Asn Thr Ile Thr Val Gln Gln Tyr Asp
                245                 250                 255

Ser Asn Gly Thr Lys Leu Glu Gly Ser Ala Val Glu Ile Thr Lys Leu
            260                 265                 270

Asp Glu Ile Lys Asn Ala Leu Lys Gly Ser Glu Ser Gln Val Arg Gln
        275                 280                 285

Gln Phe Ser Lys Asp Ile Glu Lys Leu Leu Asn Glu Val Asn Lys
    290                 295                 300

Glu Met Gln Ser Ser Asn Leu Tyr Met Ser Met Ser Ser Trp Ser Tyr
305                 310                 315                 320

Thr His Ser Leu Asp Gly Ala Gly Leu Phe Leu Phe Asp His Ala Ala
                325                 330                 335

Glu Glu Tyr Glu His Ala Lys Lys Leu Ile Ile Phe Leu Asn Glu Asn
            340                 345                 350

Asn Val Pro Val Gln Leu Thr Ser Ile Ser Ala Pro Glu His Lys Phe
        355                 360                 365

Glu Gly Leu Thr Gln Ile Phe Gln Lys Ala Tyr Glu His Glu Gln His
    370                 375                 380

Ile Ser Glu Ser Ile Asn Asn Ile Val Asp His Ala Ile Lys Cys Lys
385                 390                 395                 400

Asp His Ala Thr Phe Asn Phe Leu Gln Trp Tyr Val Ala Glu Gln His
                405                 410                 415

Glu Glu Glu Val Leu Phe Lys Asp Ile Leu Asp Lys Ile Glu Leu Ile
            420                 425                 430

Gly Asn Glu Asn His Gly Leu Tyr Leu Ala Asp Gln Tyr Val Lys Gly
        435                 440                 445

Ile Ala Lys Ser Arg Lys Ser
    450                 455

<210> SEQ ID NO 59
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Met Asp
            20                  25                  30

Glu Lys Asn Ser Val Ser Val Asp Leu Pro Gly Glu Met Lys Val Leu
        35                  40                  45

Val Ser Lys Glu Lys Asn Lys Asp Gly Lys Tyr Asp Leu Ile Ala Thr
    50                  55                  60

Val Asp Lys Leu Glu Leu Lys Gly Thr Ser Asp Lys Asn Gln Gly Ser
65                  70                  75                  80

Gly Val Leu Glu Gly Val Lys Ala Asp Lys Ser Lys Val Lys Leu Thr
                85                  90                  95
```

```
Ile Ser Asp Asp Leu Gly Gln Thr Thr Leu Glu Val Phe Lys Glu Asp
                100                 105                 110

Gly Lys Thr Leu Val Ser Lys Val Thr Ser Lys Asp Lys Ser Ser
        115                 120                 125

Thr Glu Glu Lys Phe Asn Glu Lys Gly Glu Val Ser Glu Lys Ile Ile
    130                 135                 140

Thr Arg Ala Asp Gly Thr Arg Leu Glu Tyr Thr Gly Ile Lys Ser Asp
145                 150                 155                 160

Gly Ser Gly Lys Ala Lys Glu Val Leu Lys Gly Tyr Asp Leu Lys Gly
                165                 170                 175

Glu Leu Ser Ser Glu Lys Thr Thr Leu Val Val Lys Glu Gly Thr Val
            180                 185                 190

Thr Leu Ser Lys Gln Ile Ser Lys Ser Gly Glu Val Ser Val Glu Leu
        195                 200                 205

Gln Asp Thr Asp Ser Ser Ala Ala Thr Lys Lys Thr Ala Ala Trp Asn
    210                 215                 220

Ser Gly Thr Ser Thr Leu Thr Ile Thr Val Asn Ser Lys Lys Thr Lys
225                 230                 235                 240

Asp Leu Val Phe Thr Lys Glu Asn Thr Ile Thr Val Gln Gln Tyr Asp
                245                 250                 255

Ser Gln Gly Thr Lys Leu Glu Gly Ser Ala Val Glu Ile Thr Lys Leu
            260                 265                 270

Asp Glu Ile Lys Asn Ala Leu Lys Gly Ser Glu Ser Gln Val Arg Gln
        275                 280                 285

Gln Phe Ser Lys Asp Ile Glu Lys Leu Leu Asn Glu Gln Val Asn Lys
    290                 295                 300

Glu Met Gln Ser Ser Asn Leu Tyr Met Ser Met Ser Ser Trp Ser Tyr
305                 310                 315                 320

Thr His Ser Leu Asp Gly Ala Gly Leu Phe Leu Phe Asp His Ala Ala
                325                 330                 335

Glu Glu Tyr Glu His Ala Lys Lys Leu Ile Ile Phe Leu Asn Glu Asn
            340                 345                 350

Asn Val Pro Val Gln Leu Thr Ser Ile Ser Ala Pro Glu His Lys Phe
        355                 360                 365

Glu Gly Leu Thr Gln Ile Phe Gln Lys Ala Tyr Glu His Glu Gln His
    370                 375                 380

Ile Ser Glu Ser Ile Asn Asn Ile Val Asp His Ala Ile Lys Cys Lys
385                 390                 395                 400

Asp His Ala Thr Phe Asn Phe Leu Gln Trp Tyr Val Ala Glu Gln His
                405                 410                 415

Glu Glu Glu Val Leu Phe Lys Asp Ile Leu Asp Lys Ile Glu Leu Ile
            420                 425                 430

Gly Asn Glu Asn His Gly Leu Tyr Leu Ala Asp Gln Tyr Val Lys Gly
        435                 440                 445

Ile Ala Lys Ser Arg Lys Ser
    450                 455

<210> SEQ ID NO 60
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

```
<400> SEQUENCE: 60

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Met Asp
            20                  25                  30

Glu Lys Asn Ser Val Ser Val Asp Leu Pro Gly Glu Met Lys Val Leu
        35                  40                  45

Val Ser Lys Glu Lys Asn Lys Asp Gly Lys Tyr Asp Leu Ile Ala Thr
    50                  55                  60

Val Asp Lys Leu Glu Leu Lys Gly Thr Ser Asp Lys Asn Gln Gly Ser
65                  70                  75                  80

Gly Val Leu Glu Gly Val Lys Ala Asp Lys Ser Lys Val Lys Leu Thr
                85                  90                  95

Ile Ser Asp Asp Leu Gly Gln Thr Thr Leu Glu Val Phe Lys Glu Asp
                100                 105                 110

Gly Lys Thr Leu Val Ser Lys Lys Val Thr Ser Lys Asp Lys Ser Ser
            115                 120                 125

Thr Glu Glu Lys Phe Asn Glu Lys Gly Glu Val Ser Glu Lys Ile Ile
130                 135                 140

Thr Arg Ala Asp Gly Thr Arg Leu Glu Tyr Thr Gly Ile Lys Ser Asp
145                 150                 155                 160

Gly Ser Gly Lys Ala Lys Glu Val Leu Lys Gly Tyr Thr Leu Glu Gly
                165                 170                 175

Gln Leu Ser Asp Glu Lys Thr Thr Leu Val Val Lys Glu Gly Thr Val
            180                 185                 190

Thr Leu Ser Lys Gln Ile Ser Lys Ser Gly Glu Val Ser Val Glu Leu
            195                 200                 205

Gln Asp Thr Asp Ser Ser Ala Ala Thr Lys Lys Thr Ala Ala Trp Asn
        210                 215                 220

Ser Gly Thr Ser Thr Leu Thr Ile Thr Val Asn Ser Lys Lys Thr Lys
225                 230                 235                 240

Asp Leu Val Phe Thr Lys Glu Asn Thr Ile Thr Val Gln Gln Tyr Asp
                245                 250                 255

Ser Gln Gly Thr Lys Leu Glu Gly Ser Ala Val Glu Ile Thr Lys Leu
            260                 265                 270

Asp Glu Ile Lys Asn Ala Leu Lys Gly Gly Ser Glu Ser Gln Val
            275                 280                 285

Arg Gln Gln Phe Ser Lys Asp Ile Glu Lys Leu Leu Asn Glu Gln Val
        290                 295                 300

Asn Lys Glu Met Gln Ser Ser Asn Leu Tyr Met Ser Met Ser Ser Trp
305                 310                 315                 320

Ser Tyr Thr His Ser Leu Asp Gly Ala Gly Leu Phe Leu Phe Asp His
                325                 330                 335

Ala Ala Glu Glu Tyr Glu His Ala Lys Lys Leu Ile Ile Phe Leu Asn
            340                 345                 350

Glu Asn Asn Val Pro Val Gln Leu Thr Ser Ile Ser Ala Pro Glu His
            355                 360                 365

Lys Phe Glu Gly Leu Thr Gln Ile Phe Gln Lys Ala Tyr Glu His Glu
    370                 375                 380

Gln His Ile Ser Glu Ser Ile Asn Asn Ile Val Asp His Ala Ile Lys
385                 390                 395                 400

Cys Lys Asp His Ala Thr Phe Asn Phe Leu Gln Trp Tyr Val Ala Glu
                405                 410                 415
```

-continued

```
Gln His Glu Glu Val Leu Phe Lys Asp Ile Leu Asp Lys Ile Glu
            420                 425                 430

Leu Ile Gly Asn Glu Asn His Gly Leu Tyr Leu Ala Asp Gln Tyr Val
            435                 440                 445

Lys Gly Ile Ala Lys Ser Arg Lys Ser
        450                 455

<210> SEQ ID NO 61
<211> LENGTH: 461
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Met Asp
            20                  25                  30

Glu Lys Asn Ser Val Ser Val Asp Leu Pro Gly Glu Met Lys Val Leu
            35                  40                  45

Val Ser Lys Glu Lys Asn Lys Asp Gly Lys Tyr Asp Leu Ile Ala Thr
50                  55                  60

Val Asp Lys Leu Glu Leu Lys Gly Thr Ser Asp Lys Asn Gln Gly Ser
65                  70                  75                  80

Gly Val Leu Glu Gly Val Lys Ala Asp Lys Ser Lys Val Lys Leu Thr
            85                  90                  95

Ile Ser Asp Asp Leu Gly Gln Thr Thr Leu Glu Val Phe Lys Glu Asp
            100                 105                 110

Gly Lys Thr Leu Val Ser Lys Lys Val Thr Ser Lys Asp Lys Ser Ser
            115                 120                 125

Thr Glu Glu Lys Phe Asn Glu Lys Gly Glu Val Ser Glu Lys Ile Ile
            130                 135                 140

Thr Arg Ala Asp Gly Thr Arg Leu Glu Tyr Thr Gly Ile Lys Ser Asp
145                 150                 155                 160

Gly Ser Gly Lys Ala Lys Glu Val Leu Lys Gly Tyr Thr Leu Glu Gly
            165                 170                 175

Gln Leu Ser Asp Glu Lys Thr Thr Leu Val Val Lys Glu Gly Thr Val
            180                 185                 190

Thr Leu Ser Lys Gln Ile Ser Lys Ser Gly Glu Val Ser Val Glu Leu
            195                 200                 205

Gln Asp Thr Asp Ser Ser Ala Ala Thr Lys Lys Thr Ala Ala Trp Asn
            210                 215                 220

Ser Gly Thr Ser Thr Leu Thr Ile Thr Val Asn Ser Lys Lys Thr Lys
225                 230                 235                 240

Asp Leu Val Phe Thr Lys Glu Asn Thr Ile Thr Val Gln Gln Tyr Asp
                245                 250                 255

Ser Gln Gly Thr Lys Leu Glu Gly Ser Ala Val Glu Ile Thr Lys Leu
            260                 265                 270

Asp Glu Ile Lys Asn Ala Leu Lys Gly Gly Ser Gly Gly Gly Ser
            275                 280                 285

Glu Ser Gln Val Arg Gln Gln Phe Ser Lys Asp Ile Glu Lys Leu Leu
            290                 295                 300
```

```
Asn Glu Gln Val Asn Lys Glu Met Gln Ser Ser Asn Leu Tyr Met Ser
305                 310                 315                 320

Met Ser Ser Trp Ser Tyr Thr His Ser Leu Asp Gly Ala Gly Leu Phe
            325                 330                 335

Leu Phe Asp His Ala Ala Glu Glu Tyr Glu His Ala Lys Lys Leu Ile
        340                 345                 350

Ile Phe Leu Asn Glu Asn Asn Val Pro Val Gln Leu Thr Ser Ile Ser
    355                 360                 365

Ala Pro Glu His Lys Phe Glu Gly Leu Thr Gln Ile Phe Gln Lys Ala
370                 375                 380

Tyr Glu His Glu Gln His Ile Ser Glu Ser Ile Asn Asn Ile Val Asp
385                 390                 395                 400

His Ala Ile Lys Cys Lys Asp His Ala Thr Phe Asn Phe Leu Gln Trp
            405                 410                 415

Tyr Val Ala Glu Gln His Glu Glu Val Leu Phe Lys Asp Ile Leu
        420                 425                 430

Asp Lys Ile Glu Leu Ile Gly Asn Glu Asn His Gly Leu Tyr Leu Ala
            435                 440                 445

Asp Gln Tyr Val Lys Gly Ile Ala Lys Ser Arg Lys Ser
450                 455                 460

<210> SEQ ID NO 62
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Met Asp
            20                  25                  30

Glu Lys Asn Ser Val Ser Val Asp Leu Pro Gly Glu Met Lys Val Leu
        35                  40                  45

Val Ser Lys Glu Lys Asn Lys Asp Gly Lys Tyr Asp Leu Ile Ala Thr
50                  55                  60

Val Asp Lys Leu Glu Leu Lys Gly Thr Ser Asp Lys Asn Gln Gly Ser
65                  70                  75                  80

Gly Val Leu Glu Gly Val Lys Ala Asp Lys Ser Lys Val Lys Leu Thr
            85                  90                  95

Ile Ser Asp Asp Leu Gly Gln Thr Thr Leu Glu Val Phe Lys Glu Asp
        100                 105                 110

Gly Lys Thr Leu Val Ser Lys Lys Val Thr Ser Lys Asp Lys Ser Ser
    115                 120                 125

Thr Glu Glu Lys Phe Asn Glu Lys Gly Glu Val Ser Glu Lys Ile Ile
130                 135                 140

Thr Arg Ala Asp Gly Thr Arg Leu Glu Tyr Thr Gly Ile Lys Ser Asp
145                 150                 155                 160

Gly Ser Gly Lys Ala Lys Glu Val Leu Lys Gly Tyr Thr Leu Glu Gly
            165                 170                 175

Gln Leu Ser Asp Glu Lys Thr Thr Leu Val Val Lys Glu Gly Thr Val
        180                 185                 190

Thr Leu Ser Lys Gln Ile Ser Lys Ser Gly Glu Val Ser Val Glu Leu
```

```
                    195                 200                 205

Gln Asp Thr Asp Ser Ser Ala Ala Thr Lys Lys Thr Ala Ala Trp Asn
    210                 215                 220

Ser Gly Thr Ser Thr Leu Thr Ile Thr Val Asn Ser Lys Lys Thr Lys
225                 230                 235                 240

Asp Leu Val Phe Thr Lys Glu Asn Thr Thr Val Gln Gln Tyr Asp
                245                 250                 255

Ser Gln Gly Thr Lys Leu Glu Gly Ser Ala Val Glu Ile Thr Lys Leu
                260                 265                 270

Asp Glu Ile Lys Asn Ala Leu Lys Gly Gly Ser Gly Gly Gly Ser
                275                 280                 285

Gly Gly Gly Ser Gly Gly Ser Gly Gly Gly Ser Glu Ser Gln Val
    290                 295                 300

Arg Gln Gln Phe Ser Lys Asp Ile Glu Lys Leu Leu Asn Glu Gln Val
305                 310                 315                 320

Asn Lys Glu Met Gln Ser Ser Asn Leu Tyr Met Ser Met Ser Ser Trp
                325                 330                 335

Ser Tyr Thr His Ser Leu Asp Gly Ala Gly Leu Phe Leu Phe Asp His
                340                 345                 350

Ala Ala Glu Glu Tyr Glu His Ala Lys Lys Leu Ile Ile Phe Leu Asn
                355                 360                 365

Glu Asn Asn Val Pro Val Gln Leu Thr Ser Ile Ser Ala Pro Glu His
            370                 375                 380

Lys Phe Glu Gly Leu Thr Gln Ile Phe Gln Lys Ala Tyr Glu His Glu
385                 390                 395                 400

Gln His Ile Ser Glu Ser Ile Asn Asn Ile Val Asp His Ala Ile Lys
                405                 410                 415

Cys Lys Asp His Ala Thr Phe Asn Phe Leu Gln Trp Tyr Val Ala Glu
                420                 425                 430

Gln His Glu Glu Glu Val Leu Phe Lys Asp Ile Leu Asp Lys Ile Glu
                435                 440                 445

Leu Ile Gly Asn Glu Asn His Gly Leu Tyr Leu Ala Asp Gln Tyr Val
            450                 455                 460

Lys Gly Ile Ala Lys Ser Arg Lys Ser
465                 470

<210> SEQ ID NO 63
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Met Asp
            20                  25                  30

Glu Lys Asn Ser Val Ser Val Asp Leu Pro Gly Glu Met Lys Val Leu
            35                  40                  45

Val Ser Lys Glu Lys Asn Lys Asp Gly Lys Tyr Asp Leu Ile Ala Thr
        50                  55                  60

Val Asp Lys Leu Glu Leu Lys Gly Thr Ser Asp Lys Asn Asn Gly Ala
65                  70                  75                  80
```

Gly Val Leu Glu Gly Val Lys Ala Asp Lys Ser Lys Val Lys Leu Thr
            85                  90                  95

Ile Ser Asp Asp Leu Gly Gln Thr Thr Leu Glu Val Phe Lys Glu Asp
        100                 105                 110

Gly Lys Thr Leu Val Ser Lys Val Thr Ser Lys Asp Lys Ser Ser
    115                 120                 125

Thr Glu Glu Lys Phe Asn Glu Lys Gly Glu Val Ser Glu Lys Ile Ile
130                 135                 140

Thr Arg Ala Asp Gly Thr Arg Leu Glu Tyr Thr Gly Ile Lys Ser Asp
145                 150                 155                 160

Gly Ser Gly Lys Ala Lys Glu Val Leu Lys Gly Tyr Thr Leu Glu Gly
                165                 170                 175

Gln Leu Ser Asp Glu Lys Thr Thr Leu Val Val Lys Glu Gly Thr Val
            180                 185                 190

Thr Leu Ser Lys Asn Ile Ala Lys Ser Gly Glu Val Ser Val Glu Leu
        195                 200                 205

Asn Asp Ala Asp Ser Ser Ala Thr Lys Lys Thr Ala Ala Trp Asn
210                 215                 220

Ser Gly Thr Ser Thr Leu Thr Ile Thr Val Asn Ser Lys Lys Thr Lys
225                 230                 235                 240

Asp Leu Val Phe Thr Lys Glu Asn Thr Ile Thr Val Gln Gln Tyr Asp
                245                 250                 255

Ser Asn Gly Ala Lys Leu Glu Gly Ser Ala Val Glu Ile Thr Lys Leu
            260                 265                 270

Asp Glu Ile Lys Asn Ala Leu Lys Gly Ser Glu Ser Gln Val Arg Gln
        275                 280                 285

Gln Phe Ser Lys Asp Ile Glu Lys Leu Leu Asn Glu Gln Val Asn Lys
290                 295                 300

Glu Met Gln Ser Ser Asn Leu Tyr Met Ser Met Ser Ser Trp Ser Tyr
305                 310                 315                 320

Thr His Ser Leu Asp Gly Ala Gly Leu Phe Leu Phe Asp His Ala Ala
                325                 330                 335

Glu Glu Tyr Glu His Ala Lys Lys Leu Ile Ile Phe Leu Asn Glu Asn
            340                 345                 350

Asn Val Pro Val Gln Leu Thr Ser Ile Ser Ala Pro Glu His Lys Phe
        355                 360                 365

Glu Gly Leu Thr Gln Ile Phe Gln Lys Ala Tyr Glu His Glu Gln His
370                 375                 380

Ile Ser Glu Ser Ile Asn Asn Ile Val Asp His Ala Ile Lys Cys Lys
385                 390                 395                 400

Asp His Ala Thr Phe Asn Phe Leu Gln Trp Tyr Val Ala Glu Gln His
                405                 410                 415

Glu Glu Glu Val Leu Phe Lys Asp Ile Leu Asp Lys Ile Glu Leu Ile
            420                 425                 430

Gly Asn Glu Asn His Gly Leu Tyr Leu Ala Asp Gln Tyr Val Lys Gly
        435                 440                 445

Ile Ala Lys Ser Arg Lys Ser
    450                 455

<210> SEQ ID NO 64
<211> LENGTH: 455
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 64

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Met Asp
            20                  25                  30

Glu Lys Asn Ser Val Ser Val Asp Leu Pro Gly Glu Met Lys Val Leu
        35                  40                  45

Val Ser Lys Glu Lys Asn Lys Asp Gly Lys Tyr Asp Leu Ile Ala Thr
50                  55                  60

Val Asp Lys Leu Glu Leu Lys Gly Thr Ser Asp Lys Asn Asn Gly Ser
65                  70                  75                  80

Gly Val Leu Glu Gly Val Lys Ala Asp Lys Ser Lys Val Lys Leu Thr
                85                  90                  95

Ile Ser Asp Asp Leu Gly Gln Thr Thr Leu Glu Val Phe Lys Glu Asp
            100                 105                 110

Gly Lys Thr Leu Val Ser Lys Lys Val Thr Ser Lys Asp Lys Ser Ser
        115                 120                 125

Thr Glu Glu Lys Phe Asn Glu Lys Gly Glu Val Ser Glu Lys Ile Ile
130                 135                 140

Thr Arg Ala Asp Gly Thr Arg Leu Glu Tyr Thr Gly Ile Lys Ser Asp
145                 150                 155                 160

Gly Ser Gly Lys Ala Lys Glu Val Leu Lys Gly Tyr Val Leu Glu Gly
                165                 170                 175

Thr Leu Thr Ala Glu Lys Thr Thr Leu Val Val Lys Glu Gly Thr Val
            180                 185                 190

Thr Leu Ser Lys Asn Ile Ser Lys Ser Gly Glu Val Ser Val Glu Leu
        195                 200                 205

Asn Asp Thr Asp Ser Ser Ala Ala Thr Lys Lys Thr Ala Ala Trp Asn
210                 215                 220

Ser Gly Thr Ser Thr Leu Thr Ile Thr Val Asn Ser Lys Lys Thr Lys
225                 230                 235                 240

Asp Leu Val Phe Thr Lys Glu Asn Thr Ile Thr Val Gln Gln Tyr Asp
                245                 250                 255

Ser Asn Gly Thr Lys Leu Glu Gly Ser Ala Val Glu Ile Thr Lys Leu
            260                 265                 270

Asp Glu Ile Lys Asn Ala Leu Lys Gly Ser Glu Ser Gln Val Arg Gln
        275                 280                 285

Gln Phe Ser Lys Asp Ile Glu Lys Leu Leu Asn Glu Gln Val Asn Lys
290                 295                 300

Glu Met Gln Ser Ser Asn Leu Tyr Met Ser Met Ser Ser Trp Ser Tyr
305                 310                 315                 320

Thr His Ser Leu Asp Gly Ala Gly Leu Phe Leu Phe Asp His Ala Ala
                325                 330                 335

Glu Glu Tyr Glu His Ala Lys Lys Leu Ile Ile Phe Leu Asn Glu Asn
            340                 345                 350

Asn Val Pro Val Gln Leu Thr Ser Ile Ser Ala Pro Glu His Lys Phe
        355                 360                 365

Glu Gly Leu Thr Gln Ile Phe Gln Lys Ala Tyr Glu His Glu Gln His
370                 375                 380

Ile Ser Glu Ser Ile Asn Asn Ile Val Asp His Ala Ile Lys Cys Lys
```

```
                385                 390                 395                 400

Asp His Ala Thr Phe Asn Phe Leu Gln Trp Tyr Val Ala Glu Gln His
                    405                 410                 415

Glu Glu Glu Val Leu Phe Lys Asp Ile Leu Asp Lys Ile Glu Leu Ile
                420                 425                 430

Gly Asn Glu Asn His Gly Leu Tyr Leu Ala Asp Gln Tyr Val Lys Gly
            435                 440                 445

Ile Ala Lys Ser Arg Lys Ser
        450                 455

<210> SEQ ID NO 65
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Met Asp
            20                  25                  30

Glu Lys Asn Ser Ala Ser Val Asp Leu Pro Gly Glu Met Lys Val Leu
        35                  40                  45

Val Ser Lys Glu Lys Asp Lys Asp Gly Lys Tyr Ser Leu Lys Ala Thr
    50                  55                  60

Val Asp Lys Ile Glu Leu Lys Gly Thr Ser Asp Lys Asp Asn Gly Ser
65                  70                  75                  80

Gly Val Leu Glu Gly Thr Lys Asp Lys Ser Lys Ala Lys Leu Thr
                85                  90                  95

Ile Ala Asp Asp Leu Ser Lys Thr Thr Phe Glu Leu Phe Lys Glu Asp
            100                 105                 110

Gly Lys Thr Leu Val Ser Arg Lys Val Ser Ser Lys Asp Lys Thr Ser
        115                 120                 125

Thr Asp Glu Met Phe Asn Glu Lys Gly Glu Leu Ser Ala Lys Thr Met
    130                 135                 140

Thr Arg Glu Asn Gly Thr Lys Leu Glu Tyr Thr Glu Met Lys Ser Asp
145                 150                 155                 160

Gly Thr Gly Lys Ala Lys Glu Val Leu Lys Asn Phe Thr Leu Glu Gly
                165                 170                 175

Lys Val Ala Asn Asp Lys Val Thr Leu Glu Val Lys Glu Gly Thr Val
            180                 185                 190

Thr Leu Ser Lys Glu Ile Ala Lys Ser Gly Val Thr Val Ala Leu
        195                 200                 205

Asn Asp Thr Asn Thr Thr Gln Ala Thr Lys Thr Gly Ala Trp Asp
    210                 215                 220

Ser Lys Thr Ser Thr Leu Thr Ile Ser Val Asn Ser Lys Lys Thr Thr
225                 230                 235                 240

Gln Leu Val Phe Thr Lys Gln Asp Thr Ile Thr Val Gln Lys Tyr Asp
                245                 250                 255

Ser Ala Gly Thr Asn Leu Glu Gly Thr Ala Val Glu Ile Lys Thr Leu
            260                 265                 270

Asp Glu Leu Lys Asn Ala Leu Lys Gly Ser Glu Ser Gln Val Arg Gln
        275                 280                 285
```

```
Gln Phe Ser Lys Asp Ile Glu Lys Leu Leu Asn Glu Gln Val Asn Lys
    290                 295                 300

Glu Met Gln Ser Ser Asn Leu Tyr Met Ser Met Ser Ser Trp Ser Tyr
305                 310                 315                 320

Thr His Ser Leu Asp Gly Ala Gly Leu Phe Leu Phe Asp His Ala Ala
                325                 330                 335

Glu Glu Tyr Glu His Ala Lys Lys Leu Ile Ile Phe Leu Asn Glu Asn
            340                 345                 350

Asn Val Pro Val Gln Leu Thr Ser Ile Ser Ala Pro Glu His Lys Phe
        355                 360                 365

Glu Gly Leu Thr Gln Ile Phe Gln Lys Ala Tyr Glu His Glu Gln His
    370                 375                 380

Ile Ser Glu Ser Ile Asn Asn Ile Val Asp His Ala Ile Lys Cys Lys
385                 390                 395                 400

Asp His Ala Thr Phe Asn Phe Leu Gln Trp Tyr Val Ala Glu Gln His
                405                 410                 415

Glu Glu Glu Val Leu Phe Lys Asp Ile Leu Asp Lys Ile Glu Leu Ile
            420                 425                 430

Gly Asn Glu Asn His Gly Leu Tyr Leu Ala Asp Gln Tyr Val Lys Gly
        435                 440                 445

Ile Ala Lys Ser Arg Lys Ser
    450                 455

<210> SEQ ID NO 66
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Met Asp
            20                  25                  30

Glu Lys Asn Ser Ala Ser Val Asp Leu Pro Gly Glu Met Lys Val Leu
        35                  40                  45

Val Ser Lys Glu Lys Asp Lys Asp Gly Lys Tyr Ser Leu Lys Ala Thr
    50                  55                  60

Val Asp Lys Ile Glu Leu Lys Gly Thr Ser Asp Lys Asp Gln Gly Ser
65                  70                  75                  80

Gly Val Leu Glu Gly Thr Lys Asp Asp Lys Ser Lys Ala Lys Leu Thr
            85                  90                  95

Ile Ala Asp Asp Leu Ser Lys Thr Thr Phe Glu Leu Phe Lys Glu Asp
        100                 105                 110

Gly Lys Thr Leu Val Ser Arg Lys Val Ser Ser Lys Asp Lys Thr Ser
    115                 120                 125

Thr Asp Glu Met Phe Asn Glu Lys Gly Glu Leu Ser Ala Lys Thr Met
130                 135                 140

Thr Arg Glu Gln Gly Thr Lys Leu Glu Tyr Thr Glu Met Lys Ser Asp
145                 150                 155                 160

Gly Thr Gly Lys Ala Lys Glu Val Leu Lys Gln Phe Thr Leu Glu Gly
            165                 170                 175
```

```
Lys Val Ala Asn Asp Lys Val Thr Leu Glu Val Lys Glu Gly Thr Val
                180                 185                 190

Thr Leu Ser Lys Glu Ile Ala Lys Ser Gly Glu Val Thr Val Ala Leu
            195                 200                 205

Gln Asp Thr Gln Thr Thr Gln Ala Thr Lys Lys Thr Gly Ala Trp Asp
        210                 215                 220

Ser Lys Thr Ser Thr Leu Thr Ile Ser Val Asn Ser Lys Lys Thr Thr
225                 230                 235                 240

Gln Leu Val Phe Thr Lys Gln Asp Thr Ile Thr Val Gln Lys Tyr Asp
                245                 250                 255

Ser Ala Gly Thr Asn Leu Glu Gly Thr Ala Val Glu Ile Lys Thr Leu
            260                 265                 270

Asp Glu Leu Lys Asn Ala Leu Lys Gly Ser Glu Ser Gln Val Arg Gln
        275                 280                 285

Gln Phe Ser Lys Asp Ile Glu Lys Leu Leu Asn Glu Gln Val Asn Lys
    290                 295                 300

Glu Met Gln Ser Ser Asn Leu Tyr Met Ser Met Ser Ser Trp Ser Tyr
305                 310                 315                 320

Thr His Ser Leu Asp Gly Ala Gly Leu Phe Leu Phe Asp His Ala Ala
                325                 330                 335

Glu Glu Tyr Glu His Ala Lys Lys Leu Ile Ile Phe Leu Asn Glu Asn
            340                 345                 350

Asn Val Pro Val Gln Leu Thr Ser Ile Ser Ala Pro Glu His Lys Phe
        355                 360                 365

Glu Gly Leu Thr Gln Ile Phe Gln Lys Ala Tyr Glu His Glu Gln His
    370                 375                 380

Ile Ser Glu Ser Ile Asn Asn Ile Val Asp His Ala Ile Lys Cys Lys
385                 390                 395                 400

Asp His Ala Thr Phe Asn Phe Leu Gln Trp Tyr Val Ala Glu Gln His
                405                 410                 415

Glu Glu Glu Val Leu Phe Lys Asp Ile Leu Asp Lys Ile Glu Leu Ile
            420                 425                 430

Gly Asn Glu Asn His Gly Leu Tyr Leu Ala Asp Gln Tyr Val Lys Gly
        435                 440                 445

Ile Ala Lys Ser Arg Lys Ser
    450                 455

<210> SEQ ID NO 67
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Met Asp
                20                  25                  30

Glu Lys Asn Ser Val Ser Val Asp Leu Pro Gly Gly Met Lys Val Leu
            35                  40                  45

Val Ser Lys Glu Lys Asp Lys Asp Gly Lys Tyr Ser Leu Met Ala Thr
        50                  55                  60

Val Glu Lys Leu Glu Leu Lys Gly Thr Ser Asp Lys Ser Asn Gly Ser
```

```
                65                  70                  75                  80
Gly Val Leu Glu Gly Glu Lys Ala Asp Lys Ser Lys Ala Lys Leu Thr
                    85                  90                  95
Ile Ser Gln Asp Leu Asn Gln Thr Thr Phe Glu Ile Phe Lys Glu Asp
                    100                 105                 110
Gly Lys Thr Leu Val Ser Arg Lys Val Asn Ser Lys Asp Lys Ser Ser
                    115                 120                 125
Thr Glu Glu Lys Phe Asn Asp Lys Gly Lys Leu Ser Glu Lys Val Val
                    130                 135                 140
Thr Arg Ala Asn Gly Thr Arg Leu Glu Tyr Thr Glu Ile Lys Asn Asp
145                 150                 155                 160
Gly Ser Gly Lys Ala Lys Glu Val Leu Lys Gly Phe Ala Leu Glu Gly
                    165                 170                 175
Thr Leu Thr Asp Gly Gly Glu Thr Lys Leu Thr Val Thr Glu Gly Thr
                    180                 185                 190
Val Thr Leu Ser Lys Asn Ile Ser Lys Ser Gly Glu Ile Thr Val Ala
                    195                 200                 205
Leu Asn Asp Thr Glu Thr Thr Pro Ala Asp Lys Lys Thr Gly Glu Trp
                    210                 215                 220
Lys Ser Asp Thr Ser Thr Leu Thr Ile Ser Lys Asn Ser Gln Lys Pro
225                 230                 235                 240
Lys Gln Leu Val Phe Thr Lys Glu Asn Thr Ile Thr Val Gln Asn Tyr
                    245                 250                 255
Asn Arg Ala Gly Asn Ala Leu Glu Gly Ser Pro Ala Glu Ile Lys Asp
                    260                 265                 270
Leu Ala Glu Leu Lys Ala Ala Leu Lys Gly Ser Glu Ser Gln Val Arg
                    275                 280                 285
Gln Gln Phe Ser Lys Asp Ile Glu Lys Leu Leu Asn Glu Gln Val Asn
                    290                 295                 300
Lys Glu Met Gln Ser Ser Asn Leu Tyr Met Ser Met Ser Ser Trp Ser
305                 310                 315                 320
Tyr Thr His Ser Leu Asp Gly Ala Gly Leu Phe Leu Phe Asp His Ala
                    325                 330                 335
Ala Glu Glu Tyr Glu His Ala Lys Lys Leu Ile Ile Phe Leu Asn Glu
                    340                 345                 350
Asn Asn Val Pro Val Gln Leu Thr Ser Ile Ser Ala Pro Glu His Lys
                    355                 360                 365
Phe Glu Gly Leu Thr Gln Ile Phe Gln Lys Ala Tyr Glu His Glu Gln
                    370                 375                 380
His Ile Ser Glu Ser Ile Asn Asn Ile Val Asp His Ala Ile Lys Cys
385                 390                 395                 400
Lys Asp His Ala Thr Phe Asn Phe Leu Gln Trp Tyr Val Ala Glu Gln
                    405                 410                 415
His Glu Glu Glu Val Leu Phe Lys Asp Ile Leu Asp Lys Ile Glu Leu
                    420                 425                 430
Ile Gly Asn Glu Asn His Gly Leu Tyr Leu Ala Asp Gln Tyr Val Lys
                    435                 440                 445
Gly Ile Ala Lys Ser Arg Lys Ser
    450                 455

<210> SEQ ID NO 68
<211> LENGTH: 456
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic polypeptide"

<400> SEQUENCE: 68

```
Met Asp Ser Lys Gly Ser Ser Gln Lys Gly Ser Arg Leu Leu Leu
1               5                   10                  15

Leu Val Val Ser Asn Leu Leu Leu Pro Gln Gly Val Leu Ala Met Asp
                20                  25                  30

Glu Lys Asn Ser Val Ser Val Asp Leu Pro Gly Gly Met Lys Val Leu
            35                  40                  45

Val Ser Lys Glu Lys Asp Lys Asp Gly Lys Tyr Ser Leu Met Ala Thr
50                  55                  60

Val Glu Lys Leu Glu Leu Lys Gly Thr Ser Asp Lys Ser Gln Gly Ser
65                  70                  75                  80

Gly Val Leu Glu Gly Glu Lys Ala Asp Lys Ser Lys Ala Lys Leu Thr
                85                  90                  95

Ile Ser Gln Asp Leu Gln Gln Thr Thr Phe Glu Ile Phe Lys Glu Asp
            100                 105                 110

Gly Lys Thr Leu Val Ser Arg Lys Val Asn Ser Lys Asp Lys Ser Ser
        115                 120                 125

Thr Glu Glu Lys Phe Asn Asp Lys Gly Lys Leu Ser Glu Lys Val Val
130                 135                 140

Thr Arg Ala Gln Gly Thr Arg Leu Glu Tyr Thr Glu Ile Lys Asn Asp
145                 150                 155                 160

Gly Ser Gly Lys Ala Lys Glu Val Leu Lys Gly Phe Ala Leu Glu Gly
                165                 170                 175

Thr Leu Thr Asp Gly Gly Glu Thr Lys Leu Thr Val Thr Glu Gly Thr
            180                 185                 190

Val Thr Leu Ser Lys Gln Ile Ser Lys Ser Gly Glu Ile Thr Val Ala
        195                 200                 205

Leu Gln Asp Thr Glu Thr Thr Pro Ala Asp Lys Lys Thr Gly Glu Trp
210                 215                 220

Lys Ser Asp Thr Ser Thr Leu Thr Ile Ser Lys Asn Ser Gln Lys Pro
225                 230                 235                 240

Lys Gln Leu Val Phe Thr Lys Glu Asn Thr Ile Thr Val Gln Asn Tyr
                245                 250                 255

Asn Arg Ala Gly Asn Ala Leu Glu Gly Ser Pro Ala Glu Ile Lys Asp
            260                 265                 270

Leu Ala Glu Leu Lys Ala Ala Leu Lys Gly Ser Glu Ser Gln Val Arg
        275                 280                 285

Gln Gln Phe Ser Lys Asp Ile Glu Lys Leu Leu Asn Glu Gln Val Asn
290                 295                 300

Lys Glu Met Gln Ser Ser Asn Leu Tyr Met Ser Met Ser Ser Trp Ser
305                 310                 315                 320

Tyr Thr His Ser Leu Asp Gly Ala Gly Leu Phe Leu Phe Asp His Ala
                325                 330                 335

Ala Glu Glu Tyr Glu His Ala Lys Lys Leu Ile Ile Phe Leu Asn Glu
            340                 345                 350

Asn Asn Val Pro Val Gln Leu Thr Ser Ile Ser Ala Pro Glu His Lys
        355                 360                 365

Phe Glu Gly Leu Thr Gln Ile Phe Gln Lys Ala Tyr Glu His Glu Gln
370                 375                 380
```

```
His Ile Ser Glu Ser Ile Asn Asn Ile Val Asp His Ala Ile Lys Cys
            385                 390                 395                 400

Lys Asp His Ala Thr Phe Asn Phe Leu Gln Trp Tyr Val Ala Glu Gln
                405                 410                 415

His Glu Glu Val Leu Phe Lys Asp Ile Leu Asp Lys Ile Glu Leu
            420                 425                 430

Ile Gly Asn Glu Asn His Gly Leu Tyr Leu Ala Asp Gln Tyr Val Lys
        435                 440                 445

Gly Ile Ala Lys Ser Arg Lys Ser
    450                 455

<210> SEQ ID NO 69
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Met Asp
            20                  25                  30

Glu Lys Asn Ser Val Ser Val Asp Leu Pro Gly Glu Met Lys Val Leu
            35                  40                  45

Val Ser Lys Glu Lys Asp Lys Asp Gly Lys Tyr Ser Leu Met Ala Thr
    50                  55                  60

Val Asp Lys Leu Glu Leu Lys Gly Thr Ser Asp Lys Ser Asn Gly Ser
65                  70                  75                  80

Gly Thr Leu Glu Gly Glu Lys Ser Asp Lys Ser Lys Ala Lys Leu Thr
                85                  90                  95

Ile Ser Glu Asp Leu Ser Lys Thr Thr Phe Glu Ile Phe Lys Glu Asp
            100                 105                 110

Gly Lys Thr Leu Val Ser Lys Lys Val Asn Ser Lys Asp Lys Ser Ser
        115                 120                 125

Ile Glu Glu Lys Phe Asn Ala Lys Gly Glu Leu Ser Glu Lys Thr Ile
    130                 135                 140

Leu Arg Ala Asn Gly Thr Arg Leu Glu Tyr Thr Glu Ile Lys Ser Asp
145                 150                 155                 160

Gly Thr Gly Lys Ala Lys Glu Val Leu Lys Asp Phe Ala Leu Glu Gly
                165                 170                 175

Thr Leu Ala Ala Asp Lys Thr Thr Leu Lys Val Thr Glu Gly Thr Val
            180                 185                 190

Val Leu Ser Lys His Ile Pro Asn Ser Gly Glu Ile Thr Val Glu Leu
        195                 200                 205

Asn Asp Ser Asn Ser Thr Gln Ala Thr Lys Lys Thr Gly Lys Trp Asp
    210                 215                 220

Ser Asn Thr Ser Thr Leu Thr Ile Ser Val Asn Ser Lys Lys Thr Lys
225                 230                 235                 240

Asn Ile Val Phe Thr Lys Glu Asp Thr Ile Thr Val Gln Lys Tyr Asp
                245                 250                 255

Ser Ala Gly Thr Asn Leu Glu Gly Asn Ala Val Glu Ile Lys Thr Leu
            260                 265                 270

Asp Glu Leu Lys Asn Ala Leu Lys Gly Ser Glu Ser Gln Val Arg Gln
```

```
                275                 280                 285
Gln Phe Ser Lys Asp Ile Glu Lys Leu Leu Asn Glu Gln Val Asn Lys
    290                 295                 300
Glu Met Gln Ser Ser Asn Leu Tyr Met Ser Met Ser Ser Trp Ser Tyr
305                 310                 315                 320
Thr His Ser Leu Asp Gly Ala Gly Leu Phe Leu Phe Asp His Ala Ala
                325                 330                 335
Glu Glu Tyr Glu His Ala Lys Lys Leu Ile Ile Phe Leu Asn Glu Asn
            340                 345                 350
Asn Val Pro Val Gln Leu Thr Ser Ile Ser Ala Pro Glu His Lys Phe
        355                 360                 365
Glu Gly Leu Thr Gln Ile Phe Gln Lys Ala Tyr Glu His Glu Gln His
    370                 375                 380
Ile Ser Glu Ser Ile Asn Asn Ile Val Asp His Ala Ile Lys Cys Lys
385                 390                 395                 400
Asp His Ala Thr Phe Asn Phe Leu Gln Trp Tyr Val Ala Glu Gln His
                405                 410                 415
Glu Glu Glu Val Leu Phe Lys Asp Ile Leu Asp Lys Ile Glu Leu Ile
            420                 425                 430
Gly Asn Glu Asn His Gly Leu Tyr Leu Ala Asp Gln Tyr Val Lys Gly
        435                 440                 445
Ile Ala Lys Ser Arg Lys Ser
    450                 455

<210> SEQ ID NO 70
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Met Asp Ser Lys Gly Ser Ser Gln Lys Gly Ser Arg Leu Leu Leu Leu
1               5                   10                  15
Leu Val Val Ser Asn Leu Leu Pro Gln Gly Val Leu Ala Met Asp
            20                  25                  30
Glu Lys Asn Ser Val Ser Val Asp Leu Pro Gly Glu Met Lys Val Leu
        35                  40                  45
Val Ser Lys Glu Lys Asp Lys Asp Gly Lys Tyr Ser Leu Met Ala Thr
50                  55                  60
Val Asp Lys Leu Glu Leu Lys Gly Thr Ser Asp Lys Ser Gln Gly Ser
65                  70                  75                  80
Gly Thr Leu Glu Gly Glu Lys Ser Asp Lys Ser Lys Ala Lys Leu Thr
                85                  90                  95
Ile Ser Glu Asp Leu Ser Lys Thr Thr Phe Glu Ile Phe Lys Glu Asp
            100                 105                 110
Gly Lys Thr Leu Val Ser Lys Val Asn Ser Lys Asp Lys Ser Ser
        115                 120                 125
Ile Glu Glu Lys Phe Asn Ala Lys Gly Glu Leu Ser Glu Lys Thr Ile
    130                 135                 140
Leu Arg Ala Gln Gly Thr Arg Leu Glu Tyr Thr Glu Ile Lys Ser Asp
145                 150                 155                 160
Gly Thr Gly Lys Ala Lys Glu Val Leu Lys Asp Phe Ala Leu Glu Gly
                165                 170                 175
```

```
Thr Leu Ala Ala Asp Lys Thr Thr Leu Lys Val Thr Glu Gly Thr Val
            180                 185                 190

Val Leu Ser Lys His Ile Pro Asn Ser Gly Glu Ile Thr Val Glu Leu
        195                 200                 205

Gln Asp Ser Gln Ser Thr Gln Ala Thr Lys Lys Thr Gly Lys Trp Asp
    210                 215                 220

Ser Gln Thr Ser Thr Leu Thr Ile Ser Val Asn Ser Lys Lys Thr Lys
225                 230                 235                 240

Asn Ile Val Phe Thr Lys Glu Asp Thr Ile Thr Val Gln Lys Tyr Asp
                245                 250                 255

Ser Ala Gly Thr Asn Leu Glu Gly Asn Ala Val Glu Ile Lys Thr Leu
            260                 265                 270

Asp Glu Leu Lys Asn Ala Leu Lys Gly Ser Glu Ser Gln Val Arg Gln
        275                 280                 285

Gln Phe Ser Lys Asp Ile Glu Lys Leu Leu Asn Glu Gln Val Asn Lys
    290                 295                 300

Glu Met Gln Ser Ser Asn Leu Tyr Met Ser Met Ser Ser Trp Ser Tyr
305                 310                 315                 320

Thr His Ser Leu Asp Gly Ala Gly Leu Phe Leu Phe Asp His Ala Ala
                325                 330                 335

Glu Glu Tyr Glu His Ala Lys Lys Leu Ile Ile Phe Leu Asn Glu Asn
            340                 345                 350

Asn Val Pro Val Gln Leu Thr Ser Ile Ser Ala Pro Glu His Lys Phe
        355                 360                 365

Glu Gly Leu Thr Gln Ile Phe Gln Lys Ala Tyr Glu His Glu Gln His
    370                 375                 380

Ile Ser Glu Ser Ile Asn Asn Ile Val Asp His Ala Ile Lys Cys Lys
385                 390                 395                 400

Asp His Ala Thr Phe Asn Phe Leu Gln Trp Tyr Val Ala Glu Gln His
                405                 410                 415

Glu Glu Glu Val Leu Phe Lys Asp Ile Leu Asp Lys Ile Glu Leu Ile
            420                 425                 430

Gly Asn Glu Asn His Gly Leu Tyr Leu Ala Asp Gln Tyr Val Lys Gly
        435                 440                 445

Ile Ala Lys Ser Arg Lys Ser
    450                 455

<210> SEQ ID NO 71
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Met Asp
            20                  25                  30

Glu Lys Asn Ser Val Ser Val Asp Leu Pro Gly Gly Met Lys Val Leu
        35                  40                  45

Val Ser Lys Glu Lys Asp Lys Asp Gly Lys Tyr Ser Leu Met Ala Thr
    50                  55                  60
```

-continued

Val Glu Lys Leu Glu Leu Lys Gly Thr Ser Asp Lys Asn Asn Gly Ser
65                  70                  75                  80

Gly Thr Leu Glu Gly Glu Lys Thr Asp Lys Ser Lys Val Lys Leu Thr
                85                  90                  95

Ile Ala Glu Asp Leu Ser Lys Thr Thr Phe Glu Ile Phe Lys Glu Asp
            100                 105                 110

Gly Lys Thr Leu Val Ser Lys Val Thr Leu Lys Asp Lys Ser Ser
            115                 120                 125

Thr Glu Glu Lys Phe Asn Lys Gly Glu Ile Ser Glu Lys Thr Ile
        130                 135                 140

Val Arg Ala Asn Gly Thr Arg Leu Glu Tyr Thr Asp Ile Lys Ser Asp
145                 150                 155                 160

Gly Ser Gly Lys Ala Lys Glu Val Leu Lys Asp Phe Thr Leu Glu Gly
                165                 170                 175

Thr Leu Ala Ala Asp Gly Lys Thr Thr Leu Lys Val Thr Glu Gly Thr
            180                 185                 190

Val Val Leu Ser Lys Asn Ile Leu Lys Ser Gly Glu Ile Thr Val Ala
            195                 200                 205

Leu Asp Asp Ser Asp Thr Thr Gln Ala Thr Lys Lys Thr Gly Lys Trp
    210                 215                 220

Asp Ser Lys Thr Ser Thr Leu Thr Ile Ser Val Asn Ser Gln Lys Thr
225                 230                 235                 240

Lys Asn Leu Val Phe Thr Lys Glu Asp Thr Ile Thr Val Gln Lys Tyr
                245                 250                 255

Asp Ser Ala Gly Thr Asn Leu Glu Gly Lys Ala Val Glu Ile Thr Thr
            260                 265                 270

Leu Glu Lys Leu Lys Asp Ala Leu Lys Gly Ser Glu Ser Gln Val Arg
        275                 280                 285

Gln Gln Phe Ser Lys Asp Ile Glu Lys Leu Leu Asn Glu Gln Val Asn
        290                 295                 300

Lys Glu Met Gln Ser Ser Asn Leu Tyr Met Ser Met Ser Ser Trp Ser
305                 310                 315                 320

Tyr Thr His Ser Leu Asp Gly Ala Gly Leu Phe Leu Phe Asp His Ala
            325                 330                 335

Ala Glu Glu Tyr Glu His Ala Lys Lys Leu Ile Ile Phe Leu Asn Glu
            340                 345                 350

Asn Asn Val Pro Val Gln Leu Thr Ser Ile Ser Ala Pro Glu His Lys
            355                 360                 365

Phe Glu Gly Leu Thr Gln Ile Phe Gln Lys Ala Tyr Glu His Glu Gln
        370                 375                 380

His Ile Ser Glu Ser Ile Asn Asn Ile Val Asp His Ala Ile Lys Cys
385                 390                 395                 400

Lys Asp His Ala Thr Phe Asn Phe Leu Gln Trp Tyr Val Ala Glu Gln
            405                 410                 415

His Glu Glu Glu Val Leu Phe Lys Asp Ile Leu Asp Lys Ile Glu Leu
            420                 425                 430

Ile Gly Asn Glu Asn His Gly Leu Tyr Leu Ala Asp Gln Tyr Val Lys
        435                 440                 445

Gly Ile Ala Lys Ser Arg Lys Ser
        450                 455

<210> SEQ ID NO 72
<211> LENGTH: 456
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Met Asp
            20                  25                  30

Glu Lys Asn Ser Val Ser Val Asp Leu Pro Gly Gly Met Lys Val Leu
            35                  40                  45

Val Ser Lys Glu Lys Asp Lys Asp Gly Lys Tyr Ser Leu Met Ala Thr
50                  55                  60

Val Glu Lys Leu Glu Leu Lys Gly Thr Ser Asp Lys Asn Gln Gly Ser
65                  70                  75                  80

Gly Thr Leu Glu Gly Glu Lys Thr Asp Lys Ser Lys Val Lys Leu Thr
                85                  90                  95

Ile Ala Glu Asp Leu Ser Lys Thr Thr Phe Glu Ile Phe Lys Glu Asp
            100                 105                 110

Gly Lys Thr Leu Val Ser Lys Lys Val Thr Leu Lys Asp Lys Ser Ser
            115                 120                 125

Thr Glu Glu Lys Phe Asn Glu Lys Gly Glu Ile Ser Glu Lys Thr Ile
130                 135                 140

Val Arg Ala Gln Gly Thr Arg Leu Glu Tyr Thr Asp Ile Lys Ser Asp
145                 150                 155                 160

Gly Ser Gly Lys Ala Lys Glu Val Leu Lys Asp Phe Thr Leu Glu Gly
                165                 170                 175

Thr Leu Ala Ala Asp Gly Lys Thr Thr Leu Lys Val Thr Glu Gly Thr
            180                 185                 190

Val Val Leu Ser Lys Asn Ile Leu Lys Ser Gly Glu Ile Thr Val Ala
            195                 200                 205

Leu Asp Asp Ser Asp Thr Thr Gln Ala Thr Lys Lys Thr Gly Lys Trp
210                 215                 220

Asp Ser Lys Thr Ser Thr Leu Thr Ile Ser Val Asn Ser Gln Lys Thr
225                 230                 235                 240

Lys Asn Leu Val Phe Thr Lys Glu Asp Thr Ile Thr Val Gln Lys Tyr
                245                 250                 255

Asp Ser Ala Gly Thr Asn Leu Glu Gly Lys Ala Val Glu Ile Thr Thr
            260                 265                 270

Leu Glu Lys Leu Lys Asp Ala Leu Lys Gly Ser Glu Ser Gln Val Arg
            275                 280                 285

Gln Gln Phe Ser Lys Asp Ile Glu Lys Leu Leu Asn Glu Gln Val Asn
290                 295                 300

Lys Glu Met Gln Ser Ser Asn Leu Tyr Met Ser Met Ser Ser Trp Ser
305                 310                 315                 320

Tyr Thr His Ser Leu Asp Gly Ala Gly Leu Phe Leu Phe Asp His Ala
                325                 330                 335

Ala Glu Glu Tyr Glu His Ala Lys Lys Leu Ile Ile Phe Leu Asn Glu
            340                 345                 350

Asn Asn Val Pro Val Gln Leu Thr Ser Ile Ser Ala Pro Glu His Lys
            355                 360                 365

Phe Glu Gly Leu Thr Gln Ile Phe Gln Lys Ala Tyr Glu His Glu Gln
370                 375                 380
```

His Ile Ser Glu Ser Ile Asn Asn Ile Val Asp His Ala Ile Lys Cys
385                 390                 395                 400

Lys Asp His Ala Thr Phe Asn Phe Leu Gln Trp Tyr Val Ala Glu Gln
            405                 410                 415

His Glu Glu Val Leu Phe Lys Asp Ile Leu Asp Lys Ile Glu Leu
        420                 425                 430

Ile Gly Asn Glu Asn His Gly Leu Tyr Leu Ala Asp Gln Tyr Val Lys
        435                 440                 445

Gly Ile Ala Lys Ser Arg Lys Ser
    450                 455

<210> SEQ ID NO 73
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Met Asp
            20                  25                  30

Glu Lys Asn Ser Val Ser Val Asp Leu Pro Gly Gly Met Thr Val Leu
        35                  40                  45

Val Ser Lys Glu Lys Asp Lys Asp Gly Lys Tyr Ser Leu Glu Ala Thr
50                  55                  60

Val Asp Lys Leu Glu Leu Lys Gly Thr Ser Asp Lys Asn Gln Gly Ser
65                  70                  75                  80

Gly Thr Leu Glu Gly Glu Lys Thr Asp Lys Ser Lys Val Lys Ser Thr
                85                  90                  95

Ile Ala Asp Asp Leu Ser Gln Thr Lys Phe Glu Ile Phe Lys Glu Asp
            100                 105                 110

Gly Lys Thr Leu Val Ser Lys Lys Val Thr Leu Lys Asp Lys Ser Ser
        115                 120                 125

Thr Glu Glu Lys Phe Asn Gly Lys Gly Glu Thr Ser Glu Lys Thr Ile
130                 135                 140

Val Arg Ala Gln Gly Thr Arg Leu Glu Tyr Thr Asp Ile Lys Ser Asp
145                 150                 155                 160

Gly Ser Gly Lys Ala Lys Glu Val Leu Lys Asp Phe Thr Leu Glu Gly
                165                 170                 175

Thr Leu Ala Ala Asp Gly Lys Thr Thr Leu Lys Val Thr Glu Gly Thr
            180                 185                 190

Val Val Leu Ser Lys Asn Ile Leu Lys Ser Gly Glu Ile Thr Ala Ala
        195                 200                 205

Leu Asp Asp Ser Asp Thr Thr Arg Ala Thr Lys Lys Thr Gly Lys Trp
210                 215                 220

Asp Ser Lys Thr Ser Thr Leu Thr Ile Ser Val Asn Ser Gln Lys Thr
225                 230                 235                 240

Lys Asn Leu Val Phe Thr Lys Glu Asp Thr Ile Thr Val Gln Arg Tyr
                245                 250                 255

Asp Ser Ala Gly Thr Asn Leu Glu Gly Lys Ala Val Glu Ile Thr Thr
            260                 265                 270

Leu Lys Glu Leu Lys Asn Ala Leu Lys Gly Ser Glu Ser Gln Val Arg
            275                 280                 285

Gln Gln Phe Ser Lys Asp Ile Glu Lys Leu Leu Asn Glu Gln Val Asn
    290                 295                 300

Lys Glu Met Gln Ser Ser Asn Leu Tyr Met Ser Met Ser Ser Trp Ser
305                 310                 315                 320

Tyr Thr His Ser Leu Asp Gly Ala Gly Leu Phe Leu Phe Asp His Ala
                325                 330                 335

Ala Glu Glu Tyr Glu His Ala Lys Lys Leu Ile Ile Phe Leu Asn Glu
            340                 345                 350

Asn Asn Val Pro Val Gln Leu Thr Ser Ile Ser Ala Pro Glu His Lys
        355                 360                 365

Phe Glu Gly Leu Thr Gln Ile Phe Gln Lys Ala Tyr Glu His Glu Gln
370                 375                 380

His Ile Ser Glu Ser Ile Asn Asn Ile Val Asp His Ala Ile Lys Cys
385                 390                 395                 400

Lys Asp His Ala Thr Phe Asn Phe Leu Gln Trp Tyr Val Ala Glu Gln
                405                 410                 415

His Glu Glu Glu Val Leu Phe Lys Asp Ile Leu Asp Lys Ile Glu Leu
            420                 425                 430

Ile Gly Asn Glu Asn His Gly Leu Tyr Leu Ala Asp Gln Tyr Val Lys
        435                 440                 445

Gly Ile Ala Lys Ser Arg Lys Ser
    450                 455

<210> SEQ ID NO 74
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Met Asp
            20                  25                  30

Glu Lys Asn Ser Val Ser Val Asp Leu Pro Gly Gly Met Thr Val Leu
        35                  40                  45

Val Ser Lys Glu Lys Asp Lys Asp Gly Lys Tyr Ser Leu Glu Ala Thr
50                  55                  60

Val Asp Lys Leu Glu Leu Lys Gly Thr Ser Asp Lys Asn Asn Gly Ser
65                  70                  75                  80

Gly Thr Leu Glu Gly Glu Lys Thr Asp Lys Ser Lys Val Lys Ser Thr
                85                  90                  95

Ile Ala Asp Asp Leu Ser Gln Thr Lys Phe Glu Ile Phe Lys Glu Asp
            100                 105                 110

Gly Lys Thr Leu Val Ser Lys Lys Val Thr Leu Lys Asp Lys Ser Ser
        115                 120                 125

Thr Glu Glu Lys Phe Asn Gly Lys Gly Glu Thr Ser Glu Lys Thr Ile
    130                 135                 140

Val Arg Ala Asn Gly Thr Arg Leu Glu Tyr Thr Asp Ile Lys Ser Asp
145                 150                 155                 160

Gly Ser Gly Lys Ala Lys Glu Val Leu Lys Asp Phe Thr Leu Glu Gly

```
                    165                 170                 175
Thr Leu Ala Ala Asp Gly Lys Thr Thr Leu Lys Val Thr Glu Gly Thr
            180                 185                 190

Val Val Leu Ser Lys Asn Ile Leu Lys Ser Gly Glu Ile Thr Ala Ala
        195                 200                 205

Leu Asp Asp Ser Asp Thr Thr Arg Ala Thr Lys Thr Gly Lys Trp
    210                 215                 220

Asp Ser Lys Thr Ser Thr Leu Thr Ile Ser Val Asn Ser Gln Lys Thr
225                 230                 235                 240

Lys Asn Leu Val Phe Thr Lys Glu Asp Thr Ile Thr Val Gln Arg Tyr
                245                 250                 255

Asp Ser Ala Gly Thr Asn Leu Glu Gly Lys Ala Val Glu Ile Thr Thr
            260                 265                 270

Leu Lys Glu Leu Lys Asn Ala Leu Lys Gly Ser Glu Ser Gln Val Arg
        275                 280                 285

Gln Gln Phe Ser Lys Asp Ile Glu Lys Leu Leu Asn Glu Gln Val Asn
    290                 295                 300

Lys Glu Met Gln Ser Ser Asn Leu Tyr Met Ser Met Ser Ser Trp Ser
305                 310                 315                 320

Tyr Thr His Ser Leu Asp Gly Ala Gly Leu Phe Leu Phe Asp His Ala
                325                 330                 335

Ala Glu Glu Tyr Glu His Ala Lys Lys Leu Ile Ile Phe Leu Asn Glu
            340                 345                 350

Asn Asn Val Pro Val Gln Leu Thr Ser Ile Ser Ala Pro Glu His Lys
        355                 360                 365

Phe Glu Gly Leu Thr Gln Ile Phe Gln Lys Ala Tyr Glu His Glu Gln
    370                 375                 380

His Ile Ser Glu Ser Ile Asn Asn Ile Val Asp His Ala Ile Lys Cys
385                 390                 395                 400

Lys Asp His Ala Thr Phe Asn Phe Leu Gln Trp Tyr Val Ala Glu Gln
                405                 410                 415

His Glu Glu Glu Val Leu Phe Lys Asp Ile Leu Asp Lys Ile Glu Leu
            420                 425                 430

Ile Gly Asn Glu Asn His Gly Leu Tyr Leu Ala Asp Gln Tyr Val Lys
        435                 440                 445

Gly Ile Ala Lys Ser Arg Lys Ser
    450                 455

<210> SEQ ID NO 75
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Met Asp
            20                  25                  30

Glu Lys Asn Ser Val Ser Val Asp Leu Pro Gly Glu Met Lys Val Leu
        35                  40                  45

Val Ser Lys Glu Lys Asp Lys Asp Gly Lys Tyr Ser Leu Glu Ala Thr
    50                  55                  60
```

```
Val Asp Lys Leu Glu Leu Lys Gly Thr Ser Asp Lys Asn Asn Gly Ser
 65                  70                  75                  80

Gly Val Leu Glu Gly Val Lys Ala Ala Lys Ser Lys Ala Lys Leu Thr
                 85                  90                  95

Ile Ala Asp Asp Leu Ser Gln Thr Lys Phe Glu Ile Phe Lys Glu Asp
                100                 105                 110

Gly Lys Thr Leu Val Ser Lys Val Thr Leu Lys Asp Lys Ser Ser
            115                 120                 125

Thr Glu Glu Lys Phe Asn Asp Lys Gly Lys Leu Ser Glu Lys Val Val
            130                 135                 140

Thr Arg Ala Asn Gly Thr Arg Leu Glu Tyr Thr Glu Ile Gln Asn Asp
145                 150                 155                 160

Gly Ser Gly Lys Ala Lys Glu Val Leu Lys Ser Leu Thr Leu Glu Gly
                165                 170                 175

Thr Leu Thr Ala Asp Gly Glu Thr Lys Leu Thr Val Glu Ala Gly Thr
            180                 185                 190

Val Thr Leu Ser Lys Asn Ile Ser Glu Ser Gly Glu Ile Thr Val Glu
            195                 200                 205

Leu Lys Asp Thr Glu Thr Thr Pro Ala Asp Lys Lys Ser Gly Thr Trp
210                 215                 220

Asp Ser Lys Thr Ser Thr Leu Thr Ile Ser Lys Asn Ser Gln Lys Thr
225                 230                 235                 240

Lys Gln Leu Val Phe Thr Lys Glu Asn Thr Ile Thr Val Gln Lys Tyr
                245                 250                 255

Asn Thr Ala Gly Thr Lys Leu Glu Gly Ser Pro Ala Glu Ile Lys Asp
            260                 265                 270

Leu Glu Ala Leu Lys Ala Ala Leu Lys Gly Ser Glu Ser Gln Val Arg
            275                 280                 285

Gln Gln Phe Ser Lys Asp Ile Glu Lys Leu Leu Asn Glu Gln Val Asn
            290                 295                 300

Lys Glu Met Gln Ser Ser Asn Leu Tyr Met Ser Met Ser Ser Trp Ser
305                 310                 315                 320

Tyr Thr His Ser Leu Asp Gly Ala Gly Leu Phe Leu Phe Asp His Ala
                325                 330                 335

Ala Glu Glu Tyr Glu His Ala Lys Lys Leu Ile Ile Phe Leu Asn Glu
            340                 345                 350

Asn Asn Val Pro Val Gln Leu Thr Ser Ile Ser Ala Pro Glu His Lys
            355                 360                 365

Phe Glu Gly Leu Thr Gln Ile Phe Gln Lys Ala Tyr Glu His Glu Gln
            370                 375                 380

His Ile Ser Glu Ser Ile Asn Asn Ile Val Asp His Ala Ile Lys Cys
385                 390                 395                 400

Lys Asp His Ala Thr Phe Asn Phe Leu Gln Trp Tyr Val Ala Glu Gln
                405                 410                 415

His Glu Glu Glu Val Leu Phe Lys Asp Ile Leu Asp Lys Ile Glu Leu
            420                 425                 430

Ile Gly Asn Glu Asn His Gly Leu Tyr Leu Ala Asp Gln Tyr Val Lys
            435                 440                 445

Gly Ile Ala Lys Ser Arg Lys Ser
450                 455
```

<210> SEQ ID NO 76
<211> LENGTH: 456

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76
```

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Met Asp
            20                  25                  30

Glu Lys Asn Ser Val Ser Val Asp Leu Pro Gly Glu Met Lys Val Leu
        35                  40                  45

Val Ser Lys Glu Lys Asp Lys Asp Gly Lys Tyr Ser Leu Glu Ala Thr
50                  55                  60

Val Asp Lys Leu Glu Leu Lys Gly Thr Ser Asp Lys Asn Gln Gly Ser
65                  70                  75                  80

Gly Val Leu Glu Gly Val Lys Ala Ala Lys Ser Lys Ala Lys Leu Thr
                85                  90                  95

Ile Ala Asp Asp Leu Ser Gln Thr Lys Phe Glu Ile Phe Lys Glu Asp
            100                 105                 110

Gly Lys Thr Leu Val Ser Lys Lys Val Thr Leu Lys Asp Lys Ser Ser
        115                 120                 125

Thr Glu Glu Lys Phe Asn Asp Lys Gly Lys Leu Ser Glu Lys Val Val
130                 135                 140

Thr Arg Ala Gln Gly Thr Arg Leu Glu Tyr Thr Glu Ile Gln Asn Asp
145                 150                 155                 160

Gly Ser Gly Lys Ala Lys Glu Val Leu Lys Ser Leu Thr Leu Glu Gly
                165                 170                 175

Thr Leu Thr Ala Asp Gly Glu Thr Lys Leu Thr Val Glu Ala Gly Thr
            180                 185                 190

Val Thr Leu Ser Lys Gln Ile Ser Glu Ser Gly Glu Ile Thr Val Glu
        195                 200                 205

Leu Lys Asp Thr Glu Thr Thr Pro Ala Asp Lys Lys Ser Gly Thr Trp
210                 215                 220

Asp Ser Lys Thr Ser Thr Leu Thr Ile Ser Lys Asn Ser Gln Lys Thr
225                 230                 235                 240

Lys Gln Leu Val Phe Thr Lys Glu Asn Thr Ile Thr Val Gln Lys Tyr
                245                 250                 255

Asn Thr Ala Gly Thr Lys Leu Glu Gly Ser Pro Ala Glu Ile Lys Asp
            260                 265                 270

Leu Glu Ala Leu Lys Ala Ala Leu Lys Gly Ser Glu Ser Gln Val Arg
        275                 280                 285

Gln Gln Phe Ser Lys Asp Ile Glu Lys Leu Leu Asn Glu Gln Val Asn
290                 295                 300

Lys Glu Met Gln Ser Ser Asn Leu Tyr Met Ser Met Ser Ser Trp Ser
305                 310                 315                 320

Tyr Thr His Ser Leu Asp Gly Ala Gly Leu Phe Leu Phe Asp His Ala
                325                 330                 335

Ala Glu Glu Tyr Glu His Ala Lys Lys Leu Ile Ile Phe Leu Asn Glu
            340                 345                 350

Asn Asn Val Pro Val Gln Leu Thr Ser Ile Ser Ala Pro Glu His Lys
        355                 360                 365

Phe Glu Gly Leu Thr Gln Ile Phe Gln Lys Ala Tyr Glu His Glu Gln

```
                    370             375                380
His Ile Ser Glu Ser Ile Asn Asn Ile Val Asp His Ala Ile Lys Cys
385                 390                 395                 400

Lys Asp His Ala Thr Phe Asn Phe Leu Gln Trp Tyr Val Ala Glu Gln
                405                 410                 415

His Glu Glu Glu Val Leu Phe Lys Asp Ile Leu Asp Lys Ile Glu Leu
            420                 425                 430

Ile Gly Asn Glu Asn His Gly Leu Tyr Leu Ala Asp Gln Tyr Val Lys
        435                 440                 445

Gly Ile Ala Lys Ser Arg Lys Ser
    450                 455

<210> SEQ ID NO 77
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Tyr Val Leu Glu Gly Thr Leu Thr Ala
1               5

<210> SEQ ID NO 78
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Tyr Val Ile Glu Gly Thr Ser Lys Gln
1               5

<210> SEQ ID NO 79
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Phe Thr Leu Glu Gly Lys Val Ala Asn
1               5

<210> SEQ ID NO 80
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Phe Ala Leu Glu Gly Thr Leu Thr Asp
1               5

<210> SEQ ID NO 81
```

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Tyr Thr Leu Glu Gly Gln Leu Ser Asp
1               5

<210> SEQ ID NO 82
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Tyr Asp Leu Lys Gly Glu Leu Ser Ser
1               5

<210> SEQ ID NO 83
<211> LENGTH: 273
<212> TYPE: PRT
<213> ORGANISM: Borreliella burgdorferi

<400> SEQUENCE: 83

Met Lys Lys Tyr Leu Leu Gly Ile Gly Leu Ile Leu Ala Leu Ile Ala
1               5                   10                  15

Cys Lys G

```
                225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
                260                 265                 270

Lys

<210> SEQ ID NO 84
<211> LENGTH: 273
<212> TYPE: PRT
<213> ORGANISM: Borreliella afzelii

<400> SEQUENCE: 84

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Ala Ser Val
                20                  25                  30

Asp Leu Pro Gly Glu Met Lys Val Leu Ser Lys Glu Lys Asp Lys
            35                  40                  45

Asp Gly Lys Tyr Ser Leu Lys Ala Thr Val Asp Lys Ile Glu Leu Lys
50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                85                  90                  95

Thr Thr Phe Glu Leu Phe Lys Glu Asp Gly Lys Thr Leu Val Ser Arg
                100                 105                 110

Lys Val Ser Ser Lys Asp Lys Thr Ser Thr Asp Glu Met Phe Asn Glu
                115                 120                 125

Lys Gly Glu Leu Ser Ala Lys Thr Met Thr Arg Glu Asn Gly Thr Lys
130                 135                 140

Leu Glu Tyr Thr Glu Met Lys Ser Asp Gly Thr Gly Lys Ala Lys Glu
145                 150                 155                 160

Val Leu Lys Asn Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
                180                 185                 190

Lys Ser Gly Glu Val Thr Val Ala Leu Asn Asp Thr Asn Thr Thr Gln
                195                 200                 205

Ala Thr Lys Lys Thr Gly Ala Trp Asp Ser Lys Thr Ser Thr Leu Thr
210                 215                 220

Ile Ser Val Asn Ser Lys Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
                260                 265                 270

Lys

<210> SEQ ID NO 85
<211> LENGTH: 274
<212> TYPE: PRT
<213> ORGANISM: Borreliella garinii

<400> SEQUENCE: 85
```

-continued

```
Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Gly Met Lys Val Leu Val Ser Lys Glu Lys Asp Lys
            35                  40                  45

Asp Gly Lys Tyr Ser Leu Met Ala Thr Val Glu Lys Leu Glu Leu Lys
        50                  55                  60

Gly Thr Ser Asp Lys Ser Asn Gly Ser Gly Val Leu Glu Gly Glu Lys
65                  70                  75                  80

Ala Asp Lys Ser Lys Ala Lys Leu Thr Ile Ser Gln Asp Leu Asn Gln
                85                  90                  95

Thr Thr Phe Glu Ile Phe Lys Glu Asp Gly Lys Thr Leu Val Ser Arg
            100                 105                 110

Lys Val Asn Ser Lys Asp Lys Ser Ser Thr Glu Glu Lys Phe Asn Asp
            115                 120                 125

Lys Gly Lys Leu Ser Glu Lys Val Val Thr Arg Ala Asn Gly Thr Arg
        130                 135                 140

Leu Glu Tyr Thr Glu Ile Lys Asn Asp Gly Ser Gly Lys Ala Lys Glu
145                 150                 155                 160

Val Leu Lys Gly Phe Ala Leu Glu Gly Thr Leu Thr Asp Gly Gly Glu
                165                 170                 175

Thr Lys Leu Thr Val Thr Gly Thr Val Thr Leu Ser Lys Asn Ile
            180                 185                 190

Ser Lys Ser Gly Glu Ile Thr Val Ala Leu Asn Asp Thr Glu Thr Thr
        195                 200                 205

Pro Ala Asp Lys Lys Thr Gly Glu Trp Lys Ser Asp Thr Ser Thr Leu
210                 215                 220

Thr Ile Ser Lys Asn Ser Gln Lys Pro Lys Gln Leu Val Phe Thr Lys
225                 230                 235                 240

Glu Asn Thr Ile Thr Val Gln Asn Tyr Asn Arg Ala Gly Asn Ala Leu
                245                 250                 255

Glu Gly Ser Pro Ala Glu Ile Lys Asp Leu Ala Glu Leu Lys Ala Ala
            260                 265                 270

Leu Lys
```

<210> SEQ ID NO 86
<211> LENGTH: 273
<212> TYPE: PRT
<213> ORGANISM: Borreliella bavariensis

<400> SEQUENCE: 86

```
Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asp Lys
            35                  40                  45

Asp Gly Lys Tyr Ser Leu Met Ala Thr Val Asp Lys Leu Glu Leu Lys
        50                  55                  60

Gly Thr Ser Asp Lys Ser Asn Gly Ser Gly Thr Leu Glu Gly Glu Lys
65                  70                  75                  80

Ser Asp Lys Ser Lys Ala Lys Leu Thr Ile Ser Glu Asp Leu Ser Lys
                85                  90                  95
```

```
Thr Thr Phe Glu Ile Phe Lys Glu Asp Gly Lys Thr Leu Val Ser Lys
            100                 105                 110

Lys Val Asn Ser Lys Asp Lys Ser Ser Ile Glu Glu Lys Phe Asn Ala
        115                 120                 125

Lys Gly Glu Leu Ser Glu Lys Thr Ile Leu Arg Ala Asn Gly Thr Arg
    130                 135                 140

Leu Glu Tyr Thr Glu Ile Lys Ser Asp Gly Thr Gly Lys Ala Lys Glu
145                 150                 155                 160

Val Leu Lys Asp Phe Ala Leu Glu Gly Thr Leu Ala Ala Asp Lys Thr
                165                 170                 175

Thr Leu Lys Val Thr Glu Gly Thr Val Val Leu Ser Lys His Ile Pro
            180                 185                 190

Asn Ser Gly Glu Ile Thr Val Glu Leu Asn Asp Ser Asn Ser Thr Gln
        195                 200                 205

Ala Thr Lys Lys Thr Gly Lys Trp Asp Ser Asn Thr Ser Thr Leu Thr
    210                 215                 220

Ile Ser Val Asn Ser Lys Lys Thr Lys Asn Ile Val Phe Thr Lys Glu
225                 230                 235                 240

Asp Thr Ile Thr Val Gln Lys Tyr Asp Ser Ala Gly Thr Asn Leu Glu
                245                 250                 255

Gly Asn Ala Val Glu Ile Lys Thr Leu Asp Glu Leu Lys Asn Ala Leu
            260                 265                 270

Lys

<210> SEQ ID NO 87
<211> LENGTH: 274
<212> TYPE: PRT
<213> ORGANISM: Borreliella garinii

<400> SEQUENCE: 87

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Gly Met Lys Val Leu Val Ser Lys Glu Lys Asp Lys
        35                  40                  45

Asp Gly Lys Tyr Ser Leu Met Ala Thr Val Glu Lys Leu Glu Leu Lys
    50                  55                  60

Gly Thr Ser Asp Lys Asn Asn Gly Ser Gly Thr Leu Glu Gly Glu Lys
65                  70                  75                  80

Thr Asp Lys Ser Lys Val Lys Leu Thr Ile Ala Glu Asp Leu Ser Lys
                85                  90                  95

Thr Thr Phe Glu Ile Phe Lys Glu Asp Gly Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Ile Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
            180                 185                 190
```

```
Leu Lys Ser Gly Glu Ile Thr Val Ala Leu Asp Asp Ser Asp Thr Thr
        195                 200                 205

Gln Ala Thr Lys Lys Thr Gly Lys Trp Asp Ser Lys Thr Ser Thr Leu
        210                 215                 220

Thr Ile Ser Val Asn Ser Gln Lys Thr Lys Asn Leu Val Phe Thr Lys
225                 230                 235                 240

Glu Asp Thr Ile Thr Val Gln Lys Tyr Asp Ser Ala Gly Thr Asn Leu
                245                 250                 255

Glu Gly Lys Ala Val Glu Ile Thr Thr Leu Glu Lys Leu Lys Asp Ala
            260                 265                 270

Leu Lys
```

<210> SEQ ID NO 88
<211> LENGTH: 274
<212> TYPE: PRT
<213> ORGANISM: Borreliella burgdorferi

<400> SEQUENCE: 88

```
Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Gly Met Thr Val Leu Val Ser Lys Glu Lys Asp Lys
        35                  40                  45

Asp Gly Lys Tyr Ser Leu Glu Ala Thr Val Asp Lys Leu Glu Leu Lys
    50                  55                  60

Gly Thr Ser Asp Lys Asn Asn Gly Ser Gly Thr Leu Glu Gly Glu Lys
65                  70                  75                  80

Thr Asp Lys Ser Lys Val Lys Ser Thr Ile Ala Asp Asp Leu Ser Gln
                85                  90                  95

Thr Lys Phe Glu Ile Phe Lys Glu Asp Gly Lys Thr Leu Val Ser Lys
            100                 105                 110

Lys Val Thr Leu Lys Asp Lys Ser Ser Thr Glu Glu Lys Phe Asn Gly
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
            180                 185                 190

Leu Lys Ser Gly Glu Ile Thr Ala Ala Leu Asp Asp Ser Asp Thr Thr
        195                 200                 205

Arg Ala Thr Lys Lys Thr Gly Lys Trp Asp Ser Lys Thr Ser Thr Leu
    210                 215                 220

Thr Ile Ser Val Asn Ser Gln Lys Thr Lys Asn Leu Val Phe Thr Lys
225                 230                 235                 240

Glu Asp Thr Ile Thr Val Gln Arg Tyr Asp Ser Ala Gly Thr Asn Leu
                245                 250                 255

Glu Gly Lys Ala Val Glu Ile Thr Thr Leu Lys Glu Leu Lys Asn Ala
            260                 265                 270

Leu Lys
```

```
<210> SEQ ID NO 89
<211> LENGTH: 214
<212> TYPE: PRT
<213> ORGANISM: Borreliella garinii

<400> SEQUENCE: 89
```

| Met | Lys | Lys | Tyr | Leu | Leu | Gly | Ile | Gly | Leu | Ile | Leu | Ala | Leu | Ile | Ala |
|---|---|---|---|---|---|---|---|---|---|---|---|---|---|---|---|
| 1 | | | | 5 | | | | | 10 | | | | | 15 | |

| Cys | Lys | Gln | Asn | Val | Ser | Ser | Leu | Asp | Glu | Lys | Asn | Ser | Val | Ser | Val |
| | | | 20 | | | | | 25 | | | | | 30 | | |

| Asp | Leu | Pro | Gly | Glu | Met | Lys | Val | Leu | Val | Ser | Lys | Glu | Lys | Asp | Lys |
| | | 35 | | | | | 40 | | | | | 45 | | | |

| Asp | Gly | Lys | Tyr | Ser | Leu | Glu | Ala | Thr | Val | Asp | Lys | Leu | Glu | Leu | Lys |
| | 50 | | | | | 55 | | | | | 60 | | | | |

| Gly | Thr | Ser | Asp | Lys | Asn | Asn | Gly | Ser | Gly | Val | Leu | Glu | Gly | Val | Lys |
| 65 | | | | | 70 | | | | | 75 | | | | | 80 |

| Ala | Ala | Lys | Ser | Lys | Ala | Lys | Leu | Thr | Ile | Ala | Asp | Asp | Leu | Ser | Gln |
| | | | | 85 | | | | | 90 | | | | | 95 | |

| Thr | Lys | Phe | Glu | Ile | Phe | Lys | Glu | Asp | Gly | Lys | Thr | Leu | Val | Ser | Lys |
| | | | 100 | | | | | 105 | | | | | 110 | | |

| Lys | Val | Thr | Leu | Lys | Asp | Lys | Ser | Ser | Thr | Glu | Glu | Lys | Phe | Asn | Asp |
| | | | 115 | | | | | 120 | | | | | 125 | | |

| Lys | Gly | Lys | Leu | Ser | Glu | Lys | Val | Val | Thr | Arg | Ala | Asn | Gly | Thr | Arg |
| | 130 | | | | | 135 | | | | | 140 | | | | |

| Leu | Glu | Tyr | Thr | Glu | Ile | Gln | Asn | Asp | Gly | Ser | Gly | Lys | Ala | Lys | Glu |
| 145 | | | | | 150 | | | | | 155 | | | | | 160 |

| Val | Leu | Lys | Ser | Leu | Thr | Leu | Glu | Gly | Thr | Leu | Thr | Ala | Asp | Gly | Glu |
| | | | | 165 | | | | | 170 | | | | | 175 | |

| Thr | Lys | Leu | Thr | Glu | Asn | Thr | Ile | Thr | Val | Gln | Lys | Tyr | Asn | Thr | Ala |
| | | | 180 | | | | | 185 | | | | | 190 | | |

| Gly | Thr | Lys | Leu | Glu | Gly | Ser | Pro | Ala | Glu | Ile | Lys | Asp | Leu | Glu | Ala |
| | | | 195 | | | | | 200 | | | | | 205 | | |

| Leu | Lys | Ala | Ala | Leu | Lys |
| | | | | | 210 |

```
<210> SEQ ID NO 90
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90
```

| Glu | Ser | Gln | Val | Arg | Gln | Gln | Phe | Ser | Lys | Asp | Ile | Glu | Lys | Leu | Leu |
|---|---|---|---|---|---|---|---|---|---|---|---|---|---|---|---|
| 1 | | | | 5 | | | | | 10 | | | | | 15 | |

| Asn | Glu | Gln | Val | Asn | Lys | Glu | Met | Gln | Ser | Ser | Asn | Leu | Tyr | Met | Ser |
| | | | 20 | | | | | 25 | | | | | 30 | | |

| Met | Ser | Ser | Trp | Ser | Tyr | Thr | His | Ser | Leu | Asp | Gly | Ala | Gly | Leu | Phe |
| | | 35 | | | | | 40 | | | | | 45 | | | |

| Leu | Phe | Asp | His | Ala | Ala | Glu | Glu | Tyr | Glu | His | Ala | Lys | Lys | Leu | Ile |
| | 50 | | | | | 55 | | | | | 60 | | | | |

| Ile | Phe | Leu | Asn | Glu | Asn | Asn | Val | Pro | Val | Gln | Leu | Thr | Ser | Ile | Ser |
| 65 | | | | | 70 | | | | | 75 | | | | | 80 |

| Ala | Pro | Glu | His | Lys | Phe | Glu | Gly | Leu | Thr | Gln | Ile | Phe | Gln | Lys | Ala |
| | | | | 85 | | | | | 90 | | | | | 95 | |

Tyr Glu His Glu Gln His Ile Ser Glu Ser Ile Asn Asn Ile Val Asp
                100                 105                 110

His Ala Ile Lys Cys Lys Asp His Ala Thr Phe Asn Phe Leu Gln Trp
        115                 120                 125

Tyr Val Ala Glu Gln His Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 91
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Gly Gly Gly Ser Gly Gly Gly Ser
1               5

<210> SEQ ID NO 92
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Gly Gly Gly Ser Gly Gly Gly Ser Gly Gly Gly Ser Gly Gly Gly Ser
1               5                   10                  15

Gly Gly Gly Ser
            20

<210> SEQ ID NO 93
<211> LENGTH: 154
<212> TYPE: PRT
<213> ORGANISM: Aquifex aeolicus

<400> SEQUENCE: 93

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Cys Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asn Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
        130                 135                 140

Glu Met Ala Asn Leu Phe Lys Ser Leu Arg
145                 150

<210> SEQ ID NO 94
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Asp Lys Ser Lys Val Lys
    50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
        115                 120                 125

Ser Asp Gly Ser Gly Lys Ala Lys Glu Val Leu Lys Gly Tyr Thr Leu
    130                 135                 140

Glu Gly Gln Leu Ser Asp Glu Lys Thr Thr Leu Val Val Lys Glu Gly
145                 150                 155                 160

Thr Val Thr Leu Ser Lys Asn Ile Ser Lys Ser Gly Glu Val Ser Val
                165                 170                 175

Glu Leu Asn Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
        195                 200                 205

Thr Lys Asp Leu Val Phe Thr Lys Glu Asn Thr Ile Thr Val Gln Gln
    210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys
                245                 250

<210> SEQ ID NO 95
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

```
Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Asp Lys Ser Lys Val Lys
    50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Val Thr Ser Lys Asp Lys
                85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
            115                 120                 125

Ser Asp Gly Ser Gly Lys Ala Lys Glu Val Leu Lys Gly Tyr Asp Leu
        130                 135                 140

Lys Gly Glu Leu Ser Ser Glu Lys Thr Thr Leu Val Val Lys Glu Gly
145                 150                 155                 160

Thr Val Thr Leu Ser Lys Asn Ile Ser Lys Ser Gly Glu Val Ser Val
            165                 170                 175

Glu Leu Asn Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
            195                 200                 205

Thr Lys Asp Leu Val Phe Thr Lys Glu Asn Thr Ile Thr Val Gln Gln
            210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys
                245                 250

<210> SEQ ID NO 96
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Asp Lys Ser Lys Val Lys
    50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Val Thr Ser Lys Asp Lys
                85                  90                  95

Ser Ser Thr Glu Glu Lys Phe Asn Glu Lys Gly Glu Val Ser Glu Lys
```

```
            100                 105                 110
Ile Ile Thr Arg Ala Asp Gly Thr Arg Leu Glu Tyr Thr Gly Ile Lys
            115                 120                 125

Ser Asp Gly Ser Gly Lys Ala Lys Glu Val Leu Lys Gly Phe Thr Leu
        130                 135                 140

Glu Gly Lys Val Ala Asn Glu Lys Thr Thr Leu Val Val Lys Glu Gly
145                 150                 155                 160

Thr Val Thr Leu Ser Lys Asn Ile Ser Lys Ser Gly Glu Val Ser Val
                    165                 170                 175

Glu Leu Asn Asp Thr Asp Ser Ser Ala Ala Thr Lys Lys Thr Ala Ala
                180                 185                 190

Trp Asn Ser Gly Thr Ser Thr Leu Thr Ile Thr Val Asn Ser Lys Lys
            195                 200                 205

Thr Lys Asp Leu Val Phe Thr Lys Glu Asn Thr Ile Thr Val Gln Gln
        210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys
                    245                 250

<210> SEQ ID NO 97
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
                20                  25                  30

Ala Thr Val Asp Lys Leu Glu Leu Lys Gly Thr Ser Asp Lys Asn Asn
            35                  40                  45

Gly Ser Gly Val Leu Glu Gly Val Lys Ala Asp Lys Ser Lys Val Lys
        50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Val Thr Ser Lys Asp Lys
                    85                  90                  95

Ser Ser Thr Glu Glu Lys Phe Asn Glu Lys Gly Glu Val Ser Glu Lys
                100                 105                 110

Ile Ile Thr Arg Ala Asp Gly Thr Arg Leu Glu Tyr Thr Gly Ile Lys
            115                 120                 125

Ser Asp Gly Ser Gly Lys Ala Lys Glu Val Leu Lys Gly Phe Ala Leu
        130                 135                 140

Glu Gly Thr Leu Thr Asp Glu Lys Thr Thr Leu Val Val Lys Glu Gly
145                 150                 155                 160

Thr Val Thr Leu Ser Lys Asn Ile Ser Lys Ser Gly Glu Val Ser Val
                    165                 170                 175

Glu Leu Asn Asp Thr Asp Ser Ser Ala Ala Thr Lys Lys Thr Ala Ala
                180                 185                 190

Trp Asn Ser Gly Thr Ser Thr Leu Thr Ile Thr Val Asn Ser Lys Lys
            195                 200                 205
```

```
Thr Lys Asp Leu Val Phe Thr Lys Glu Asn Thr Ile Thr Val Gln Gln
    210                 215                 220

Tyr Asp Ser Asn Gly Thr Lys Leu Glu Gly Ser Ala Val Glu Ile Thr
225                 230                 235                 240

Lys Leu Asp Glu Ile Lys Asn Ala Leu Lys
                245                 250

<210> SEQ ID NO 98
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
                20                  25                  30

Ala Thr Val Asp Lys Leu Glu Leu Lys Gly Thr Ser Asp Lys Asn Gln
            35                  40                  45

Gly Ser Gly Val Leu Glu Gly Val Lys Ala Asp Lys Ser Lys Val Lys
50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
        115                 120                 125

Ser Asp Gly Ser Gly Lys Ala Lys Glu Val Leu Lys Gly Tyr Thr Leu
130                 135                 140

Glu Gly Gln Leu Ser Asp Glu Lys Thr Thr Leu Val Val Lys Glu Gly
145                 150                 155                 160

Thr Val Thr Leu Ser Lys Gln Ile Ser Lys Ser Gly Glu Val Ser Val
                165                 170                 175

Glu Leu Gln Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
        195                 200                 205

Thr Lys Asp Leu Val Phe Thr Lys Glu Asn Thr Ile Thr Val Gln Gln
    210                 215                 220

Tyr Asp Ser Gln Gly Thr Lys Leu Glu Gly Ser Ala Val Glu Ile Thr
225                 230                 235                 240

Lys Leu Asp Glu Ile Lys Asn Ala Leu Lys
                245                 250

<210> SEQ ID NO 99
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 99

```
Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Gln
        35                  40                  45

Gly Ser Gly Val Leu Glu Gly Val Lys Ala Asp Lys Ser Lys Val Lys
    50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
        115                 120                 125

Ser Asp Gly Ser Gly Lys Ala Lys Glu Val Leu Lys Gly Phe Thr Leu
    130                 135                 140

Glu Gly Lys Val Ala Asn Glu Lys Thr Thr Leu Val Val Lys Glu Gly
145                 150                 155                 160

Thr Val Thr Leu Ser Lys Gln Ile Ser Lys Ser Gly Glu Val Ser Val
                165                 170                 175

Glu Leu Gln Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
        195                 200                 205

Thr Lys Asp Leu Val Phe Thr Lys Glu Asn Thr Ile Thr Val Gln Gln
    210                 215                 220

Tyr Asp Ser Gln Gly Thr Lys Leu Glu Gly Ser Ala Val Glu Ile Thr
225                 230                 235                 240

Lys Leu Asp Glu Ile Lys Asn Ala Leu Lys
                245                 250
```

<210> SEQ ID NO 100
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 100

```
Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Gln
        35                  40                  45

Gly Ser Gly Val Leu Glu Gly Val Lys Ala Asp Lys Ser Lys Val Lys
    50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
```

```
                85                  90                  95
Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
            115                 120                 125

Ser Asp Gly Ser Gly Lys Ala Lys Glu Val Leu Lys Gly Phe Ala Leu
            130                 135                 140

Glu Gly Thr Leu Thr Asp Glu Lys Thr Thr Leu Val Val Lys Glu Gly
145                 150                 155                 160

Thr Val Thr Leu Ser Lys Gln Ile Ser Lys Ser Gly Glu Val Ser Val
                165                 170                 175

Glu Leu Gln Asp Thr Asp Ser Ser Ala Ala Thr Lys Lys Thr Ala Ala
            180                 185                 190

Trp Asn Ser Gly Thr Ser Thr Leu Thr Ile Thr Val Asn Ser Lys Lys
            195                 200                 205

Thr Lys Asp Leu Val Phe Thr Lys Glu Asn Thr Ile Thr Val Gln Gln
            210                 215                 220

Tyr Asp Ser Gln Gly Thr Lys Leu Glu Gly Ser Ala Val Glu Ile Thr
225                 230                 235                 240

Lys Leu Asp Glu Ile Lys Asn Ala Leu Lys
                245                 250

<210> SEQ ID NO 101
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Gln
            35                  40                  45

Gly Ser Gly Val Leu Glu Gly Val Lys Ala Asp Lys Ser Lys Val Lys
    50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
            115                 120                 125

Ser Asp Gly Ser Gly Lys Ala Lys Glu Val Leu Lys Gly Tyr Asp Leu
            130                 135                 140

Lys Gly Glu Leu Ser Ser Glu Lys Thr Thr Leu Val Val Lys Glu Gly
145                 150                 155                 160

Thr Val Thr Leu Ser Lys Gln Ile Ser Lys Ser Gly Glu Val Ser Val
                165                 170                 175

Glu Leu Gln Asp Thr Asp Ser Ser Ala Ala Thr Lys Lys Thr Ala Ala
            180                 185                 190
```

```
Trp Asn Ser Gly Thr Ser Thr Leu Thr Ile Thr Val Asn Ser Lys Lys
        195                 200                 205

Thr Lys Asp Leu Val Phe Thr Lys Glu Asn Thr Ile Thr Val Gln Gln
    210                 215                 220

Tyr Asp Ser Gln Gly Thr Lys Leu Glu Gly Ser Ala Val Glu Ile Thr
225                 230                 235                 240

Lys Leu Asp Glu Ile Lys Asn Ala Leu Lys
                245                 250

<210> SEQ ID NO 102
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (48)..(48)
<223> OTHER INFORMATION: /replace="Gln"
<220> FEATURE:
<221> NAME/KEY: MOD_RES
<222> LOCATION: (142)..(150)
<223> OTHER INFORMATION: Any amino acid
<220> FEATURE:
<221> NAME/KEY: VARIANT
<222> LOCATION: (167)..(167)
<223> OTHER INFORMATION: /replace="Gln"
<220> FEATURE:
<221> NAME/KEY: VARIANT
<222> LOCATION: (179)..(179)
<223> OTHER INFORMATION: /replace="Gln"
<220> FEATURE:
<221> NAME/KEY: VARIANT
<222> LOCATION: (228)..(228)
<223> OTHER INFORMATION: /replace="Gln"
<220> FEATURE:
<221> NAME/KEY: SITE
<222> LOCATION: (1)..(250)
<223> OTHER INFORMATION: /note="Variant residues given in the sequence
      have no preference with respect to those in the annotations for
      variant positions"

<400> SEQUENCE: 102

Met Asp Glu Lys Asn Ser Val Ser Val Asp Leu Pro Gly Glu Met Lys
1               5                   10                  15

Val Leu Val Ser Lys Glu Lys Asn Lys Asp Gly Lys Tyr Asp Leu Ile
            20                  25                  30

Ala Thr Val Asp Lys Leu Glu Leu Lys Gly Thr Ser Asp Lys Asn Asn
        35                  40                  45

Gly Ser Gly Val Leu Glu Gly Val Lys Ala Asp Lys Ser Lys Val Lys
    50                  55                  60

Leu Thr Ile Ser Asp Asp Leu Gly Gln Thr Thr Leu Glu Val Phe Lys
65                  70                  75                  80

Glu Asp Gly Lys Thr Leu Val Ser Lys Lys Val Thr Ser Lys Asp Lys
                85                  90                  95

Ser Ser Thr Glu Glu Lys Phe Asn Glu Lys Gly Glu Val Ser Glu Lys
            100                 105                 110

Ile Ile Thr Arg Ala Asp Gly Thr Arg Leu Glu Tyr Thr Gly Ile Lys
        115                 120                 125

Ser Asp Gly Ser Gly Lys Ala Lys Glu Val Leu Lys Gly Xaa Xaa Xaa
    130                 135                 140

Xaa Xaa Xaa Xaa Xaa Xaa Glu Lys Thr Thr Leu Val Val Lys Glu Gly
```

-continued

```
            145                 150                 155                 160
        Thr Val Thr Leu Ser Lys Asn Ile Ser Lys Ser Gly Glu Val Ser Val
                        165                 170                 175
        Glu Leu Asn Asp Thr Asp Ser Ser Ala Ala Thr Lys Lys Thr Ala Ala
                    180                 185                 190
        Trp Asn Ser Gly Thr Ser Thr Leu Thr Ile Thr Val Asn Ser Lys Lys
                    195                 200                 205
        Thr Lys Asp Leu Val Phe Thr Lys Glu Asn Thr Ile Thr Val Gln Gln
                210                 215                 220
        Tyr Asp Ser Asn Gly Thr Lys Leu Glu Gly Ser Ala Val Glu Ile Thr
        225                 230                 235                 240
        Lys Leu Asp Glu Ile Lys Asn Ala Leu Lys
                        245                 250
```

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

```
<400> SEQUENCE: 111
000

<210> SEQ ID NO 112
<400> SEQUENCE: 112
000

<210> SEQ ID NO 113
<400> SEQUENCE: 113
000

<210> SEQ ID NO 114
<400> SEQUENCE: 114
000

<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

<210> SEQ ID NO 118
<400> SEQUENCE: 118
000

<210> SEQ ID NO 119
<400> SEQUENCE: 119
000

<210> SEQ ID NO 120
<400> SEQUENCE: 120
000

<210> SEQ ID NO 121
<400> SEQUENCE: 121
000

<210> SEQ ID NO 122
<400> SEQUENCE: 122
```

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

```
<210> SEQ ID NO 168
<400> SEQUENCE: 168
000

<210> SEQ ID NO 169
<400> SEQUENCE: 169
000

<210> SEQ ID NO 170
<400> SEQUENCE: 170
000

<210> SEQ ID NO 171
<400> SEQUENCE: 171
000

<210> SEQ ID NO 172
<400> SEQUENCE: 172
000

<210> SEQ ID NO 173
<400> SEQUENCE: 173
000

<210> SEQ ID NO 174
<400> SEQUENCE: 174
000

<210> SEQ ID NO 175
<400> SEQUENCE: 175
000

<210> SEQ ID NO 176
<400> SEQUENCE: 176
000

<210> SEQ ID NO 177
<400> SEQUENCE: 177
000

<210> SEQ ID NO 178
<400> SEQUENCE: 178
000
```

-continued

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191
<400> SEQUENCE: 191

000

<210> SEQ ID NO 192
<400> SEQUENCE: 192

000

<210> SEQ ID NO 193
<400> SEQUENCE: 193

000

<210> SEQ ID NO 194
<400> SEQUENCE: 194

000

<210> SEQ ID NO 195
<400> SEQUENCE: 195

000

<210> SEQ ID NO 196
<400> SEQUENCE: 196

000

<210> SEQ ID NO 197
<400> SEQUENCE: 197

000

<210> SEQ ID NO 198
<400> SEQUENCE: 198

000

<210> SEQ ID NO 199
<400> SEQUENCE: 199

000

<210> SEQ ID NO 200
<400> SEQUENCE: 200

000

<210> SEQ ID NO 201
<211> LENGTH: 173
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 201
```

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Cys
            20                  25                  30

Met Ser Ser Trp Ser Tyr Thr His Ser Leu Asp Gly Ala Gly Leu Phe
        35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
            100                 105                 110

His Ala Ile Lys Ser Lys Asp His Ala Thr Phe Asn Phe Leu Gln Trp
        115                 120                 125

Tyr Val Ala Glu Gln His Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

```
<210> SEQ ID NO 202
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 202
```

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
            20                  25                  30

Met Ser Ser Trp Ser Tyr Thr His Ser Leu Asp Gly Ala Gly Leu Phe
        35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Cys Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
            100                 105                 110

His Ala Ile Lys Ser Lys Asp His Ala Thr Phe Asn Phe Leu Gln Trp
        115                 120                 125

Tyr Val Ala Glu Gln His Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 203
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 203

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
                20                  25                  30

Met Ser Ser Trp Ser Tyr Thr His Ser Leu Asp Gly Ala Gly Leu Phe
            35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Ser Ile Ser
65                  70                  75                  80

Cys Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
                100                 105                 110

His Ala Ile Lys Ser Lys Asp His Ala Thr Phe Asn Phe Leu Gln Trp
            115                 120                 125

Tyr Val Ala Glu Gln His Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 204
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 204

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
                20                  25                  30

Met Ser Ser Trp Ser Tyr Thr His Ser Leu Asp Gly Ala Gly Leu Phe
            35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Ser Ile Ser
65                  70                  75                  80

Ala Pro Glu His Cys Phe Glu Gly Leu Thr Gln Ile Phe Gln Lys Ala

-continued

```
                85                  90                  95

Tyr Glu His Glu Gln His Ile Ser Glu Ser Ile Asn Asn Ile Val Asp
            100                 105                 110

His Ala Ile Lys Ser Lys Asp His Ala Thr Phe Asn Phe Leu Gln Trp
        115                 120                 125

Tyr Val Ala Glu Gln His Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 205
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 205

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
            20                  25                  30

Met Ser Ser Trp Ser Tyr Thr His Ser Leu Asp Gly Ala Gly Leu Phe
        35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Cys Ile Asn Asn Ile Val Asp
            100                 105                 110

His Ala Ile Lys Ser Lys Asp His Ala Thr Phe Asn Phe Leu Gln Trp
        115                 120                 125

Tyr Val Ala Glu Gln His Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 206
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 206

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
            20                  25                  30
```

Met Ser Ser Trp Ser Tyr Thr His Ser Leu Asp Gly Ala Gly Leu Phe
            35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
            100                 105                 110

His Ala Ile Lys Cys Lys Asp His Ala Thr Phe Asn Phe Leu Gln Trp
            115                 120                 125

Tyr Val Ala Glu Gln His Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 207
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 207

Glu Ser Gln Val Arg Gln Gln Phe Ser Lys Asp Ile Glu Lys Leu Leu
1               5                   10                  15

Asn Cys Gln Val Asn Lys Glu Met Gln Ser Ser Asn Leu Tyr Met Ser
            20                  25                  30

Met Ser Ser Trp Ser Tyr Thr His Ser Leu Asp Gly Ala Gly Leu Phe
            35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
            100                 105                 110

His Ala Ile Lys Ser Lys Asp His Ala Thr Phe Asn Phe Leu Gln Trp
            115                 120                 125

Tyr Val Ala Glu Gln His Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 208
<211> LENGTH: 173
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 208

Glu Ser Gln Val Arg Gln Gln Phe Ser Lys Asp Ile Glu Lys Leu Leu
1               5                   10                  15

Asn Glu Gln Val Asn Lys Glu Met Asn Ser Ser Asn Leu Tyr Met Ser
            20                  25                  30

Met Ser Ser Trp Cys Tyr Thr His Ser Leu Asp Gly Ala Gly Leu Phe
        35                  40                  45

Leu Phe Asp His Ala Ala Glu Glu Tyr Glu His Ala Lys Lys Leu Ile
50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
            100                 105                 110

His Ala Ile Lys Ser Lys Asp His Ala Thr Phe Asn Phe Leu Gln Trp
        115                 120                 125

Tyr Val Ala Glu Gln His Glu Glu Val Leu Phe Lys Asp Ile Leu
130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170

<210> SEQ ID NO 209
<211> LENGTH: 166
<212> TYPE: PRT
<213> ORGANISM: Helicobacter pylori

<400> SEQUENCE: 209

Leu Ser Lys Asp Ile Ile Lys Leu Leu Asn Glu Gln Val Asn Lys Glu
1               5                   10                  15

Met Asn Ser Ser Asn Leu Tyr Met Ser Met Ser Ser Trp Cys Tyr Thr
            20                  25                  30

His Ser Leu Asp Gly Ala Gly Leu Phe Leu Phe Asp His Ala Ala Glu
        35                  40                  45

Glu Tyr Glu His Ala Lys Lys Leu Ile Ile Phe Leu Asn Glu Asn Asn
    50                  55                  60

Val Pro Val Gln Leu Thr Ser Ile Ser Ala Pro Glu His Lys Phe Glu
65                  70                  75                  80

Gly Leu Thr Gln Ile Phe Gln Lys Ala Tyr Glu His Glu Gln His Ile
                85                  90                  95

Ser Glu Ser Ile Asn Asn Ile Val Asp His Ala Ile Lys Ser Lys Asp
            100                 105                 110

His Ala Thr Phe Asn Phe Leu Gln Trp Tyr Val Ala Glu Gln His Glu
        115                 120                 125

Glu Val Leu Phe Lys Asp Ile Leu Asp Lys Ile Glu Leu Ile Gly
    130                 135                 140

Asn Glu Asn His Gly Leu Tyr Leu Ala Asp Gln Tyr Val Lys Gly Ile
145                 150                 155                 160

Ala Lys Ser Arg Lys Ser
                165

<210> SEQ ID NO 210
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
tgactgtgaa cgttcgagat ga                                              22

<210> SEQ ID NO 211
<211> LENGTH: 191
<212> TYPE: PRT
<213> ORGANISM: Trichoplusia ni

<400> SEQUENCE: 211

Thr Gln Cys Asn Val Asn Pro Val Gln Ile Pro Lys Asp Trp Ile Thr
1               5                   10                  15

Met His Arg Ser Cys Arg Asn Ser Met Arg Gln Gln Ile Gln Met Glu
            20                  25                  30

Val Gly Ala Ser Leu Gln Tyr Leu Ala Met Gly Ala His Phe Ser Lys
        35                  40                  45

Asp Val Val Asn Arg Pro Gly Phe Ala Gln Leu Phe Phe Asp Ala Ala
    50                  55                  60

Ser Glu Glu Arg Glu His Ala Met Lys Leu Ile Glu Tyr Leu Leu Met
65                  70                  75                  80

Arg Gly Glu Leu Thr Asn Asp Val Ser Ser Leu Leu Gln Val Arg Pro
                85                  90                  95

Pro Thr Arg Ser Ser Trp Lys Gly Gly Val Glu Ala Leu Glu His Ala
            100                 105                 110

Leu Ser Met Glu Ser Asp Val Thr Lys Ser Ile Arg Asn Val Ile Lys
        115                 120                 125

Ala Cys Glu Asp Asp Ser Glu Phe Asn Asp Tyr His Leu Val Asp Tyr
    130                 135                 140

Leu Thr Gly Asp Phe Leu Glu Glu Gln Tyr Lys Gly Gln Arg Asp Leu
145                 150                 155                 160

Ala Gly Lys Ala Ser Thr Leu Lys Lys Leu Met Asp Arg His Glu Ala
                165                 170                 175

Leu Gly Glu Phe Ile Phe Asp Lys Lys Leu Leu Gly Ile Asp Val
            180                 185                 190

<210> SEQ ID NO 212
<211> LENGTH: 212
<212> TYPE: PRT
<213> ORGANISM: Trichoplusia ni

<400> SEQUENCE: 212

Ala Asp Thr Cys Tyr Asn Asp Val Ala Leu Asp Cys Gly Ile Thr Ser
1               5                   10                  15

Asn Ser Leu Ala Leu Pro Arg Cys Asn Ala Val Tyr Gly Glu Tyr Gly
            20                  25                  30

Ser His Gly Asn Val Ala Thr Glu Leu Gln Ala Tyr Ala Lys Leu His
        35                  40                  45

Leu Glu Arg Ser Tyr Asp Tyr Leu Leu Ser Ala Ala Tyr Phe Asn Asn
    50                  55                  60

```
Tyr Gln Thr Asn Arg Ala Gly Phe Ser Lys Leu Phe Lys Lys Leu Ser
 65                  70                  75                  80

Asp Glu Ala Trp Ser Lys Thr Ile Asp Ile Lys His Val Thr Lys
                 85                  90                  95

Arg Gly Asp Lys Met Asn Phe Asp Gln His Ser Thr Met Lys Thr Glu
            100                 105                 110

Arg Lys Asn Tyr Thr Ala Glu Asn His Glu Leu Glu Ala Leu Ala Lys
        115                 120                 125

Ala Leu Asp Thr Gln Lys Glu Leu Ala Glu Arg Ala Phe Tyr Ile His
    130                 135                 140

Arg Glu Ala Thr Arg Asn Ser Gln His Leu His Asp Pro Glu Ile Ala
145                 150                 155                 160

Gln Tyr Leu Glu Glu Glu Phe Ile Glu Asp His Ala Glu Lys Ile Arg
                165                 170                 175

Thr Leu Ala Gly His Thr Ser Asp Leu Lys Lys Phe Ile Thr Ala Asn
            180                 185                 190

Asn Gly His Asp Leu Ser Leu Ala Leu Tyr Val Phe Asp Glu Tyr Leu
        195                 200                 205

Gln Lys Thr Val
    210

<210> SEQ ID NO 213
<211> LENGTH: 174
<212> TYPE: PRT
<213> ORGANISM: Pyrococcus furiosus

<400> SEQUENCE: 213

Met Leu Ser Glu Arg Met Leu Lys Ala Leu Asn Asp Gln Leu Asn Arg
  1               5                  10                  15

Glu Leu Tyr Ser Ala Tyr Leu Tyr Phe Ala Met Ala Ala Tyr Phe Glu
                 20                  25                  30

Asp Leu Gly Leu Glu Gly Phe Ala Asn Trp Met Lys Ala Gln Ala Glu
             35                  40                  45

Glu Glu Ile Gly His Ala Leu Arg Phe Tyr Asn Tyr Ile Tyr Asp Arg
         50                  55                  60

Asn Gly Arg Val Glu Leu Asp Glu Ile Pro Lys Pro Pro Lys Glu Trp
 65                  70                  75                  80

Glu Ser Pro Leu Lys Ala Phe Glu Ala Ala Tyr Glu His Glu Lys Phe
                 85                  90                  95

Ile Ser Lys Ser Ile Tyr Glu Leu Ala Ala Leu Ala Glu Glu Glu Lys
            100                 105                 110

Asp Tyr Ser Thr Arg Ala Phe Leu Glu Trp Phe Ile Asn Glu Gln Val
        115                 120                 125

Glu Glu Glu Ala Ser Val Lys Lys Ile Leu Asp Lys Leu Lys Phe Ala
    130                 135                 140

Lys Asp Ser Pro Gln Ile Leu Phe Met Leu Asp Lys Glu Leu Ser Ala
145                 150                 155                 160

Arg Ala Pro Lys Leu Pro Gly Leu Leu Met Gln Gly Gly Glu
                165                 170

<210> SEQ ID NO 214
<211> LENGTH: 183
<212> TYPE: PRT
<213> ORGANISM: Homo sapiens

<400> SEQUENCE: 214
```

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Gln
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Gln Glu Ser
            180

<210> SEQ ID NO 215
<211> LENGTH: 204
<212> TYPE: PRT
<213> ORGANISM: Homo sapiens

<400> SEQUENCE: 215

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Ser Ser
            20                  25                  30

Gln Ile Arg Gln Asn Tyr Ser Thr Asp Val Glu Ala Ala Val Asn Ser
        35                  40                  45

Leu Val Asn Leu Tyr Leu Gln Ala Ser Tyr Thr Tyr Leu Ser Leu Gly
    50                  55                  60

Phe Tyr Phe Asp Arg Asp Asp Val Ala Leu Glu Gly Val Ser His Phe
65                  70                  75                  80

Phe Arg Glu Leu Ala Glu Glu Lys Arg Glu Gly Tyr Glu Arg Leu Leu
                85                  90                  95

Lys Met Gln Asn Gln Arg Gly Gly Arg Ala Leu Phe Gln Asp Ile Lys
            100                 105                 110

Lys Pro Ala Glu Asp Glu Trp Gly Lys Thr Pro Asp Ala Met Lys Ala
        115                 120                 125

Ala Met Ala Leu Glu Lys Lys Leu Asn Gln Ala Leu Leu Asp Leu His
    130                 135                 140

Ala Leu Gly Ser Ala Arg Thr Asp Pro His Leu Cys Asp Phe Leu Glu
145                 150                 155                 160

Thr His Phe Leu Asp Glu Glu Val Lys Leu Ile Lys Lys Met Gly Asp
                165                 170                 175

His Leu Thr Asn Leu His Arg Leu Gly Gly Pro Glu Ala Gly Leu Gly
            180                 185                 190

Glu Tyr Leu Phe Glu Arg Leu Thr Leu Lys His Asp
            195                 200

<210> SEQ ID NO 216
<211> LENGTH: 154
<212> TYPE: PRT
<213> ORGANISM: Aquifex aeolicus

<400> SEQUENCE: 216

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Cys Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asn Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150

<210> SEQ ID NO 217
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Bullfrog linker sequence"

<400> SEQUENCE: 217

Glu Ser Gln Val Arg Gln Gln Phe
1               5

<210> SEQ ID NO 218
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Cys Leu Val Pro Arg Gly Ser Leu Glu His His His His His His
1               5                   10                  15

<210> SEQ ID NO 219
<211> LENGTH: 156
<212> TYPE: PRT
<213> ORGANISM: Escherichia coli

<400> SEQUENCE: 219

```
Met Asn Ile Ile Glu Ala Asn Val Ala Thr Pro Asp Ala Arg Val Ala
1               5                   10                  15

Ile Thr Ile Ala Arg Phe Asn Asn Phe Ile Asn Asp Ser Leu Leu Glu
                20                  25                  30

Gly Ala Ile Asp Ala Leu Lys Arg Ile Gly Gln Val Lys Asp Glu Asn
            35                  40                  45

Ile Thr Val Val Trp Val Pro Gly Ala Tyr Glu Leu Pro Leu Ala Ala
        50                  55                  60

Gly Ala Leu Ala Lys Thr Gly Lys Tyr Asp Ala Val Ile Ala Leu Gly
65                  70                  75                  80

Thr Val Ile Arg Gly Gly Thr Ala His Phe Glu Tyr Val Ala Gly Gly
                85                  90                  95

Ala Ser Asn Gly Leu Ala His Val Ala Gln Asp Ser Glu Ile Pro Val
            100                 105                 110

Ala Phe Gly Val Leu Thr Thr Glu Ser Ile Glu Gln Ala Ile Glu Arg
        115                 120                 125

Ala Gly Thr Lys Ala Gly Asn Lys Gly Ala Glu Ala Ala Leu Thr Ala
            130                 135                 140

Leu Glu Met Ile Asn Val Leu Lys Ala Ile Lys Ala
145                 150                 155
```

```
<210> SEQ ID NO 220
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220
```

```
Gly Gly Gly Gly Ser Gly Gly Gly Ser Gly Gly Gly Gly Ser Gly
1               5                   10                  15
```

```
<210> SEQ ID NO 221
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221
```

```
Gly Gly Ser Gly Ser Gly Ser Asn Ser Ser Ala Ser Ser Gly Ala Ser
1               5                   10                  15

Ser Gly Gly Ala Ser Gly Gly Ser Gly Gly Ser Gly
            20                  25
```

```
<210> SEQ ID NO 222
<211> LENGTH: 46
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 222
```

```
Gly Gly Ser Gly Ser Ala Ser Ser Gly Ala Ser Ala Ser Gly Ser Ser
1               5                   10                  15
```

```
Asn Gly Ser Gly Ser Gly Ser Gly Ser Asn Ser Ser Ala Ser Ser Gly
                    20                  25                  30

Ala Ser Ser Gly Gly Ala Ser Gly Gly Ser Gly Gly Ser Gly
            35                  40                  45

<210> SEQ ID NO 223
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Gly Gly Ser Gly Ser Ala Ser Ala Glu Ala Ala Ala Lys Glu Ala Ala
1               5                   10                  15

Ala Lys Ala Gly Gly Ser Gly Gly Ser Gly
            20                  25

<210> SEQ ID NO 224
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 224

Gly Gly Ser Gly Ser Ala Ser Ala Glu Ala Ala Ala Lys Glu Ala Ala
1               5                   10                  15

Ala Lys Glu Ala Ala Ala Lys Ala Ser Gly Gly Ser Gly Gly Ser Gly
            20                  25                  30

<210> SEQ ID NO 225
<211> LENGTH: 47
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 225

Ser Gly Gly Gly Ser Gly Ser Ala Ser Ser Gly Ala Ser Ala Ser Gly
1               5                   10                  15

Ser Ser Cys Ser Gly Ser Gly Ser Gly Ser Ser Ala Ser Ser Gly
            20                  25                  30

Ala Ser Ser Gly Gly Ala Ser Gly Gly Ser Gly Gly Ser Gly
            35                  40                  45

<210> SEQ ID NO 226
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Gly Gly Gly Ser
1
```

```
<210> SEQ ID NO 227
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 227

His His His His His His
1               5

<210> SEQ ID NO 228
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
tgactgtgaa cgttcgagat g                                              21
```

We claim:

1. A composition comprising (a) an antigenic outer surface protein A (OspA) serotype 1 polypeptide of *Borrelia* and (b) a ferritin protein, wherein the OspA serotype 1 polypeptide of *Borrelia* does not comprise the sequence of SEQ ID NO: 77, wherein the OspA serotype 1 polypeptide of *Borrelia* comprises a sequence with at least 90% identity to the sequence of any one of SEQ ID NOS: 1, 3, 4, 53, or 94-102, and wherein the ferritin protein comprises a bullfrog linker that has the sequence of SEQ ID NO: 217, and wherein the ferritin protein comprises a sequence having at least 90% identity to SEQ ID NO: 90.

2. The composition of claim 1, wherein the ferritin protein comprises a mutation replacing a surface-exposed amino acid with a cysteine.

3. The composition of claim 1, wherein the ferritin protein comprises one or more of E1 2C, S26C, S72C, A75C, K79C, S100C, and S111C mutations of *H. pylori* ferritin or one or more corresponding mutations in a non-*H. pylori* ferritin as determined by pairwise or structural alignment.

4. The composition of claim 1, comprising one or more immune-stimulatory moieties linked to the ferritin protein via a surface-exposed amino acid, wherein the surface-exposed amino acid is a cysteine resulting from a mutation.

5. A ferritin particle comprising the composition of claim 1.

6. The composition of claim 1, further comprising a pharmaceutically acceptable carrier.

* * * * *